United States Patent
Rybtchinski et al.

(10) Patent No.: US 9,623,381 B2
(45) Date of Patent: Apr. 18, 2017

(54) SEPARATION OF NANOPARTICLES

(71) Applicant: YEDA RESEARCH AND DEVELOPMENT CO. LTD., Rehovot (IL)

(72) Inventors: Boris Rybtchinski, Givaataim (IL); Elisha M. Krieg, Rehovot (IL); Haim Weissman, Rehovot (IL); Shira Albeck, Rehovot (IL); Yaron Tidhar, Rehovot (IL); Erez Cohen, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 0 days.

(21) Appl. No.: 14/753,096

(22) Filed: Jun. 29, 2015

(65) Prior Publication Data
US 2015/0375180 A1 Dec. 31, 2015

Related U.S. Application Data

(63) Continuation-in-part of application No. 14/636,227, filed on Mar. 3, 2015, and a continuation-in-part of
(Continued)

(51) Int. Cl.
| | | |
|---|---|---|
| H01L 51/54 | (2006.01) |
| C09K 11/06 | (2006.01) |
| B01D 71/64 | (2006.01) |
| C07C 319/28 | (2006.01) |
| C07C 209/86 | (2006.01) |
| B01D 65/02 | (2006.01) |
| B01D 69/14 | (2006.01) |
| B01D 67/00 | (2006.01) |
| B01D 69/02 | (2006.01) |
| C07C 51/42 | (2006.01) |
| C08G 65/30 | (2006.01) |
| C07F 15/00 | (2006.01) |
| C07D 471/06 | (2006.01) |
| C07F 1/10 | (2006.01) |
| C08G 83/00 | (2006.01) |
| C08G 61/12 | (2006.01) |
| B82Y 30/00 | (2011.01) |

(Continued)

(52) U.S. Cl.
CPC ............ *B01D 71/64* (2013.01); *B01D 65/02* (2013.01); *B01D 67/0016* (2013.01); *B01D 69/02* (2013.01); *B01D 69/14* (2013.01); *C07C 51/42* (2013.01); *C07C 209/86* (2013.01); *C07C 319/28* (2013.01); *C07D 471/06* (2013.01); *C07F 1/10* (2013.01); *C07F 15/0066* (2013.01); *C07F 15/0093* (2013.01); *C08G 61/122* (2013.01); *C08G 65/30* (2013.01); *C08G 83/008* (2013.01); *B01D 2325/04* (2013.01); *B01D 2325/20* (2013.01); *B82Y 30/00* (2013.01); *B82Y 40/00* (2013.01); *C08G 2261/1424* (2013.01); *C08G 2261/226* (2013.01); *C08G 2261/3221* (2013.01); *C08G 2261/3328* (2013.01); *C08G 2261/344* (2013.01); *C08G 2261/37* (2013.01); *C08G 2261/374* (2013.01); *C08G 2261/90* (2013.01); *C08G 2261/964* (2013.01); *C08L 65/00* (2013.01)

(58) Field of Classification Search
CPC .... C07F 1/00; C07F 1/10; C07F 15/00; C07F 15/006; C07F 15/0066; C07F 15/0086; C07F 15/0093; C08G 61/00; C08G 61/122; C08G 2261/00; C08G 2261/3241; C08G 2261/142; C08G 2261/1424; C08G 2261/226; C08G 2261/3221; C08G 2261/3328; C08G 2261/344; C08G 2261/37; C08G 2261/374; C08G 2261/90; C08G 2261/964; C08G 83/008; B82Y 30/00; B82Y 40/00; C09K 11/06; C09K 2211/00; C09K 2211/14; C09K 2211/1408; C09K 2211/1416; C07D 471/00; C07D 471/06; H01L 51/0032; H01L 51/0034; H01L 51/0043; H01L 51/0053; H01L 51/0067; H01L 51/0087; H01L 51/0091
USPC ..................... 428/690, 691, 917, 411.4, 336; 313/500–512; 257/40, 88–104, 257/E51.001–E51.052; 252/301.16–301.35; 546/10, 37; 528/367; 536/241; 977/773, 810
See application file for complete search history.

(56) References Cited

U.S. PATENT DOCUMENTS

| | | | |
|---|---|---|---|
| 6,143,905 A | 11/2000 | Böhm et al. |
| 6,184,378 B1 | 2/2001 | Böhm et al. |

(Continued)

FOREIGN PATENT DOCUMENTS

| | | |
|---|---|---|
| CN | 1706842 | 5/2005 |
| CN | 101157757 A | 4/2008 |

(Continued)

OTHER PUBLICATIONS

Supporting Information Nature Nanotechnology 2011, 6, 141-146, SI pp. 1-21. Date of publication: Jan. 23, 2011.*

(Continued)

*Primary Examiner* — Andrew K Bohaty
(74) *Attorney, Agent, or Firm* — Mark S. Cohen; Pearl Cohen Zedek Latzer Baratz LLP

(57) ABSTRACT

This invention is directed to separation, optimization and purification of nano-materials using self-assembled perylene diimide membranes, wherein said perylene diimide membrane is recyclable.

31 Claims, 48 Drawing Sheets

Related U.S. Application Data application No. 13/779,248, filed on Feb. 27, 2013, now Pat. No. 9,067,181, which is a continuation-in-part of application No. PCT/IL2011/000687, filed on Aug. 25, 2011.

(60) Provisional application No. 61/377,540, filed on Aug. 27, 2010.

(51) Int. Cl.
　　*B82Y 40/00*　　　(2011.01)
　　*C08L 65/00*　　　(2006.01)

(56) References Cited

U.S. PATENT DOCUMENTS

| | | |
|---|---|---|
| 6,326,494 B1 | 12/2001 | Böhm et al. |
| 8,859,772 B2 | 10/2014 | Rybtchinski et al. |
| 8,968,886 B2 | 3/2015 | Rybtchinski et al. |
| 2005/0176970 A1 | 8/2005 | Marks et al. |
| 2007/0202353 A1 | 8/2007 | Inagaki et al. |
| 2008/0241090 A1 | 10/2008 | Speckbacher et al. |
| 2011/0137008 A1 | 6/2011 | Yeh et al. |

FOREIGN PATENT DOCUMENTS

| | | |
|---|---|---|
| EP | 0422535 A1 | 4/1991 |
| WO | WO 97/22607 | 6/1997 |
| WO | WO 02/14318 A1 | 2/2002 |
| WO | WO 02/14414 A3 | 2/2002 |
| WO | WO 2005/124453 A2 | 12/2005 |
| WO | WO 2008/139452 A3 | 11/2008 |
| WO | WO 2009/118742 | 10/2009 |

OTHER PUBLICATIONS

Addicott et al. "Synthesis of a bis(pyridyl)-substituted perylene diimide ligand and incorporation into a supramolecular rhomboid and rectangle via coordination driven self-assembly" J Org Chem.;70(3):797-801, Feb, 4, 2005.

Ahrens et al.; "Self-Assembly of Supramolecular Light-Harvesting Arrays from Covalent Multi-Chromophore Perylene-3,4:9,10-bis(dicarboximide) Building Blocks", J. Am. Chem. Soc. 2004, 126, 8284-8294.

Aprahamian; "Anions and Polyanions of Oligoindenopyrenes: Modes of Electron Delocalization and Dimerization", Chem. Asian J. 2006, 1, 678-685.

Baram et al.; "Control over Self-Assembly through Reversible Charging of the Aromatic Building Blocks in Photofunctional Supramolecular Fibers", J. Am. Chem. Soc. 2008, 130, 14966-14967.

Becke; "Density-functional thermochemistry. III. The role of exact exchange," J. Chem. Phys.98 (7), pp. 5648-5652, (1993).

Beginn; "Supramolecular Templates as Porogenes", Adv. Mater. 1998, 10, 1391-1394.

Benfer et al.; "Ceramic Membranes for Filtration Applications—Preparation and Characterization", Eng. Mater. 2004, 6, 495-500.

Bhattacharjee et al.; "Studies on the fractionation of β-lactoglobulin from casein whey using ultrafiltration and ion-exchange membrane chromatography", J. Membr. Sci. 2006, 275, 141-150.

Binsilong et al.; "Synthesis and Structure of a Novel Silver(1) Perchlorate 2,2':6',2"-Terpyridine Adduct Solvated with Acetonitrile", Aust. J. Chem. 1994, 47, 1545-1551.

Breeze et al. "Polymer—perylene diimide heterojunction solar cells," Appl. Phys. Lett., 81, 3085, (2002).

Brust; "Synthesis of thiol-derivatised gold nanoparticles in a two-phase Liquid-Liquid system", J. Chem. Soc., Chem. Commun., 801 (1994).

Busbee et al.; "An Improved Synthesis of High-Aspect-Ratio Gold Nanorods", Adv. Mater.15, 414 (2003).

Che et al.; "Ultralong Nanobelts Self-Assembled from an Asymmetric Perylene Tetracarboxylic Diimide", J. Am. Chem. Soc. 2007, 129, 7234-7235.

Chen et al.; "Self-assembled Π-stacks of functional dyes in solution: structural and thermodynamic features", Chem. Soc. Rev. 2009, 38, 564-584.

Cohen et al.; "The Charge Alternation Concept: Application to Cyclic Conjugated Doubly Charged Systems", J. Am. Chem. Soc. 1988, 110, 4634-4640.

Corbin et al.; "Self-Association without Regard to Prototropy. A Heterocycle That Forms Extremely Stable Quadruply Hydrogen-Bonded Dimers", J. Am. Chem. Soc. 1998, 120, 9710-9711.

Cui et al.; "Block Copolymer Assembly via Kinetic Control", Science 2007, 317, 647-650.

Dalsin et al.; "Protein Resistance of Titanium Oxide Surfaces Modified by Biologically Inspired mPEG—DOPA", Langmuir 2004, 21, 640-646.

Demmig et al. "Easily soluble and photostable perylene fluorescent dyes," Chemische Berichte, vol. 121 Issue 2, pp. 225-230, (1988).

Dimitrakopoulos et al. "Organic thin film transistors for large area electronics," Advanced Materials, 14, pp. 99-117, (2002).

Dreiss; "Wormlike micelles: where do we stand? Recent developments, linear rheology and scattering techniques", Soft Matter 2007, 3, 956-970.

Ebeid et al. "Emission characteristics and photostability of N, N'-bis (2, 5-di-tert-butylphenyl)-3, 4:9, 10-perylenebis (dicarboximide)," Journal of physical chemistry, vol. 92, No. 15, pp. 4565-4568, (1988).

Ego et al.; "Attaching perylene dyes to polyfluorene: three simple, efficient methods for facile color tuning of light-emitting polymers" J. Am. Chem. Soc, 125, 437, (2003).

Fan et al. "1,6-Disubstituted perylene bisim ides: concise synthesis and characterization as near-infrared fluorescent dyes," Tetrahedron Letters, vol. 46, Issue 26, pp. 4443-4447, Jun. 27, 2005.

Ford et al.; "Photochemistry of 3,4,9,10-perylenetetracarboxylic dianhydride dyes. 4. Spectroscopic and redox properties of oxidized and reduced forms of the bis(2,5-di-tert-butylphenyl)imide derivative" J. Phys. Chem., 93 (18), pp. 6692-6696, (1989).

Fox; "The Photoexcited States of Organic Anions", Chem. Rev. 1979, 79, 253-273.

Frim et al.; "Helicene Dianions : Paratropicity of Twisted Phenanthrene Dianions", Chem. Int. Ed. 1990, 29, 919-921.

Gibb; "Supramolecular Assembly and Binding in Aqueous Solution: Useful Tips Regarding the Hofmeister and Hydrophobic Effects", Isr. J. Chem. 2011, 51, 798-806.

Golubkov et al.; "Economical Design in Noncovalent Nanoscale Synthesis: Diverse Photofunctional Nanostructures Based on a Single Covalent Building Block", Angew. Chem. Int. Ed. 2009, 48, 926-930, Jan. 7, 2009.

Gosztola; "Excited Doublet States of Electrochemically Generated Aromatic Imide and Diimide Radical Anions", J. Phys. Chem. A 2000, 104, 6545-6551.

Holy; "Reactions of the Radical Anions and Dianions of Aromatic Hydrocarbons", N. L., Chem. Rev. 1974, 74, 243-277.

Huber et al.; "Effects of Electron-Transfer Processes on Conformation", Acc. Chem. Res. 1986, 19, 300-306.

Ichikawa et al; "Hydrogen Absorption and Hydrogen Exchange Reactions in Solution by 1 : 2 Electron Donor-Acceptor Complexes of Anthracene with Various Alkali Metals", J. Am. Chem. Soc. 1971, 93, 2079-2080.

International Search Report for PCT Application No. PCT/IL2011/000687 mailed on Nov. 7, 2011.

Jain et al.; "Consequences of Nonergodicity in Aqueous Binary PEO-PB Micellar Dispersions", Macromolecules 2004, 37, 1511-1523.

Jones et al. "High-Mobility Air-Stable n-Type Semiconductors with Processing Versatility: Dicyanoperylene-3, 4:20049, 10-bis (dicarboximides)," Angew. Chem. Int. Ed. 43, 6363-6366, (2004).

Kaminker et al.; "Molecular Structure—Function Relations of the Optical Properties and Dimensions of Gold Nanoparticle Assemblies", Angew. Chem. 2010, 122, 1240-1243.

Kane et al.; "Kosmotropes Form the Basis of Protein-Resistant Surfaces", Langmuir 2003, 19, 2388-2391.

(56) References Cited

OTHER PUBLICATIONS

Katz; "The Cyclootatetraenyl Dianion", J. Am. Chem. Soc. 1960, 82, 3784-3785.
Keller et al.; "The bioseparation needs for tomorrow", Trends Biotechnol. 2001, 19, 438-441.
Kimling et al.; "Turkevich Method for Gold Nanoparticle Synthesis Revisited", J. Phys. Chem. B 2006, 110, 15700-15707.
Kingshott et al.; "Effects of cloud-point grafting, chain length, and density of PEG layers on competitive adsorption of ocular proteins", Biomaterials 2002, 23, 2043-2056.
Krieg et al.; "A recyclable supramolecular membrane for size-selective separation of nanoparticles", Nature Nanotech. 2011, 6, 141-146.
Krieg et al.; "Supramolecular Gel Based on a Perylene Diimide Dye: Multiple Stimuli Responsiveness, Robustness, and Photofunction", Am. Chem. Soc. 2009, 131, 14365-14373.
Langhals et al.; "Novel Fluorescent Dyes by the Extension of the Core of Perylenetetracarboxylic Bisimides," European Journal of Organic Chemistry, vol. 2000, Iss. 2, pp. 365-380, (2000).
Langhals; "Control of the Interactions in Multichromophores: Novel Concepts. Perylene Bis-imides as Components for Larger Functional Units," Helvetica Chimica Acta vol. 88, Issue 6, pp. 1309-1343, (2005).
Langhals; "Synthesis of highly pure perylene fluorescent dyes in large scale amounts-specific preparation of atropisomers," Chemische Berichte, vol. 118, No. 11, pp. 4641-4645, (1985).
Langhals;. "A novel fluorescent dye with strong, anisotropic solid-state fluorescence, small stokes shift, and high photostability," Angew Chem Int Ed Engl. 44(16):2427-8, Apr. 15, 2005.
Li et al. "Energy transfer switching in a bistable molecular machine," Org Lett.; 7(22):4835-8. Oct. 27, 2005.
Li et al.; "Synthesis and characterization of ferrocene-perylenetetracarboxylic diimide-fullerene triad", Tetrahedron, vol. 61, Issue 6, pp. 1563-1569, Feb. 7, 2005.
Li et al.; "Synthesis, Characterization, and Self-Assembly of Nitrogen-Containing Heterocoronenetetracarboxylic Acid Diimide Analogues: Photocyclization of N-Heterocycle-Substituted Perylene Bisimides," Chem. Eur. J., 12, pp. 8378-8385, (2006).
Li et al.; "Ultrafast Aggregate-to-Aggregate Energy Transfer within Self-assembled Light-Harvesting Columns of Zinc Phthalocyanine Tetrakis(Perylenediimide)," J. Am. Chem. Soc. 126, 10810-10811, (2004).
Li et al.; "Multicompartment Micelles from ABC Miktoarm Stars in Water", Science 2004, 306, 98-101.
Lightfoot et al.; "Bioseparations", Biotechnol. Bioeng. 2004, 87, 259-273.
Lim et al.; "Rod—coil block molecules: their aqueous self-assembly and biomaterials applications", Mater. Chem. 2008, 18, 2909-2909.
Locklin et al.; "Organic Thin Film Transistors Based on Cyclohexyl-Substituted Organic Semiconductors," Chem. Mater., 17 (13), pp. 3366-3374, (2005).
Lu et al.; "Electrochemical Characterization, Electrochroism, and Voltage-Dependent Fluorescence of Novel Perylene-Containing Polyimides", Macromolecules 1999, 32, 8880-8885.
Lu et al.; "Nanofiltration Membranes based on Rigid Star Amphiphiles", Chem. Mater. 2007, 19, 3194-3204.
Lu et al.; "Fractionation of Lysozyme and Chicken Egg Albumin Using Ultrafiltration with 30-kDa Commercial Membranes", Ind. Eng. Chem. Res. 2005, 44, 7610-7616.
Müllen et al.; "Dianion and Tetraanion of Octalene", Chem. Int. Ed. 1979, 18, 229-231.
Müllen et al.; "Highly Reduced Annulenes. Novel Probes for Spectroscopy and Theory", J. Am. Chem. Soc. 1982, 104, 5403-5411.
Müllen; "The Dianions of Phenanthrene and 1,2,3,4-Dibenzocyclooctatetraene", Helv. Chim. Acta 1978, 61, 1296-1304.
Müllen; "The Dianions of Pyrene and Pyrene Isomers as (4n)π-Perimeters')", Helv. Chim. Acta 1978, 61, 2307-2317.
Nunes et al.; "Switchable pH-Responsive Polymeric Membranes Prepared via Block Copolymer Micelle Assembly", ACS Nano 2011, 5, 3516-3522.
Peeva et al.; "Performance of Thin-Layer Hydrogel Polyethersulfone Composite Membranes during Dead-End Ultrafiltration of Various Protein Solutions", Ind. Eng. Chem. Res. 2012, 51, 7231-7241.
Peinemann et al.; "Asymmetric superstructure formed in a block copolymer via phase separation", Nat. Mater. 2007, 6, 992-996.
Peng; "Using redundant internal coordinates to optimize equilibrium geometries and transition states," Journal of Computational Chemistry, vol. 17 Issue 1, pp. 49-56, (1996).
Prathapan et al.; "Synthesis and Excited-State Photodynamics of Perylene—Porphyrin Dyads. 1. Parallel Energy and Charge Transfer via a Diphenylethyne Linker," J. Phys. Chem. B, 105 (34), pp. 8237-8248, (2001).
Prins et al.; "Noncovalent Synthesis Using Hydrogen Bonding", Chem. Int. Ed. 2001, 40, 2382-2426.
Qu et al.; "Dendronized perylenetetracarboxdiimides with peripheral triphenylamines for intramolecular energy and electron transfer," Chem. Eur. J. 10, 528-537, (2004).
Rabinovitz et al.; "From Charged to Super-chargedl Systems: The Problem of "Aromaticity" in Polycyclic Ions ", Acc. Chem. Res. 1983, 16, 298-304.
Rabinovitz et al.; "Π-Conjugated polycyclic anions; interplay between topology, electronic structure and patterns of charge distribution", Pure Appl. Chem. 1993, 65, 111-118.
Rajasingh et al.; "Selective Bromination of Perylene Diimides under Mild Conditions" J. Org. Chem., 72, 5973-5979, (2007).
Roger et al.; "Efficient Energy Transfer from Peripheral Chromophores to the Self-Assembled Zinc Chlorin Rod Antenna: A Bioinspired Light-Harvesting System to Bridge the „Green Gap", Am. Chem. Soc. 128, 6542-6543, (2006).
Rybtchinski B et al.; "Combining Light-Harvesting and Charge Separation in a Self-Assembled Artificial Photosynthetic System Based on Perylenediimide Chromophores," J. Am. Chem. Soc.126 (39), pp. 12268-12269, (2004).
Ryu et al.; Aqueous self-assembly of aromatic rod building blocks Chem. Commun. 2008, 1043-1054.
Sautter A et al.; "Ultrafast Energy-Electron Transfer Cascade in a Multichromophoric Light-Harvesting Molecular Square," J. Am. Chem. Soc. 127 (18), pp. 6719-6729, (2005).
Saxena et al.; "Membrane-based techniques for the separation and purification of proteins: An overview", Adv. Coll. Int. Sci. 2009, 145, 1-22.
Schlegel; "Optimization of equilibrium geometries and transition structures," Journal of Computational Chemistry, vol. 3 Iss. 2, pp. 214-218, (1982).
Schmidt-Mende; et al. "Self-Organized Discotic Liquid Crystals for High-Efficiency Organic Photovoltaics," Science: vol. 293. No. 5532, pp. 1119-1122, Aug. 10, 2001.
Schmuck et al.; "Highly Stable Self-Assembly in Water: Ion Pair Driven Dimerization of a Guanidiniocarbonyl Pyrrole Carboxylate Zwitterion", J. Am. Chem. Soc. 2003, 125, 452-459.
Shin et al.; "Effects of functional groups at perylene diimide derivatives on organic photovoltaic device application," J. Mater. Chem.16, 384-390, (2006).
Shirman et al.; "Stable Aromatic Dianion in Water", J. Phys. Chem. B, 2008, 112, 8855-8858.
Srere et al.; "Citrate condensing enzyme of pigeon breast muscle and moth flight muscle", Acta Chem. Scand. 1963, 17, S129-S134.
Struijk et al.; "Liquid Crystalline Perylene Diimides: Architecture and Charge Carrier Mobilities," J. Am. Chem. Soc. 122 (45), pp. 11057-11066, (2000).
Tidhar et al.; "Pathway-Dependent Self-Assembly of Perylene Diimide/Peptide Conjugates in Aqueous Medium", Chem. Eur. J. 2011, 17, 6068-6075.
Tokarev et al.; "Multiresponsive, Hierarchically Structured Membranes: New, Challenging, Biomimetic Materials for Biosensors, Controlled Release, Biochemical Gates, and Nanoreactors", Adv. Mater. 2009, 21, 241-247.

(56) References Cited

OTHER PUBLICATIONS

Turkevich et al.; "A Study of the Nucleationand Growth Processes in the Synthesis of Colloidal Gold", Discuss. Faraday Soc. 11, 55 (1951).

Tyagi et al.; "Dynamic Interactive Membranes with Pressure-Driven Tunable Porosity and Self-Healing Ability", Chem. Int. Ed. 2012, 51, 7166-7170.

Uehara et al.; "Size-Selective Diffusion in Nanoporous but Flexible Membranes for Glucose Sensors", ACS Nano 2009, 3, 924-932.

Ulbricht; "Advanced functional polymer membranes", Polymer 2006, 47, 2217-2262.

Vanburgel et al.; "The dynamics of one-dimensional excitons in liquids", J. Chem. Phys. 1995, 102, 20-33.

Wang et al.' "Alternating DNA and Π-Conjugated Sequences. Thermophilic Foldable Polymers," J. Am. Chem. Soc.125 (18), pp. 5248-5249, (2003).

Wasielewski; "Energy, Charge, and Spin Transport in molecules and Self-Assembled Nanostructures Inspired by Photosynthesis," J. Org. Chem. 71, pp. 5051-5066, (2006).

Willner et al.; "Manifestation of Dual Aromaticity in Doubly Charged Annelated Pentalenes", Am. Chem. Soc. 1979, 101, 395-401.

Wuelfing et al.; "Nanometer Gold Clusters Protected by Surface-Bound Monolayers of Thiolated Poly(ethylene glycol) Polymer Electrolyte", J. Am. Chem. Soc.120, 12696 (1998).

Würthner et al.; "Preparation and Characterization of Regioisomerically Pure 1, 7-Disubstituted Perylene Bisimide Dyes," J. Org. Chem. 69, 7933-7939, (2004).

Würthner et al.; "Metallosupramolecular squares: from structure to function," Chem. Soc. Rev.,33, pp. 133-146, (2004).

Würthner; "Perylene bisimide dyes as versatile building blocks for functional supramolecular architectures," Chemical communications 2004, No. 14, pp. 1564-1579.

Xiao et al.; "Dyads and triads containing perylenetetracarboxylic diimide and porphyrin: efficient photoinduced electron transfer elicited via both excited singlet states," J Phys Chem B.;109(8):3658-67,Mar, 3, 2005.

Yakimov et al.; "High photovoltage multiple-heterojunction organic solar cells incorporating interfacial metallic nanoclusters," Appl. Phys. Lett. 80, 1667, (2002).

Yang et al.; "Single File Diffusion of Protein Drugs through Cylindrical Nanochannels", ACS Nano 2010, 4, 3817-3822.

Yoo et al.; "High-mobility bottom-contact n-channel organic transistors and their use in complementary ring oscillators," Appl. Phys. Lett. 88, 082104, (2006).

You et al.; "Light-harvesting metallosupramolecular squares composed of perylene bisimide walls and fluorescent antenna dyes," Chemistry.12 (28):7510-9, Sep, 2006, 25.

Zang et al.; "A Single-Molecule Probe Based on Intramolecular Electron Transfer," J. Am. Chem. Soc.124 (36), pp. 10640-10641, (2002).

Zhang et al.; "Morphology Control of Fluorescent Nanoaggregates by Co-Self-Assembly of Wedge- and Dumbbell-Shaped Amphiphilic Perylene Bisimides", J. Am. Chem. Soc. 2007, 129, 4886-4887.

Zhang et al.; "The Influence of Carboxyl Groups on the Photoluminescence of Mercaptocarboxylic Acid-Stabilized CdTe Nanoparticles", J. Phys. Chem. B107, 8 (2003).

Zhao et al;. "3, 4:9, 10-Perylenebis (dicarboximide) chromophores that function as both electron donors and acceptors," Tetrahedron Letters, vol. 40, Iss. 39, pp. 7047-7050, (1999).

Zollinger; "Color Chemistry. 3rd ed" Verlag Helvetica Chimica Acta, Zurich, Wiley-VCH, Weinheim, (2003).

Gao et al. "Chinese Chemical Letters", vol. 18, Issue 3, Mar. 2007, pp. 283-286.

\* cited by examiner

PEG = polyethylene glycol

Before filtration:

Filtrate:

Before filtration:

Filtrate:

A

B

SEPARATION OF NANOPARTICLES

CROSS REFERENCE TO RELATED APPLICATIONS

This application is a Continuation-In-Part of U.S. patent application Ser. No. 13/779,248, filed 27 Feb. 2013, which is a Continuation-in-Part application of International Application Number PCT/IL2011/000687 filed 25 Aug. 2011, which claims priority of United-States Provisional Ser. No. 61/377,540 filed 27 Aug. 2010; This application is a Continuation-In-Part of U.S. patent application Ser. No. 14/636,227, filed 3 Mar. 2015; which are incorporated in their entirety herein by reference.

FIELD OF THE INVENTION

This invention is directed to separation, optimization and purification of nano-materials using self-assembled perylene diimide membranes, wherein said perylene diimide membrane is recyclable.

BACKGROUND OF THE INVENTION

Separation and purification of nanoparticles (NPs) or biomolecules become increasingly important both for fundamental studies and applications. Known separation techniques include size exclusion chromatography, size-selective precipitation, gel electrophoresis and (ultra) centrifugation. Although these techniques can be used to separate according to size they are usually time- or energy consuming. An emerging alternative to these methods is represented by filtration techniques. In particular, ultrafiltration is a pressure-driven separation process in which porous membranes retain particles larger than the membrane cut-off (ranging from 2 to 100 nm). Membrane processes allow fast separation, the use of small solvent volumes, and are suitable for separation and purification of various NPs. Filtration can be easily scaled up, allowing separation and purification on the industrial scale. All commercially available filtration membranes used today are either polymer-based or ceramic. Supramolecular structures have been used as templates for porous membranes and for modification of membrane pores. The challenge in creating supramolecular filtration membranes relates to the robustness and the structure that is adequate for filtration, requiring a uniform porous array that maintains its integrity and pore sizes under the forces created by percolation of solvents and solutes during the filtration process.

Membrane filtration is an essential tool in the biotechnological industry and appears to be particularly useful for the purification and concentration of proteins. Moreover, membranes can be used for immobilization and biocatalytic utilization of enzymes. As enzymes catalyze reactions under very mild conditions, exhibiting efficiency and selectivity largely unmatched by synthetic catalysts, such membrane reactors are emerging components in new, environmentally friendly industrial processes (heterogeneous biocatalysis), which may supplement or replace traditional chemical methods.

Separation of chiral compounds is of great interest since the majority of bioorganic compounds (sugars, amino-acids, sugar, proteins, nucleic acids) are chiral. Chirality is a major concern also in the pharmaceutical industry, since drugs with different chirality may have different pharmacological activities as well different pharmacokinetic and pharmacodynamic effects. Chiral HPLC and chiral GC have proven to be one of the methods for the direct separation of enantiomers. However, there is still no one universal column that has the ability to separate all classes of racemic compounds.

Filtration membranes which are used today are based on polymers or ceramics. Supramolecular systems have been utilized as templates for polymer membrane pores, rather than the membrane material itself. Recently, substantial progress has been made in fabricating supramolecular membranes. However, these membranes employ conventional high molecular weight polymers, and those that were applied to biological systems underwent elaborate modifications of the self-assembled material prior to use.

SUMMARY OF THE INVENTION

In one embodiment, this invention is directed to noncovalent self-assembled porous membrane comprising a perylene diimide supramolecular structure.

In one embodiment, this invention is directed to a non-covalent self-assembled porous membrane comprising a perylene diimide supramolecular structure, and provides a chromatography medium for size-selective separation of nano-material;
wherein said perylene diimide supramolecular structure comprises a mixture of perylene diimide compounds,
wherein each perylene diimide compound is a monomeric unit represented by the structure of formula I:

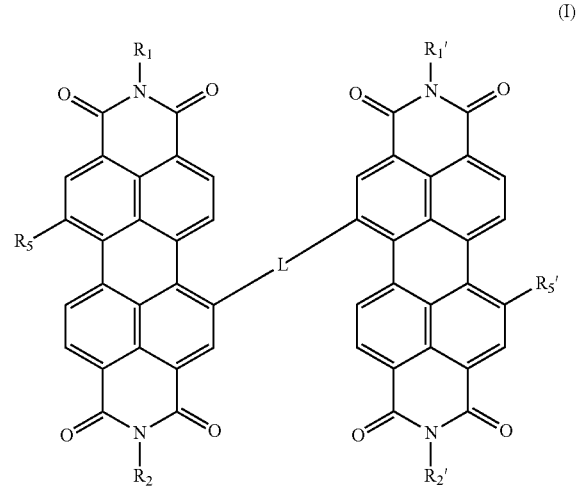

(I)

wherein
$R_1$ and $R_1'$ are each independently $[(CH_2)_qO]_rCH_3$, $[(CH_2)_qO]_rH$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$ alkyl, $(C_3-C_8)$ cycloalkyl, aryl, heteroaryl, chiral group, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$ alkyl; and wherein $R_3$ in said $[C(O)CHR_3NH]_1H$ is an alkyl, haloalkyl, hydroxyalkyl, hydroxyl, aryl, phenyl, alkylphenyl, alkylamino and independently the same or different when p is larger than 1;

$R_2$ and $R_2'$ are each independently $[(CH_2)_q O]_r CH_3$, $[(CH_2)_q C(O)O]_r CH_3$, $[(CH_2)_q C(O)NH]_r CH_3$, $[(CH_2)_q CH_2=CH_2]_r CH_3$, $[(CH_2)_q CH=CH]_r CH_3$, $[(CH_2)_q NH]_r CH_3$, $[(alkylene)_q O]_r CH_3$, $[(alkylene)_q C(O)O]_r CH_3$, $[(alkylene)_q C(O)NH]_r CH_3$, $[(alkylene)_q CH_2=CH_2]_r CH_3$, $[(alkylene)_q CH=CH]_r CH_3$, $[(alkylene)_q NH]_r CH_3$, $(C_1-C_{32})$ alkyl, $(C_3-C_8)$cycloalkyl, aryl, heteroaryl, chiral group, $(C_1-C_{32})$alkyl-COOH, $(C_1-C_{32})$alkyl-Si-A, or $[C(O)CHR_4NH]_s H$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$ alkyl; and wherein $R_4$ in said $[C(O)CHR_4NH]_s H$ is an alkyl, haloalkyl, hydroxyalkyl, hydroxyl, aryl, phenyl, alkylphenyl, alkylamino and independently the same or different when s is larger than 1;

$R_5$ and $R_5'$ are each independently H, —$OR_x$ where $R_x$ is $C_1-C_6$ alkyl, $[(CH_2)_n O]_o CH_3$ or $[(CH_2)_n O]_o H$; $[(CH_2)_n C(O)O]_o CH_3$, $[(CH_2)_n C(O)NH]_o CH_3$, $[(CH_2)_n CH_2=CH_2]_o CH_3$, $[(CH_2)_n CH=CH]_o CH_3$, $[(CH_2)_n NH]_o CH_3$, $[(alkylene)_n O]_o CH_3$, $[(alkyl ene)_n C(O)O]_o CH_3$, $[(alkylene)_n C(O)NH]_o CH_3$, $[(alkylene)_n CH_2=CH_2]_o CH_3$, $[(alkylene)_n CH=CH]_o CH_3$, $[(alkylene)_n NH]_o CH_3$, aryl, heteroaryl, C≡C—$R_7$, CH=$CR_8R_9$, $NR_{10}R_{11}$, chiral group, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_7$ is H, halo, $(C_1-C_{32})$alkyl, aryl, $NH_2$, alkyl-amino, COOH, C(O)H, alkyl-COOH heteroaryl, $Si(H)_3$ or $Si[(C_1-C_8)$alkyl$]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_8$, $R_9$, $R_{10}$ and $R_{11}$ are each independently H, $(C_1-C_{32})$ alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

L is a linker;

n is an integer from 1-5;

o is an integer from 1-100;

p is an integer from 1-100;

q is an integer from 1-5;

r is an integer from 1-100; and s is an integer from 1-100;

wherein if $R_5$ and/or $R_5'$ are chiral; said membrane will form a chiral membrane;

wherein said mixture comprises between 2 to 10 different perylene diimide compounds of formula I.

In another embodiment, the perylene diimide supramolecular structure comprises a mixture of perylene diimide compounds, wherein each compound is a monomeric unit represented by the structure of formula of formula XV:

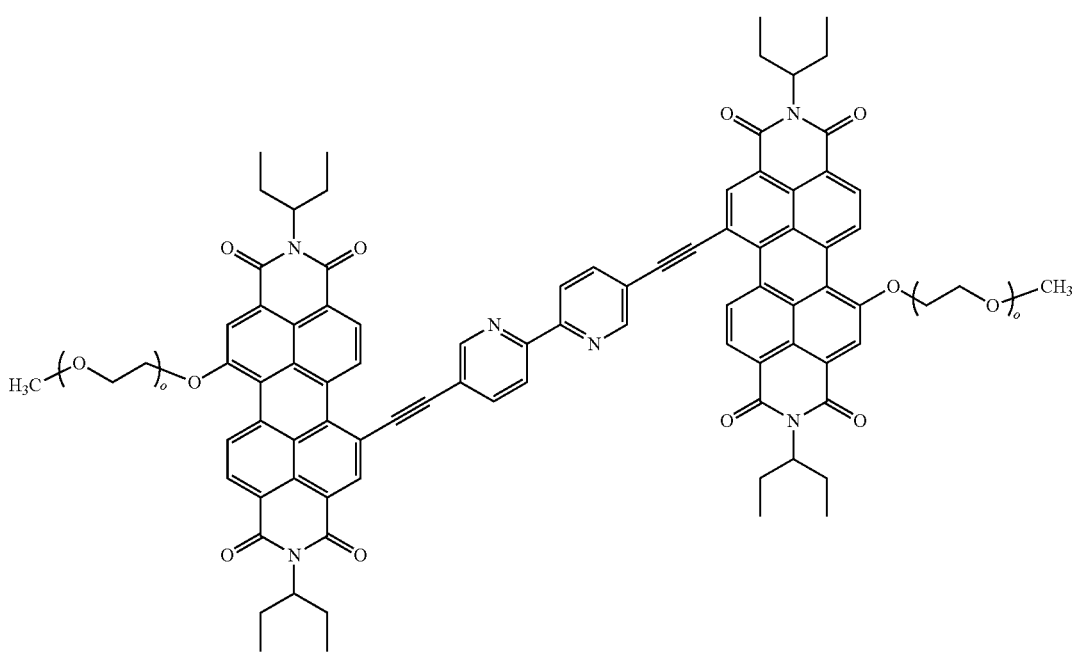

(XV)

wherein o is between 1 to 100; wherein said mixture comprises between 2 to 10 different perylene diimide compounds of formula XV, and wherein said compounds in said mixture, are different in their "o" integer.

In another embodiment, the perylene diimide supramolecular structure comprises a mixture of two different perylene diimide compounds. In another embodiment, the mixture comprises of 95% (% mol) of compound of formula XV wherein o is 17 and 5% (% mol) of a compound of formula XV, wherein o is 23. In another embodiment, the mixture comprises 95% (% mol) of compound of formula XV wherein o is 17 and 5% (% mol) of a compound of formula XV, wherein o is 13. In another embodiment, the mixture comprises 95% (% mol) of compound of formula XV wherein o is 13 and 5% (% mol) of a compound of formula XV, wherein o is 23.

In one embodiment the pores size of the membrane of this invention have a cutoff size of between 2-100 nm. In another embodiment, the size of said pores depends on the thickness of the membrane, wherein the thickness of said membrane is between 5-100 μm.

In one embodiment, this invention is directed to a method of preparing a noncovalent self-assembled perylene diimide based membrane comprising:
   a. preparing an organic solution of a mixture of perylene diimide compounds, wherein the organic solvent in said organic solution is miscible in water;
   b. adding excess of water to said solution of (a); wherein the ratio between said organic solvent to water is between about 1:99% to 8:92% v/v;
   c. evaporating said organic solvent; and
   d. transferring the remaining aqueous solution or emulsion through a solid support;
   thereby obtaining a noncovalent self-assembled perylene diimide based membrane.
   In another embodiment, the organic solvent is tetrahydrofurane (THF), dimethylacetamide (DMA), dimethylformamide (DMF), acetonitrile, acetone, methanol, ethanol or any combination thereof. In another embodiment, the organic solvent is THF. In another embodiment, the organic solvent is ethanol.

In one embodiment, this invention provides a method of separation/filtration or purification of nanoparticles comprising (a) transferring an aqueous solution or emulsion comprising a membrane of this invention through porous solid support, thereby forming a noncovalent self assembled perylene diimide based membrane on said porous solid support; (b) transferring nanoparticles through said noncovalent self-assembled perylene diimide based membrane of step (a); wherein the particles which are larger than the pores of said membrane remain on said membrane.

In another embodiment, the noncovalent self-assembled perylene diimide based membrane is further recycled.

In another embodiment, the recycling of said self-assembled perylene diimide based membrane comprises: (a) washing said solid support with the noncovalent self-assembled perylene diimide based membrane and the retentate deposited thereon, with a solution of alcohol and water; (b) extracting said perylene diimide structure from said solution with an organic solvent; and (c) isolating said perylene diimide from said organic solvent. In another embodiment, said isolated perylene diimide can be further used to form a noncovalent self-assembled perylene diimide based membrane in aqueous conditions.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5A depict membrane fabrication and recycling. FIG. 5B depicts the molecular structure of Perylene diimide V resulting in supramolecular fibers, 3D network, and membrane. The Hydrophobic groups of Perylene diimide V are located in the fibers' core, whereas their hydrophilic PEG shell provides a biocompatible interface. Recycling of the membrane is achieved by disaggregation or physical removal of the supramolecular layer from the support, followed by purification, and subsequent reassembly in aqueous solution.

FIG. 33A depicts UV/V is spectra of the protein mixture before and after filtration over the pristine cellulose acetate (CA) membrane. FIG. 33B depicts UV/V is spectra of the protein mixture before filtration through the supramolecular membrane, the filtrate (collected in 5×1.5 ml fractions, F1-F5), and filtered buffer solution as a reference (F0). FIG. 33C depicts the total protein concentration in the filtrate fractions F1-F5 as compared to the feed solution, determined from absorbance at 280 nm. Error bars correspond to the standard deviation of 5 independent filtration experiments.

FIG. 34A presents a typical SDS-PAGE used for densitometric quantification of individual protein concentrations. MWM=molecular weight marker (170, 130, 95, 72, 55, 43, 34, 26, 17, 11 kDa). FIG. 34B presents the concentrations of individual proteins in fractions F1-F5 (normalized with respect to the non-filtered solution), and recycled proteins. FIG. 34C presents the protein retention against molecular weight (data points) and sigmoid fit (curve). Protein structures of KE70 (PDB; 3Q2D), Aldolase (PDB; 1DZU) and CS hexamer (PDB; 1NXG) and their long-axis diameters are shown. FIG. 34D presents the dependence of protein retention on the hydrodynamic diameter (data points) and sigmoid fit (curve). All error bars represent the standard deviation of 5 independent filtration experiments. (PDB refers to protein data bank).

FIG. 35A depicts UV/V is spectra of the protein mixture before filtration, and filtered fractions. FIG. 35B depicts SDS-PAGE of the filtration experiment. BF=Before filtration, M=Molecular weight marker (170, 130, 95, 72, 55, 43, 34, 26, 17, 11 kDa), R=Recycled, P=Pellet (highly concentrated). Selected areas for densitometric protein quantification are marked. FIG. 35C depicts total protein concentration in the filtrate fractions F1-F5 as compared to the feed solution. FIG. 35D depicts protein concentrations (normalized with respect to the non-filtered solution) of fractions F1-F5, and recycled proteins. FIG. 35E depicts a plot of protein retention against molecular weight (data points) and sigmoid fit (curve). FIG. 35F depicts a plot of protein retention against hydrodynamic diameter (data points) and sigmoid fit (curve).

FIG. 37A: Full experiment. FIG. 37B: Linear range of enzyme kinetics and regression lines.

FIG. 38A: Full experiment. FIG. 38B: Linear range of enzyme kinetics and regression lines.

FIG. 39A presents hydrolysis of ONPG into Galactose and ONP. FIG. 39B presents the yield of ONP as a function of time during several hours of continuous flux of substrate.

FIG. 41A depicts deposition of a mixture of 5% perylene diimide monomeric unit of formula XV wherein o=23 with 95% perylene diimide monomeric unit of formula XV wherein o=13 on 13 mm diameter PES (0.45 μm) support. FIG. 41B depicts gold NP's solution before (left) and after filtration (right) on the membrane of the invention. FIG. 41C depicts UV/V is spectra of gold NP's before filtration (black), filtrate (light gray) and 20% EtOH filtrate (dark gray).

Figure 1:
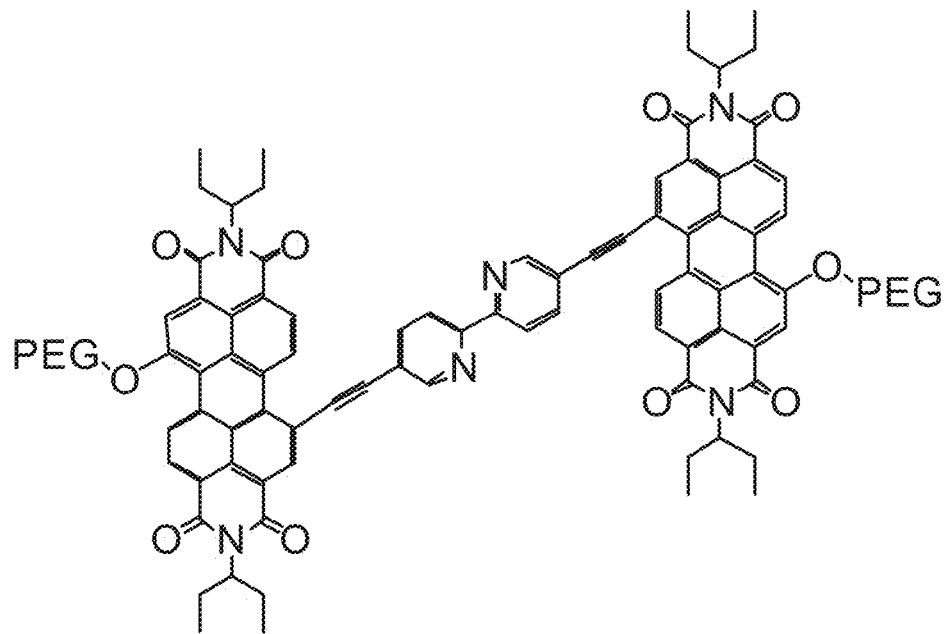
FIG. 1 depicts a Perylene diimide of this invention, wherein the PEG has between 17-21 repeating units.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to (i) a noncovalent self-assembled porous membrane comprising a perylene diimide supramolecular structure; (ii) a noncovalent self-assembled porous membrane comprising a perylene diimide supramolecular structure and provides a chromatography medium for size-selective separation; (iii) a noncovalent self-assembled porous chiral membrane comprising a chiral perylene diimide supramolecular structure and provides a chiral separation for chiral molecules (nanometer and subnanometer size) (iv) a method of filtration, purification, optimization and/or separation of nano-materials (nanoparticles, biomolecules) using the noncovalent self-assembly perylene diimide based porous membrane of this invention; (v) a method of chiral separation using chiral membrane comprising a chiral perylene diimide supramolecular structure; (v) a method of preparing the noncovalent self-assembly perylene diimide based porous membrane; (vi) a method of recycling the membrane of this invention; (vii) a biocatalytic membrane comprising the membrane of this invention and an enzyme wherein the enzyme is immobilized within the membrane; and (viii) a method of heterogenous biocatalysis using the biocatalytic membrane of this invention; comprising and make use of perylene diimide monomeric unit of formula I-XV or mixtures thereof.

In one embodiment, this invention is directed to noncovalent self-assembled porous membrane and methods of use thereof comprising a supramolecular structure of perylenes, perylene diimide, pyrenes, other extended aromatics or mixtures thereof wherein said supramolecular structure is formed by self assembly of the perylene diimide, perylenes, pyrenes, or other extended aromatics. In one embodiment, this invention is directed to noncovalent self-assembled porous membrane and methods of use thereof comprising a supramolecular structure of perylene diimide compounds of this invention. The self assembled supramolecular structure is formed by noncovalent interactions such as hydrogen bonds, π-π interactions and/or hydrophoboic interactions between the perylene groups or the pyrene groups. In another embodiment, the monomer unit of the supramolecular structure comprises between one to five covalently attached perylene diimide groups, perylene groups or pyrene groups. In another embodiment, the monomer unit of the supramolecular polymer structures comprises between one to five covalently attached perylene diimide groups or pyrene groups comprising a PEG (polyethylene glycol) side chains linked by an unsaturated bridge. In another embodiment, the PEG side chains comprise between 17-21 repeating units. In another embodiment, the PEG side chains comprise between 18-22 repeating units. In another embodiment, the perylene diimides, perylenes or pyrenes comprise different lengths of PEG size chains, wherein the average lengths is of the side chains is between 17-22, 13-25, 13-50, or 18-22 repeating units. In another embodiment, the PEG side chains comprise 13 repeating units [PEG13=—(CH$_2$CH$_2$O)$_{13}$—CH$_3$ or —(CH$_2$CH$_2$O)$_{13}$—H]. In another embodiment, the PEG side chains comprise 17 repeating units [PEG17=—(CH$_2$CH$_2$O)$_{17}$—CH$_3$ or —(CH$_2$CH$_2$O)$_{17}$—H). In another embodiment, the PEG side chains comprise 23 repeating units [PEG23=—(CH$_2$CH$_2$O)$_{23}$—CH$_3$ or —(CH$_2$CH$_2$O)$_{23}$—H.

Figure 5A:
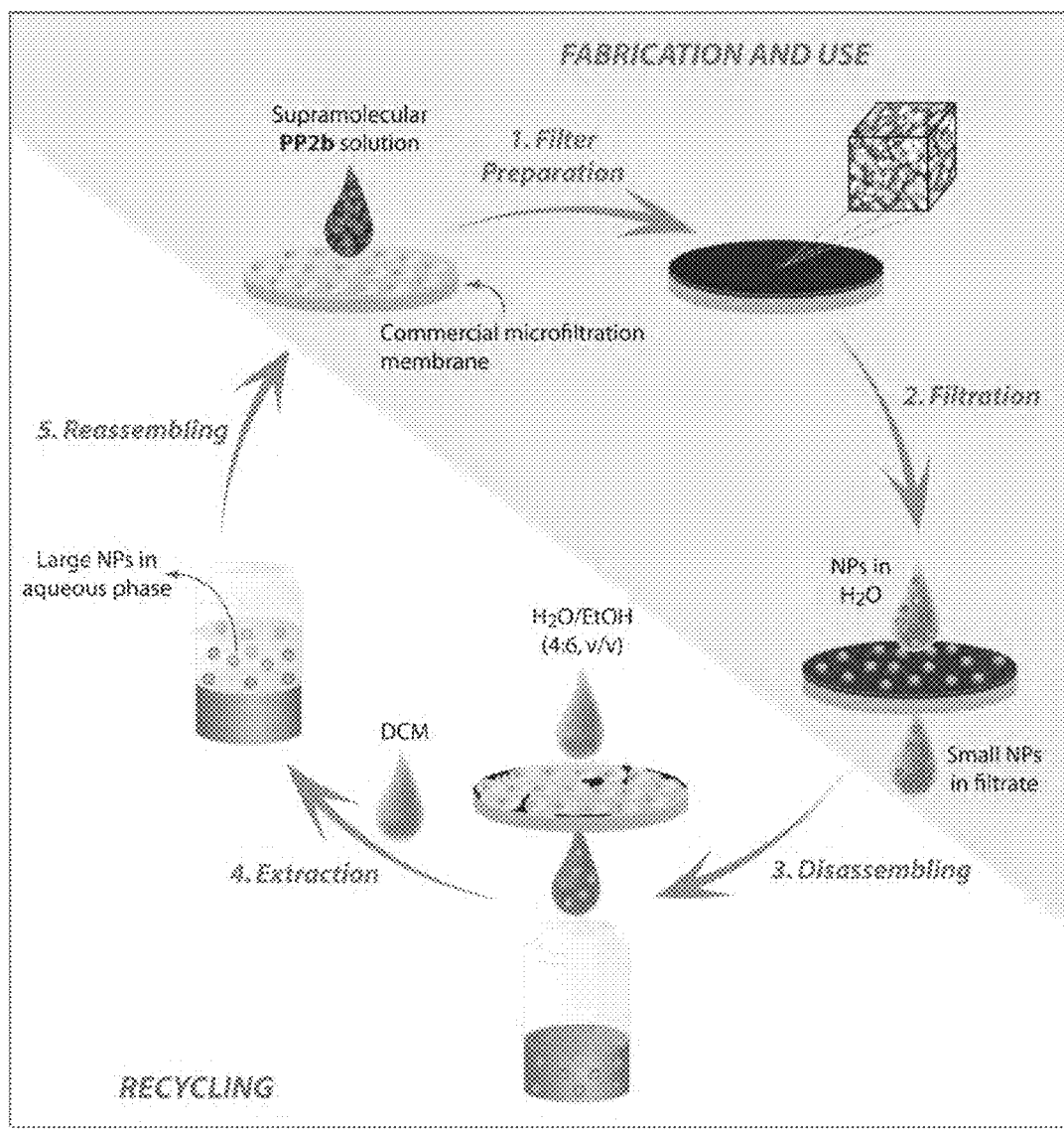
FIGS. 5A and 5B depicts schemes of fabrication, use, and recycling of the supramolecular membrane of this invention.
Figure 5B:
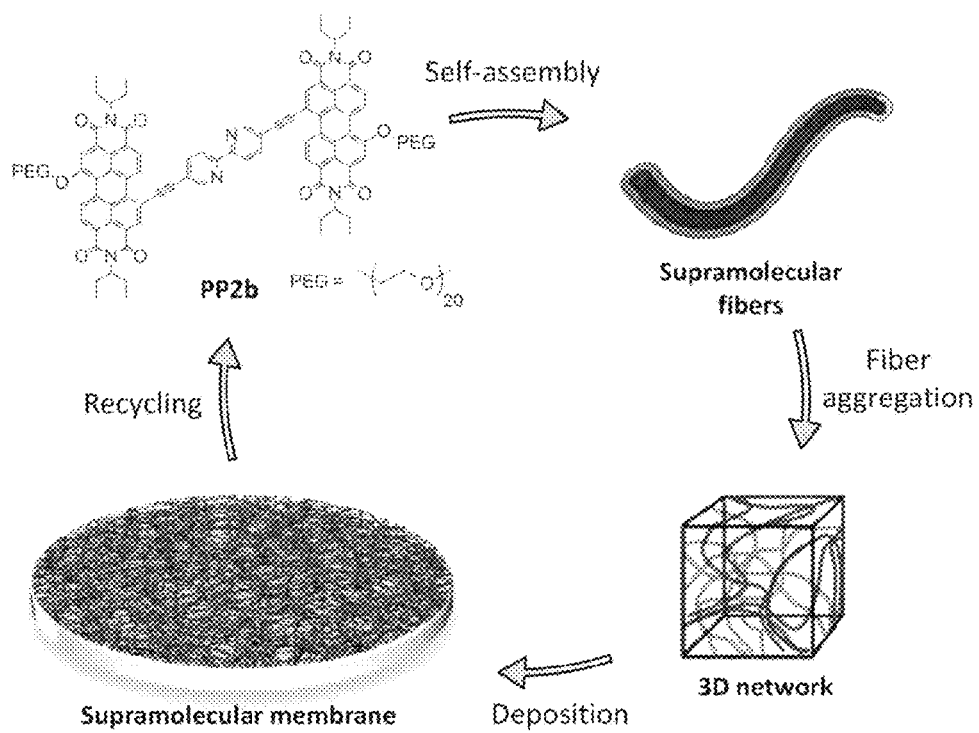

Hydrophobic interactions between large nonpolar groups of amphiphilic molecules in aqueous solution can be remarkably strong, driving self-assembly towards very stable supramolecular systems. The monomer unit of the supramolecular structure of this invention comprises two covalently attached perylene-3,4,9,10-tetracarboxylic acid diimide (PDI) units. The PDI monomeric unit self-assembles in aqueous media into a robust three dimensional (3D) fibrous network, resulting in a stable and multiple-stimuli-responsive material (FIGS. 5A and 5B).

In another embodiment, the membrane of this invention is based on very strong hydrophobic interactions, preventing exposure of the hydrophobic moieties to bulk water. It is also enclosed by a shell of polyethylene glycol (PEG) groups (Error! Reference source not found.), which are known to preserve the native structure of proteins and resist undesired biomolecule adsorption. Thus, in water, the membrane of this invention is robust and potentially biocompatible.

In one embodiment, this invention is directed to noncovalent self-assembled porous membrane and methods of use thereof comprising a supramolecular structure comprising perylene diimide, a salt thereof or a metal complex thereof as a monomeric unit wherein said perylene diimide is represented by the structure of formula I:

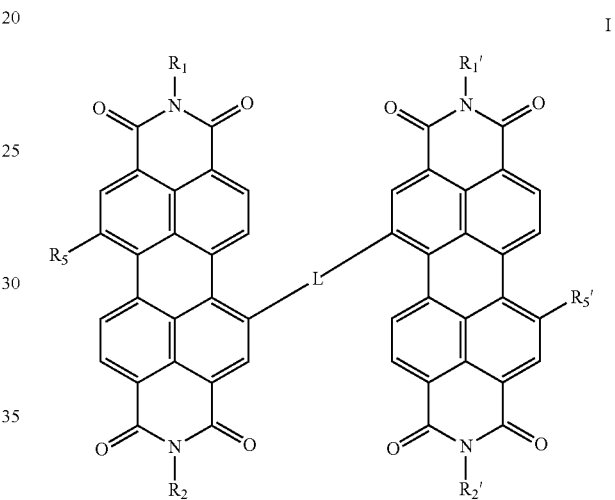

wherein $R_1$ and $R_1'$ are each independently [(CH$_2$)$_q$O]$_r$CH$_3$, [(CH$_2$)$_q$O]$_r$H [(CH$_2$)$_q$C(O)O]$_r$CH$_3$, [(CH$_2$)$_q$C(O)NH]$_r$CH$_3$, [(CH$_2$)$_q$CH$_2$=CH$_2$]$_r$CH$_3$, [(CH$_2$)$_q$CH=CH]$_r$CH$_3$, [(CH$_2$)NH]$_r$CH$_3$, [(alkylene)$_q$O]$_r$CH$_3$, [(alkylene)$_q$C(O)O]$_r$CH$_3$, [(alkylene)$_q$C(O)NH]$_r$CH$_3$, [(alkylene)$_q$CH$_2$=CH$_2$]$_r$CH$_3$, [(alkylene)$_q$CH=CH]$_r$CH$_3$, [(alkylene)$_q$NH]$_r$CH$_3$, (C$_1$-C$_{32}$)alkyl, (C$_3$-C$_8$)cycloalkyl, aryl, heteroaryl, chiral group, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl);

wherein A comprises three same or different of the following substituents Cl, Br, I, O(C$_1$-C$_8$)alkyl or (C$_1$-C$_8$)alkyl; and wherein $R_3$ in said [C(O)CHR$_3$NH]$_p$H is an alkyl, haloalkyl, hydroxyalkyl, hydroxyl, aryl, phenyl, alkylphenyl, alkylamino and independently the same or different when p is larger than 1;

$R_2$ and $R_2'$ are each independently [(CH$_2$)$_q$O]$_r$CH$_3$, [(CH$_2$)$_q$C(O)O]$_r$CH$_3$, [(CH$_2$)$_q$C(O)NH]$_r$CH$_3$, [(CH$_2$)$_q$CH$_2$—CH$_2$]$_r$CH$_3$, [(CH$_2$)$_q$CH=CH]$_r$CH$_3$, [(CH$_2$)NH]$_r$CH$_3$, [(alkylene)$_q$O]$_r$CH$_3$, [(alkylene)$_q$C(O)O]$_r$CH$_3$, [(alkylene)$_q$C(O)NH]$_r$CH$_3$, [(alkylene)CH$_2$=CH$_2$]$_r$CH$_3$, [(alkylene)$_q$CH=CH]$_r$CH$_3$, [(alkylene)$_q$NH]$_r$CH$_3$, (C$_1$-C$_{32}$)alkyl, (C$_3$-C$_8$)cycloalkyl, aryl, heteroaryl, chiral group, (C$_1$-C$_{32}$)alkyl-COOH, (C$_1$-C$_{32}$)alkyl-Si-A, or [C(O)CHR$_4$NH]$_s$H wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$)alkyl; and wherein $R_4$ in said $[C(O)CHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are each independently H, —$OR_x$ where $R_x$ is $C_1$-$C_6$ alkyl, $[(CH_2)_nO]_oCH_3$ or $[(CH_2)_nO]_oH$; $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, aryl, heteroaryl, C≡C—$R_7$, CH=$CR_8R_9$, $NR_{10}R_{11}$, chiral group, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_8$ alkyl) or O—($C_1$-$C_8$ alkyl);

$R_7$ is H, halo, ($C_1$-$C_{32}$)alkyl, aryl, $NH_2$, alkyl-amino, COOH, C(O)H, alkyl-COOH heteroaryl, Si(H)$_3$ or Si[($C_1$-$C_8$)alkyl]$_3$ wherein said aryl or heteroaryl groups are optionally substituted by 1-3 groups comprising halide, aryl, heteroaryl, CN, $CO_2H$, OH, SH, $NH_2$, $CO_2$—($C_1$-$C_8$ alkyl) or O—($C_1$-$C_8$ alkyl);

$R_8$, $R_9$, $R_{10}$ and $R_{11}$ are each independently H, ($C_1$-$C_{32}$) alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—($C_1$-$C_8$ alkyl) or O—($C_1$-$C_8$ alkyl);

L is a linker;
n is an integer from 1-5;
o is an integer from 1-100;
p is an integer from 1-100;
q is an integer from 1-5;
r is an integer from 1-100; and
s is an integer from 1-100;

wherein if $R_5$ and/or $R_5'$ are chiral groups; said membrane will form a chiral membrane.

In one embodiment, this invention is directed to noncovalent self-assembled porous membrane and methods of use thereof comprising a supramolecular structure comprising perylene diimide, a salt thereof or a metal complex thereof as a monomeric unit wherein said perylene diimide is represented by the structure of formula II:

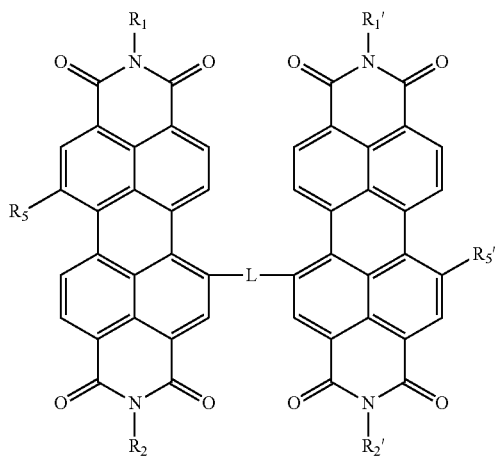

II wherein $R_1$, $R_2$, $R_1'$, $R_2'$, $R_5$, $R_5'$ and L are as described in formula I.

In one embodiment, the noncovalent self-assembled porous membrane of this invention and methods of use thereof comprise a supramolecular structure comprising perylene diimide, a salt thereof or a metal complex thereof as a monomeric unit wherein said perylene diimide is represented by the structure of formula III:

Perylene diimide III

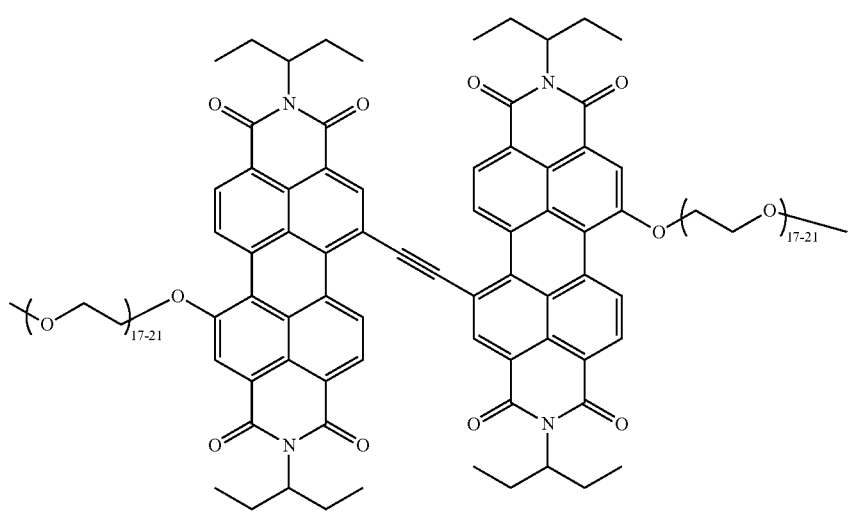

In one embodiment, the noncovalent self-assembled porous membrane of this invention and methods of use thereof comprise a supramolecular structure comprising perylene diimide, a salt thereof or a metal complex thereof as a monomeric unit wherein said perylene diimide is represented by the structure of formula IV:

Perylene diimide IV

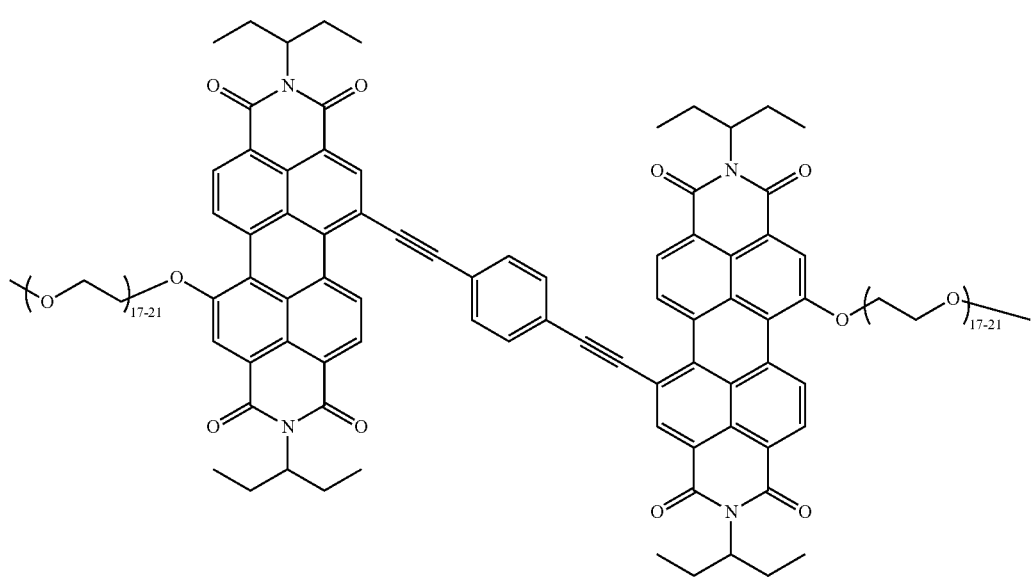

In one embodiment, the noncovalent self-assembled porous membrane of this invention and methods of use thereof comprise a supramolecular structure comprising perylene diimide, a salt thereof or a metal complex thereof as a monomeric unit wherein said perylene diimide is represented by the structure of formula V:

Perylene diimide V

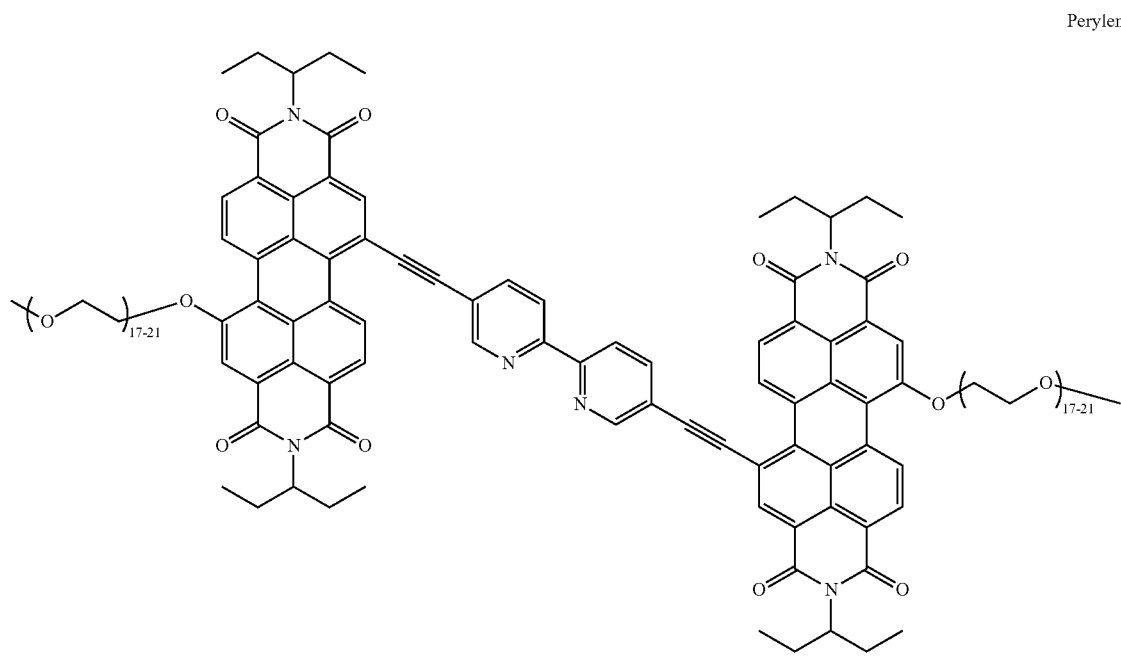

In one embodiment, the noncovalent self-assembled porous membrane of this invention and methods of use thereof comprise a supramolecular structure comprising perylene diimide, a salt thereof as a monomeric unit wherein said perylene diimide is represented by the structure of formula Perylene diimide V-Pt complex:

Perylene diimide V

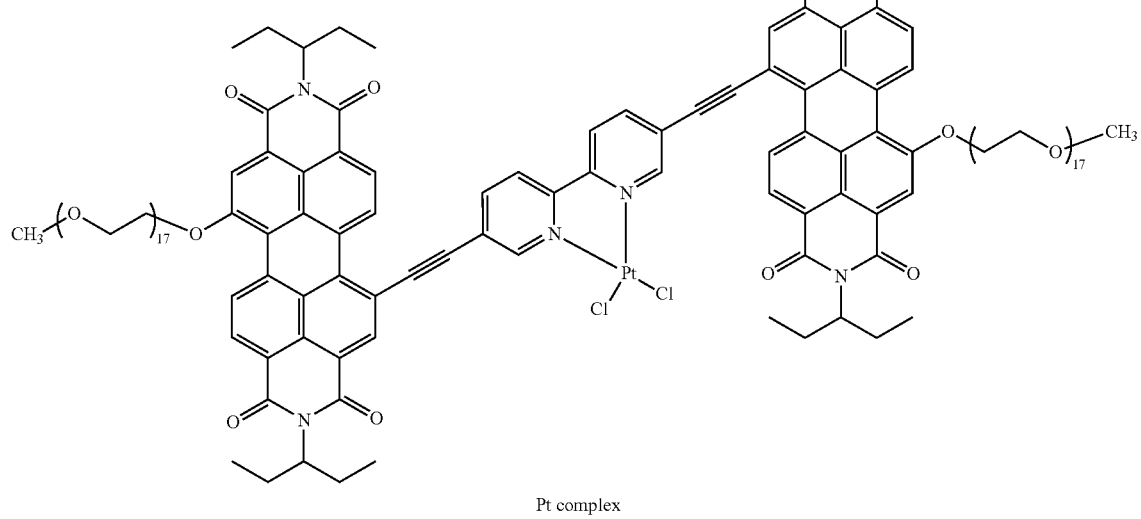

Pt complex

In one embodiment, this invention is directed to noncovalent self-assembled porous membrane and methods of use thereof comprising a supramolecular structure comprising perylene diimide, a salt thereof or a metal complex thereof as a monomeric unit wherein said perylene diimide is represented by the structure of formula VI:

Perylene diimide VI

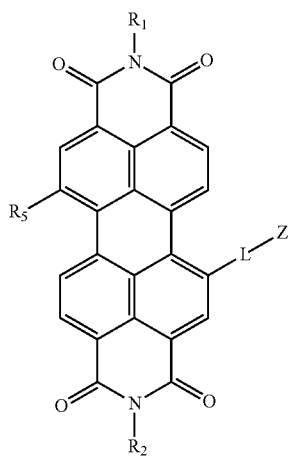

wherein $R_1$ is $[(CH_2)_qO]_rCH_3$, $[(CH_2)_qO]_rH$ $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$ alkyl, $(C_3-C_8)$cycloalkyl, aryl, heteroaryl, chiral group, $(C_1-C_{32})$alkyl-COOH, $(C_1-C_{32})$alkyl-Si-A, or $[C(O)CHR_3NH]_pH$; wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_5$ alkyl);

wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is an alkyl, haloalkyl, hydroxyalkyl, hydroxyl, aryl, phenyl, alkylphenyl, alkylamino and independently the same or different when p is larger than 1

$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_q NH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_q NH]_rCH_3$, $(C_1-C_{32})$ alkyl, $(C_3-C_8)$cycloalkyl, aryl, heteroaryl, chiral group, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_5$ alkyl);

wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is an alkyl, haloalkyl, hydroxyalkyl, hydroxyl, aryl, phenyl, alkylphenyl, alkylamino and independently the same or different when s is larger than 1;

$R_5$ is H, $-OR_x$ where $R_x$ is $C_1$-$C_6$ alkyl, $[(CH_2)_nO]_oCH_3$ or $[(CH_2)_nO]_oH$; $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, aryl, heteroaryl, $C\equiv C-R_7$, $CH=CR_8R_9$, $NR_{10}R_{11}$, chiral group, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

Z is $-OR_x$ where $R_x$ is $C_1$-$C_6$ alkyl, $[(CH_2)_qO]_rH$ or $[(CH_2)_qO]_rCH_3$, peptide, amino-acid, chiral group, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qCH_2=CH_2]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_q CH=CH]_rCH_3$, $[(alkylene)_qNH]_rCH_3$, aryl, heteroaryl, $C\equiv C-R_7$, $CH=CR_8R_9$, $NR_{10}R_{11}$ or a saturated carbocyclic or heterocyclic ring wherein said saturated heterocyclic ring or heteroaryl contains at least one nitrogen atom and Z is connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, $NH_2$, alkyl-amino, COOH, C(O)H, alkyl-COOH heteroaryl, $Si(H)_3$ or $Si[C_1$-$C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are each independently H, ($C_1$-$C_{32}$) alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

L is a linker or a bond;

n is an integer from 1-5;

o is an integer from 1-100;

p is an integer from 1-100;

q is an integer from 1-5;

r is an integer from 1-100; and s is an integer from 1-100;

wherein if Z is a chiral group; said membrane will form a chiral membrane.

In one embodiment, the noncovalent self-assembled porous membrane of this invention and methods of use thereof comprise a supramolecular structure comprising perylene diimide, a salt thereof or a metal complex thereof as a monomeric unit wherein said perylene diimide is represented by the structure of formula VII:

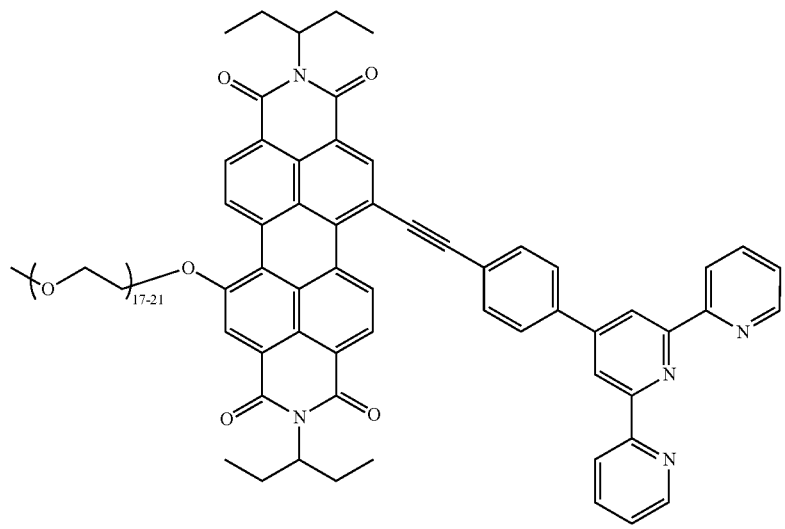

Perylene diimide VII

In one embodiment, the noncovalent self-assembled porous membrane of this invention and methods of use thereof comprise a supramolecular structure comprising perylene diimide or a salt thereof as a monomeric unit wherein said perylene diimide is represented by the structure of formula VII-Pd Complex:

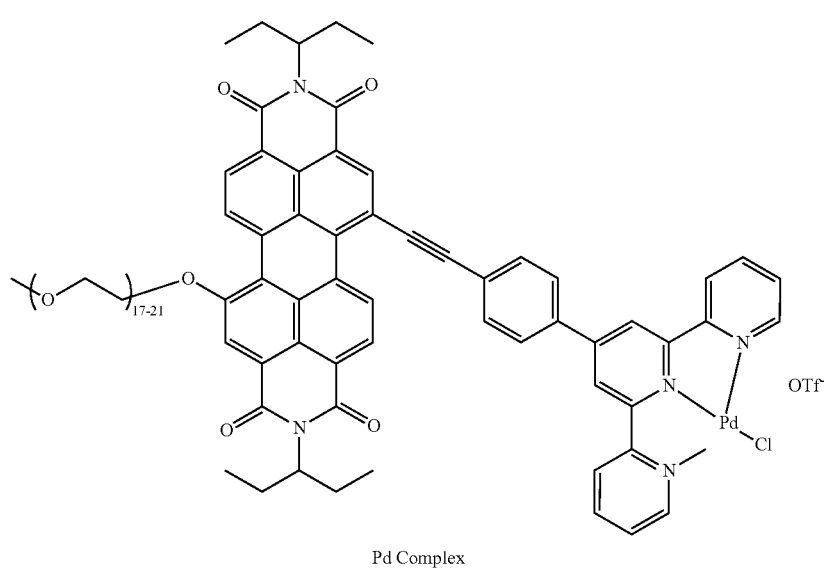

Pd Complex

Perylene diimide VII

In one embodiment, the noncovalent self-assembled porous membrane of this invention and methods of use thereof comprise a supramolecular structure comprising perylene diimide or a salt thereof as a monomeric unit wherein said perylene diimide is represented by the structure of formula VII-Pt Complex:

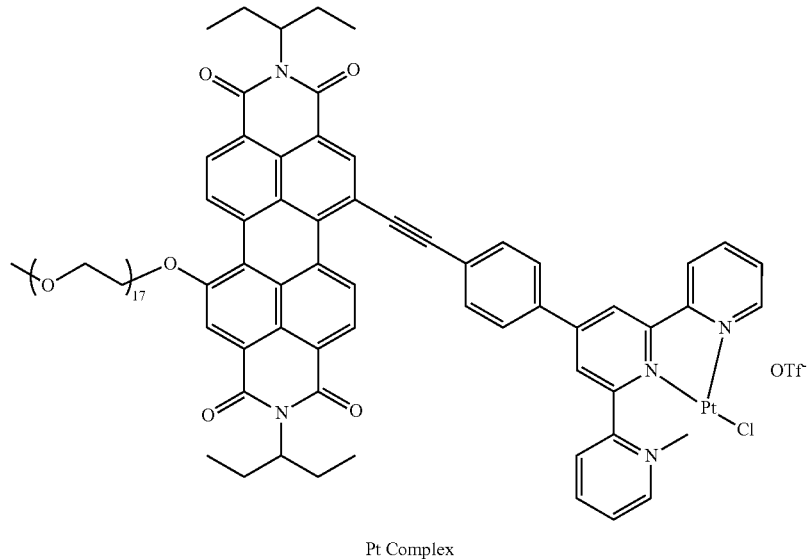

Pt Complex

Perylene diimide VII

In one embodiment, the noncovalent self-assembled porous membrane of this invention and methods of use thereof comprise a supramolecular structure comprising perylene diimide, or a salt thereof as a monomeric unit wherein said perylene diimide is represented by the structure of formula VII-Ag Complex:

Perylene diimide VII

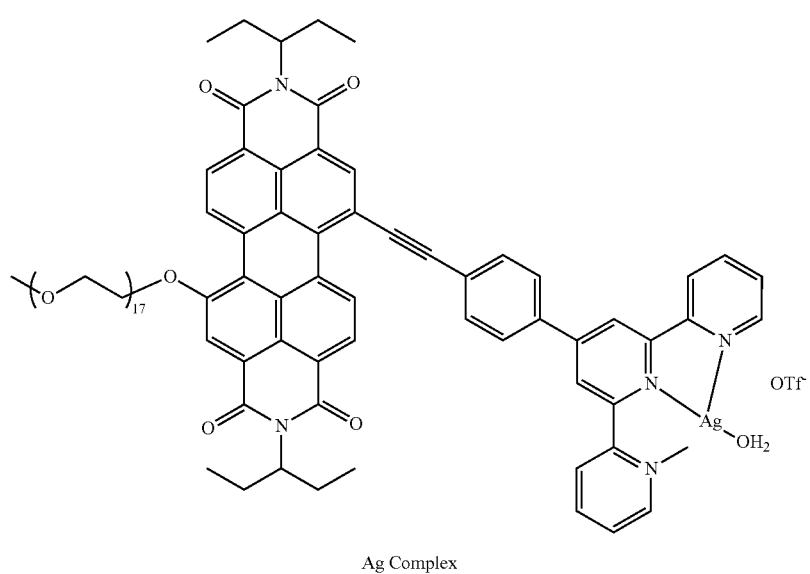

Ag Complex

In one embodiment, this invention is directed to noncovalent self-assembled porous and chiral membrane and methods of use thereof comprising a supramolecular structure comprising a chiral perylene diimide, a salt thereof or a metal complex thereof as a monomeric unit wherein said perylene diimide is represented by the structure of formula I wherein $R_5$ or $R_5'$ are independently a chiral group, an amino acid or a peptide. In another embodiment, said perylene diimide is represented by the structure of formula VI wherein Z is a chiral group, an amino acid or a peptide.

In another embodiment, said perylene diimide is represented by the structure of formula VI wherein Z is a chiral group, an amino acid or a peptide and $R_5$ is a PEG substituted by a chiral group.

In one embodiment, the noncovalent self-assembled porous and chiral membrane of this invention comprising a supramolecular structure comprising a chiral perylene diimide, a salt thereof or a metal complex thereof as a monomeric unit wherein said perylene diimide is represented by the following structures:

Perylene diimide VIII

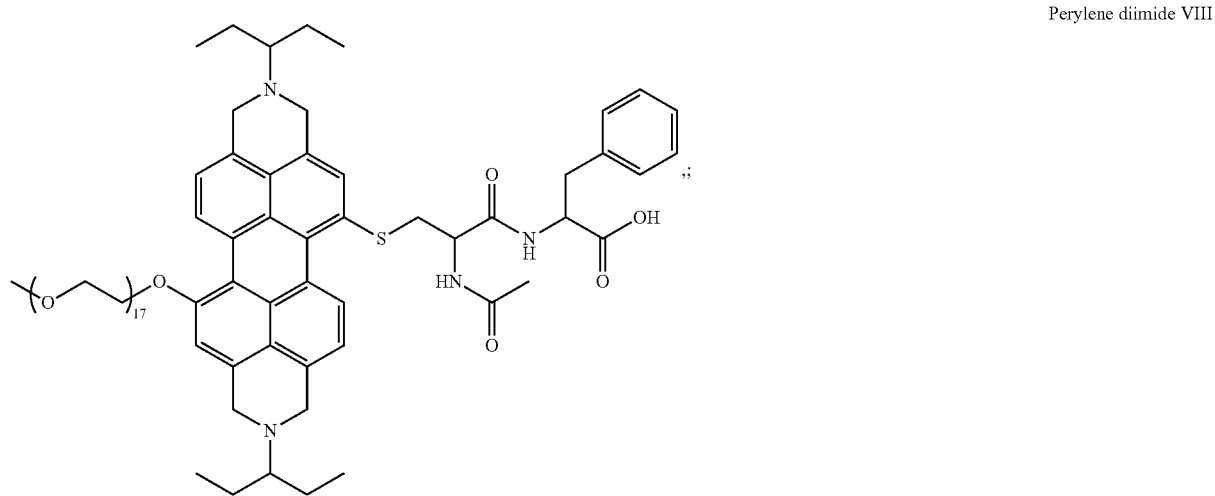

-continued
Perylene diimide IX
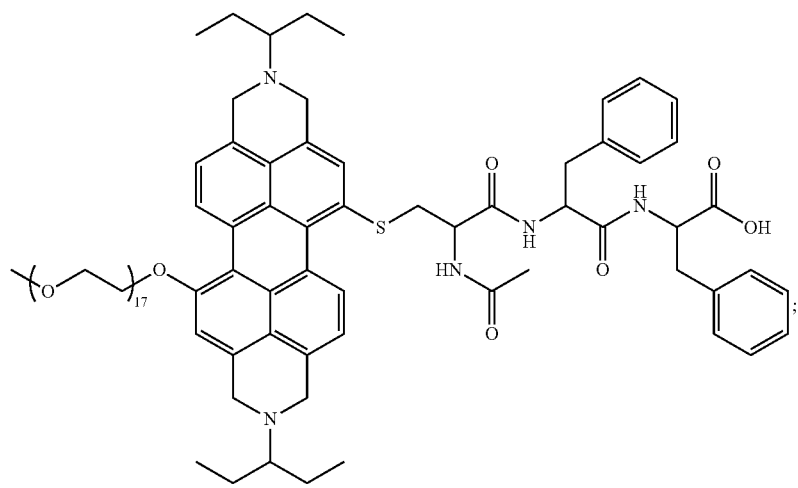
Perylene diimide X
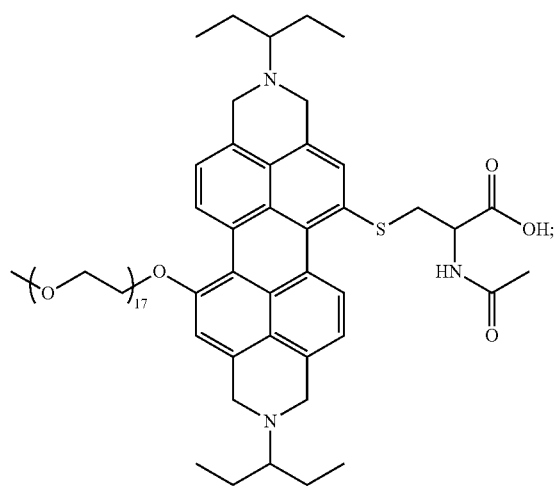
Perylene diimide XI
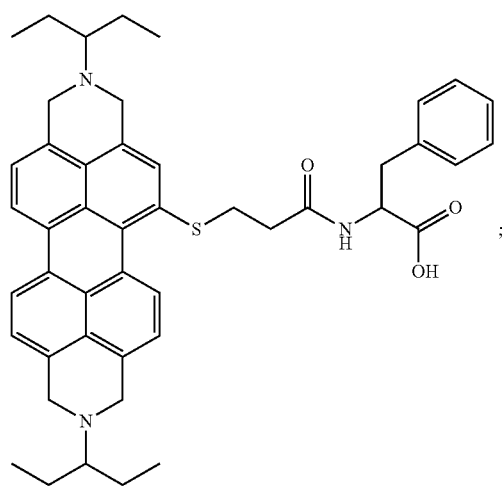
Perylene diimide XII
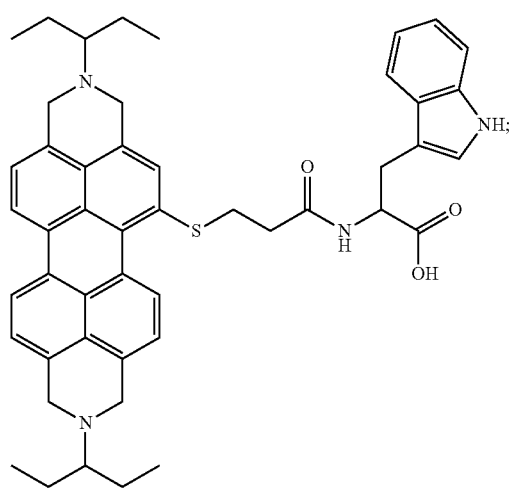
Perylene diimide XIII
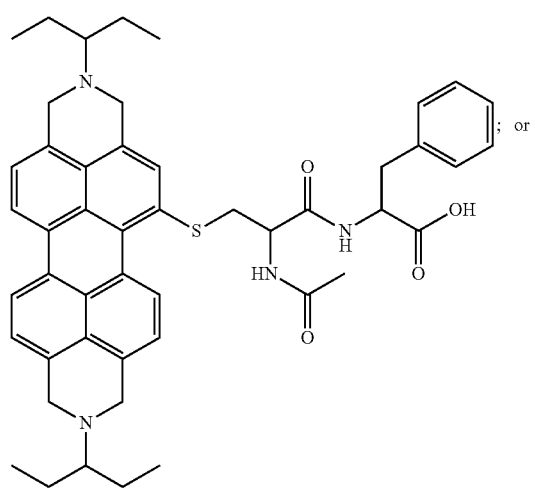
; or Perylene diimide XIV

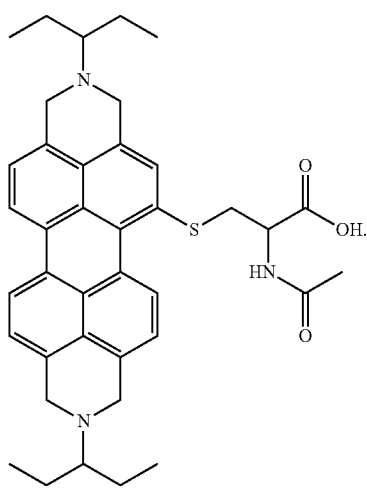

In one embodiment, the noncovalent self-assembled porous membrane of this invention and methods of use thereof comprise a supramolecular structure comprising mixture of perylene diimides monomeric units, wherein each of said perylene diimide monomeric units is represented by the structure of formula XV:

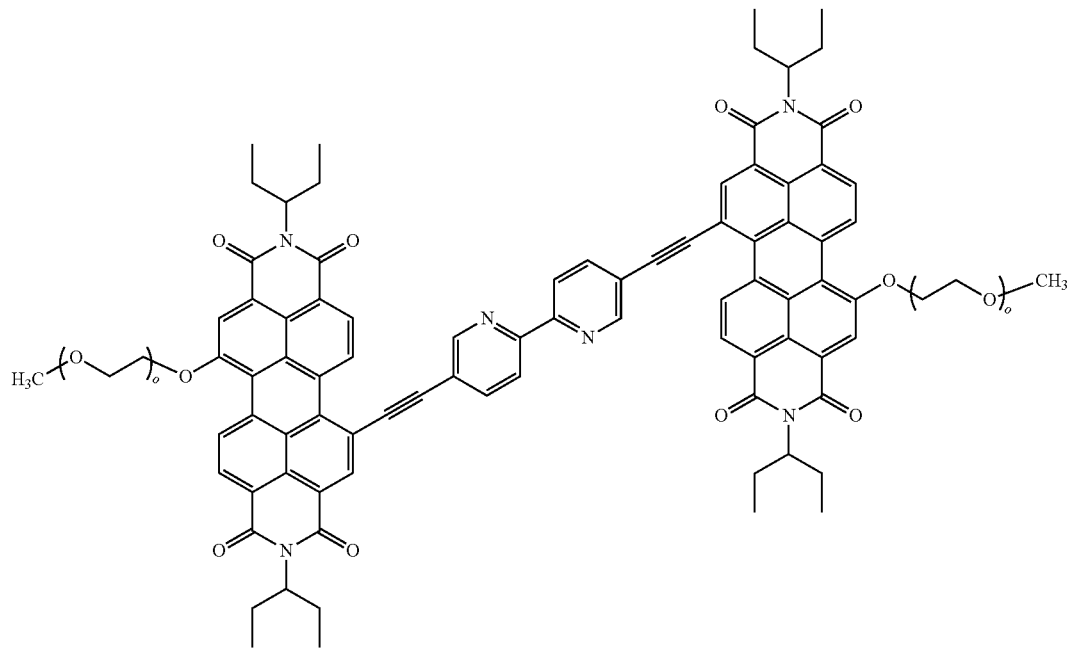

(XV)

a salt thereof or a metal complex thereof,
wherein o is between 1 to 100; and wherein said monomeric units comprised in said mixture, are optionally different from each other in their o integer.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula I, wherein said mixture comprises between 2 to 10 different perylene diimide compounds of formula I.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula II, wherein said mixture comprises between 2 to 10 different perylene diimide compounds of formula II.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula III, wherein said mixture comprises between 2 to 5 different perylene diimide compounds of formula III, and wherein said monomeric units comprised in said mixture, are different from in their PEG size. In one embodiment, the PEG size of each monomeric unit is independently PEG17, PEG18, PEG19, PEG20 or PEG21.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula IV, wherein said mixture comprises between 2 to 5 different perylene diimide compounds of formula IV, and wherein said monomeric units comprised in said mixture, are different in their PEG size. In one embodiment, the PEG size of each monomeric unit is independently PEG17, PEG18, PEG19, PEG20 or PEG21.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula V, wherein said mixture comprises between 2 to 5 different perylene diimide compounds of formula V, and wherein said monomeric units comprised in said mixture, are different in their PEG size. In one embodiment, the PEG size of each monomeric unit is independently PEG17, PEG18, PEG19, PEG20 or PEG21.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula VI, wherein said mixture comprises between 2 to 10 different perylene diimide compounds of formula VI.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula VII, wherein said mixture comprises between 2 to 10 different perylene diimide compounds with different PEG size or different metal complexes formula V of formula VII.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula VIII-XIV, wherein said mixture comprises between 2 to 10 different perylene diimide compounds of formula VIII-XIV.

In one embodiment, this invention is directed to a non-covalent self-assembled porous membrane comprising a perylene diimide supramolecular structure, and provides a chromatography medium for size-selective separation of nano-material; wherein said perylene diimide supramolecular structure comprises a mixture of perylene diimide compounds, wherein each perylene diimide compound is a monomeric unit represented by the structure of formula of formula XV:

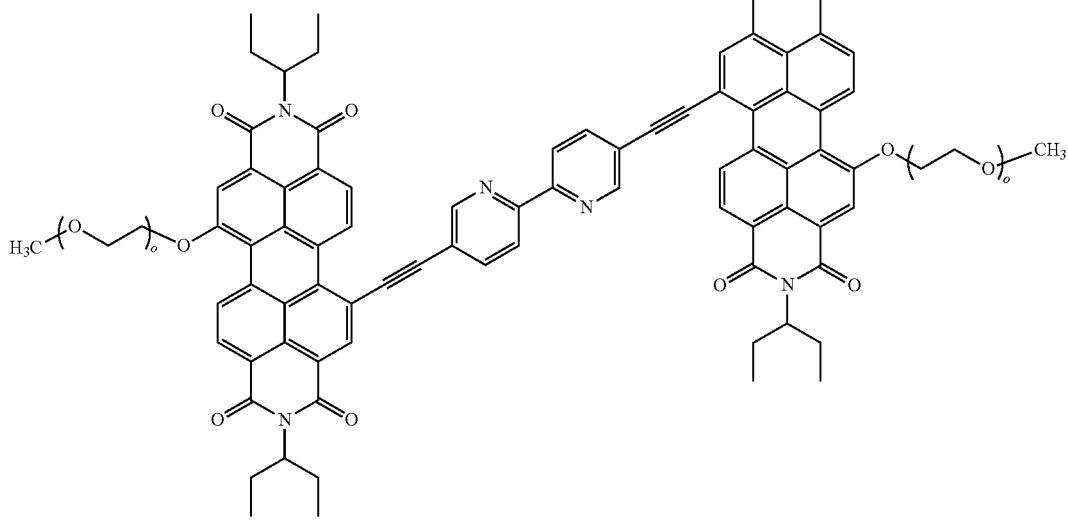

wherein o is between 1 to 100; wherein said mixture comprises between 2 to 10 different perylene diimide compounds of formula XV, and wherein said monomeric units/compounds comprised in said mixture, are different in their "o" integer.

In one embodiment, the membrane of this invention comprises a mixture of between 2 to 10 different perylene diimide compounds of this invention. In another embodiment, the membrane comprises 2 different perylene diimide compounds of this invention. In another embodiment, the membrane comprises 3 different perylene diimide compounds of this invention. In another embodiment, the membrane comprises 4 different perylene diimide compounds of this invention. In another embodiment, the membrane comprises 5 different perylene diimide compounds of this invention. In another embodiment, the membrane comprises 6 different perylene diimide compounds of this invention. In another embodiment, the membrane comprises between 7 to 10 different perylene diimide compounds of this invention.

In one embodiment, the noncovalent self-assembled porous membrane of this invention and methods of use thereof comprise a supramolecular structure comprising perylene diimide of formula XV, wherein o is 13, as a monomeric unit. In another embodiment, the noncovalent self-assembled porous membrane of this invention and methods of use thereof comprise a supramolecular structure comprising perylene diimide of formula XV, wherein o is 23, as a monomeric unit. In another embodiment, the noncovalent self-assembled porous membrane of this invention and methods of use thereof comprise a supramolecular structure comprising perylene diimide of formula XV, wherein o is 44, as a monomeric unit.

In another embodiment, the noncovalent self-assembled porous membrane of this invention and methods of use thereof comprise a supramolecular structure comprising a mixture of perylene diimide monomeric units of this invention.

In another embodiment, the noncovalent self-assembled porous membrane of this invention and methods of use thereof comprise a supramolecular structure comprising a mixture is of perylene diimide monomeric unit of formula XV wherein o is 23, with a perylene diimide monomeric unit of formula XV wherein o is 13.

In another embodiment, the noncovalent self-assembled porous membrane of this invention and methods of use thereof comprise a supramolecular structure comprising a mixture is of perylene diimide monomeric unit of formula XV wherein o is 13 with a perylene diimide monomeric unit of formula XV wherein o is 44.

In another embodiment, the noncovalent self-assembled porous membrane of this invention and methods of use thereof comprise a supramolecular structure comprising a mixture is of perylene diimide monomeric unit of formula XV wherein o is 13, with a perylene diimide monomeric unit of formula XV wherein o is 17.

In another embodiment, the membrane of this invention comprises a mixture of 95% (% mol) of compound of formula XV wherein o is 17, and 5% (% mol) of a compound of formula XV, wherein o is 13. In another embodiment, the pores size of said membrane have a cutoff size of about 8 nm.

In another embodiment, the membrane of this invention comprises 95% (% mol) of compound of formula XV wherein o is 13 and 5% (% mol) of a compound of formula XV, wherein o is 23. In another embodiment, the pores size of said membrane have a cutoff size of about 5 nm.

In one embodiment, a cutoff size refers to the size larger than 95% of the particles in the filtrate. In one embodiment L of formula I, II or VI is an unsaturated bridge. In another embodiment, L of formula VI is saturated or unsaturated bridge. In one embodiment an unsaturated bridge of this invention is acetylene. In one embodiment an unsaturated bridge of this invention is phenylacetylene. In another embodiment an unsaturated bridge of this invention comprises an acetylene. In another embodiment an unsaturated bridge of this invention comprises a pyridyl. In another embodiment an unsaturated bridge of this invention comprises a bipyridyl. In another embodiment an unsaturated bridge of this comprises a terpyridyl. In another embodiment an unsaturated bridge of this invention comprises a phenyl. In another embodiment an unsaturated bridge of this comprises a dibenzene. In another embodiment an unsaturated bridge of this invention comprises diethynylbenzene. In another embodiment an unsaturated bridge of this invention comprises aryl. In another embodiment an unsaturated bridge of this invention comprises diethynyl-bipyridyl. In one embodiment an unsaturated bridge of this invention comprises bis-acetylene. In another embodiment an unsaturated bridge of this invention is a pyridyl group. In another embodiment an unsaturated bridge of this invention is a bipyridyl group. In another embodiment an unsaturated bridge of this invention is a terpyridyl group. In one embodiment L of formula I and II is a saturated bridge. In another embodiment a saturated bridge of this invention comprises an alkyl, cycloalkyl, heterocycle, ether, polyether, or haloalkyl. In one embodiment L of formula I and II is a combination of a saturated and unsaturated groups as defined hereinabove. In another embodiment, L of formula VI is an unsaturated bridge. In another embodiment, L of formula VI is an unsaturated bridge including —S—$(CH_2)_t$—C(O)—, —S—$(CH_2)_t$—O—, —O—$(CH_2)_t$—O—, —NH—$(CH_2)_t$—C(O)—, —C(O)—$(CH_2)_t$—CO—, —C(O)—$(CH_2)_t$—NH— wherein t is between 1 to 6.

In another embodiment L of formula I, II or VI is:

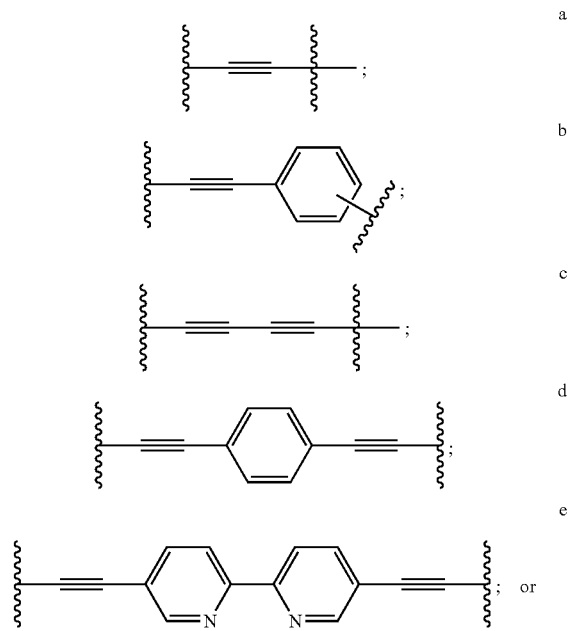

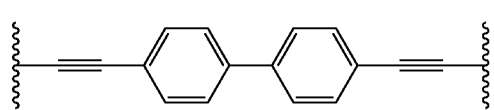
f

In one embodiment $R_5$ and/or $R_5'$ of formula I, II and VI are each independently a hydrophilic side chain. In another embodiment $R_5$ and/or $R_5'$ of formula I and II and VI are each independently a PEG (polyethylene glycol). In another embodiment the PEG of this invention comprises between 15-20 units. In another embodiment the PEG comprises between 17-21 repeating units. In another embodiment the PEG comprises between 18-22 repeating units. In another embodiment the PEG comprises about 19 repeating units. In another embodiment the PEG comprises between 13 to 25 repeating units. In another embodiment the PEG comprises between 18 to 24 repeating units. In another embodiment the PEG comprises between 10 to 30 repeating units. In one embodiment, $R_5$ and/or $R_5'$ of formula I, II and VI (or the side chains of the perylene diimide monomers) are each independently $-OR^x$ where $R^x$ is $C_1$-$C_6$ alkyl, $[(CH_2)_nO]_oCH_3$ or $[(CH_2)_nO]_oH$. In another embodiment, $R_5$ and/or $R_5'$ of formula I, II and VI are each independently $-OR^x$ where $R^x$ is $[(CH_2)_nO]_oCH_3$ or $[(CH_2)_nO]_oH$ and n is 2 or 3. In another embodiment, $R_5$ and/or $R_5'$ are each independently $-OR^x$ where $R^x$ is $[(CH_2)_nO]_oCH_3$, n is 2 and o is 17. In another embodiment, the perylene diimides comprise different lengths of PEG size chains, wherein the average lengths is of the side chains is between 13-25, 17-22 or 18-22 repeating units.

In one embodiment $R_1$, $R_1'$, $R_2$ and $R_2$ are the same. In another embodiment, $R_1$, $R_1'$, $R_2$ and $R_2$ are different. In another embodiment, $R_1$, $R_1'$, $R_2$ and/or $R_2$ are each independently an alkyl. In another embodiment, $R_1$, $R_1'$, $R_2$ and/or $R_2$ are each independently $-CH(CH_2CH_3)_2$. In another embodiment, $R_1$, $R_1'$, $R_2$ and/or $R_2$ are each independently a phenyl. In another embodiment, $R_1$, $R_1'$, $R_2$ and/or $R_2$ are each independently a $CH_2$-phenyl. In another embodiment, $R_1$, $R_1'$, $R_2$ and/or $R_2$ are each independently a PEG. In another embodiment, $R_1$, $R_1'$, $R_2$ and/or $R_2$ are each independently a chiral group.

In one embodiment, "r" of $R_1$, $R_1'$, $R_2$, and/or $R_2'$ of formula I, II and VI in the following substituents $[(CH_2)_qO]_rCH_3$, $[(CH_2)_qO]_rH$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rH_3$, $[(alkylene)_qCH=CH]_rCH_3$, $[(alkylene)_qNH]_rCH_3$, is between 1-100. In another embodiment "r" is between 15-20. In another embodiment "r" is between 10-20. In another embodiment "r" is between 17-22. In another embodiment "r" is about 19. In another embodiment "r" is between 10-30. In another embodiment "r" is between 20-40. In another embodiment "r" is between 20-50.

In one embodiment, "o" of $R_5$ and/or $R_5'$ formula I, II and VI in the following substituents $OR_x$, wherein $R_x$ is $[(CH_2)_nO]_oCH_3$ or $[(CH_2)_nO]_oH$; or wherein $R_5$ and/or $R_5'$ formula I, II and VI are independently each $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$ is between 1-100. In another embodiment "o" is between 15-20. In another embodiment "o" is between 10-20. In another embodiment is between 17-22. In another embodiment "o" is about 19. In another embodiment "o" is between 13-23. In another embodiment "o" is between 10-30. In another embodiment "o" is between 20-40. In another embodiment "o" is between 20-50.

In one embodiment "p" of $R_3$ formula I, II and VI in the following substituent $[C(O)CHR_3NH]_pH$ is between 1-100. In another embodiment "p" is between 15-20. In another embodiment "p" is between 10-20. In another embodiment "p" is between 17-22. In another embodiment "p" is about 19. In another embodiment "p" is between 10-30. In another embodiment "p" is between 20-40. In another embodiment "p" is between 20-50.

In one embodiment "n" of $R_5$ and/or $R_5'$ formula I, II and VI in the following substituent $[(CH_2)_nO]_oCH_3$, $[(CH_2)_nO]_oH$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$ is between 1-5. In another embodiment "n" is 1. In another embodiment "n" is 2. In another embodiment "n" is 3. In another embodiment "n" is 4. In another embodiment "n" is 5.

In one embodiment "q" of $R_1$, $R_1'$, $R_2$ and/or $R_2'$ formula I, II and VI in the following substituent independently $[(CH_2)_qO]_r$ $CH_3$, $[(CH_2)_qO]_rH$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, is between 1-5. In another embodiment "q" is 1. In another embodiment "q" is 2. In another embodiment "q" is 3. In another embodiment "q" is 4. In another embodiment "q" is 5.

In one embodiment "s" of $R_4$ formula I, II and VI in the following substituent $[C(O)CHR_4NH]_sH$ is between 1-100. In another embodiment "s" is between 15-20. In another embodiment "s" is between 10-20. In another embodiment "s" is between 17-22. In another embodiment "s" is about 19. In another embodiment "s" is between 10-30. In another embodiment "s" is between 20-40. In another embodiment "s" is between 20-50.

In one embodiment, Z of formula VI is $-OR_x$ where $R_x$ is $C_1$-$C_6$ alkyl or $[(CH_2)_qO]_rCH_3$.

In one embodiment, Z of formula VI is a peptide. In another embodiment, Z is a peptide including between 2-4 amino acids. In another embodiment, Z is a peptide including between 2-6 amino acids. In another embodiment, Z is a peptide including between 2-10 amino acids. In another embodiment, the amino acids are protected amino acids. In another embodiment, Z of formula VI is a peptide wherein the peptide is attached to the linker (L) via one of the side chains of the amino acid. In another embodiment, Z of formula VI is a peptide wherein the peptide is attached to the linker (L) via the amino end. In another embodiment, Z of formula VI is a peptide wherein the peptide is attached to the linker (L) via the carboxylic end. In another embodiment, Z of formula VI is a peptide, L is a bond and the peptide is attached the perylene diimide directly via one of the side chains of the amino acid. In another embodiment, Z of formula VI is a peptide, L is a bond and the peptide is attached the perylene diimide directly via the amino end. In another embodiment, Z of formula VI is a peptide, L is a bond and the peptide is attached the perylene diimide directly via the carboxylic acid end. In another embodiment, Z of formula VI is a peptide, L is a bond and the peptide is attached the perylene diimide directly via the SH side chain of a cysteine amino acid. In another embodiment, the peptide is -Cys-Phe, In another embodiment, the peptide is -Cys-Phe-Phe. In another embodiment, the peptide is chiral.

In one embodiment, Z of formula VI is an amino acid. In another embodiment, the amino acid is Phe. In another embodiment, the amino acid is Trp. In another embodiment, the amino acid is Cys. In another embodiment, the amino acid is Tyr. In another embodiment the amino acid is not an enantiomeric mixture. In another embodiment, the amino acid is a pure enantiomer. In one embodiment, Z of formula VI is a chiral group. In another embodiment, $R_1$, $R_1'$, $R_2$, $R_2'$, $R_5$ and/or $R_5'$ of formula I, II, and VI are each independently a chiral group. In another embodiment, "chiral group" refers to any group that lack symmetry. Non limiting examples of chiral group include an amino acid, an artificial amino acid, a peptide, a protein, a sugar, DNA, RNA, a nucleic acid, chiral drug, chiral molecule or combination thereof.

In one embodiment, Z of formula VI is $[(CH_2)_qC(O)O]_rCH_3$. In another embodiment, Z of formula VI is $[(CH_2)_qC(O)NH]_rCH_3$. In another embodiment, Z of formula VI is $[(CH_2)_qCH_2=CH_2]_rCH_3$. In another embodiment, Z of formula VI is $[(CH_2)_qCH=CH]_rCH_3$. In another embodiment, Z of formula VI is $[(CH_2)_qNH]_rCH_3$. In another embodiment, Z of formula VI is $[(alkylene)_qO]_rCH_3$. In another embodiment, Z of formula VI is $[(alkylene)_qC(O)O]_rCH_3$. In another embodiment, Z of formula VI is $[(alkylene)_qC(O)NH]_rCH_3$. In another embodiment, Z of formula VI is $[(alkylene)_qCH_2=CH_2]_rCH_3$. In another embodiment, Z of formula VI is $[(alkylene)_qCH=CH]_rCH_3$. In another embodiment, Z of formula VI is $[(alkylene)_qNH]_rCH_3$. In another embodiment, Z of formula VI is aryl. In another embodiment, Z of formula VI is heteroaryl. In another embodiment, Z of formula VI is $C\equiv C-R_7$. In another embodiment, Z of formula VI is $CH=CR_8R_9$. In another embodiment, Z of formula VI is $NR_{10}R_{11}$. In another embodiment, Z of formula VI is saturated carbocyclic or heterocyclic ring. In another embodiment, Z of formula VI is bipyridyl, terpyridyl or metal complex thereof.

In one embodiment, the self-assembled membrane, and methods of filtration/separation or purification comprise the use of perylene diimide of this invention or a salt thereof which may be produced, by reaction of a compound of this invention with an acid or base. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyOmethylamines, triethylamines, triethanolamines, trimethylamines, tromethamines and ureas.

In one embodiment, the self-assembled membrane, and methods of filtration/separation or purification comprise perylene diimide of this invention or its metal complex. In another embodiment the metal complex is a Pd (IV), Pt(II), Ag(T) or any other transition metal complex of pyridyls, bipyridyls, terpyridyl or any other chelating linkers known in the art.

An "alkyl" or "alkylene" group refers, in one embodiment, to a saturated aliphatic hydrocarbon, including straight-chain and branched-chain groups. In one embodiment, the alkyl group has 1-12 carbons. In another embodiment, the alkyl group has 1-8 carbons. In another embodiment, the alkyl group has 1-6 carbons. In another embodiment, the alkyl group has 1-4 carbons. The alkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the alkyl group is $-CH_3$, $-CH(CH_3)_2$, $-CH_2CH(CH_3)_2$, $-CH(CH_3)CH_2CH_3$, and the like.

A "cycloalkyl" group refers, in one embodiment, to a saturated aliphatic cyclic hydrocarbon group. In one embodiment, the cycloalkyl group has 3-12 carbons. In another embodiment, the cycloalkyl group has 3-8 carbons. In another embodiment, the cycloalkyl group has 3-6 carbons. In another embodiment, the cycloalkyl group has 3 carbons. The cycloalkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the cycloalkyl group is cyclopropyl, cyclobutyl, cyclopentyl, cyclohexyl, and the like. In another embodiment, the cycloalkyl comprises of between 1-4 rings.

The term "carbocyclic ring" refers to a saturated or unsaturated ring composed exclusively of carbon atoms. In one embodiment, the carbocyclic ring is a 3-12 membered ring. In another embodiment, the carbocyclic ring is a 3-8 membered ring. In one embodiment, the carbocyclic ring is a five membered ring. In one embodiment, the carbocyclic ring is a six membered ring. In one embodiment the carbocyclic ring may be unsubstituted or substituted by one or more groups selected from halogen, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of carbocyclic ring are benzene, cyclohexane, and the like. In another embodiment, the carbocyclic ring comprises of between 1-4 rings.

The term "aryl" refers to an aromatic group having at least one carbocyclic aromatic ring, which may be unsubstituted or substituted by one or more groups selected from halogen, cyano, aryl, heteroaryl, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, and the like. In one embodiment, the aryl group is a 5-12 membered ring. In another embodiment, the aryl group is a 5-8 membered ring. In one embodiment, the aryl group is a five membered ring. In one embodiment, the aryl group is a six membered ring. In another embodiment, the aryl group comprises of 1-4 fused rings.

The term "arylalkyl" refers to an alkyl group as defined above substituted by an aryl group as defined above. Examples of arylalkyl, but not limited to are —CH$_2$Ph or —CH$_2$CH$_2$Ph.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

The terms "halide" and "halogen" refer to in one embodiment to F, in another embodiment to Cl, in another embodiment to Br, in another embodiment to I.

A "heterocyclic" group refers to a heterocycle. In one embodiment, said heterocycle refers to a ring structure comprising in addition to carbon atoms, sulfur, oxygen, nitrogen, silicon or phosphorous or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halide, haloalkyl, hydroxyl, alkoxy, carbonyl, amido, alkylamido, dialkylamido, cyano, nitro, CO$_2$H, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

The term "hydroxylalkyl" refers to an alkyl as described above substituted by hydroxyl group. Nonlimiting examples of hydroxyalkyl are —CH$_2$OH, —CH$_2$CH$_2$OH and the like.

The term "alkylamino" refers to an alkyl as described above substituted by an amine group. Nonlimiting examples of alkylamono are —CH$_2$NH$_2$—CH$_2$CH$_2$N(CH$_3$)$_2$, —(CH$_2$)$_5$NH$_2$ and the like.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of nano-materials of between 1-5 nm particle sizes. In another embodiment, the perylene diimide supramolecular structure (membrane) provides a chromatography medium for size-selective separation of nano-materials of between 7-10 nm particle sizes. In another embodiment, the perylene diimide supramolecular structure (membrane) provides a chromatography medium for size-selective separation of nano-materials of between 5-10 nm particle sizes. In another embodiment, the perylene diimide supramolecular structure (membrane) provides a chromatography medium for size-selective separation of nano-materials of between 5-20 nm particle sizes. In another embodiment, the perylene diimide supramolecular structure (membrane) provides a chromatography medium for size-selective separation of nano-materials of between 2-10 nm particle sizes. In another embodiment, the nano-materials are nanoparticles or biomolecules. In another embodiment, size-selective separation of nanoparticles is conducted on a membrane having pores size with a cutoff size of between 1-5 nm. In another embodiment, size-selective separation of biomolecules is conducted on a membrane having pores size with a cutoff size of between 7-10 nm.

In another embodiment, membrane cutoff values are known to depend on shape and deformability of the filtered particles. In another embodiment, the membrane pores depend on the thickness of the membrane. In another embodiment, enlargement of the pores can be obtained by heating the membrane. In another embodiment, enlargement of the pores can be obtained by increasing the temperature of the membrane to a temperature between 30-60° C. In another embodiment, enlargement of the pores can be obtained by increasing the temperature of the membrane to a temperature between 30-100° C.

In one embodiment, this invention is directed to noncovalent self-assembled porous chiral membrane comprising a chiral perylene diimide supramolecular structure, having a cutoff size of ultrafiltration of between 2-100 nm; which provides a chromatography medium for size-selective separation of nano-materials and provides chiral separation for chiral nano-materials. In another embodiment, the chiral membrane of this invention provides chiral separation between chiral biomolecules. In another embodiment, the chiral membrane of this invention provides chiral separation between chiral nanoparticles, biomolecules or chiral nano-materials. In another embodiment, chiral nano-materials include any chiral material/molecule having a chiral center, an amino acid, an artificial amino acid, a peptide, a protein, a sugar, DNA, RNA, a nucleic acid, chiral drug, chiral molecule or any combination thereof.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of nanoparticles of between 1-5 nm particle sizes. In another embodiment, the membrane of this invention has a cutoff size of ultrafiltration of between 5 to 10 nm.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of biomolecules of between 7-10 nm particle sizes or a biomolecule of about 150 kDa.

In one embodiment, the membrane of this invention has a cutoff size of between 2 nm to 4 nm. In another embodiment, the membrane of this invention has a cutoff size of between 2 nm to 5 nm. In another embodiment, the membrane of this invention has a cutoff size of between 3 nm to 10 nm. In another embodiment, the membrane of this invention has a cutoff size of between 2 nm to 15 nm. In another embodiment, the membrane of this invention has a cutoff size of between 5 nm to 10 nm. In another embodiment, the membrane of this invention has a cutoff size of between 5 nm to 20 nm. In another embodiment, the membrane of this invention has a cutoff size of between 5 nm to 50 nm. In another embodiment, the membrane of this invention has a cutoff size of between 5 nm to 15 nm. In another embodiment, the membrane of this invention has a cutoff size of between 20 nm to 50 nm.

In one embodiment, this invention is directed to porous membrane wherein the cutoff size of the pores is between 2-100 nm. In another embodiment, the cutoff size depends on the thickness of the membrane. In another embodiment, the thickness of the membrane is between 5-100 μm. In another embodiment, the thickness of the membrane is between 10-50 μm. In another embodiment, the thickness of the membrane is between 10-20 μm. In another embodiment, the thickness of the membrane is between 15-30 μm. In another embodiment, the thickness of the membrane is between 10-40 μm. In another embodiment, the thickness of the membrane is between 30-40 μm. In another embodiment, the thickness of the membrane is between 10-20 μm.

In one embodiment, a membrane thickness of between 10-15 μm provides a cutoff size of 5 nm. In another embodiment, a membrane thickness of between 40-50 μm provides a cutoff size of between 2-4 nm. In another embodiment, this invention is directed to a membrane providing a chromatography medium for size-selective separation of nano-materials of between 1-5 nm particle size comprising self assembled perylene diimide of this invention. In another embodiment, a thicker layer of self assembled perylene diimide of this invention provide better separation between the nano-materials. (i.e smaller nano-materials will pass faster through the membrane than larger nano-materials, and thereby provide size separation between the nano-materials.)

In one embodiment, the term "nano-materials" refers to mixture of materials (same or different) having different particle sizes wherein one of the materials has particle size of between 1-200 nm. In another embodiment, the term "nano-materials" refers to same materials having different particle size or to different materials having different particle size. In another embodiment, the term "nano-materials" refers to nanoparticles. In another embodiment, the term "nano-material" refers to sub nanometer size materials including small molecules. In another embodiment, the nano-materials refers to biomolecules. In another embodiment, the term "chiral nano-materials" refers to chiral compounds in the nanometer and sub nanometer size material.

In one embodiment, this invention provides a method for separation/filtration, purification and optimization of nanoparticles. In another embodiment, this invention provides a method for separation/filtration, purification and optimization of nanoparticles in a size domain of sub 5 nm. In another embodiment, applications in separation/filtration, purification and optimization of nanoparticles in a size domain is highly relevant to optical, catalytic, and biological applications. In another embodiment, the nanoparticles refer to gold nanoparticles, metal nanoparticles, metal oxide nanoparticles, nanoparticles which are soluble in water, quantum dots (CdS nanoparticles, CdSe nanoparticles, CdTe nanoparticles), polymers, biomacromolecules, such as peptides, DNA, RNA, viruses, and proteins.

In one embodiment, this invention provides a method for separation/filtration, purification and optimization of biomolecules. In another embodiment, this invention provides a method for separation/filtration, purification and optimization of nanoparticles in a size domain of sub 5 nm. In another embodiment, applications in separation/filtration, purification and optimization of biomolecules in a size domain is highly relevant for medical and biological systems. In another embodiment, the biomolecules refer to peptides, DNA, RNA, proteins and separation of viruses. In another embodiment separation of proteins is disclosed in Examples 13 and 16.

The cutoff value of the supramolecular membrane is in the upper range of commonly used ultrafiltration membranes in biotechnology, allowing the retention of large proteins, nucleic acids, lipids and other large lysate components.

In one embodiment, this invention provides a method of rapid separation of protein monomers from protein aggregates using the perylene diimide membrane of this invention. In another embodiment, this invention provides a method of separation of protein monomers from protein aggregates as described in Example 18.

In one embodiment, this invention provides a biocatalytic membrane comprising a noncovalent self-assembled porous membrane comprising a perylene diimide supramolecular structure of this invention and an enzyme; wherein said enzyme is immobilized within said membrane; wherein said noncovalent self-assembled perylene diimide supramolecular structure comprises a perylene diimide, a salt thereof or a metal thereof of formula I-XV as a monomeric unit. In another embodiment, noncovalent self-assembled perylene diimide supramolecular structure comprises a perylene diimide, a salt thereof or a metal thereof of formula I as a monomeric unit. In another embodiment, noncovalent self-assembled perylene diimide supramolecular structure comprises a perylene diimide, a salt thereof or a metal thereof of formula II as a monomeric unit. In another embodiment, noncovalent self-assembled perylene diimide supramolecular structure comprises a perylene diimide, a salt thereof or a metal thereof of formula III as a monomeric unit. In another embodiment, noncovalent self-assembled perylene diimide supramolecular structure comprises a perylene diimide, a salt thereof or a metal thereof of formula IV as a monomeric unit. In another embodiment, noncovalent self-assembled perylene diimide supramolecular structure comprises a perylene diimide, a salt thereof or a metal thereof of formula V as a monomeric unit. In another embodiment, noncovalent self-assembled perylene diimide supramolecular structure comprises a perylene diimide, a salt thereof or a metal thereof of formula VI-XIV as a monomeric unit. In another embodiment, noncovalent self-assembled perylene diimide supramolecular structure comprises a perylene diimide, a salt thereof or a metal thereof of formula XV as a monomeric unit. In another embodiment, noncovalent self-assembled perylene diimide supramolecular structure comprises a mixture of perylene diimide of formula I-XV, a salt thereof or a metal thereof.

In one embodiment, this invention provides a method of heterogenous catalysis comprising (a) transferring an aqueous solution or emulsion comprising a perylene diimide supramolecular structure through porous solid support, thereby forming a noncovalent self-assembled perylene diimide based membrane layer on said porous solid support; (b) transferring a biocatalyst through said membrane layer; wherein said biocatalyst is immobilized within said membrane; and (c) passing through said immobilized biocatalyst a substrate wherein a catalytic reaction occurs between said biocatalyst and said substrate. In another embodiment, the biocatalyst is an enzyme.

Immobilization on the supramolecular membranes is versatile and applicable to various enzymes provided that they are large enough to be retained. In order to extend the method to smaller enzymes, one can use standard procedures to enlarge the enzyme without affecting its activity, either by fusing the enzyme to a large inactive protein, or by formation of cross-linked enzyme aggregates (CLEAs) prior to filtration. Since the design of effective immobilization techniques has been described as one of the main obstacles for industrial-scale biocatalysis, we note that enzyme entrapment in the supramolecular membrane is accomplished in a simple filtration step within 20 minutes. The reactant conversion can be controlled by adjusting the amount of enzyme deposited on the supramolecular membrane. Having a substantial thickness of ~6 μm the noncovalent matrix functions as a depth filter, allowing very high enzyme loading (e.g. 0.4 g enzyme/1 g perylene diimide membrane) without membrane clogging.

Biocatalysis in membrane reactors takes place within the short time of the substrate's passing through the membrane layer. Thus, high enzyme loading is important in order to achieve satisfying reaction yields.

In another embodiment, heterogeneous biocatalysis facilitates more complex cascade reactions, wherein two or more enzymes are immobilized in a sequential manner. As membrane fabrication and enzyme immobilization are carried out by simple deposition steps, preparation of complex layered structures with alternating membrane/enzyme arrays.

In another embodiment, the advantages of the biocatalytic membrane and methods of heterogenous catalysis include: (i) no synthetic modification or covalent attachment of the enzyme to a stationary phase is necessary. (ii) Enzymes/biocatalysts can be easily retrieved from the membrane by disassembly of the noncovalent membrane material, which is important considering the high cost of enzyme synthesis.

In one embodiment, this invention provides a method for separation/filtration, purification and optimization of chiral nano-materials. In another embodiment, the chiral nano-materials refer to nano-sized materials and subnanometer sized materials, possessing at least one chiral center. Non limiting examples include an amino acid, an artificial amino acid, a peptide, a protein, a sugar, DNA, RNA, a nucleic acid, chiral drug, chiral molecule or combination thereof.

In one embodiment, this invention is directed to a method of separation/filtration or purification of nanoparticles comprising (a) transferring an aqueous solution or emulsion comprising a perylene diimide supramolecular structure of this invention through porous solid support, thereby forming a noncovalent self assembled perylene diimide based membrane on said porous solid support; (b) transferring nanoparticles through said noncovalent self-assembled perylene diimide based membrane of step (a); wherein the particles which are larger than the pores of said membrane remain on said membrane. In another embodiment, the method includes further chiral separation/filtration or purification of chiral nanoparticles.

In one embodiment, this invention is directed to a method of separation/filtration or purification of biomolecules comprising (a) transferring an aqueous solution or emulsion comprising a perylene diimide supramolecular structure of this invention through porous solid support, thereby forming a noncovalent self-assembled perylene diimide based membrane on said porous solid support; (b) transferring a solution of biomolecules through said noncovalent self-assembled perylene diimide based membrane of step (a); wherein the particles which are larger than the pores of said membrane remain on said membrane. In another embodiment, the method includes further chiral separation/filtration or purification of chiral biomolecules.

In one embodiment, this invention is directed to a method of separation/filtration or purification of chiral nano-materials comprising (a) transferring an aqueous solution or emulsion comprising a chiral perylene diimide supramolecular structure of this invention through porous solid support, thereby forming a noncovalent self-assembled chiral perylene diimide based membrane on said porous solid support; (b) transferring chiral nano-materials through said noncovalent self-assembled perylene diimide based membrane of step (a); wherein the chiral-nano-materials are separated/filtered or purified.

In one embodiment, the biomolecules solution is an aqueous solution. In another embodiment, the biomolecules solution is a buffered solution. In another embodiment, the biomolecules solution is a solution under physiological conditions.

In one embodiment, the methods of this invention provide separation between nanoparticles or separation between biomolecules at a size range of between 3-40 nm. In one embodiment, the methods of this invention provide separation between nanoparticles or separation between biomolecules at a size range of between 1-5 nm. In one embodiment, the methods of this invention provide separation between nanoparticles or separation between biomolecules at a size range of between 5-10 nm. In one embodiment, the methods of this invention provide separation between nanoparticles or separation between biomolecules at a size range of between 7-10 nm.

In one embodiment, the methods of this invention fractionate nanoparticles or fractionate biomolecules between 5 and 40 nm. In another embodiment this invention is directed to fractionates nanoparticles or fractionate biomolecules between 3 and 10 nm. In another embodiment this invention is directed to fractionates nanoparticles or fractionate biomolecules between 1 and 5 nm. In another embodiment this invention is directed to fractionates nanoparticles or fractionate biomolecules between 5 and 10 nm. In another embodiment this invention is directed to fractionates nanoparticles or fractionate biomolecules between 7 and 10 nm.

In one embodiment, this invention provides a method for separation/filtration, purification and optimization of nanoparticles or biomolecules in a size domain. In another embodiment, the separation/filtration or purification is based on the thickness of the membrane. In another embodiment particles with a cap off of 5 nm are separated on a membrane of between 10-15 μm thickness. In another embodiment quantum dots of a size between 1-5 nm, are separated on a membrane of between 40-50 μm thickness. In another embodiment, this invention provides a chromatography medium for size-selective separation of nanoparticles or biomolecules.

In one embodiment the separated and/or fractionate nanoparticles do not aggregate or fuse using the methods of this invention.

In one embodiment the separated and/or fractionate biomolecules do not aggregate or fuse using the methods of this invention.

In one embodiment, the membrane of this invention is deposited on a solid support. In another embodiment, the solid support is a microfiltration filter. In another embodiment, the microfiltration filter comprises cellulose acetate (CA). In another embodiment, the microfiltration filter comprises polyether sulfone (PES). In another embodiment, the microfiltration filter comprises Teflon (PTFE). In another embodiment, the microfiltration filter comprises polycarbonate. In another embodiment, the microfiltration filter is commercially available having a pore size smaller or equal to 0.45 microns and larger than 5 nm. In another embodiment, the microfiltration filter has a pore size which is larger than 5 nm. In another embodiment, the microfiltration filter has a pore size smaller or equal to 0.45 microns.

Figure 2:
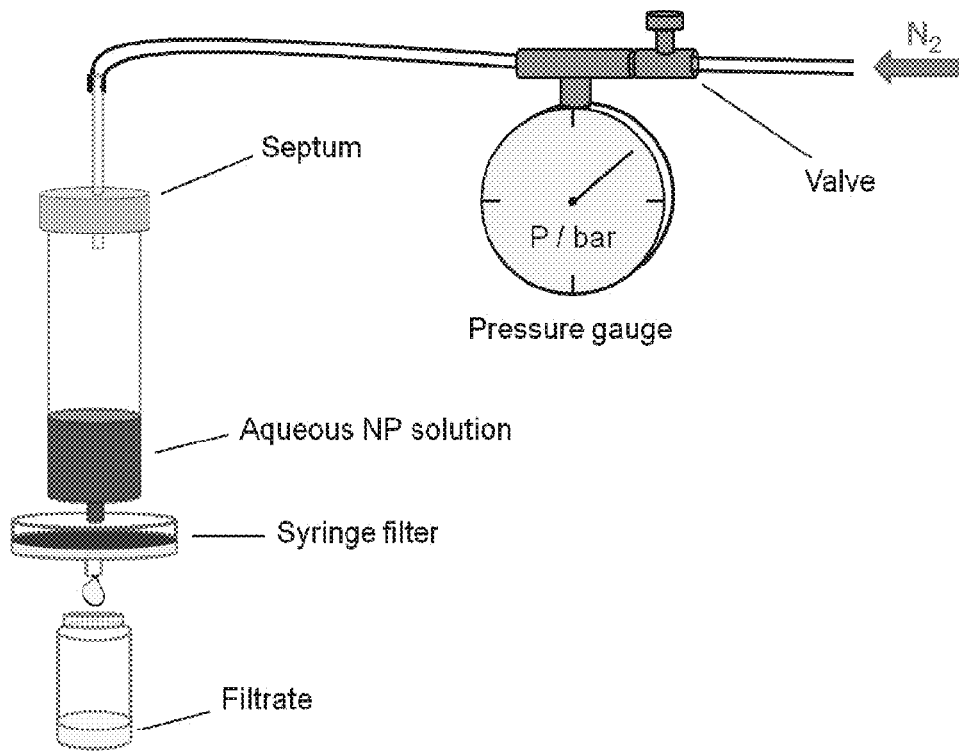
FIG. 2 provides a schematic setup for filter preparation and filtration experiments. Nitrogen entering the system produces the pressure that can be adjusted using a valve and a pressure gauge. Aqueous solution of perylene diimide of this invention, nano-material solutions and rinsing water are injected into the system through the septum.

In one embodiment, the method of separation/filtration or purification of nanoparticles is depicted in FIGS. 5(A)-(B) and FIG. 2.

In one embodiment, the method of separation/filtration or purification of nanoparticles comprises transferring nanoparticles through the noncovalent self-assembled perylene diimide based membrane. In another embodiment, the transfer of nanoparticles through the membrane is done under pressure. In another embodiment, ultrafiltration is a pressure-driven separation process in which porous membranes retain particles larger than the membrane cut-off (ranging from 2 to 100 nm).

In one embodiment, the method of separation/filtration or purification of biomolecules comprises transferring biomolecules through the noncovalent self-assembled perylene diimide based membrane. In another embodiment, the transfer of biomolecules through the membrane is done under pressure. In another embodiment, ultrafiltration is a pressure-driven separation process in which porous membranes retain particles larger than the membrane cut-off (ranging from 2 to 100 nm).

In one embodiment, the method of separation/filtration or purification of chiral nano-materials comprises transferring nano-materials through the noncovalent self-assembled chiral perylene diimide based membrane. In another embodiment, the transfer of nano-materials through the membrane is done under pressure. In another embodiment, ultrafiltration is a pressure-driven separation process in which porous membranes retain particles larger than the membrane cut-off (ranging from 2 to 100 nm), and/or separate particles having different chirality.

Figure 9:
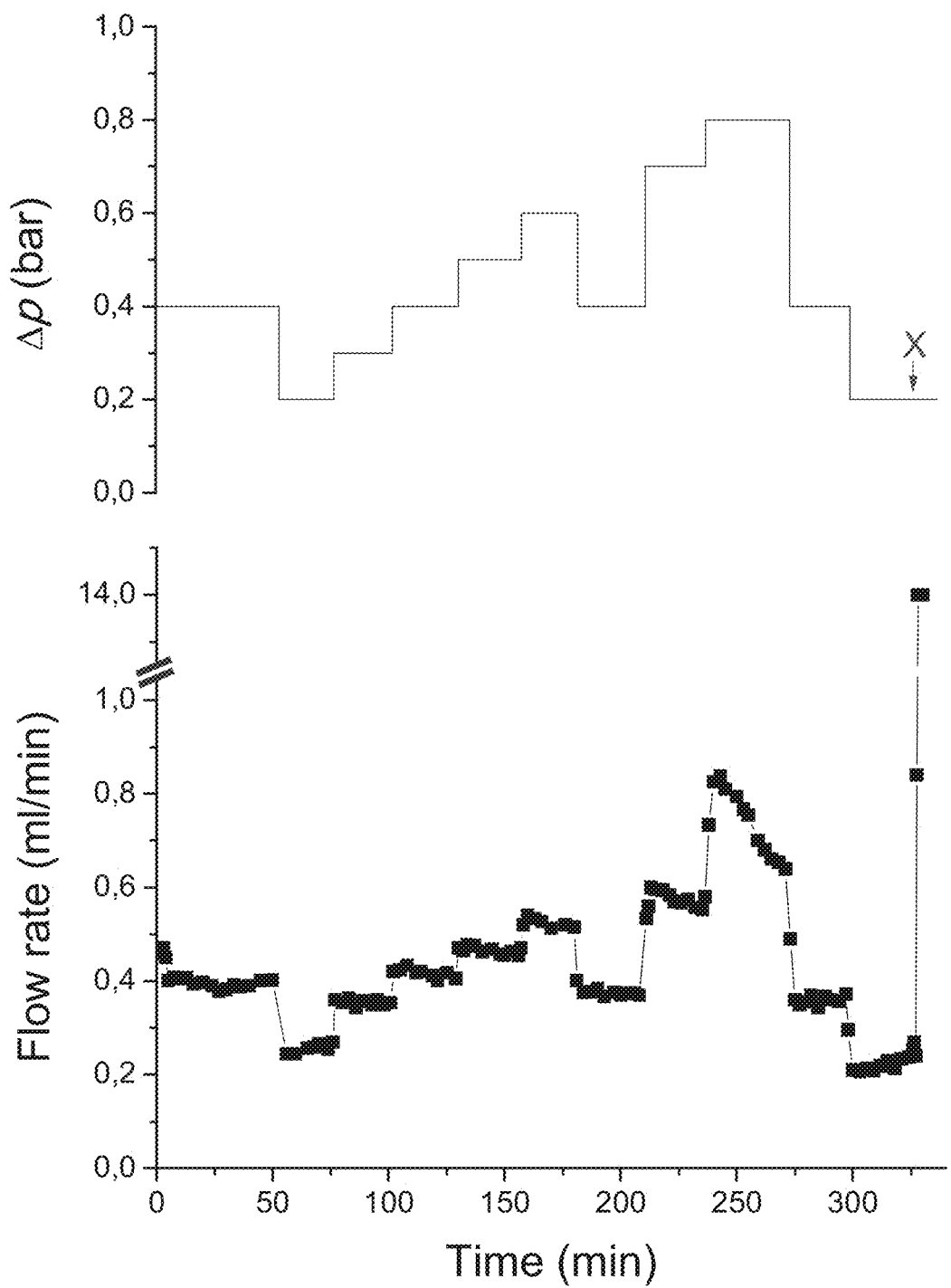
FIG. 9 depicts flow rate of water through a supramolecular membrane prepared from 0.5 ml Perylene diimide V ($5 \cdot 10^{-4}$ M) on CA support (0.45 μm pore size, 5.7 cm$^2$ surface area; 0.13 mg Perylene diimide V/cm$^2$) at 25° C. The top graph presents the stepwise variation of the transmembrane pressure, $\Delta p$, with time. The bottom graph presents flow rate during that time and its response to changes in $\Delta p$. Flow rates are stable at pressures up to 0.7 bar. At 0.8 bar unstable flow is observed (minutes 240-270). The 'X' denotes the time of addition of water/ethanol (4:6, v/v) mixture, which causes disassembly of the supramolecular filter and a resulting jump in flow rate by almost two orders of magnitude. The flow rates were determined using the setup depicted in FIG. 2 in combination with a digital balance recording the weight gain caused by the change in filtrate volume.

In one embodiment the flow rate of water through 12 μm membrane can be adjusted via the trans-membrane pressure, and stable flow rates are observed at pressures up to 0.7 bar over several hours (FIG. 9). The flow rate at 0.4 bar is 0.4 ml/min, corresponding to permeance (pressure normalized flux) of $1.1 \cdot 10^2$ 1 $h^{-1}$ $m^{-2}$ $bar^{-1}$ (Example 9).

In one embodiment, the membranes of this invention are readily prepared via one-step deposition of an aggregated perylene diimide of formula I-XV solution on a microfiltration support. Owing to its noncovalent nature, the material is easily disassembled by organic solvent (e.g. ethanol), the retained particles are released, and the membrane material itself can be recycled and reused multiple times.

In one embodiment, this invention provides a method of recycling the noncovalent self-assembled perylene diimide based membrane comprising: (a) washing said microfiltration filter with the membrane of this invention and the retentate deposited thereon, with a solution of alcohol and water; (b) extracting said perylene diimide structure from said solution with an organic solvent; and (c) isolating said perylene diimide from said organic solvent. In another embodiment, the isolated perylene diimide can be further used to form a noncovalent self-assembled perylene diimide based membrane in aqueous conditions. In another embodiment the perylene diimide is isolated from said organic solvent by evaporation of the organic solvent. In another embodiment the perylene diimide is isolated from said organic solvent by precipitation of the perylene diimide from said organic solvent.

In one embodiment, a retentate is any material retained on the membrane of this invention during the separation/purification process. In another embodiment the retentate refers to nanoparticles. In another embodiment, the retentate refers to biomolecules. In another embodiment, the retentate refers to chiral compounds.

Figure 10:
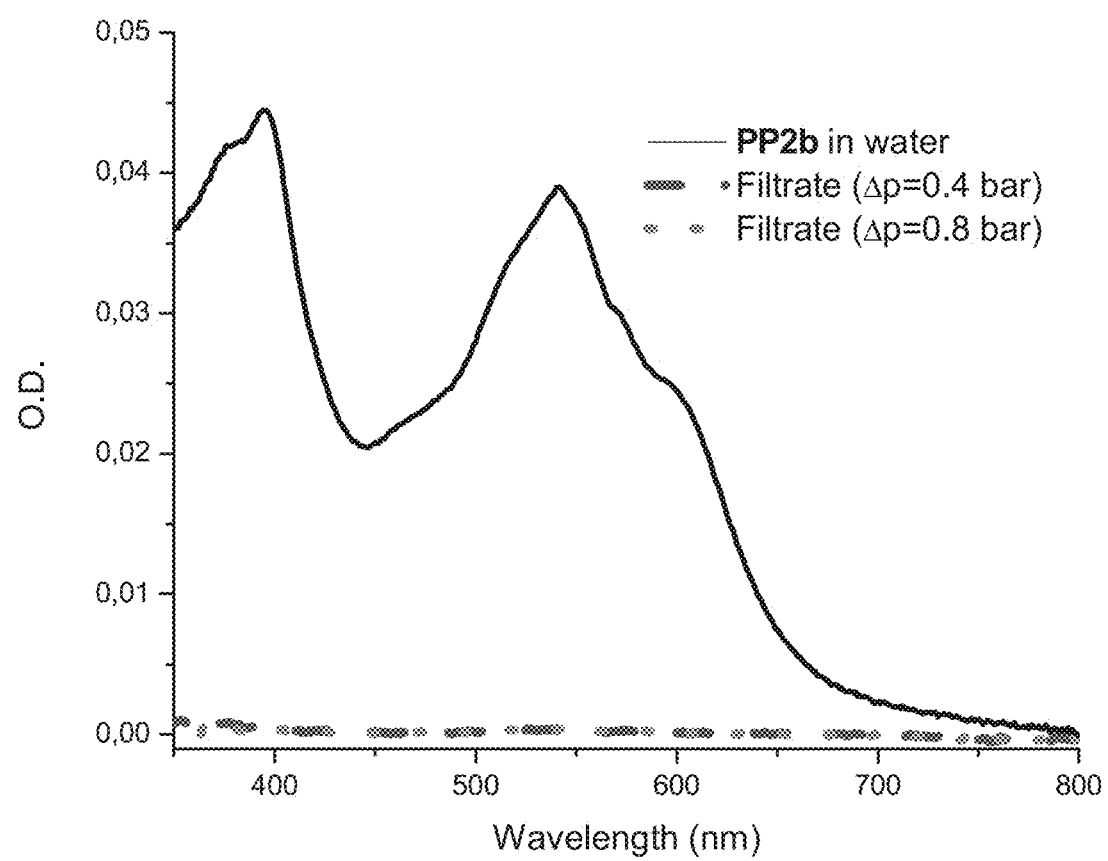
FIG. 10 depicts UV/Vis spectra of a dilute solution of Perylene diimide V in water ($5 \cdot 10^6$ M, solid line), the filtrates obtained from flow of water through a Perylene diimide V supramolecular membrane at $\Delta p=0.4$ bar (dashed line) and at $\Delta p=0.8$ bar (dotted line). No traces of Perylene diimide V are detectable in both filtrates.

In another embodiment, the supramolecular membrane material is disassembled by organic solvent, cleaned, and can be reassembled, and reused in aqueous conditions, maintaining the same performance. In another embodiment, the perylene diimide maintained its performance as described in Example 10 and FIGS. 10 and 5.

In one embodiment, this invention provides a method of isolating the retentate on the membrane of this invention comprising (a) washing said microfiltration filter with said membrane of this invention and said retentate deposited thereon with a solution of alcohol and water; (b) extraction of said perylene diimide structure from said solution with an organic solvent, and extracting said retentate from the remaining aqueous phase. In another embodiment, the retentate refers to nanoparticles. In another embodiment, the retentate refers to biomolecules. In another embodiment, the retentate refers to chiral compounds.

In one embodiment, this invention provides a method of recycling the noncovalent self-assembled perylene diimide based membrane and isolating the retentate on the membrane comprising washing said microfiltration filter with the membrane of this invention and the retentate deposited thereon with a mixture of alcohol and water. In another embodiment, the water:alcohol ratio in said mixture is between about 5:5 to 3:7 v/v. In another embodiment, the water:alcohol ratio is about 4:6 v/v. In another embodiment, the alcohol is ethanol, methanol or isopropanol. In another embodiment, the retentate refers to nanoparticles. In another embodiment, the retentate refers to biomolecules.

In one embodiment, this invention provides a method of recycling the noncovalent self-assembly perylene diimide based membrane and isolating the retentate on the membrane comprising: (a) washing the microfiltration filter with the membrane of this invention and the retentate deposited thereon with a mixture of alcohol and water and (b) extracting said perylene diimide structure with an organic solvent, wherein the retentate remains in the aqueous phase. In another embodiment the organic solvent is methylene chloride, chloroform, ethyl acetate, ether, benzene toluene or any organic solvent that is immiscible in water.

In one embodiment, this invention is directed to a method of preparing a noncovalent self-assembled perylene diimide based membrane of this invention comprising (a) prepare an organic solution of perylene diimide of this invention, wherein the organic solvent in said organic solution is miscible in water; (b) adding excess of water to said solution of (a); wherein the organic solvent:water ratio is between about 1:99 to 8:92 v/v; (c) evaporating said organic solvent; and (d) transferring the remaining aqueous solution or emulsion of (c) through a solid support; thereby obtaining a noncovalent self-assembled perylene diimide based membrane.

In another embodiment, this invention is directed to a method of preparing a noncovalent self-assembled perylene diimide based membrane comprising dissolving the perylene diimide in a mixture of an organic solvent which is miscible in water and water wherein the organic solvent:water ratio is between about 10:90 to 3:97 v/v. In another embodiment the organic solvent:water ratio is about 5:95 v/v. In another embodiment the organic solvent:water ratio is about 1:99 to 8:92 v/v.

In another embodiment, the miscible organic solvent is THF, acetonitrile, acetone, methanol, ethanol, DMF, any other miscible organic solvent known in the art, or any combination thereof.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, and preferably up to 10% of a given value; such as within 7.5%, within 5%, within 2%, within 1%, within 0.5% of a given value.

The following examples are presented in order to more fully illustrate the preferred embodiments of the invention. They should in no way be construed, however, as limiting the broad scope of the invention.

EXAMPLES

Materials and Methods

Solvents and reagents were purchased from commercial sources and used as received, unless otherwise specified.

PEG-SH (CH$_3$—(OCH$_2$CH$_2$)$_n$—SH, M$_p$=840 Da, PD=1.04) was purchased from Rapp Polymere. For all aqueous mixtures double-distilled water was used (Barnstead NANO pure Diamond™ water system). Organic solvents for spectroscopic studies were of spectroscopic or HPLC grade, dried over molecular sieves (3 Å), and filtered over 0.2 μm PTFE syringe filters prior to use. All procedures with air-sensitive compounds were performed under inert gas atmosphere (dried N$_2$ or Argon) using a glovebox (MBRAUN, Labmaster) or standard Schlenk techniques. Organic solvents used for these procedures were degassed with Argon and stored over molecular sieves (3 Å) in the glovebox. Water used for air-sensitive samples was degassed by the freeze-pump-thaw technique and kept in the glovebox as well. Cellulose acetate (CA) syringe filters were purchased from Whatman (Puradisc FP 30/0.45 CA-S). PTFE syringe filters were purchased from Pall (Valuprep 25 mm Syringe Filter, 0.45 μm pore size) and from MS (SFPTFE025022NB, 25 mm syringe filter, 0.22 μm pore size). Polycarbonate membranes were purchased from SPI (Black Membrane, 25 mm, 0.4 μm pore size). CA membranes for size-selective chromatography experiments were purchased from Advantec (C045A025A, 25 mm, 0.45 μm pore size). The filter holder for these membranes was purchased from Pall (25 mm Easy Pressure Syringe Filter Holder).

$^1$H NMR spectra were recorded at room temperature on a 300 MHz spectrometer (Bruker).

UV/V is absorption and luminescence measurements were carried out on a Cary-5000 spectrometer (Varian) and a Cary Eclipse fluorimeter (Varian), respectively.

MALDI-TOF mass spectrometry was carried out using a REFLEX™ reflector time-of-flight instrument with SCOUT™ multiprobe (384) inlet. ESI mass spectrometry was performed using a Micromass Platform instrument. Chloroform was the solvent for all samples analyzed by mass spectrometry.

TEM was performed on a Philips T12 transmission electron microscope operated at 120 kV and equipped with a TVIPS F224HD CCD digital camera. 5 μl of the sample were applied to a 300-mesh copper grid (SPI supplies) coated with nitrocellulose and carbon. Samples were blotted after one minute and dried in air. The images of nanoparticles were analyzed using ImageJ 1.410 (Wayne Rasband, NIH, USA). For creation of particle size histograms, an area containing >100 particles was chosen and diameters of all particles were measured.

Cryo-TEM was performed using a Tecnai F20 transmission electron microscope operating at 200 kV and using a Gatan 626 cooling holder and transfer station with a Gatan US4000 CCD digital camera. For sample-preparation, 8 μl of the sample was applied to a 300-mesh copper grid coated with holey carbon (Pacific Grid-Tech). Samples were blotted in N$_2$-enriched environment at 25° C. and 100% relative humidity, and subsequently plunged into liquid ethane using a CEVS plunger (2). Specimens were equilibrated at −178° C. in the microscope prior to imaging. The images were analyzed using AnalySIS 5.0 (2004, Soft Imaging System GmbH).

Cryo-SEM sample preparation involved the high pressure freezing (HPF) technique. For this purpose, a ~1×1 mm small rectangle was cut out from the membrane and placed inside the inner cavity of an aluminium planchette (size=3.0×0.5 mm, inner cavity=2.0×0.15 mm). The vacant space in the cavity was filled with hexadecene and it was capped with the flat side of another aluminium planchette.HPF was carried out using a Bal-Tec HPM 010 high pressure freezing machine. Subsequently, the sandwich was transferred into a Bal-Tech BAF 060 freeze fracture system where it was opened with a pre-cooled razorblade and solvent was allowed to sublime (−105° C., 60 min). Subsequently, it was coated with Ta/W or Pt employing double axis rotary shadowing (DARS). Images were taken in a Zeiss Ultra 55 cryogenic scanning electron microscope operated at 2-5 kV with an aperture size set to 10 μm, utilizing in-lens secondary or backscattered electrons detectors. Importantly, as the preparation of the cryo-SEM samples may slighty affect the supramolecular network (enlargement of the pores due to ice crystals formation), we employed the cryogenic methodology based on HPF that is designed to minimize ice formation.

Example 1

Synthesis of 1,2-bis(N,N'-bis(1-ethylpropyl)-3,4,9,10-tetracarboxylic diimide-7-(polyethylene glygol)-perylen-1-yl)ethyne (Compound III)

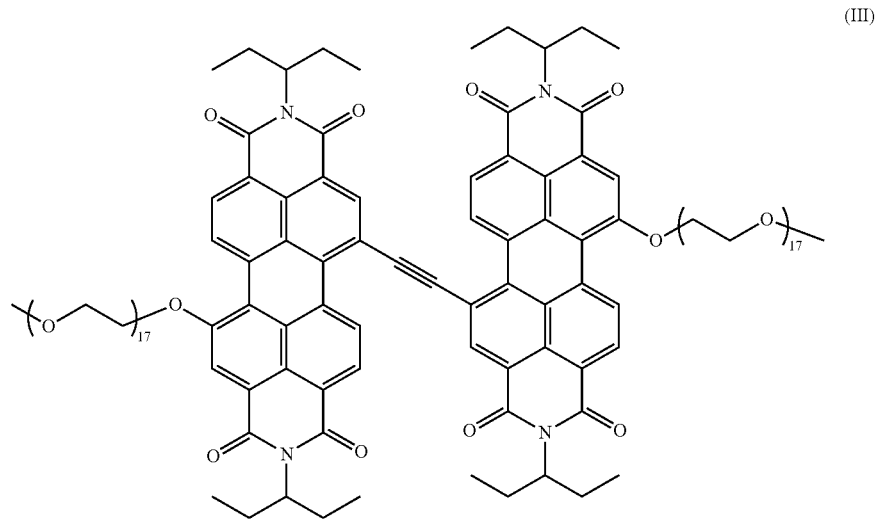

(III)

A mixture of PEG-PDI-Br (50 mg, 0.036 mmol) and Bis-(tributylstannyl)acetylene (11 mg, 0.018 mmol) was dissolved in toluene (1 ml) and stirred for 10 min. Di-Palladium-tri-Dibenzylideneacetone (1.65 mg, 1.8 μmol) and tri-(t-Butyl)phosphine (0.727 mg, 3.6 μmol) were dissolved in toluene (1 ml) and stirred for 10 min in a separate vial. Then the mixtures were combined and stirred at r.t. for 6 h. accompanied by color change from red to deep purple. Then the reaction mixture was washed with brine and purified by column chromatography (silica 60-200 micron, eluted with acetone/methanol (1:1)) to afford 43 mg of Compound III (Perylene diimide III) as a dark purple solid. Yield 90%.

GPC showed polydispersity of 1.06. $^1$H NMR (CDCl3): δ=10.12 (d, 2H, $J_{HH}$=8.4, perylene-H), 9.76 (d, 2H, $J_{HH}$=8.4 Hz, perylene-H), 8.97 (s, 2H, perylene-H), 8.72 (d, 2H, perylene-H), 8.54 (d, 2H, JHH=8.0 Hz, perylene-H), 8.52 (s, 2H, perylene-H), 5.07 (m, 4H, N(CH(CH2CH3)2), 4.69 (m, 4H, PEG), 4.13 (m, 4H, PEG), 3.88 (m, 4H, PEG), 3.80 (m, 4H, PEG), 3.64 (bs, 88H, PEG), 3.37 (m, 6H, PEG-OCH3), 2.27 (m, 8H, N(CH(CH2CH3)2), 1.93 (m, 8H, N(CH(CH2CH3)2), 0.93 (m, 24H, N(CH(CH2CH3)2). $^{13}$C NMR (CDCl3): 157.6, 135.62, 133.39, 129.21, 128.92, 128.4, 128.16, 127.62, 124.09, 120.8, 117.81, 97.69 (PDI-C≡C-PDI), 71.93, 71.08, 70.87, 70.74, 70.57, 69.48, 69.42, 59.04, 57.71, 25.02, 11.39, 11.35.

MS-MALDI-TOF calcd for C140H198N4O44:2639.34. found 2639 [M+]. UV/vis (CHCl$_3$): λmax/nm (ε/M−1 cm-1)=412.4 (12704), 461.25 (13798), 537.9 (29425), 573.5 (28482), Fluorescence: λmax=693 nm, quantum yield φf=0.06.

Example 2

Synthesis of Diethynylbenzene-Bridged Perylene Dimmers (Compound IV)

2 eq. of PEG-PDIBr (obtained in a reaction of equimolar amounts of 1,7-PDIBr$_2$, PEGOH and NaH in THF, purified by SiO$_2$ column, yield 79%) was mixed with 1 eq. of diethynyl benzene in diisopropyl amine at room temperature overnight in the presence of Pd catalyst. The product was separated using column chromatography (SiO$_2$, chloroform/MeOH as an eluent). Yield 90%.

Example 3

Synthesis of 5,5'-Bis(1-PEG-PDI-7-ethynyl)-2,2'-bipyridine (Compound V; having PEG17)

Synthesis of 5,5'-dibromo-2,2'-bipyridine (3)

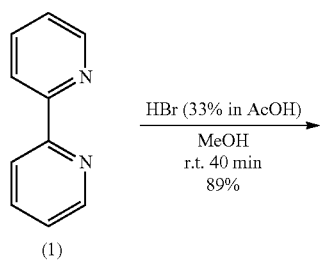

(1)

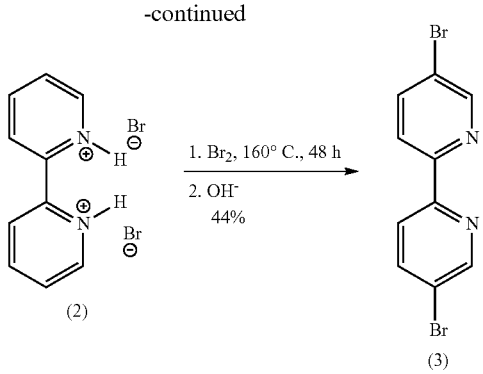

(2)

(3)

A solution of HBr in acetic acid (5 ml, 33 wt %) was added dropwise to a solution of 1 (0.992 g, 6.35 mmol) in MeOH (2 ml). The instantly forming precipitate was filtered and dried to yield 1.80 g (5.66 mmol, 89%) of 2 as a crude salt. Subsequently, a mixture of 2 (0.975 g, 3.07 mmol) and bromine (981 mg, 6.14 mmol) was heated in a pressure flask to 160° C. for 48 hours with stirring. The reaction was stopped and the hard solid was powdered using mortar and pestle. In order to remove unreacted bromine, a concentrated aqueous solution of Na$_2$S$_2$O$_3$ (60 ml) was added to the brown powder and the mixture was stirred for 10 minutes. Subsequently, it was treated with 1 N NaOH (10 ml) and the product was extracted with CH$_2$Cl$_2$ (6×40 ml). The combined organic phases were concentrated under reduced pressure. This lead to partial precipitation of 3 together with unreacted 1. The precipitate was filtered and the two compounds were separated by flash column chromatography on silica gel, using CH$_2$Cl$_2$ as an eluent. The mother liquor contained 3, mono-brominated bipyridine, and other products of bromination. 3 was separated from the side products by silica flash column chromatography of the mother liquor using CH$_2$Cl$_2$ as an eluent. A total amount of 420 mg (1.34 mmol, 44%) of pure 3 as a white solid was obtained. $^1$H NMR (CDCl$_3$, 250 MHz): δ=8.70 (dd, 2H, $J_{HH}$=0.6 Hz, 2.4 Hz), 8.28 (dd, 2H, $J_{HH}$=0.6 Hz, 8.5 Hz), 7.93 (dd, 2H, $H_{HH}$=2.3 Hz, 8.5 Hz).

Synthesis of 5,5'-Bis((trimethylsilyl)ethynyl)-2,2'-bipyridine (4)

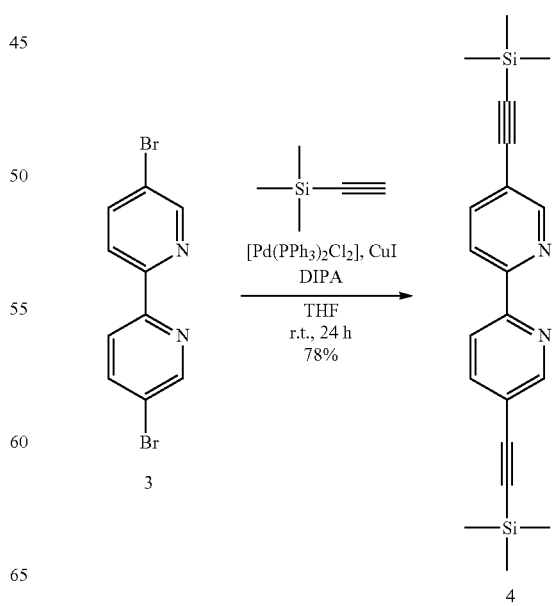

3

4

Under dry nitrogen atmosphere, successively trimethylsilyl-acetylene (619 mg, 6.30 mmol), [Pd(PPh$_3$)$_2$Cl$_2$] (112 mg, 159 µmol), CuI (54.5 mg, 286 µmol) and DIPA (4 ml) were added to a stirred suspension of 3 (500 mg, 1.59 mmol) in 30 ml THF. While the mixture was stirred for 24 hours at room temperature, its color turned black. It was stirred together with activated carbon for 20 minutes and filtered over celite. Then the solvent was removed under reduced pressure, the residue was resuspended in hexane, sonicated for 15 minutes and filtered over celite again yielding an orange solution. The solvent was removed under reduced pressure and the residue was purified by flash column chromatography on silica (eluent: CH$_2$Cl$_2$) to yield 430 mg (1.23 mmol, 78%) of pure 4 as an off-white solid. $^1$H NMR (CDCl$_3$, 250 MHz): δ=8.71 (s, 2H, bpy-H), 8.33 (d, 2H, $J_{HH}$=8.3 Hz, bpy-H), 7.85 (d, 2H, $J_{HH}$=7.8 Hz, bpy-H), 0.27 (s, 18H, Si(CH$_3$)$_3$).

Synthesis of 5,5'-diethynyl-2,2'-bipyridine (5)

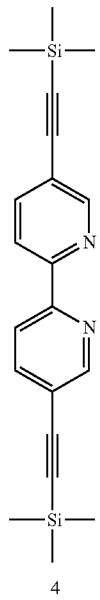

4

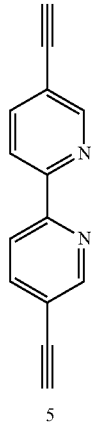

5

4 (390 mg, 1.12 mmol) was dissolved in a mixture of 40 ml MeOH and 10 ml THF; then KF powder (400 mg, 6.88 mmol) was added and the solution was stirred at room temperature overnight. Subsequently, the solvents were removed under reduced pressure. The residue was redissolved in 200 ml CH$_2$Cl$_2$ and washed four times with 100 ml H$_2$O each, in order to remove inorganic salts. The organic phase was dried over Na$_2$SO$_4$, concentrated under reduced pressure and purified by silica flash column chromatography (eluent: CH$_2$Cl$_2$) to yield a colorless powder of 204 mg (1.0 mmol, 81%) pure 5. $^1$H NMR (CDCl$_3$, 250 MHz): δ=8.76 (d, 2H, $J_{HH}$=1.0 Hz, bpy-H), 8.39 (d, 2H, $J_{HH}$=6.0 Hz, bpy-H), 7.90 (dd, 2H, $J_{HH}$=1.1 Hz, 5.1 Hz, bpy-H), 3.31 (s, 2H, bpy-CCH).

Synthesis of 1-Br-7-PEG-N,N'-Bis(ethylpropyl) perylene-3,4:9,10-tetracarboxylic diimide (7)

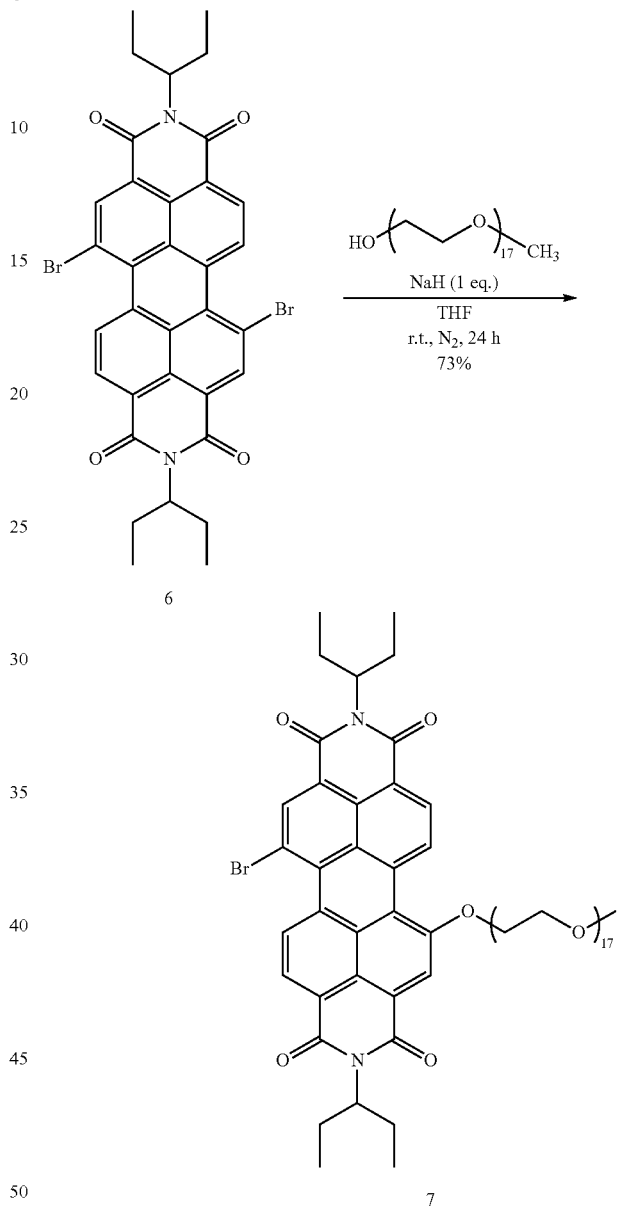

Under dry nitrogen atmosphere, 6 (255.7 mg, 372.7 µmol) was dissolved in 30 ml THF in a 100 ml round bottom flask equipped with a magnetic stirrer. Subsequently, dry PEG17 HO (CH$_2$CH$_2$O)$_{17}$CH$_3$, 371.2 mg, 485 µmol) was added to the stirring solution, followed by NaH (60 wt %, 20 mg, 500 µmol). Instantly, the color turned darker and after a short time a dark red precipitate formed. The reaction was stopped after 24 hours and the solvent was evaporated under reduced pressure. In order to remove inorganic salts and an excess of PEG, the mixture was treated with 30 ml of water, a few drops of HCl (1N), and 7 was extracted with CH$_2$Cl$_2$ (3×30 ml). The combined organic extracts were washed with brine (3×30 ml). The solvent was removed under reduced pressure and the resulting dark purple solid was purified by silica gel flash column chromatography. Initially, CHCl$_3$ was used as an eluent, followed by CHCl$_3$/methanol mixtures with a content of methanol rising gradually from 1 to 6 percent. The second band collected contained a red solid yielding 370 mg (269 μmol, 73%) of pure 7. $^1$H NMR (CDCl$_3$, 250 MHz): δ=9.58 (d, 2H, J$_{HH}$=8.3 Hz, perylene-H), 8.91 (s, 1H, perylene-H), 8.65 (d, 1H, J$_{HH}$=8.5 Hz, perylene-H), 8.57 (d, 1H, J$_{HH}$=8.0, perylene-H), 8.45 (s, 1H, perylene-H), 5.05 (m, 2H, N(CH(CH$_2$CH$_3$)$_2$). 4.63 (m, 2H, PEG), 4.07 (m, 2H, PEG), 3.82 (m, 2H, PEG), 3.78 (m, 2H, PEG) 3.70-3.50 (m, 56H, PEG), 3.37 (s, 3H, PEG-OCH$_3$), 2.24 (m, 4H, N(CH(CH$_2$CH$_3$)$_2$), 1.92 (m, 4H, N(CH(CH$_2$CH$_3$)$_2$), 0.90 (m, 12H, N(CH(CH$_2$CH$_3$)$_2$).

Synthesis of 5,5'-Bis(1-PEG-PDI-7-ethynyl)-2,2'-bipyridine (Compound V)

A modified Sonogashira cross-coupling reaction was carried out under nitrogen atmosphere. In contrast to typical Sonogashira reactions, no copper iodide was used as a co-catalyst, in order to prevent coordination of the bpy units to copper ions. To a stirred solution of 7 (315.3 mg, 227 μmol) in 50 ml of dry toluene was added successively a mixture of allyl palladium chloride (6.76 mg, 17.2 μmol) and tris(tert-butyl)phosphine (6.93 mg, 34.3 μmol) in 5 ml toluene, 5,5'-diethynyl-2,2'-bipyridine 5 (20.7 mg, 101 μmol), and 20 ml of DIPA. After stirring for 24 hours at room temperature, the solvents were evaporated and the crude product was dried in high vacuum for several hours. It was purified using silica gel flash column chromatography with CHCl$_3$/MeOH mixtures as an eluent, starting from pure

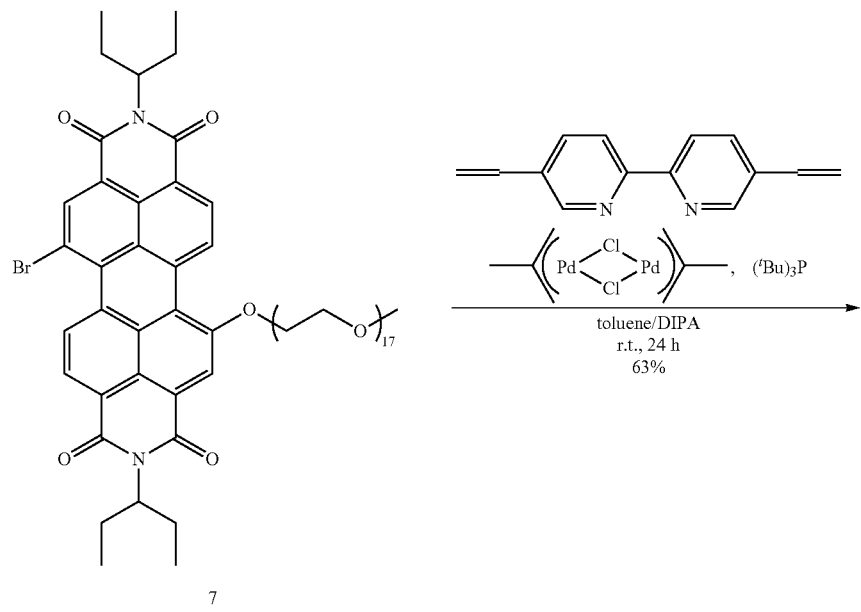

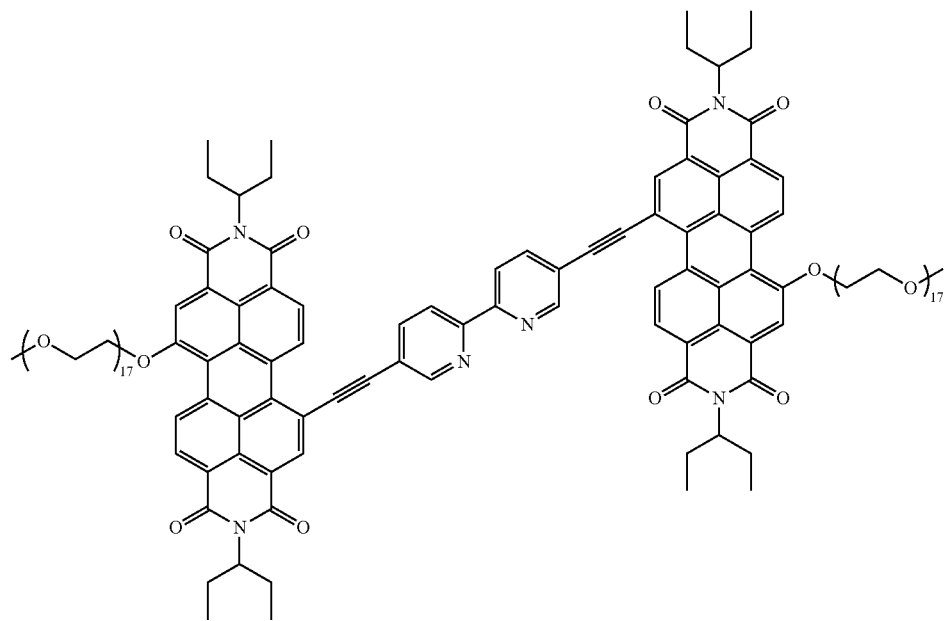

Compound V (Perylene diimide V)

CHCl₃, and subsequently raising the MeOH content to 6%. A red solid was obtained from the second band, yielding 179.2 mg (64 µmol, 63%) of pure Compound V.

$^1$H NMR (CDCl₃, 500 MHz): δ=10.08 (d, 2H, $J_{HH}$=8.5 Hz, perylene-H), 9.73 (d, 2H, $J_{HH}$=8.5 Hz, perylene-H), 8.97 (s, 2H, bpy-H), 8.94 (s, 2H, perylene-H), 8.68 (dd, 4H, $J_{HH}$=8.5 Hz, 8.0 Hz, perylene-H, bpy-H), 8.62 (d, 2H, $J_{HH}$=8.0 Hz, perylene-H), 8.51 (s, 2H, perylene-H), 8.10 (d, 2H, $J_{HH}$=8.0 Hz, bpy-H), 5.09 (m, 4H, N(CH(CH₂CH₃)₂), 4.67 (m, 4H, PEG), 4.11 (m, 4H, PEG), 3.50-3.75 (m, 120H, PEG), 3.37 (s, 6H, PEG-OCH₃), 2.29 (m, 8H, N(CH(CH₂CH₃)₂), 1.96 (m, 8H, N(CH(CH₂CH₃)₂), 0.94 (m, 24H, N(CH(CH₂CH₃)₂). $^{13}$C {$^1$H} NMR (CDCl₃, 125 MHz): δ=164 (br., carbonyl), 157.65, 154.88, 152.05, 139.64, 137.57 (br.) 135.47, 134.34, 133.73, 132.11 (br. s), 129.30, 129.17, 128.5 (br.), 128.41, 128.22, 124.4 (br.), 124.21, 123.6 (br.), 122.1 (br.), 121.29, 121.01, 120.12, 118.24, 95.64 (ethynyl), 93.70 (ethynyl), 72.09 (PEG), 71.23 (PEG), 71.02-70.05 (PEG), 69.63 (PEG), 69.56 (PEG), 59.20 (PEG-O—CH₃), 57.98, 57.83 (N(CH(CH₂CH₃)₂), 25.20 (N(CH(CH₂CH₃)₂), 11.51 (N(CH(CH₂CH₃)₂).

MALDI-TOF-MS m/z calc. for $C_{148}H_{196}N_6O_{42}$: 1730.3. found: 1754.7 [M+Na⁺]. UV/Vis (CHCl₃):$\lambda_{max}$/nm (ϵ/M$^{-1}$ cm$^{-1}$) 577.8 (42,700), 539.3 (33,400), 386.4 (39800). Fluorescence (CHCl3): $\lambda_{max}$/nm: 604.0, fluorescence quantum yield, $\phi_f$) 0.58. GPC: Polydispersity 1.15, molecular weight≈3000 Da. Redox potentials (E vs. SCE): +1.49 V (M⁺+e⁻⇌M), −0.68 V (M+e⁻⇌M⁻), −0.88 V (M⁻+e⁻⇌M²⁻).

The large and rigid aromatic core of Compounds III-V containing PDI, bipyridyl, and acetylene moieties, is highly hydrophobic, whereas the two PEG tails are hydrophilic. This amphiphilicity allows a bottom-up approach for the design of supramolecular structures. The hydrophobic moieties guarantee aggregation driven by π-π interactions and the hydrophobic effect, whereas the hydrophilic PEG tails are dissolved well in aqueous medium preventing precipitation.

Example 4A

Synthesis of Gold/MPA Nanoparticles (Au1-4)

Mercaptopropionic acid (MPA)—stabilized gold nanoparticles of different sizes were prepared according to a modified literature procedure [T. Yonezawa, T. Kunitake, Practical preparation of anionic mercapto ligand-stabilized gold nanoparticles and their immobilization. Colloids Surf, A149, 193 (1999)] which is incorporated herein by reference.

Round bottom flasks and magnetic stirrers were washed carefully with aqua regia, Piranha (H₂SO₄/H₂O₂, 7:1), and double distilled water (Nanopure system). MPA-Na was prepared by neutralizing MPA with NaOH.

A solution of HAuCl₄·3H₂O (57 mg, 0.145 mmol) in 25 ml water was added to 250 ml of refluxing water. Then 25 ml of a mixed solution of MPA-Na (see Table 1) and trisodium citrate 2H₂O (500 mg, 1.70 mmol) was added rapidly. The solutions were refluxed for 6 hours. For separation from the excess of salts, the dispersions were treated with HCl (2M) until aggregated particles precipitated. The precipitate was removed from the mother liquor by centrifugation. Then it was re-dispersed by adding 250 ml of water and adjusting the pH to 9 using NaOH (1M).

TABLE 1

MPA-Na used for synthesis of Au1-4.

| | Au1 | Au2 | Au3 | Au4 |
|---|---|---|---|---|
| MPA-Na (mmol) | 0.435 | 0.145 | 0.073 | 0.015 |
| Average particle diameter (nm) | 1.6 ± 0.6 | 2.8 ± 1.5 | 7.1 ± 5.9 | 17.5 ± 3.9 |

Example 4B

Synthesis of Gold/Citrate Nanoparticles (Au5)

Au5 was synthesized according to a literature procedure [R. Kaminker et al., Molecular Structure-Function Relations of the Optical Properties and Dimensions of Gold Nanoparticle Assemblies. Angew. Chem. Int. Ed. 49, 1218 (2010)] that employs a modified Turkevich method [J. Kimling et al., Turkevich Method for Gold Nanoparticle Synthesis Revisited. J. Phys. Chem. B110, 15700 (2006); J. Turkevich, P. C. Stevenson, J. Hillier, A study of the nucleation and growth processes in the synthesis of colloidal gold. Discuss. Faraday Soc. 11, 55 (1951)] which are incorporated herein by reference.

Example 4C

Synthesis of Gold/CTAB Polydisperse Nanoparticles (Au6) and Nanorods (Au7)

Au6 was formed in water by addition of NaBH₄ (55 µl, 0.25 µM) into a growth solution containing previously recrystallized cetryl trimethyl ammonium bromide (CTAB) (10 ml, 0.2 M), HAuCl₄ (200 µl, 1 mM), AgNO₃ (40 µl, 0.2 mM) and ascorbic acid (400 µl, 2 mM). The color of the solution turned blue within a few minutes. The mixture was kept at r.t. overnight. The particles were purified by repetitive (3×) centrifugation and redispersion in water.

Au7 was synthesized according to the seed mediated procedure reported by Murphy et al. B. D. Busbee, S. O. Obare, C. J. Murphy, An Improved Synthesis of High-Aspect-Ratio Gold Nanorods. Adv. Mater. 15, 414 (2003); which is incorporated herein by reference.

Example 5

Synthesis of Gold/PEG-SH Nanoparticles (Au8)

PEG-SH stabilized nanoparticles were prepared using a modified Brust-Schiffrin method [M. Brust, M. Walker, D. Bethell, D. J. Schiffrin, R. Whyman, Synthesis of thiol-derivatised gold nanoparticles in a two-phase Liquid-Liquid system. J. Chem. Soc., Chem. Commun., 801 (1994); and W. P. Wuelfing, S. M. Gross, D. T. Miles, R. W. Murray, Nanometer Gold Clusters Protected by Surface-Bound Monolayers of Thiolated Poly(ethylene glycol) Polymer Electrolyte. J Am. Chem. Soc. 120, 12696 (1998)] which are incorporated herein by reference. In the glovebox, tetraoctylammonium bromide (TOAB, 23 mg, 42 µmol) in toluene (6 ml) was added to HAuCl₄·3H₂O (10 mg, 25 µmol) in water (3 ml) and the mixture was stirred for 30 minutes transferring Au(III) ions to the organic phase. The aqueous phase was removed, then PEG-SH (2.0 mg, 2.4 µmol) in toluene (100 µl) was added and the mixture was taken out of the glove box. To this solution, a freshly prepared solution of NaBH₄ (11.2 mg, 0.30 mmol) in H₂O (3 ml) was added under vigorous stirring over a period of 15 seconds. During that time the organic phase became brown and within 1 min this color was transferred to the aqueous phase. The mixture was stirred for 90 minutes. Subsequently, the two phases were separated, dichloromethane (DCM) (6 ml) was added to the aqueous phase, and the nanoparticles were salted out into the organic phase with a minimal amount of NaCl. The organic phase was dried in high vacuum. Then acetonitrile (3 ml) was added to re-dissolve the nanoparticles, leaving behind a small amount of white precipitate. The solution was filtered over a 0.2 µm cellulose acetate (CA) filter and dried in high vacuum, yielding 5.5 mg nanoparticles, which were dissolved in water (20 ml). The nanoparticles were protected from light and aged for 6 months at room temperature prior to use.

Example 6

Synthesis of CdTe/MPA Quantum Dots (QD1, QD2)

Quantum dots QD1 and QD2 were synthesized according to a literature procedure [H. Zhang, Z. Zhou, B. Yang, M. Gao, The Influence of Carboxyl Groups on the Photoluminescence of Mercaptocarboxylic Acid-Stabilized CdTe Nanoparticles. *J. Phys. Chem. B* 107, 8 (2003)] which is incorporated herein by reference. The synthesis was carried out under argon atmosphere. Briefly, a solution of $CdCl_2 \cdot H_2O$ (114.5 mg, 1.25 mM) and MPA (105 µl, 3.0 mM) in water (400 ml) was adjusted to pH 9 using NaOH (1 M). Subsequently, a freshly prepared solution of NaHTe (250 µl, 1 M) (14) was added and the mixture was refluxed. QD2 was obtained after 240 min and QD1 was obtained after 24 h reaction time. The particles were purified as described in the literature Zhang et al. *J. Phys. Chem. B* 107, 8 (2003).

Example 7

Self-Assembly of Compound V (Having PEG17)

Figure 28:
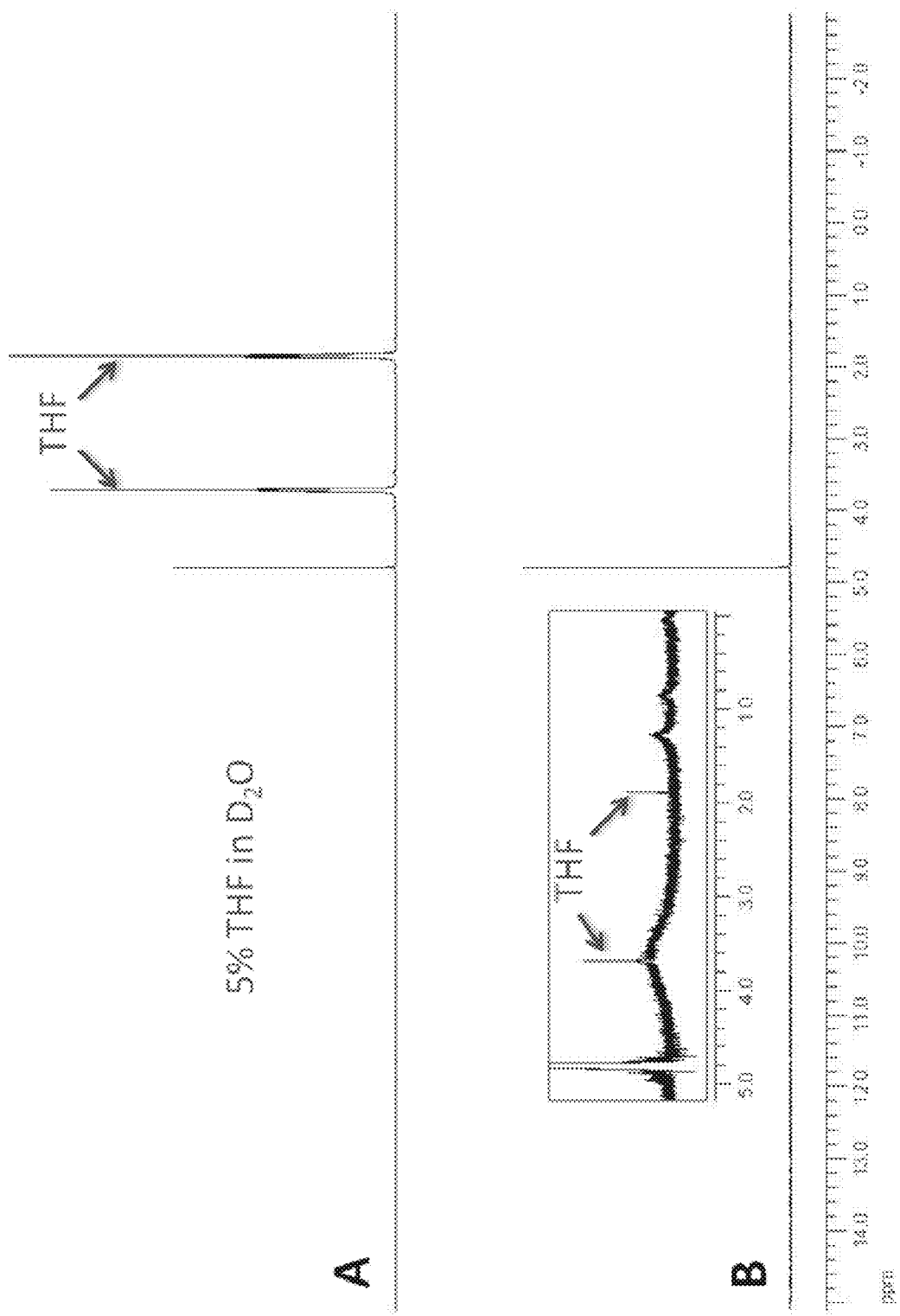
FIG. 28(A)-(B) depicts $^1$H-NMR spectra of Perylene diimide V supramolecular solution ($5 \cdot 10^{-4}$ M) (A) before and (B) after removal of THF. Inset: Only traces (≤0.01%) of THF are detectable after the removal procedure. Perylene diimide V peaks are strongly broadened and poorly visible due to aggregation.

In a typical experiment, Compound V (100 mg, ~36 µmol) was first dissolved in THF (3.6 ml). Then water was added in portions (3×22.5 ml), each addition was followed by vigorous mixing of the solution and sonication for 5 minutes. After adding the last portion, the mixture contained 5% THF and 95% water at a Compound V concentration of $5 \cdot 10^{-4}$ M. It was sonicated for 20 min. Subsequently, THF was removed by evaporating ~40 vol % of the solution at room temperature in the high vacuum and the reduced volume was refilled with water. Removal of THF was confirmed by $^1$H NMR spectroscopy of a $THF/D_2O$ solution of Compound V after applying this procedure (FIG. 28A-B). The aggregated solution of Compound V in water was aged for one day and used as a stock solution for preparation of supramolecular filtration membranes.

Example 8

Preparation of Supramolecular Filtration Membranes

In a typical experiment, 0.5 ml of self-assembled Compound V (having PEG17) in water ($5 \cdot 10^{-4}$ M) was filtered over a syringe filter (Whatman Puradisc FP 30, CA, effective filtration area=5.7 cm$^2$, pore size=0.45 µm). Care was taken to avoid the presence of air bubbles in the chamber, which would affect the formation of a homogeneous layer of supramolecular material. Subsequently, 3 ml rinsing water (containing 0.1 mM nanoparticle capping agent (e.g. MPA) adjusted to the pH of the nanoparticle solution) was filtered over the membrane at a constant trans-membrane pressure of 0.4 bar, in order to stabilize material packing and flow rate. The filter housing was kept filled with aqueous solvent and the supramolecular membrane was used directly for filtration experiments. (FIG. 2)

Figure 11:
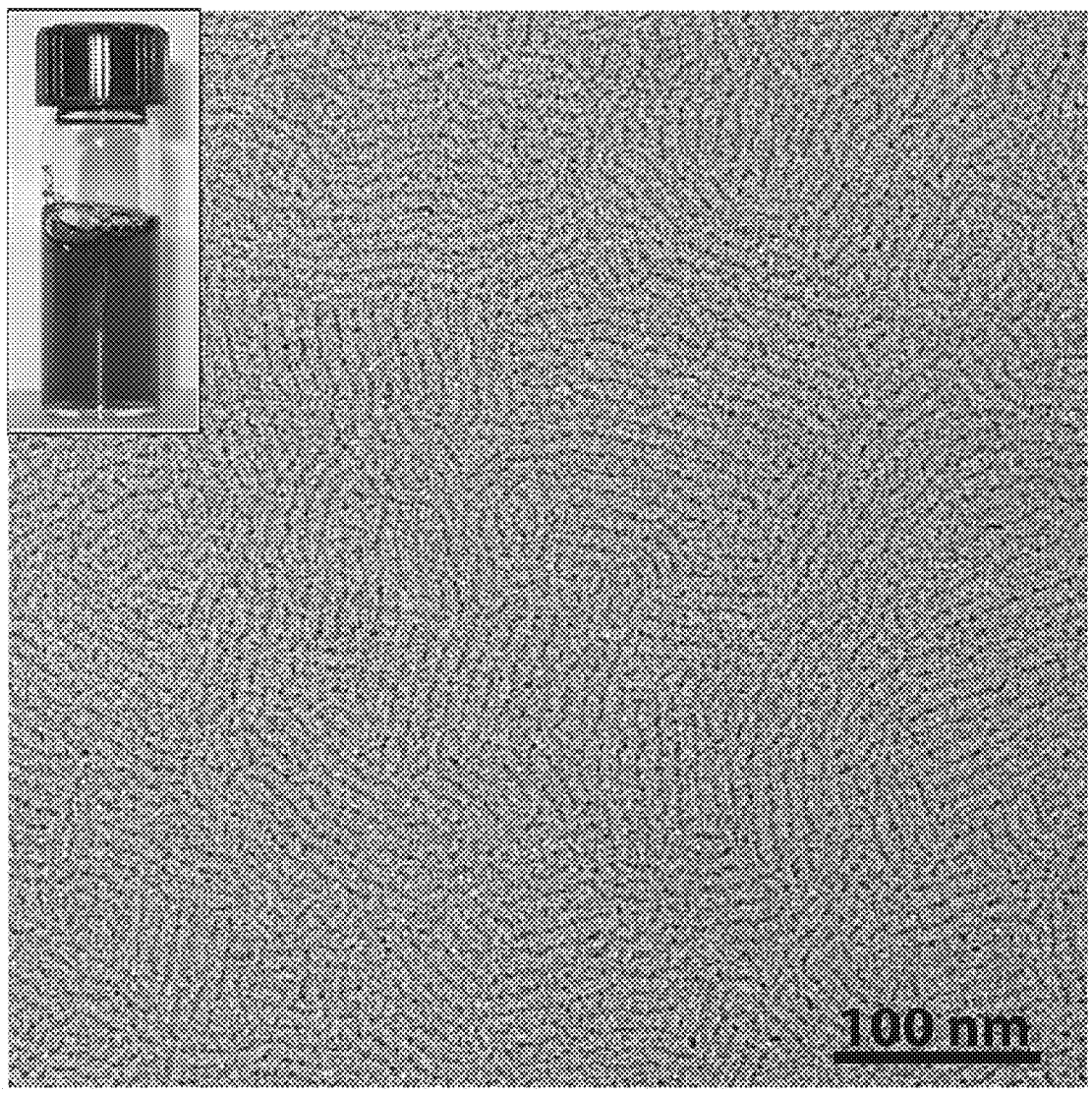
FIG. 11 depicts Cryo-TEM image of the solution of Perylene diimide V ($10^{-4}$ M) in water. Inset: Photograph of the corresponding sample. Perylene diimide V supramolecular fibers in water are composed of an inner core of stacked aromatic units (high contrast), and an outer PEG-shell (low contrast). The inner core is 2.8±0.5 nm wide. The total fiber width (inner core plus PEG-shell) is 8.3±1.1 nm. The fibers are uniform and very similar to previously reported Perylene diimide V in water/THF mixtures.

Cryogenic transmission electron microscopy (cryo-TEM) of the aqueous solution confirms the presence of interacting supramolecular fibers (FIG. 11).

Example 9

Figure 29:
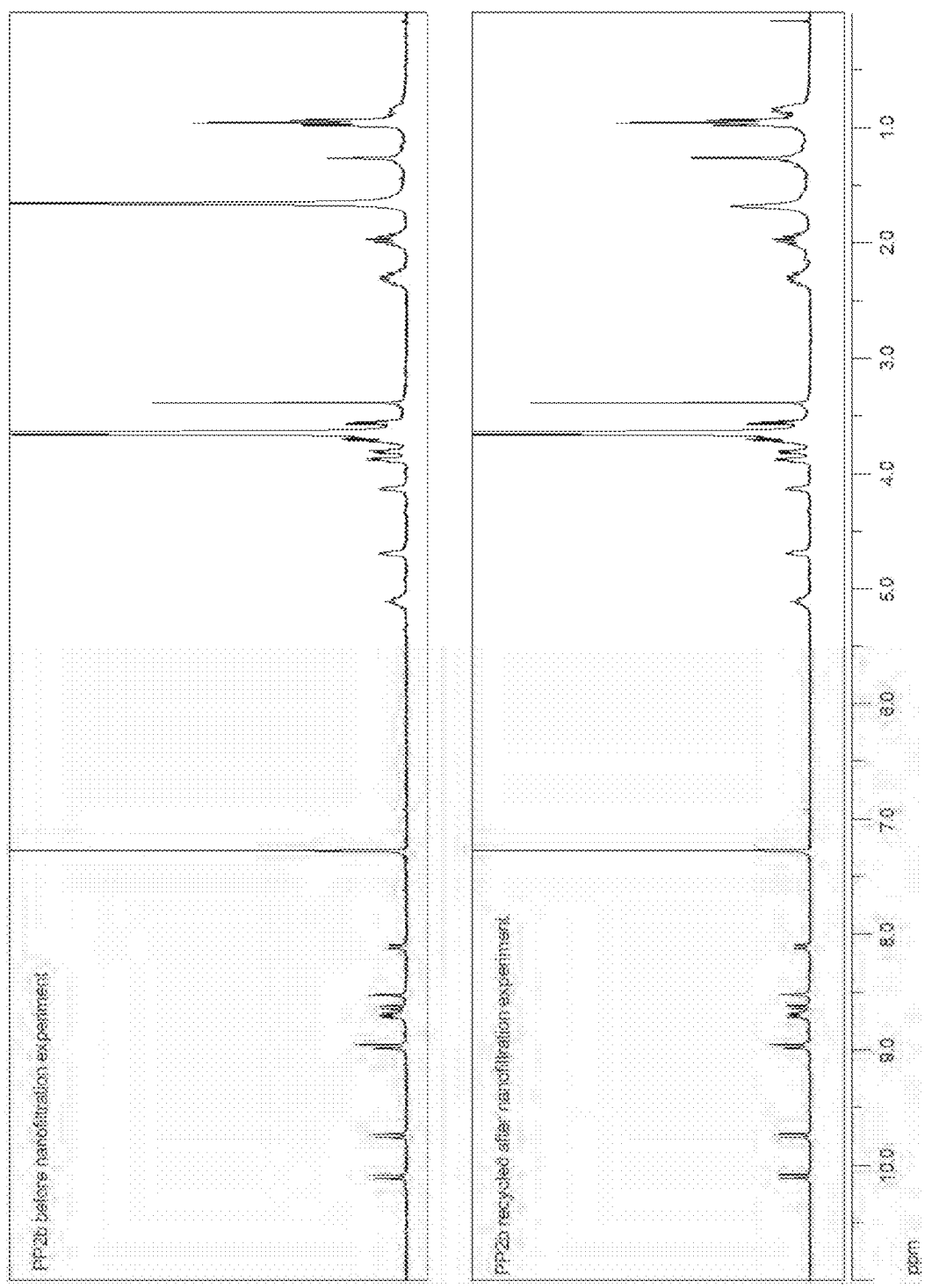
FIG. 29 $^1$H-NMR spectra of Perylene diimide V in CDCl$_3$ before (top) and after recycling (bottom).

Filtration of Particles 3 ml of the nanoparticle solution was filtered over the supramolecular filtration membrane at a constant pressure of 0.4 bar using the setup depicted in FIG. 29. 3 ml of filtrate was collected after the dead volume of 1 ml solution passed through the filter housing. Subsequently, the filter was rinsed with 6 ml water (containing 0.1 mM nanoparticle capping agent at the pH of the nanoparticle solution).

Figure 3:
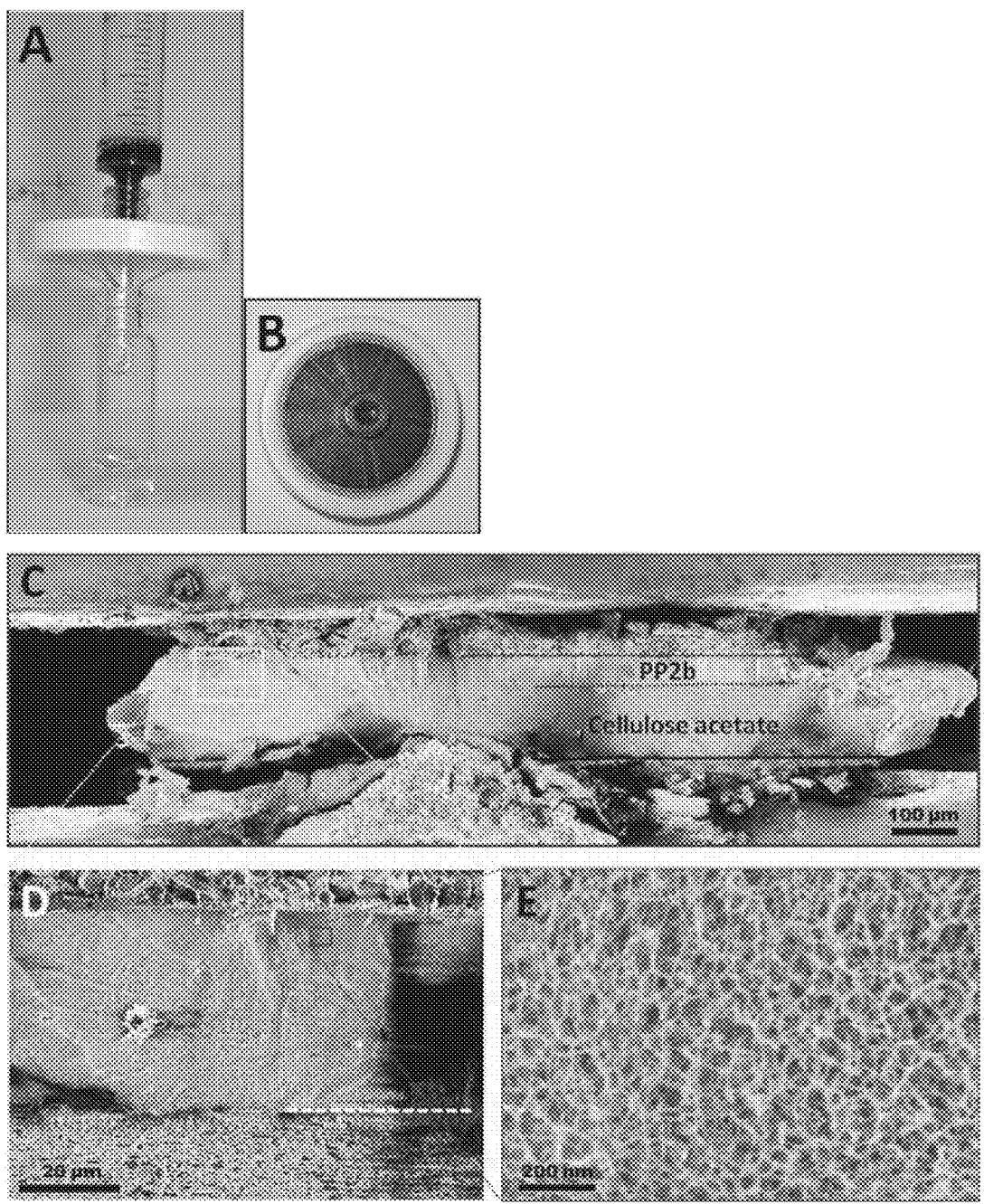
FIG. 3 (A) presents a photograph showing filtration of a supramolecular solution of Perylene diimide V ($5 \cdot 10^{-4}$ M) in water over cellulose acetate (CA) filter (0.45 μm pore size). (B) Photograph of supramolecular material deposited on top of the cellulose acetate (CA) support in the commercial syringe filter. (C) Cryo-SEM image of the cross-section of a ~1×1 mm piece of the supramolecular membrane (0.65 mg Perylene diimide V/cm$^2$) on CA support. (D) Magnified image showing the sharp border between coarse CA and smooth Perylene diimide V layer (dashed line). (E) High magnification image of the supramolecular Perylene diimide V layer.

Filtration of the supramolecular solution over commercial microfiltration syringe filters results in a colorless filtrate and quantitative deposition of Compound V on top of the microfiltration support (FIG. 3A, B). While this simple one-step deposition is feasible using various commercial microfiltration membranes (e.g. cellulose acetate (CA), teflon (PTFE) or polycarbonate; 0.22 or 0.45 µm pore size), in the further experiments, CA was chosen as support membrane, since it is inexpensive and allows high flow rates for water.

A deposited supramolecular layer prepared by filtration of 2.5 ml of aqueous perylene diimide of formula V (Compound V, having PEG17) ($5 \cdot 10^{-4}$ M) over CA (0.45 µm pore size, 5.7 cm$^2$ surface area; 0.65 mg Perylene diimide V/cm$^2$) was investigated using cryogenic scanning electron microscopy (cryo-SEM). Images of the filter cross-section show a homogeneous 45 µm thick layer of the supramolecular material on top of the CA support (FIG. 3C).

A sharp border between the coarse CA and the smooth supramolecular layer suggests that Perylene diimide V (Compound V) fibers do not penetrate notably into the pores of the CA (FIG. 3D). Higher magnifications reveal the three dimensional fibrous network in the supramolecular layer (FIG. 3E). Importantly, the deposited supramolecular system exhibits uniform nanostructured network, with voids that may play a role of nanopores during filtration.

Figure 12:
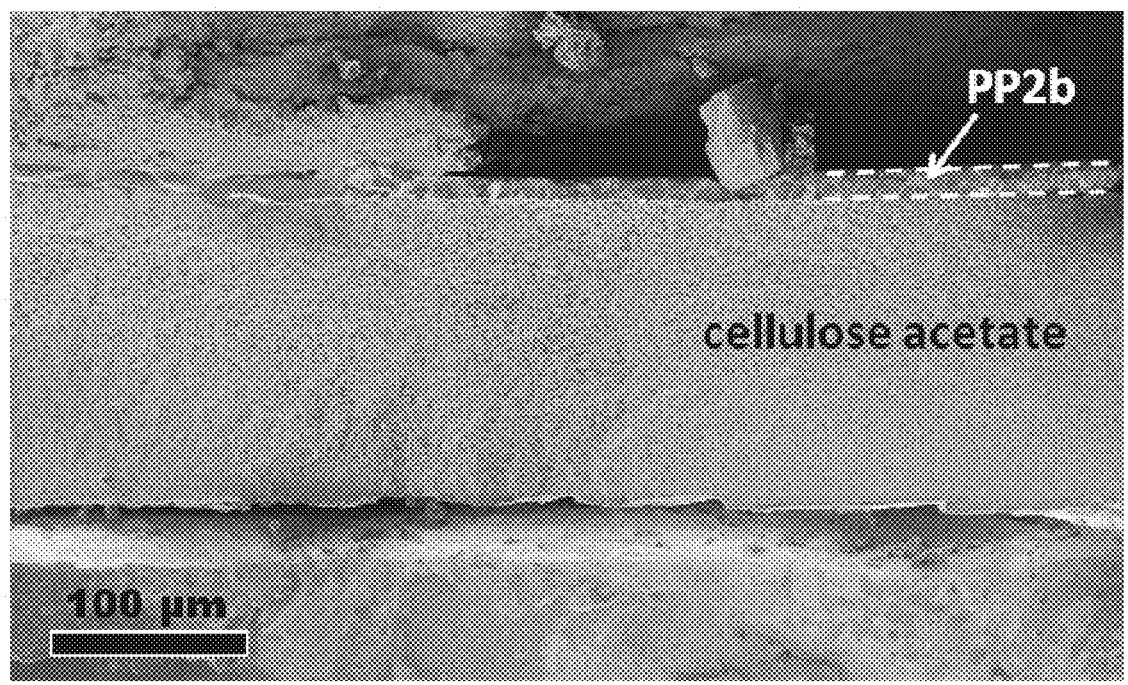
FIG. 12 depicts cryo-SEM image of the cross-section of the supramolecular filtration membrane (0.13 mg Perylene diimide V/cm$^2$) on the CA support.
Figure 13:
FIG. 13(A)-(E) depicts filtration experiment of Au1. (A) Photograph of filtration. (B) Representative TEM image of particles before filtration, and (C) particle size histogram. (D) Representative TEM image of particles in the filtrate, and (E) particle size histogram.
Figure 13:
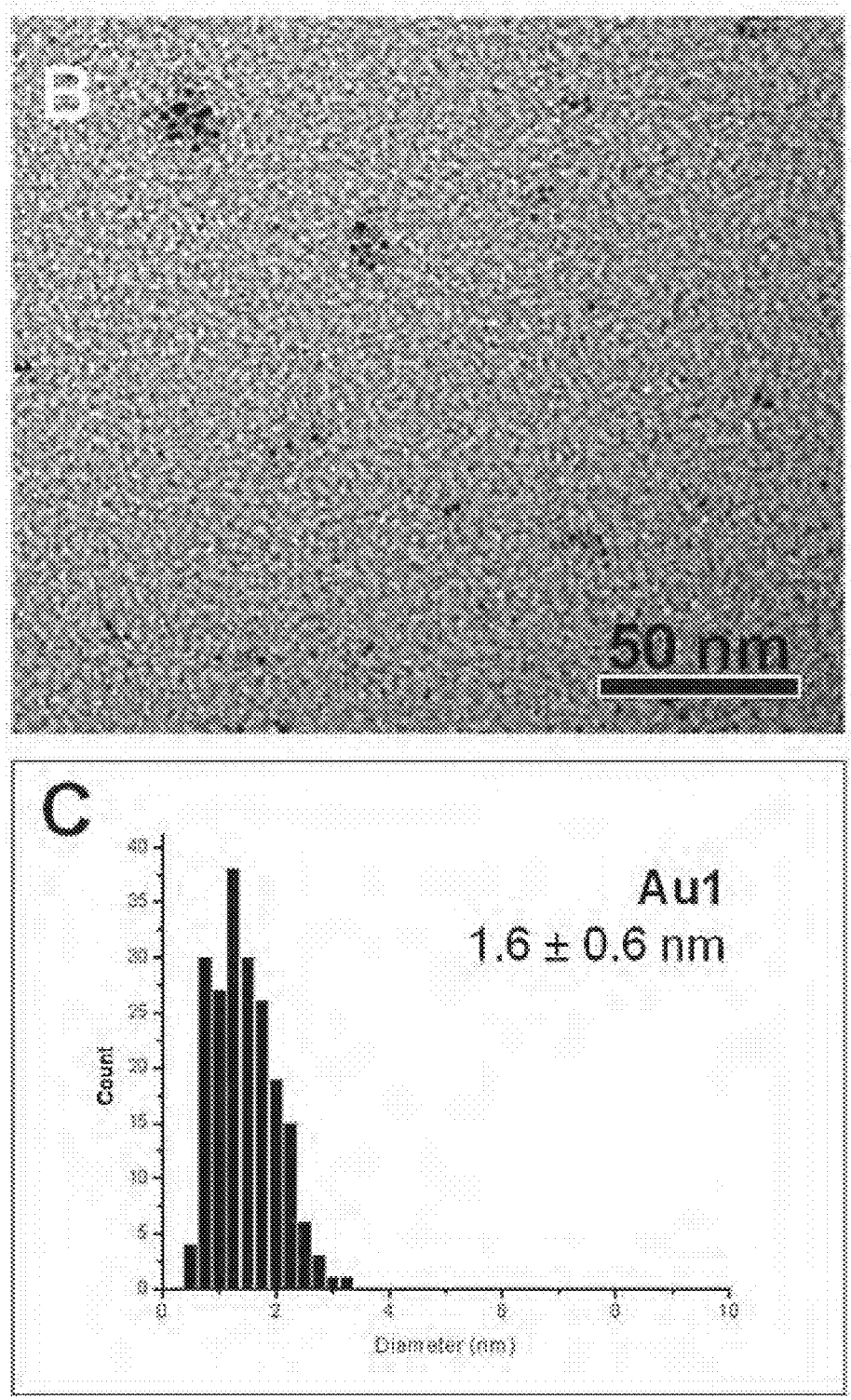
Figure 13:
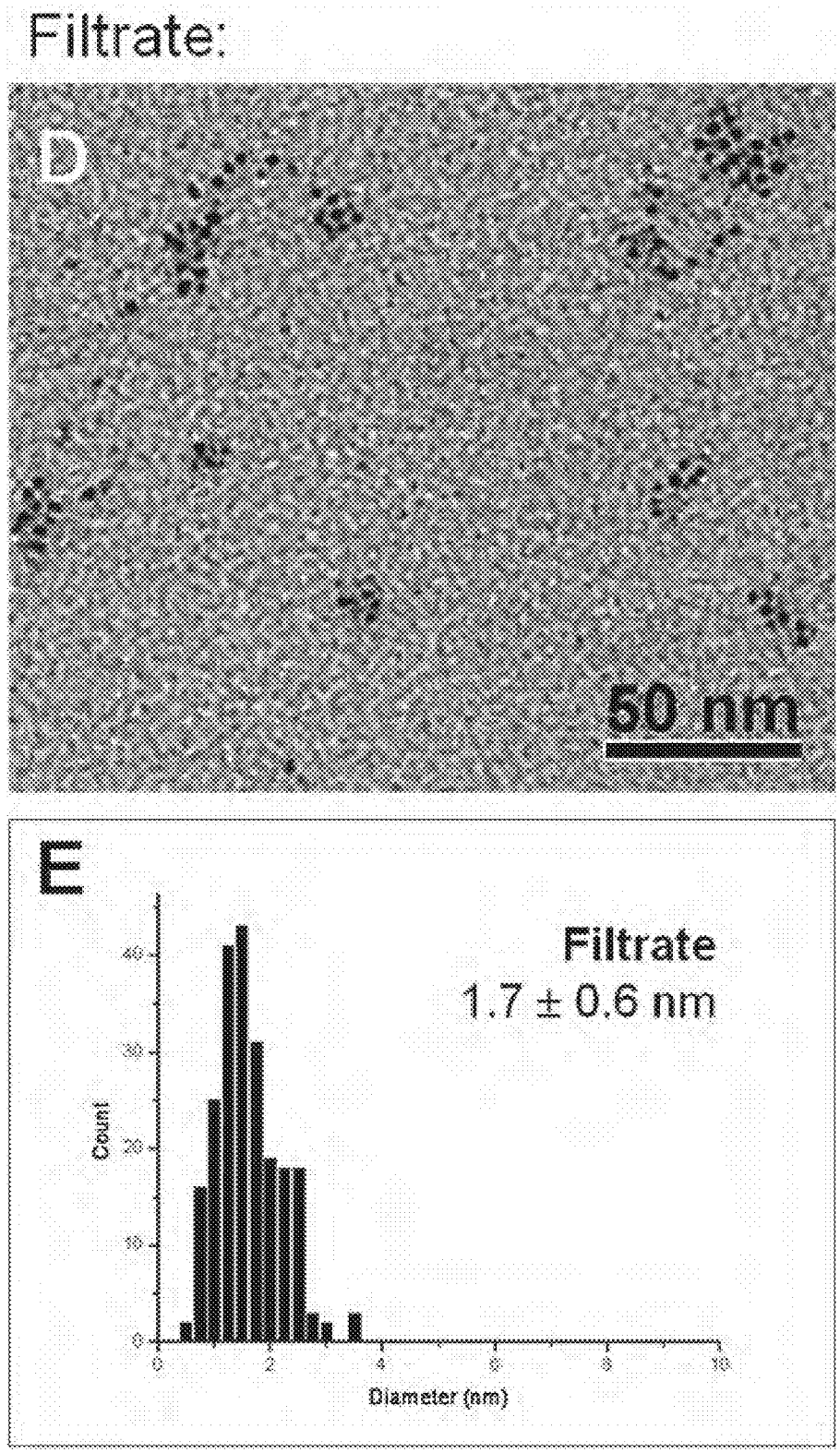
Figure 14:
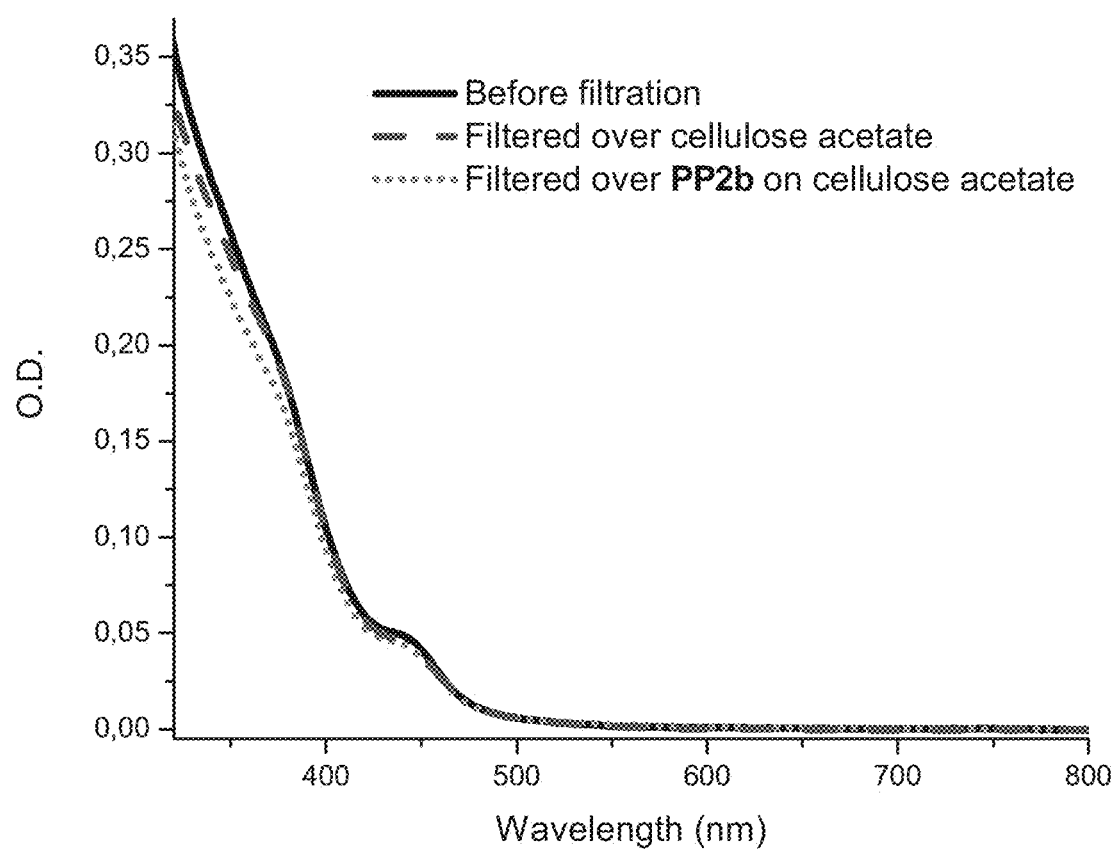
FIG. 14 depicts UV/Vis spectra of a Au1 solution before filtration (solid line), after filtration over CA only (dashed line), and after filtration over the Perylene diimide V membrane (dotted line).
Figure 15:
FIG. 15(A)-(E) Filtration experiment of Au4. (A) Photograph of filtration. (B) Representative TEM image of particles before filtration, and (C) particle size histogram. (D) Representative TEM image of the filtrate. (E) magnified area. Low contrast dark areas in the filtrate are not nanoparticles, but may be excess of organic capping agent (MPA-Mercaptopropionic acid) that passes the membrane).
Figure 15:
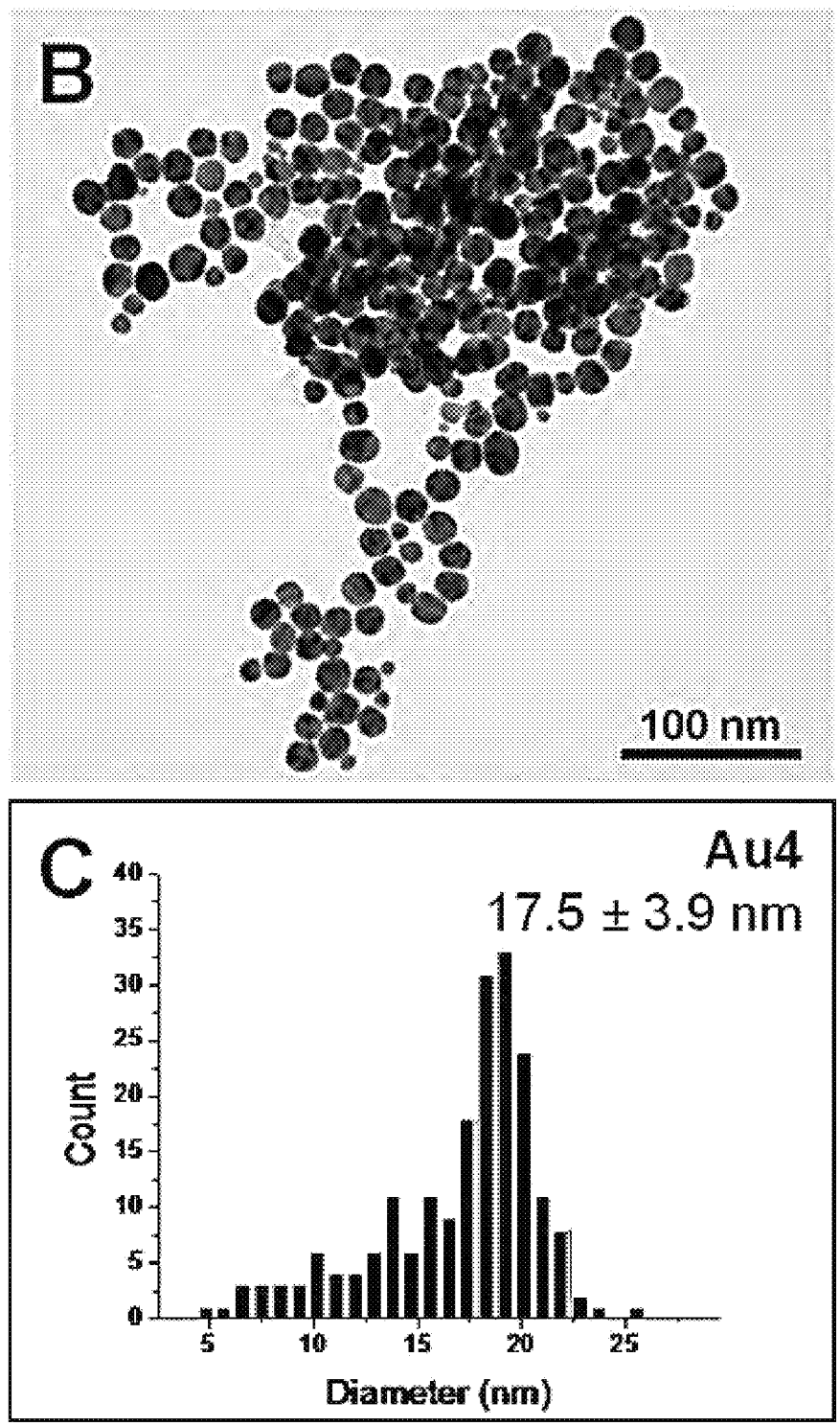
Figure 15:
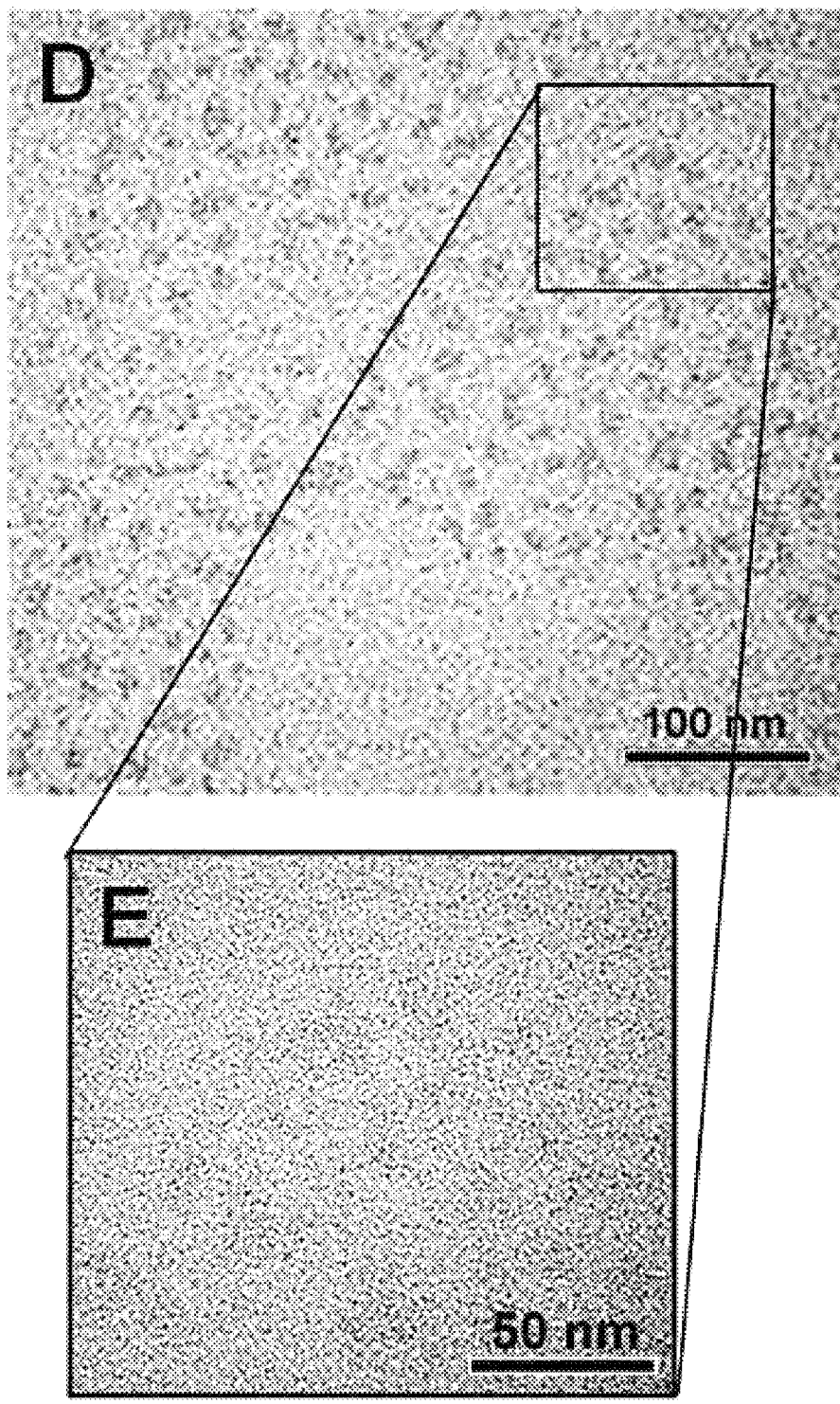
Figure 16:
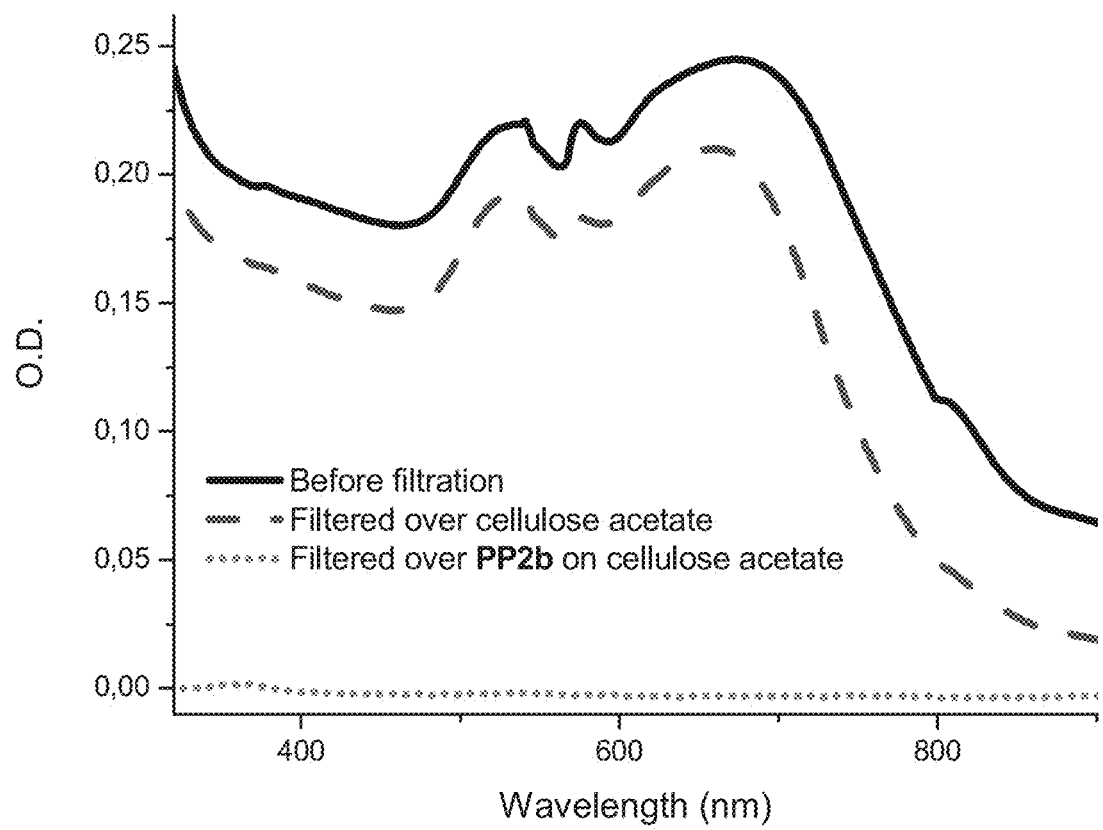
FIG. 16 depicts UV/Vis spectra of a Au4 solution before filtration (solid line), after filtration over CA as a control experiment (dashed line), and after filtration over the Perylene diimide V membrane (dotted line).
Figure 17:
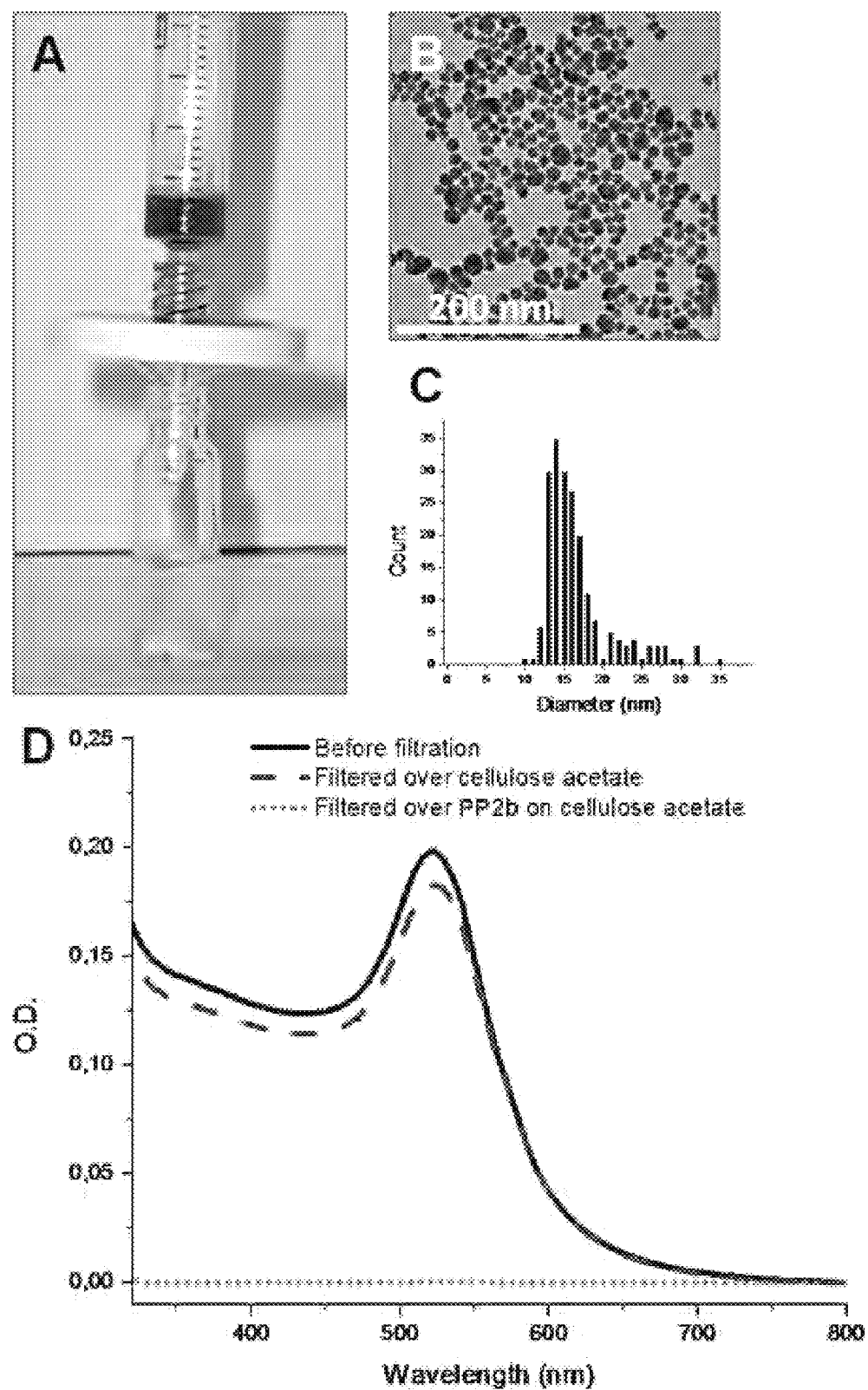
FIG. 17(A)-(D) depicts filtration experiment of Au5. (A) photograph of filtration. (B) Representative TEM image of particles before filtration. (C) corresponding histogram. (D) UV/V is spectra of Au5 solution before filtration (solid line), after filtration over CA as a control experiment (dashed line), and after filtration over the Perylene diimide V membrane (dotted line).
Figure 18:
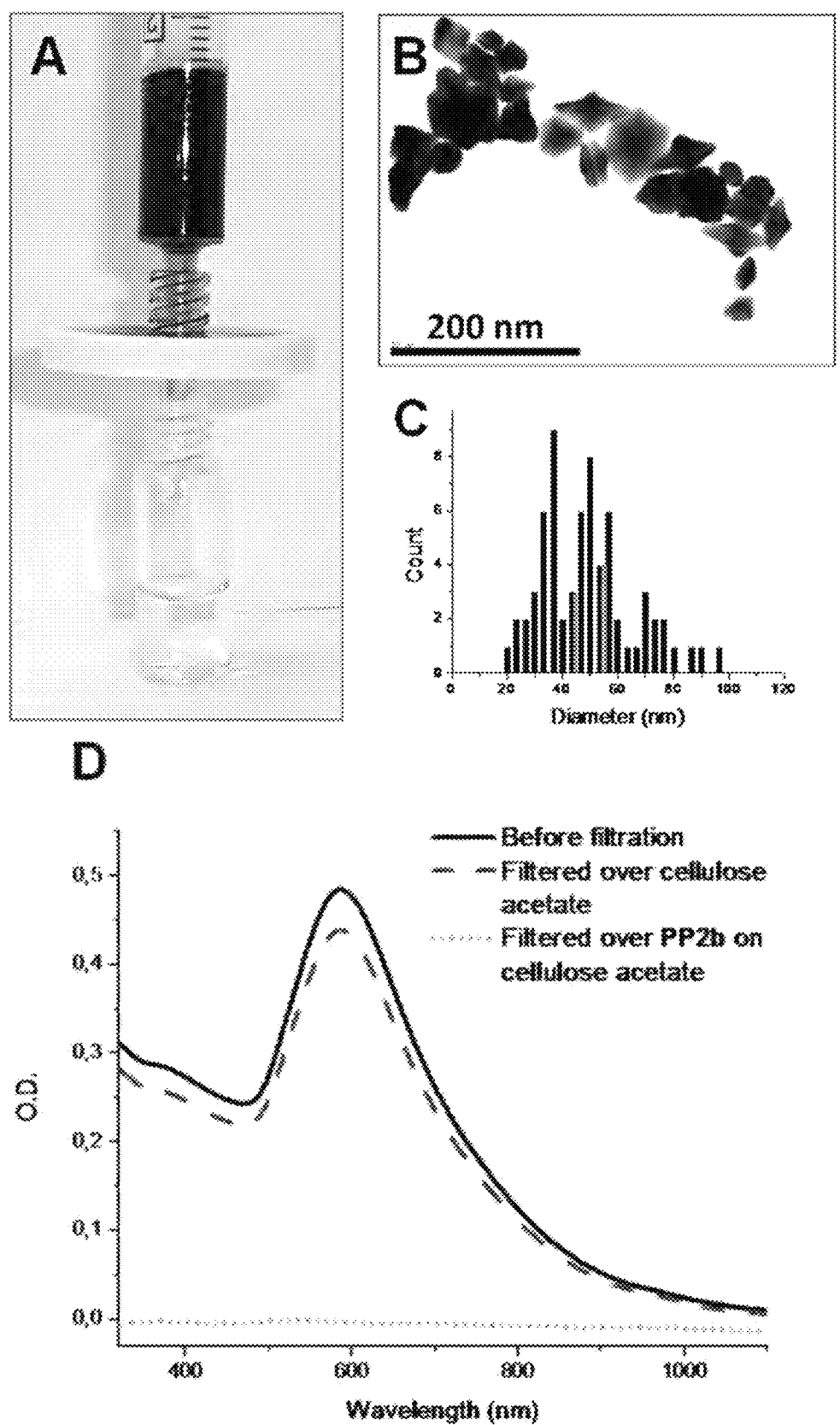
FIG. 18(A)-(D) depicts filtration experiment of Au6. (A) photograph of filtration. (B) Representative TEM image of particles before filtration. (C) corresponding histogram. (D) UV/V is spectra of Au6 solution before filtration (solid line), after filtration over CA only (dashed line), and after filtration over the Perylene diimide V membrane (dotted line).
Figure 19:
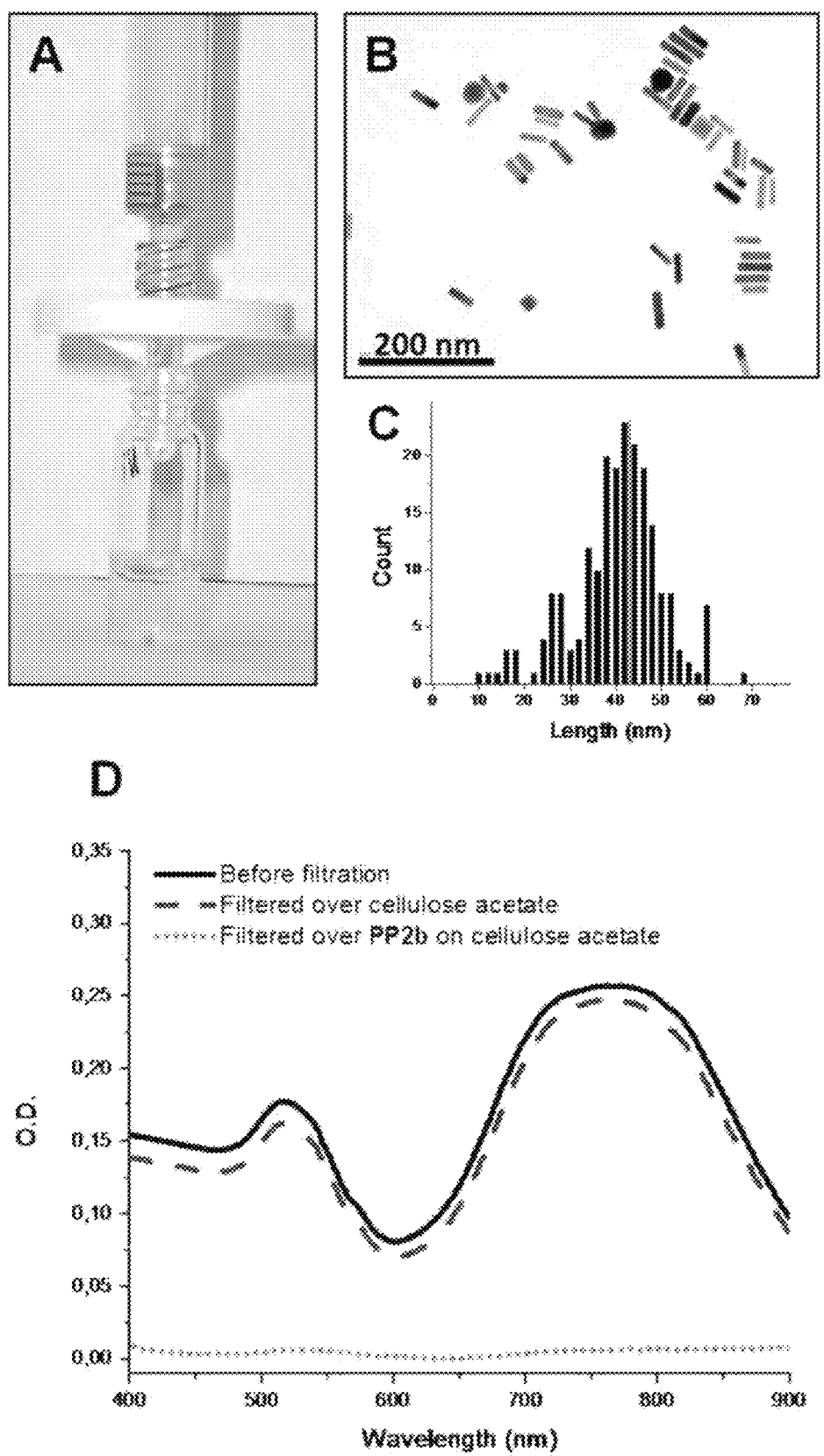
FIG. 19(A)-(D) depicts filtration experiment of Au7. (A) photograph of filtration. (B) Representative TEM image of particles before filtration. (C) corresponding histogram. (D) UV/V is spectra of Au7 solution before filtration (solid line), after filtration over CA only (dashed line), and after filtration over the Perylene V membrane (dotted line).

The membrane thickness can be readily controlled by the ratio of Perylene diimide V solution volume to filter surface area. Thus, filtering only 0.5 ml Perylene diimide V ($5 \cdot 10^{-4}$ M) over CA (0.13 mg Perylene diimide V/cm$^2$) resulted in reduction of Perylene diimide V layer thickness to ~12 µm (FIG. 12). The one-step fabrication of the supramolecular membrane is exceedingly simple and preparation from a stock solution of self-assembled Perylene diimide V takes ~15 minutes.

The flow rate of water through the 12 µm membrane can be adjusted via the trans-membrane pressure, and stable flow rates are observed at pressures up to 0.7 bar over several hours (FIG. 9). The flow rate at 0.4 bar is 0.4 ml/min, corresponding to permeance (pressure normalized flux) of $1.1 \cdot 10^2$ l h$^{-1}$ m$^{-2}$ bar$^{-1}$, which is comparable to commercial ultrafiltration membranes with similar rejection properties. Importantly, no traces of Perylene diimide V (Compound V) are detectable in the filtrate of the water solution (FIG. 10), revealing the robustness of the supramolecular membrane material under the solvent flow.

Example 10

Recycling of Filtration Membrane and Nanoparticles 5 ml of water/ethanol (4:6, v/v), containing nanoparticle capping agent (0.04 mM), was flown through the supramolecular membrane in order to wash Perylene diimide V (Compound V) and retained NPs off the CA support. Subsequently, Perylene diimide V was extracted with 12 ml DCM. The organic phase was partially evaporated in high vacuum; Perylene diimide V was precipitated with hexane and dried in high vacuum.

Aunts in the aqueous phase were purified by successive addition of 3 ml EtOH and 12 ml DCM, leading to removal of traces of Perylene diimide V. The aqueous phase was washed with DCM and partially evaporated in high vacuum in order to remove traces of organic solvent. Then it was refilled to 3 ml with an aqueous solution containing NP capping agent (0.1 mM).

Figure 20:
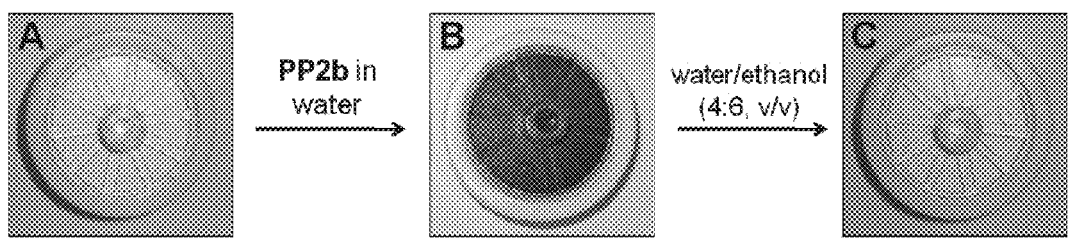
FIG. 20(A)-(C) presents photographs of (A) unused CA syringe filter, (B) Perylene diimide V(=PP2b) supramolecular membrane on the filter, and (C) the same filter after rinsing with water/ethanol mixture.
Figure 21:
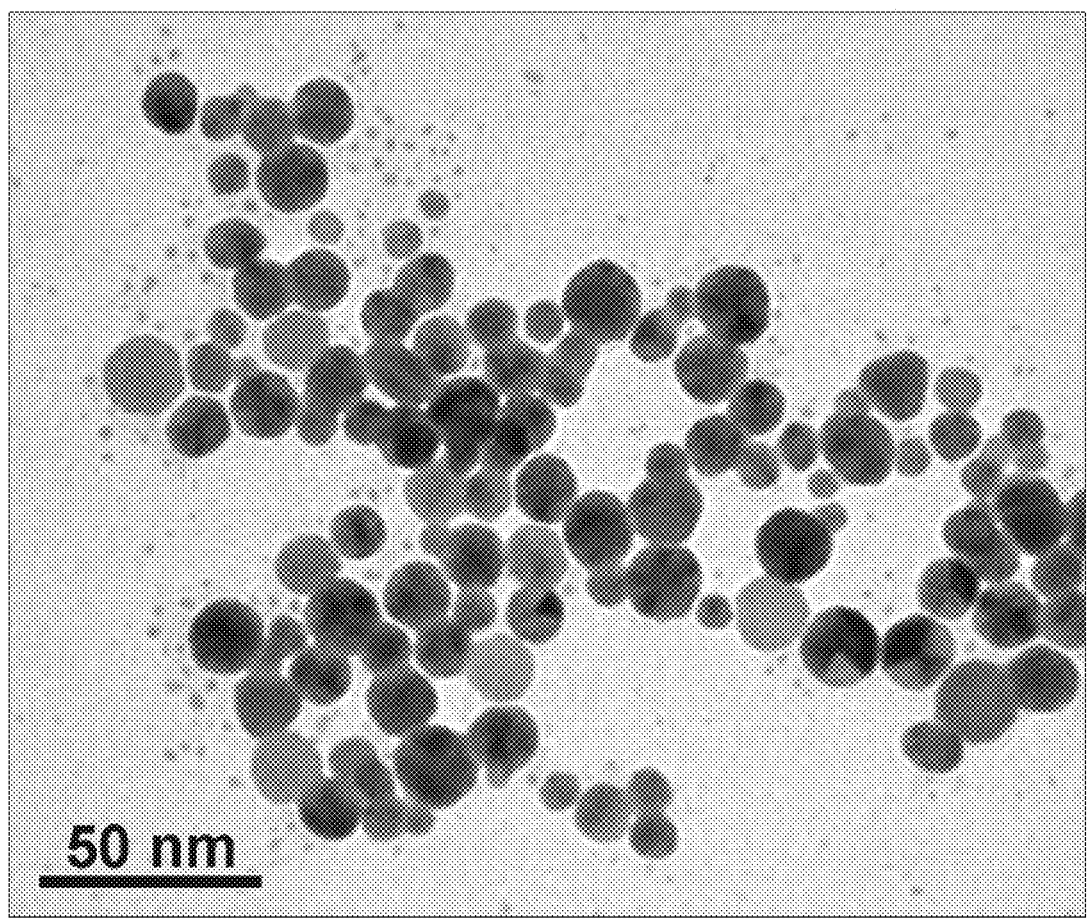
FIG. 21 depicts TEM image of Au3 before filtration.
Figure 22:
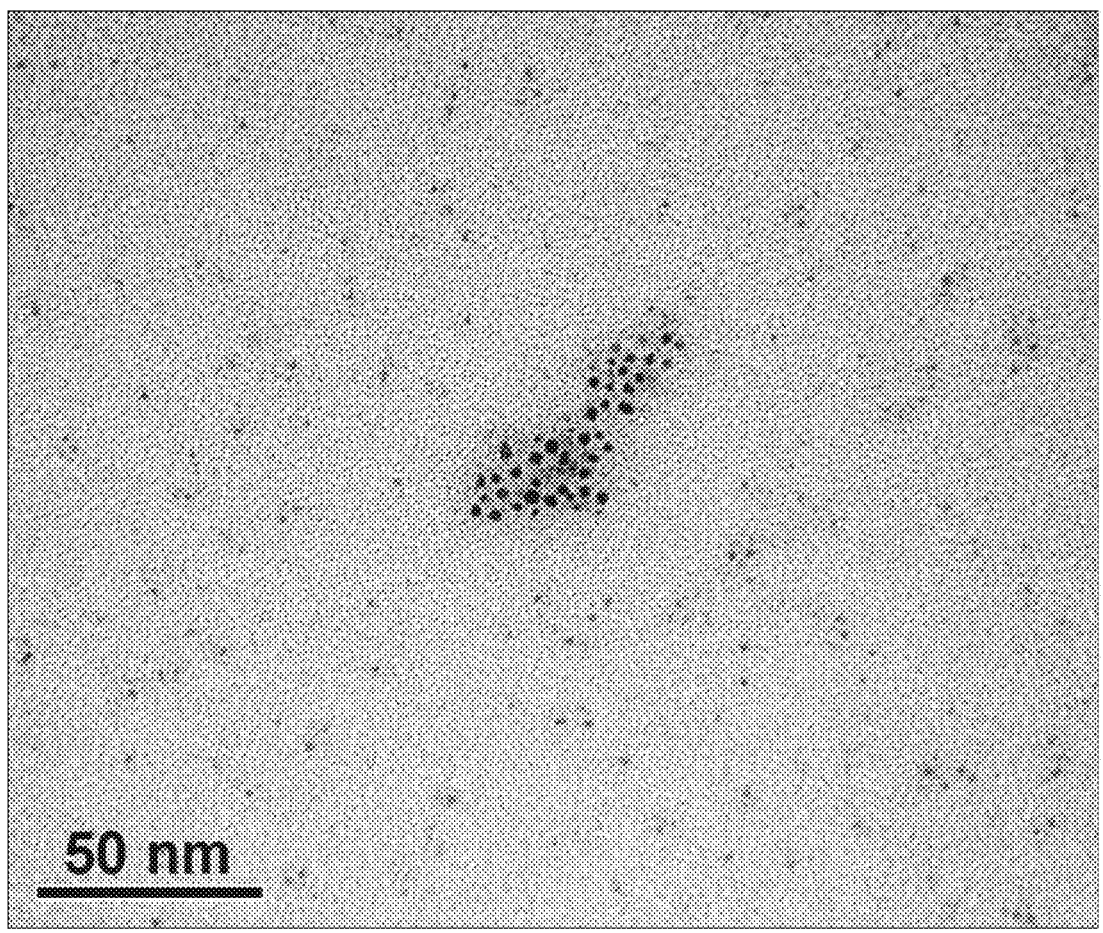
FIG. 22 depicts TEM image of Au3 filtrate.
Figure 23:
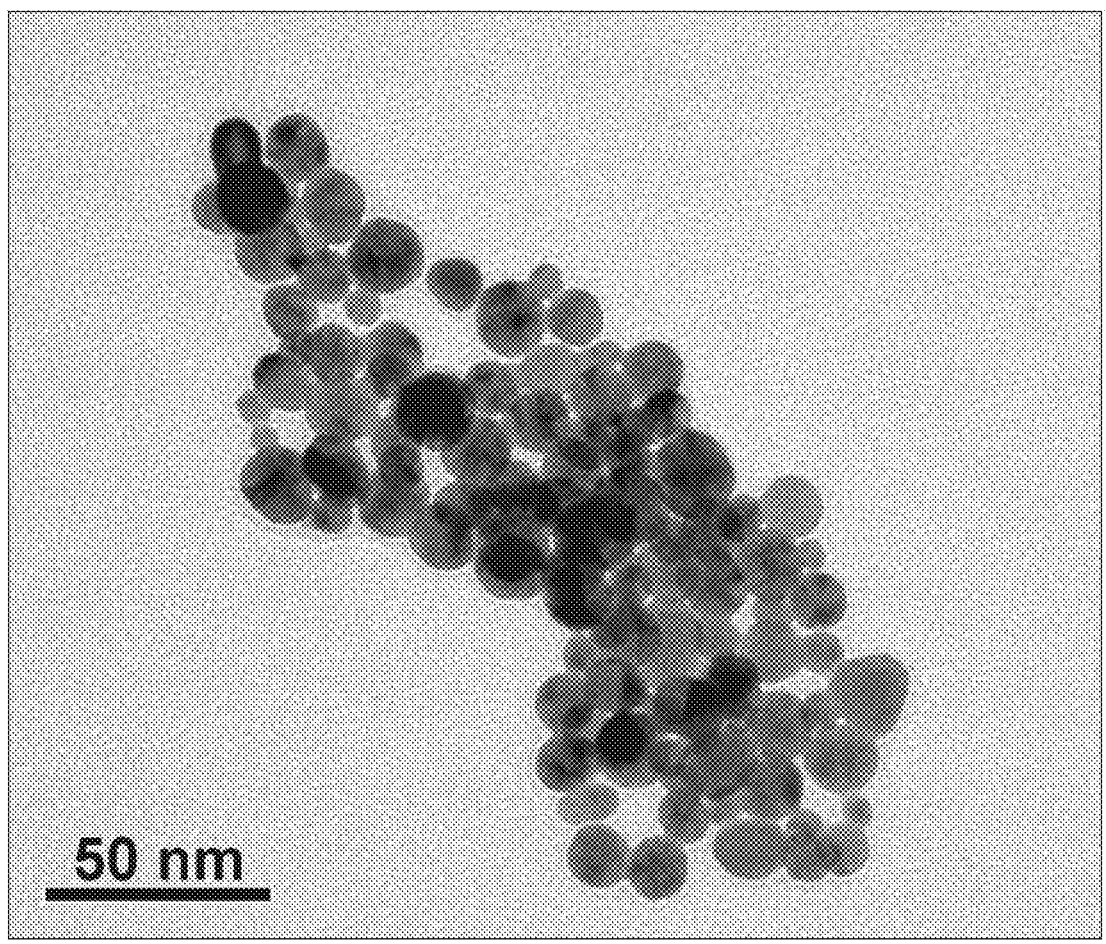
FIG. 23 depicts TEM image of Au3 retentate.
Figure 24:
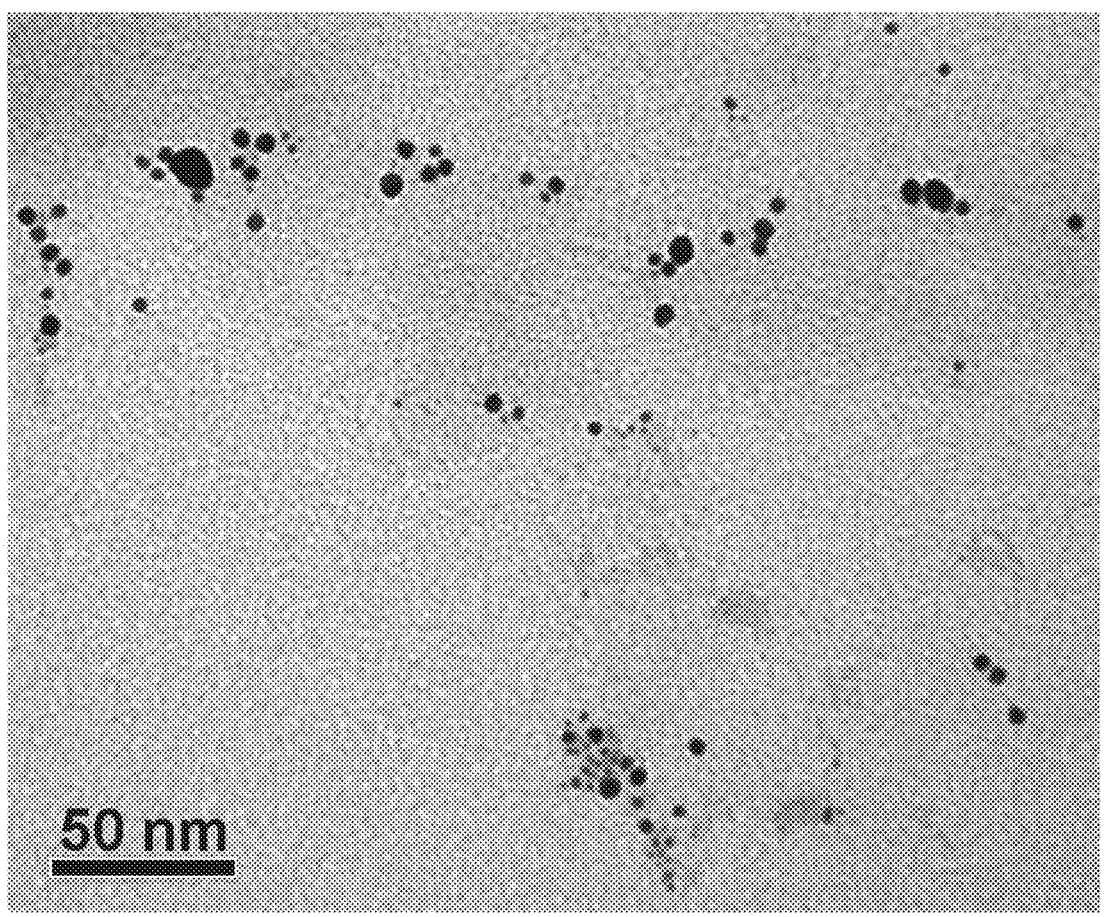
FIG. 24 depicts TEM image of Au2 before filtration.
Figure 25:
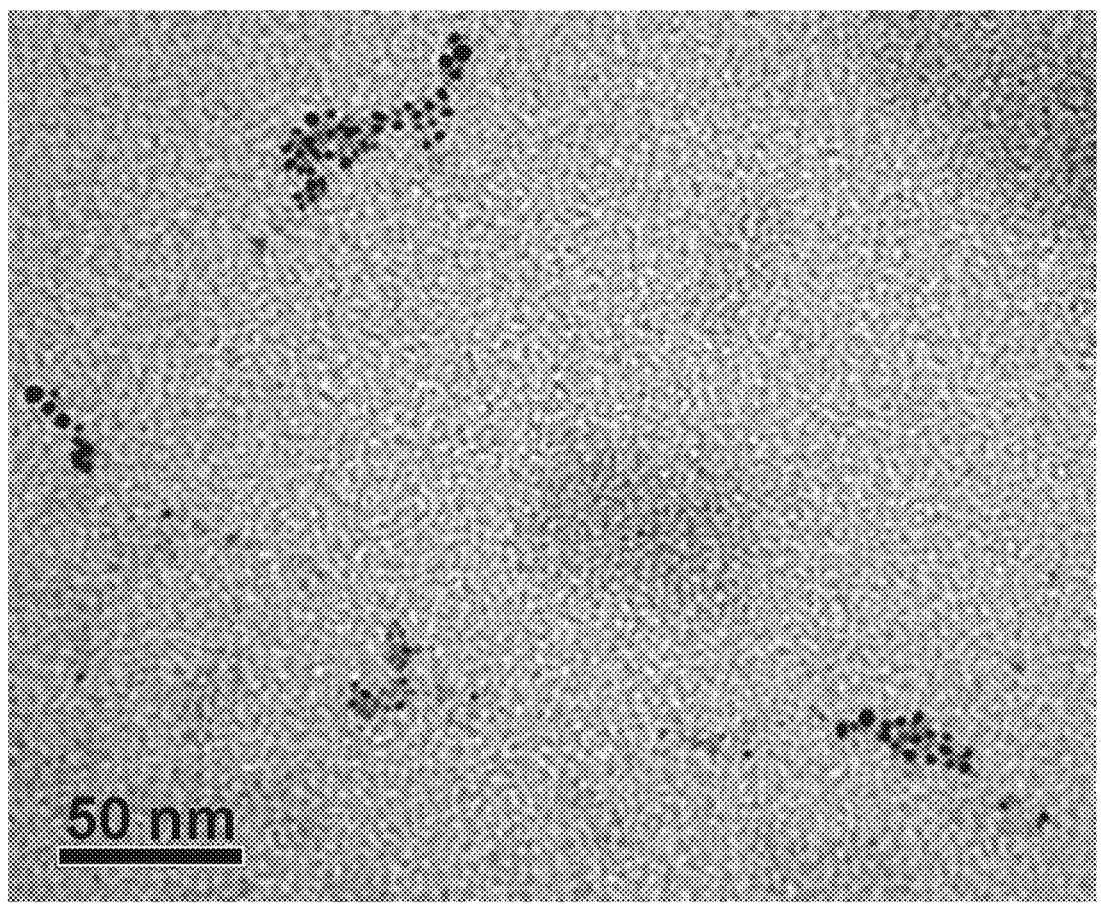
FIG. 25 depicts TEM image of Au2 filtrate.
Figure 26:
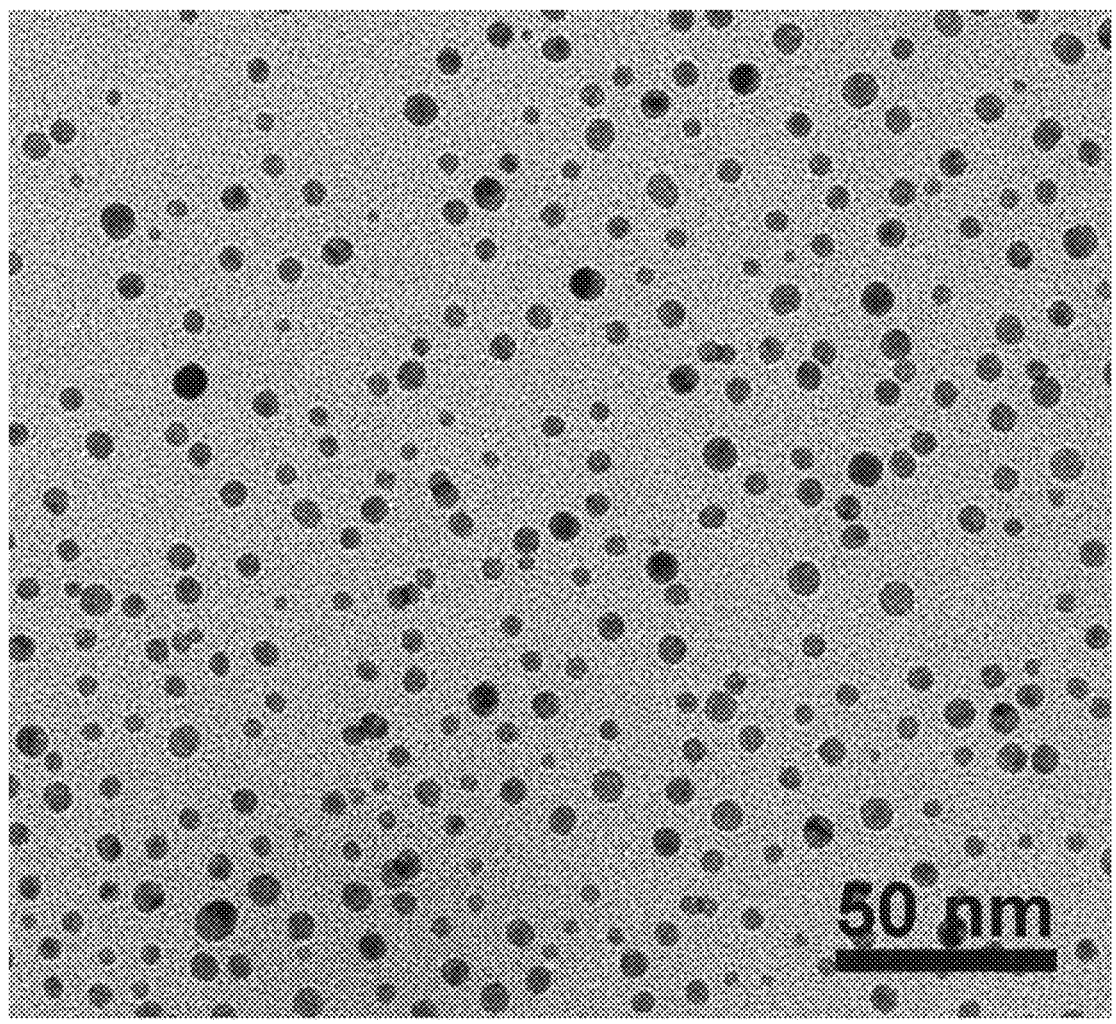
FIG. 26 depicts TEM image of Au8 before filtration.
Figure 27:
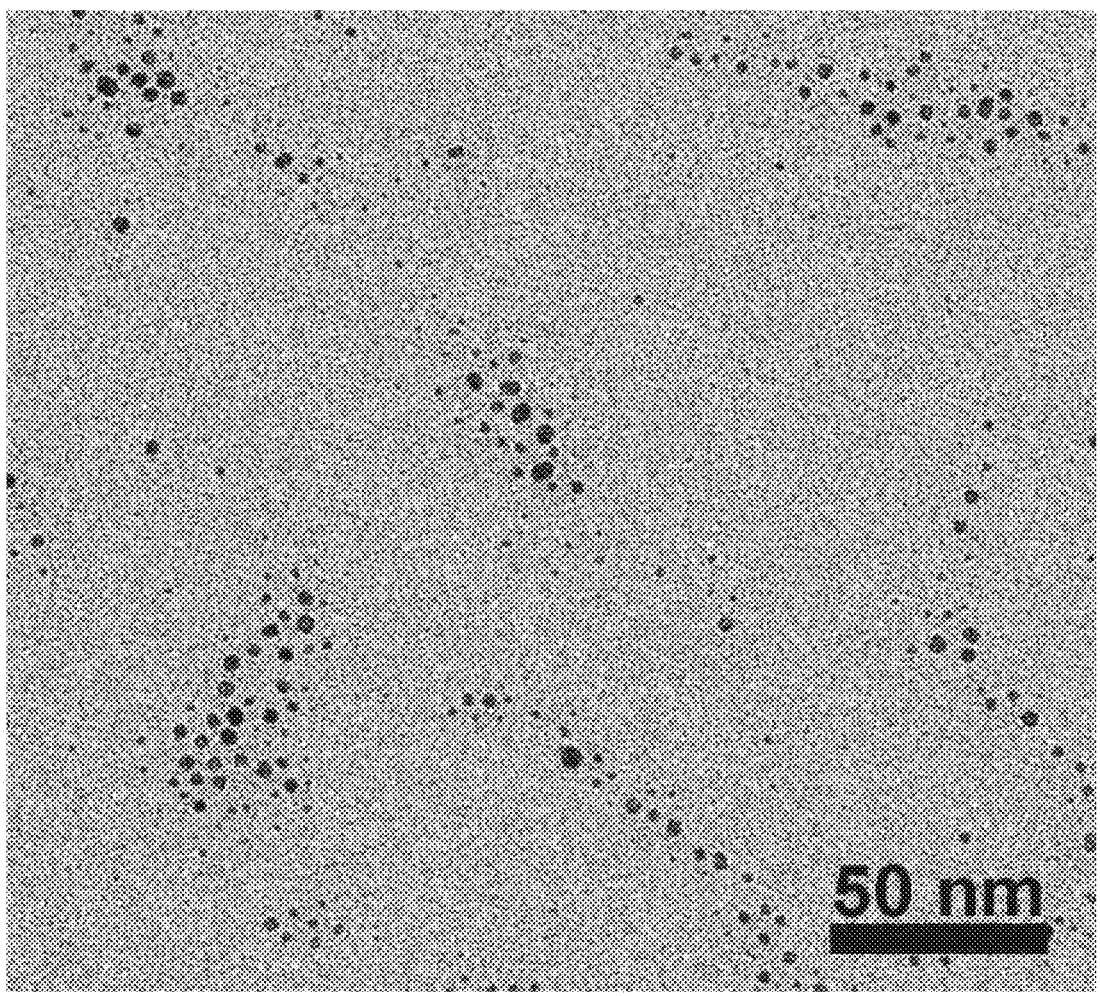
FIG. 27 depicts TEM image of Au8 filtrate.

Thus, rinsing the supramolecular filter with a water/ethanol mixture (4:6, v/v) results in disassembly of Perylene diimide V and its complete removal from the CA support (FIG. 20A-C). The Perylene diimide V can be dried, reassembled in water, and reused as a membrane.

Figure 4:
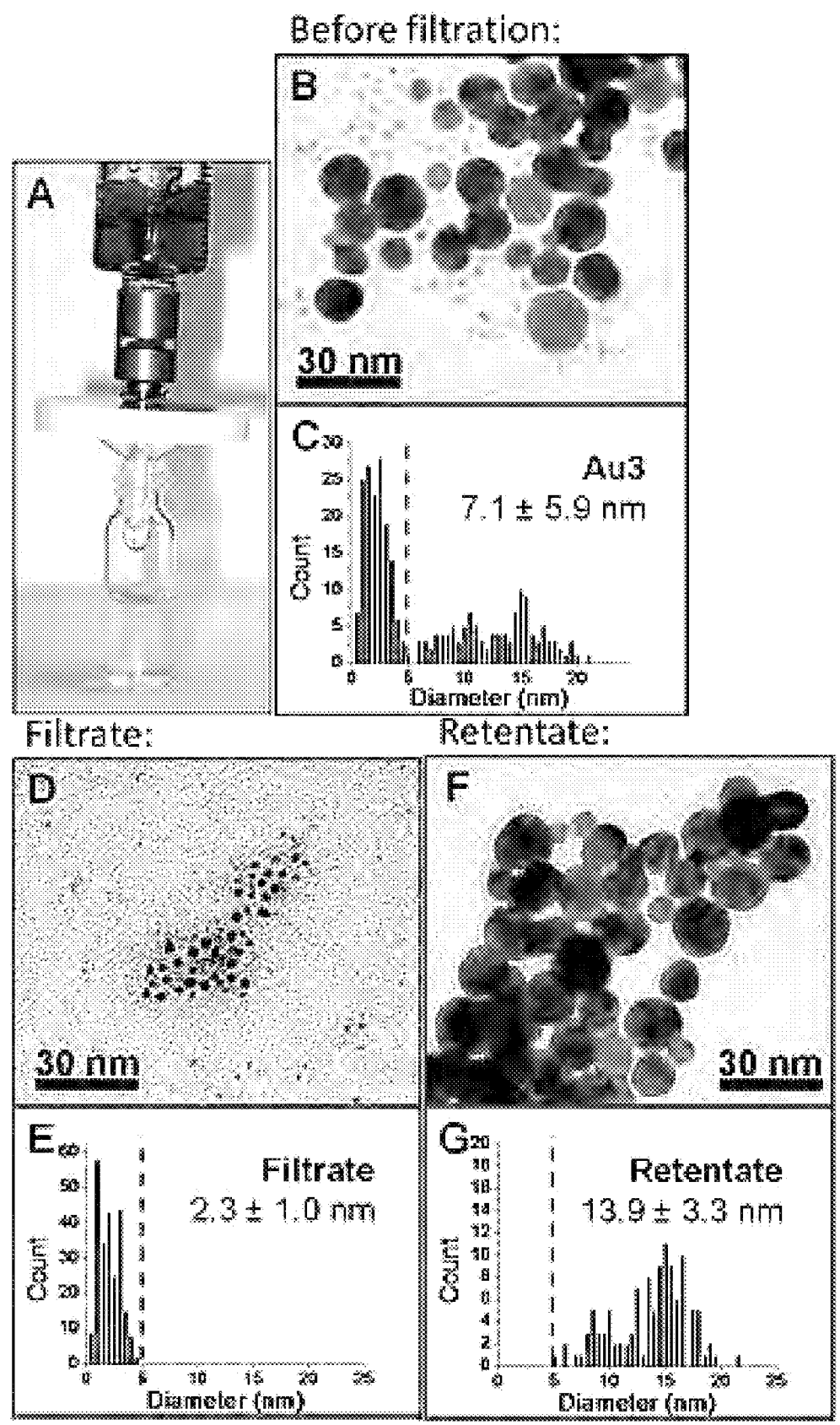
FIG. 4 (A) presents photograph of the filtration experiment of Au3. (B) Representative TEM image of Au3 before filtration and (C) corresponding particle size histogram. (D) TEM image of the filtrate and (E) corresponding histogram. (F) TEM image of the retentate and (G) corresponding histogram; dashed lines in the histograms indicate the cut-off of the filter. Representative TEM images of larger areas are provided in FIG. 21-23. (H) UV/Vis spectra of Au3 solution before filtration (solid line), retentate (dashed line), and filtrate (dotted line). (I) Photographs showing the retrieval of Perylene diimide V and AuNPs from the water/ethanol mixture.
Figure 4:
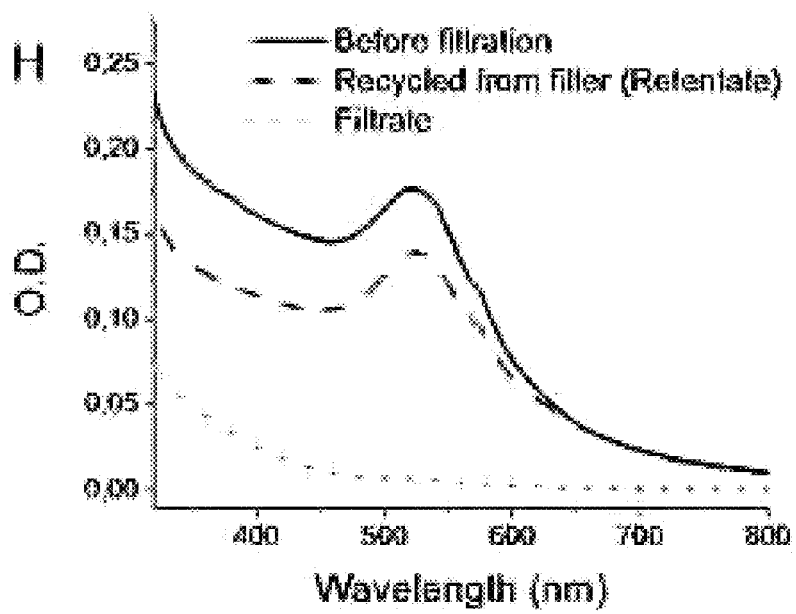
Figure 4:
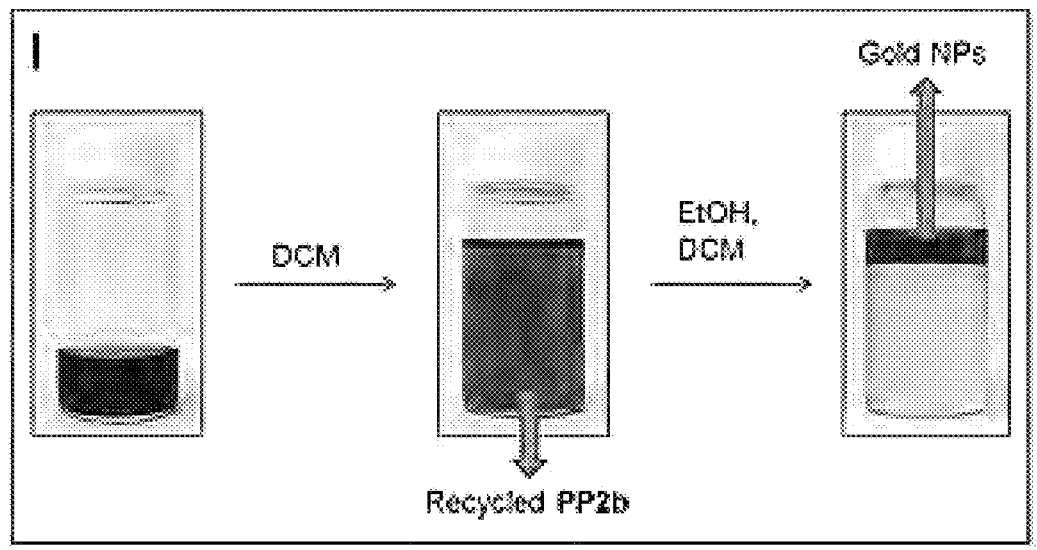

Through this procedure, both Perylene diimide V and retained NPs (retentate) could be recycled (FIG. 4I). As revealed by TEM, the retentate contains particles larger than 5 nm, matching well with the fraction of particles that are missing in the filtrate (FIG. 4F, G). In agreement with this observation, the UV/V is spectrum of the retentate solution shows a strong Plasmon resonance band SPB at 524 nm, characteristic of the larger AuNPs in Au3 (FIG. 4H). The absence of Perylene diimide V absorption peaks ($\lambda_{max,1}$=394 nm, $\lambda_{max,2}$=540 nm) in the isolated retentate solution shows that the extraction of the strongly absorbing amphiphile with DCM is quantitative.

$^1$H-NMR spectra measured before and after the recycling procedure do not indicate any decomposition or contamination of Perylene diimide V(FIG. 29), which is important for its multiple recycling and reproducible use as supramolecular membrane.

The Perylene diimide V material was recycled and reused 3 times, showing consistent performance. The experiments demonstrate that reversible bonding in Perylene diimide V supramolecular structures allows facile recycling of both the membrane material and retained NPs. The CA support can be recycled as well. A scheme depicting membrane fabrication, use, and recycling is shown in FIGS. 5A and 5B.

Example 11

Size-Selective Chromatography

In order to study applicability for ultrafiltration, gold nanoparticles (AuNPs) of various sizes were filtered over a ~12 μm thick Perylene diimide V (Compound V, having PEG17) supramolecular membrane (0.13 mg Perylene diimide V/cm$^2$, FIG. 12). Filtration experiments were preformed in a setup (FIG. 2) that allows filtration under a constant trans-membrane pressure (0.4 bar was used in all filtration experiments). AuNP solutions were characterized before and after filtration using transmission electron microscopy (TEM). In addition, UV/V is was used for qualitative corroboration of TEM image analysis, since a surface plasmon band (SPB) is dependent on the particle size.

Mercaptopropionic acid (MPA)-stabilized AuNPs Au3 (7.1±5.9 nm) have a bimodal, highly polydisperse particle size distribution with particles ranging from 0.5 to ~20 nm in diameter (FIG. 4B, C). Filtration of the red solution over the supramolecular Perylene diimide V membrane results a pale yellow filtrate (FIG. 4A). The UV-Vis spectrum shows the absence of a SPB in the filtrate (FIG. 4H), suggesting the removal of particles larger than ~5 nm. TEM images of the filtrate show size-selective removal of large particles (~5 nm cutoff size) and reduction of average particle size from 7.1 to 2.3 nm (FIG. 4D, E).

Figure 6:
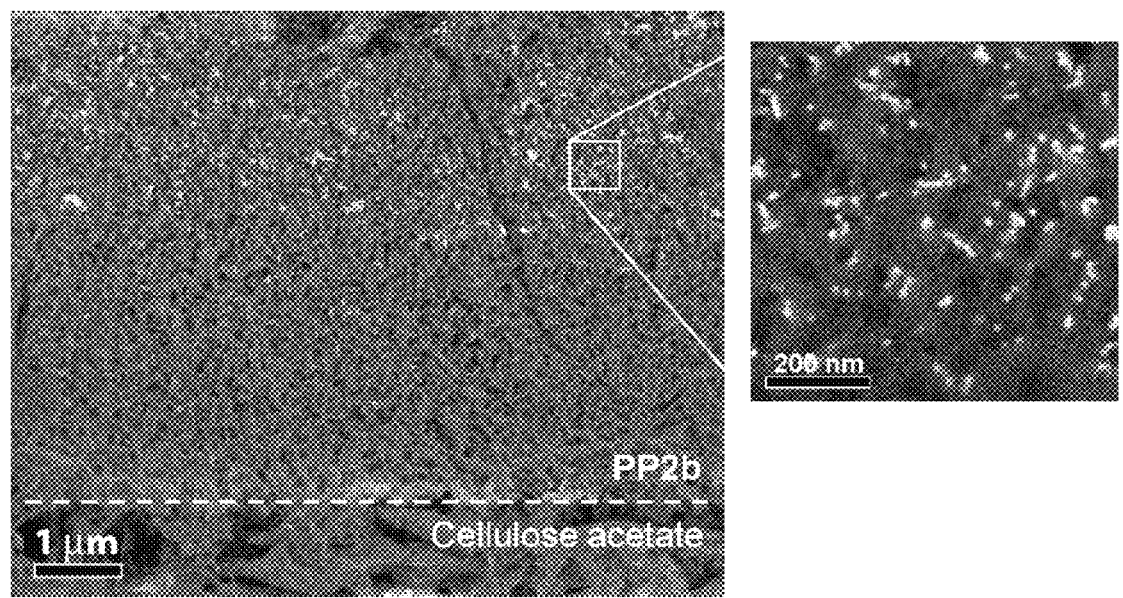
FIG. 6 depicts a cryo-SEM image (back-scattered electron analysis) of the supramolecular membrane that was used for filtration of Au3 solution. AuNPs (appearing as bright spots) have sizes of 10-20 nm.

In order to visualize filtered nanoparticles embedded in the supramolecular membrane, filtration of Au3 was investigated using cryo-SEM. When detecting back-scattered electrons, AuNPs appear as a band of bright spots that penetrated into the filtration membrane rather than being retained on its surface and forming a filter cake (FIG. 6). The magnified area shows individual particles with diameters corresponding to the larger particle fraction in the Au3 size distribution. The particles appear to be neither fused nor aggregated.

Figure 7:
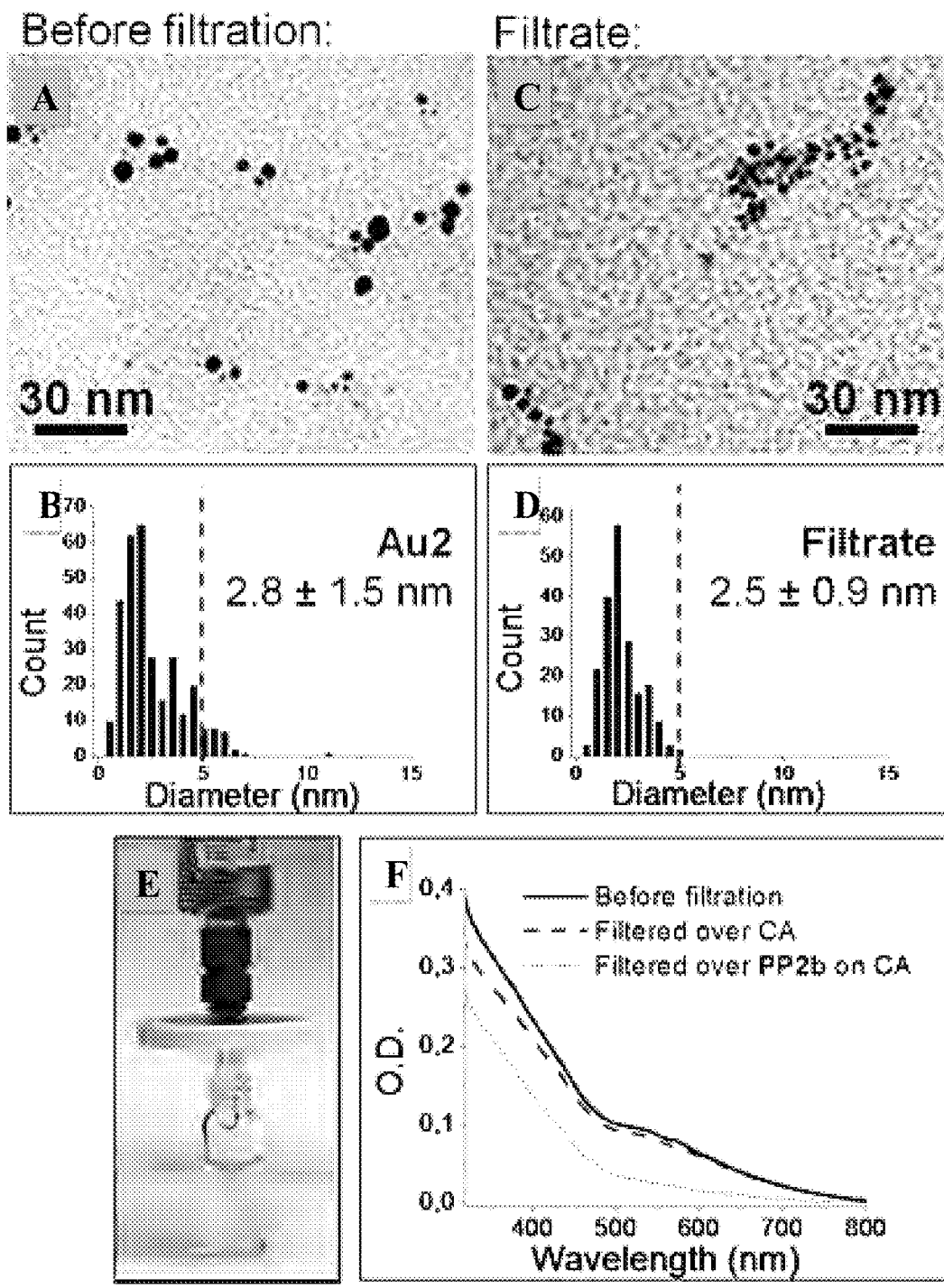
FIG. 7(A)-(L) Filtration experiment of Au2. (A) Representative TEM image of particles before filtration, and (B) particle size histogram. (C) Representative TEM image of particles in the filtrate, and (D) particle size histogram. (E) Photograph of filtration. (F) UV/Vis spectra of an Au2 solution before filtration (solid line), after filtration over CA (control measurement, dashed line), and after filtration over the Perylene diimide V supramolecular membrane (dotted line). Filtration of Au2 over CA does not change any spectral features and the SPB (surface plasmon band) at ~520 nm remains unchanged, indicating that all particles pass CA. In contrast, no SPB is visible in the sample filtered over the supramolecular Perylene diimide V membrane, indicating removal of particles larger than 5 nm. (G)-(L) Filtration experiment of Au8. (G) Representative TEM image of particles before filtration, and (H) particle size histogram. (I) Representative TEM image of particles in the filtrate, and (J) particle size histogram. (K) Photograph of filtration. (L) UV/Vis spectra of an Au8 solution before filtration (solid line), after filtration over CA (control measurement, dashed line), and after filtration over the Perylene diimide V membrane (dotted line). Since even small (~2 nm) charge-neutral (PEG-SH stabilized) AuNPs still exhibit a weak SPB, the SPB does not vanish completely in the filtrate but weakens, and a resulting peak shift from 512 to 502 nm is observed.
Figure 7:
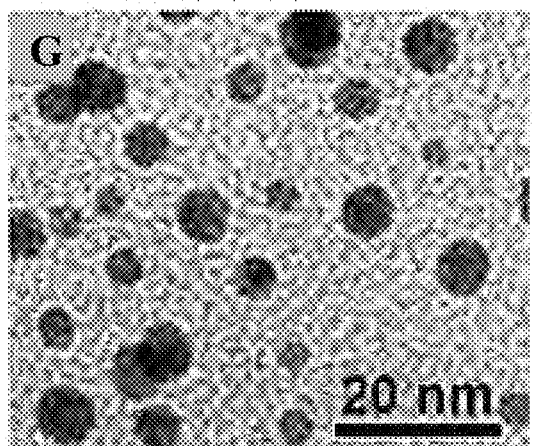
Figure 7:
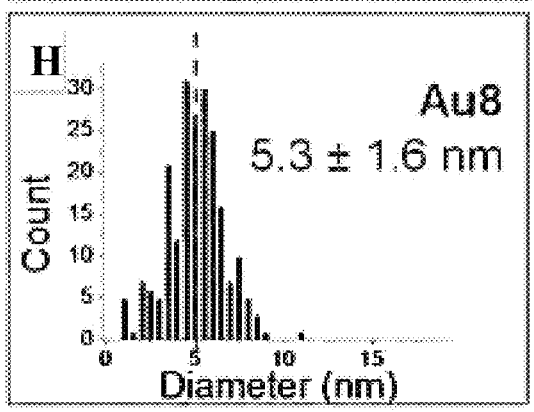
Figure 7:
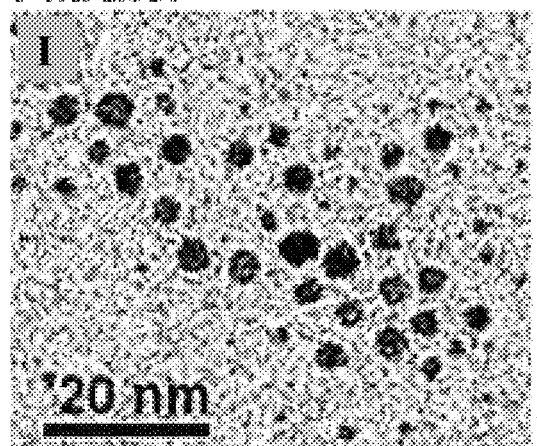
Figure 7:
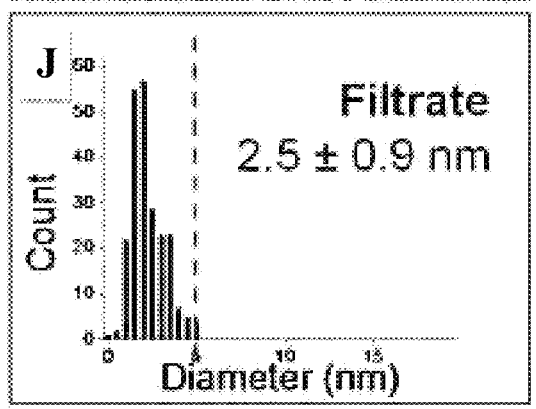
Figure 7:
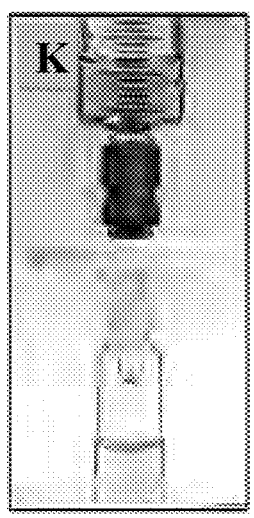
Figure 7:
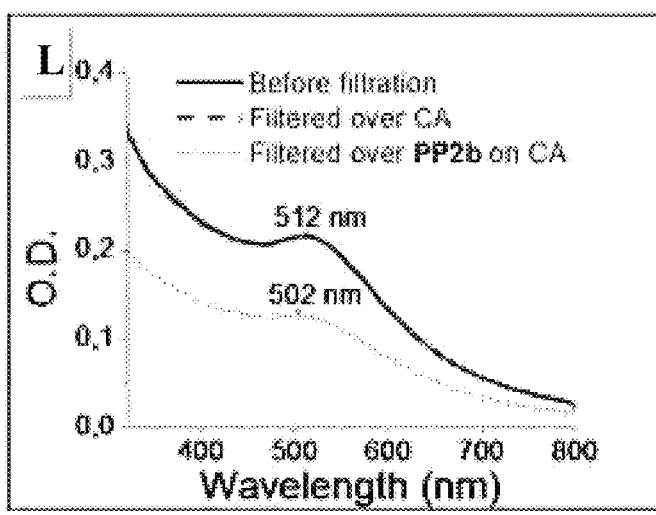

Filtration experiments with other MPA-stabilized AuNPs are in agreement with the filter's ~5 nm cutoff size: small Au1 (1.6±0.6 nm) pass the supramolecular membrane (FIG. 13(A)-(E), 14), while large Au4 (17.5±3.9 nm) are filtered off quantitatively (FIGS. 15(A)-(E) and FIG. 16). Filtration of polydisperse Au2 (2.8±1.5 nm) resulted in removal of particles larger than 5 nm and improved monodispersity of the nanoparticles (FIG. 7 A-F).

The supramolecular membrane maintains similar rejection properties when AuNPs are stabilized by other capping layers: Filtration of PEG-SH-stabilized Au8 (5.3±1.6 nm) leads to removal of particles larger than 5 nm (FIG. 7G-L). Large citrate-stabilized Au5 (17±5 nm), very polydisperse CTAB-stabilized Au6 (51±17 nm), and CTAB-stabilized nanorods Au7 (41±10 nm in length) are filtered off quantitatively (FIGS. 17A-D, 18A-D and 19A-D). Thus, the outcome of our filtration experiments did not depend on the capping layer of the filtered NPs but on particle size as demonstrated in Table 2:

TABLE 2

Filtration of various water-soluble AuNPs.

| | Diameter (nm) | Capping layer | Filtration result |
|---|---|---|---|
| Au1 | 1.6 ± 0.6 | MPA | complete passing |
| Au2 | 2.8 ± 1.5 | MPA | separation |
| Au3 | 7.1 ± 5.9 | MPA | separation |
| Au4 | 17.5 ± 3.9 | MPA | complete removal |
| Au5 | 17.0 ± 5.0 | Citrate | complete removal |
| Au6 | 51 ± 17 | CTAB | complete removal |
| Au7 | 41 ± 10 (length) | CTAB | complete removal |
| Au8 | 5.3 ± 1.6 | PEG-SH | separation |

Separation of Quantum Dots (QDs).

2 ml of QD1+2 mixture was run over a supramolecular layer (0.65 mg Perylene diimide V/cm$^2$) on a CA support (Advantec C045A025A, effective filtration area=3.7 cm$^2$, pore size=0.45 μm) in a PallEasy Pressure Syringe Filter Holder at a trans-membrane pressure of 1.2 bar. An aqueous solution of capping agent (adjusted to the pH 9 with NaOH) was used as the eluent and 5 fractions (2 ml) were collected.

As shown above, a thin supramolecular membrane (0.13 mg Perylene diimide V/cm$^2$) allows filtration and separation of NPs with ~5 nm cutoff size. While, MPA-capped quantum dots QD1 (~4 nm) quickly pass the filter, it was observed that if a significantly thicker membrane is fabricated, QD1 permeate after a notable delay. Based on this observation we expected that particles of different sizes might pass the filter within different times, thus allowing for chromatographic size-selective separation of sub-5 nm NPs. Accessing this size range bears great potential, in particular for post-synthetic purification of quantum dots, as NPs size range between 2 and 5 nm is typical for widely utilized CdS, CdSe and CdTe particles.

Figure 8:
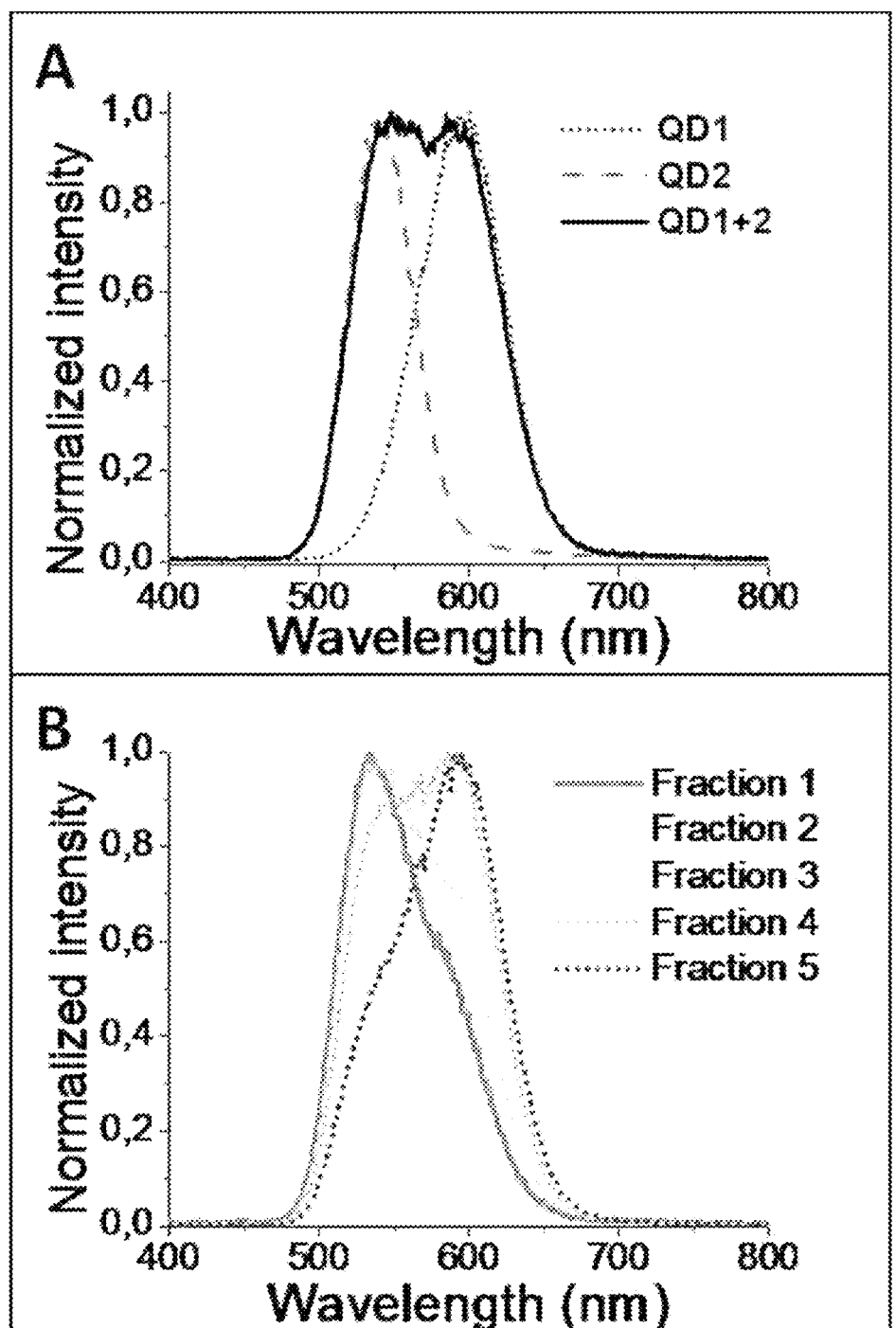
FIG. 8 (A)-(C) depicts normalized luminescence spectra ($\lambda_{ex}$=390 nm) of (A) QD1 (dotted line), QD2 (dashed line), and their mixture (solid line), and (B) successive fractions collected by filtration of the QD mixture. (C) Photograph of the mixture (top) and the collected fractions (bottom) under UV light (365 nm).
Figure 8:
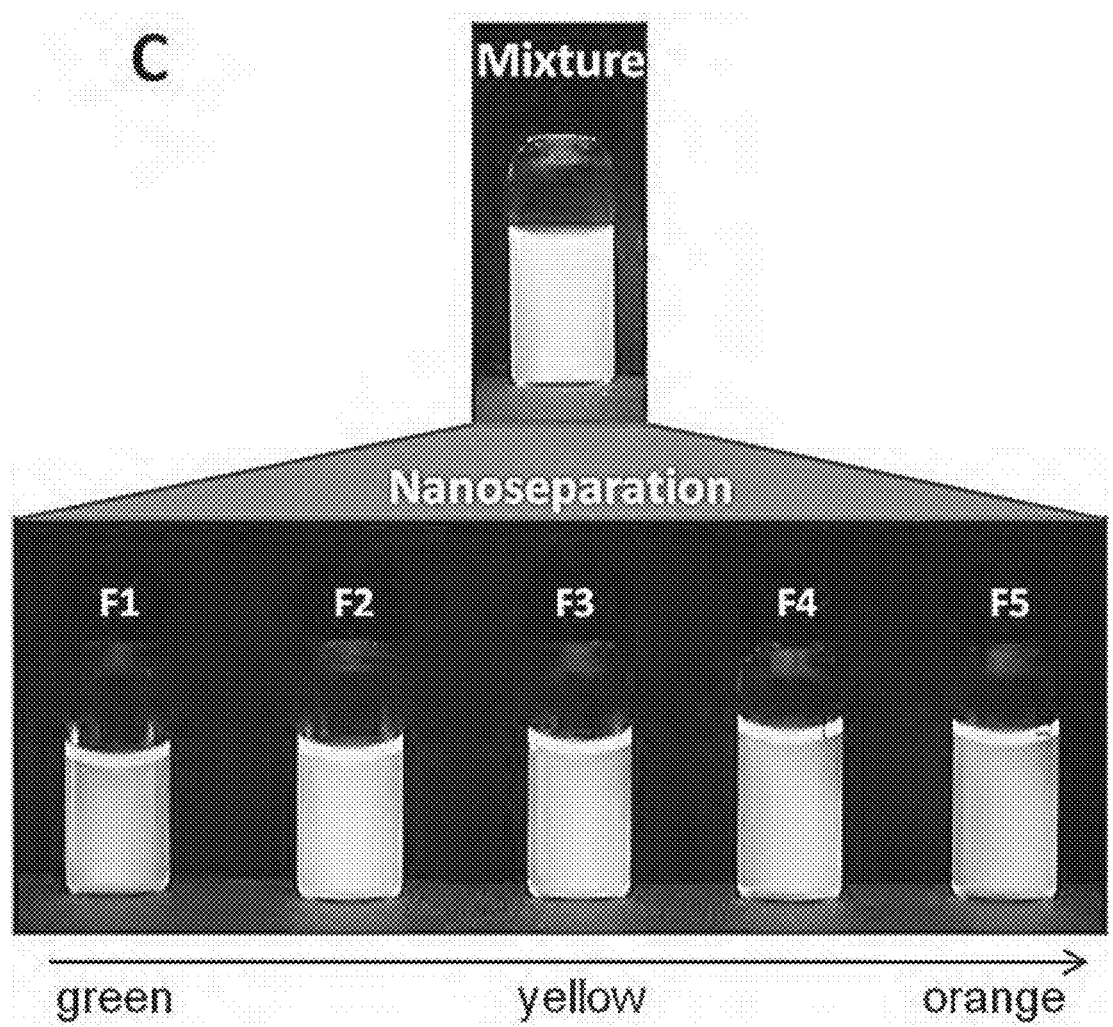

Quantum dot luminescence is a function of particle size. In order to investigate size selective chromatography, a mixture of MPA-capped CdTe quantum dots QD1 (~4.0 nm) and smaller QD2 (~2.5 nm) was prepared, such that emissions of both particles had equal intensities (FIG. 8A). The mixture (2 ml) was run over a thick (~45 μm; 0.65 mg Perylene diimide V/cm$^2$) supramolecular membrane (eluting with aqueous MPA solution (0.1 M)) and 5 fractions (2 ml) were collected successively. A gradual color change of fractions 1 (green) through 5 (orange) was observed (FIG. 8C). The emission spectrum of the first fraction corresponds mainly to QD2, while the last fraction contains predominantly QD1 (FIG. 8B, and intermediate fractions 2 to 4 contain mixtures of both particle types, with gradually rising QD1:QD2 ratio. However, the results indicate that it is possible to achieve considerable size-selective separation of sub-5 nm semiconductor nanoparticles over a 45 μm thick supramolecular membrane. As opposed to size exclusion chromatography, only minute amounts of (recyclable) stationary phase and small elution volumes are required to separate preparative amounts of nanoparticles. Notably, small particles pass the membrane faster than large particles, demonstrating different separation mechanism in the 3D fibrous network, as opposed to porous polymer beads used in size exclusion chromatography.

Example 12

Stability at Solutions with High Ionic Strength

Biological systems are commonly kept in solutions with higher ionic strength (i.e. in the presence of buffer, with ion concentrations similar to physiological conditions). The stability of the supramolecular membranes of this invention at these conditions was determined. The flow rates of solutions of different compositions and ionic strength were monitored. Changes and instabilities in the flow rate would indicate that the membranes are not stable under biologically relevant conditions.

Figure 30:
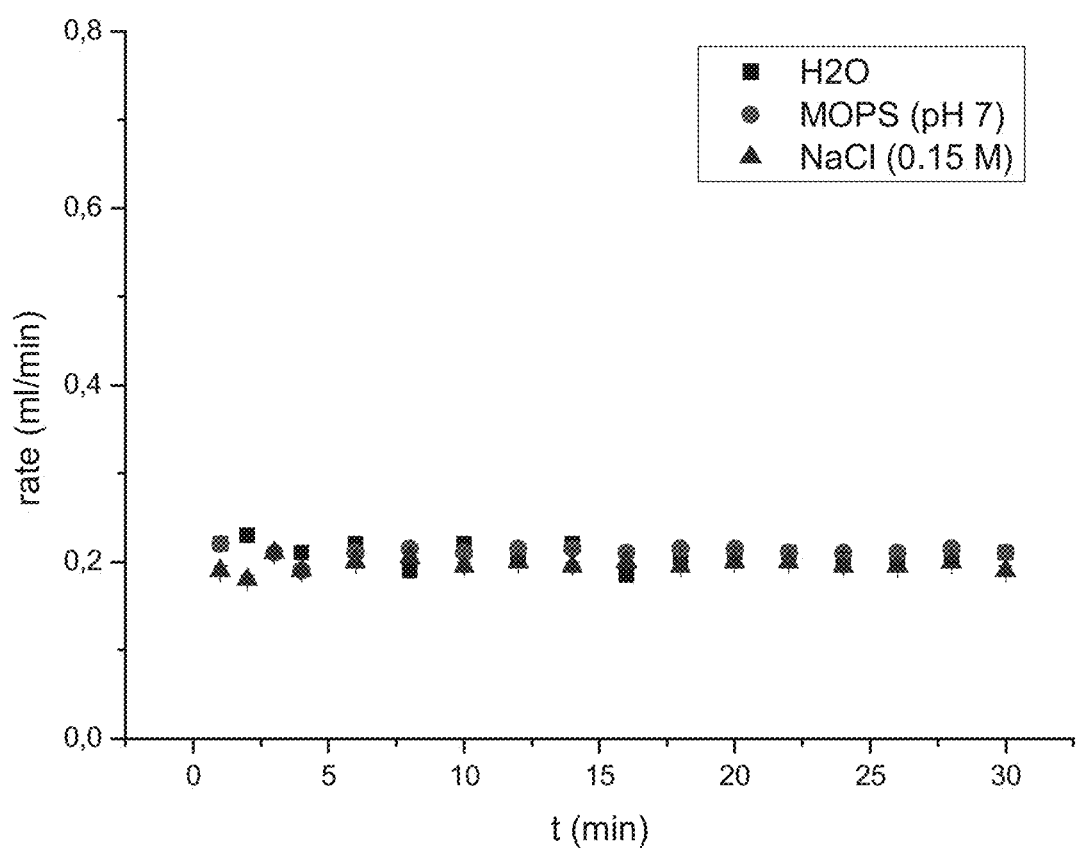
FIG. 30 a scheme presenting the flow rate of H$_2$O, MOPS (((3-(N-morpholino)propanesulfonic acid)) buffer solution (pH=7), and NaCl(aq) at constant pressure (0.4 bar) over a supramolecular membrane composed of 3.7 mg Perylene diimide V deposited on 5.7 cm$^2$ cellulose acetate (thickness: ~12 μm).

Filtration of solutions of a) buffer solution at pH=7 (3-(N-morpholino)propanesulfonic acid, MOPS (20 mM), KCl (70 mM), MgCl$_2$ (10 mM)) and b) NaCl(aq) (150 mM) over the supramolecular membranes of Perylene diimide V (Compound V) for 30 minutes took place at essentially identical flow rates, compared to filtration of neat double distilled water (FIG. 30).

Thus, the presence of higher salt concentrations does neither destabilize/dissolve the membrane, nor critically alter the membrane's nanoscopic structure, and the membrane can perform under conditions relevant to biological systems.

Example 13

Purification of Biological Macromolecules

In order to study applicability for purification or filtration of biological supramolecules, two proteins bovine serum albumin (BSA) and Kemp eliminase (KE70) were filtered through the Perylene diimide V (Compound V) based membrane. BSA has a molecular weight of ~67 kDa, and dimensions of ~5×9×9 nm. KE70 has a molecular weight of ~30 kDa, and dimensions of ~5×4×4 nm. Considering the membranes' 5 nm cut-off, KE70 was expected to pass the supramolecular membrane, whereas BSA, being significantly larger than the membrane's pores, was expected to be retained.

A mixture of BSA (0.1 mg/ml) and KE70 (0.1 mg/ml) in 2 ml 3-(N-morpholino)propanesulfonic acid (MOPS) buffer solution at pH=7 was filtered over a freshly prepared supramolecular membrane (~12 μm thick). After the filtrate solutions had passed the membrane, additional 5.5 ml of neat MOPS buffer solution was run over the membrane. The filtrate was collected in fractions (5×1.5 ml). In order to obtain retained proteins, the used supramolecular membrane was scratched off its cellulose acetate support, dispersed in MOPS buffer solution, and centrifuged. The supernate contained the retained proteins, whilst the precipitage contained the membrane material Perylene diimide V.

Figure 31:
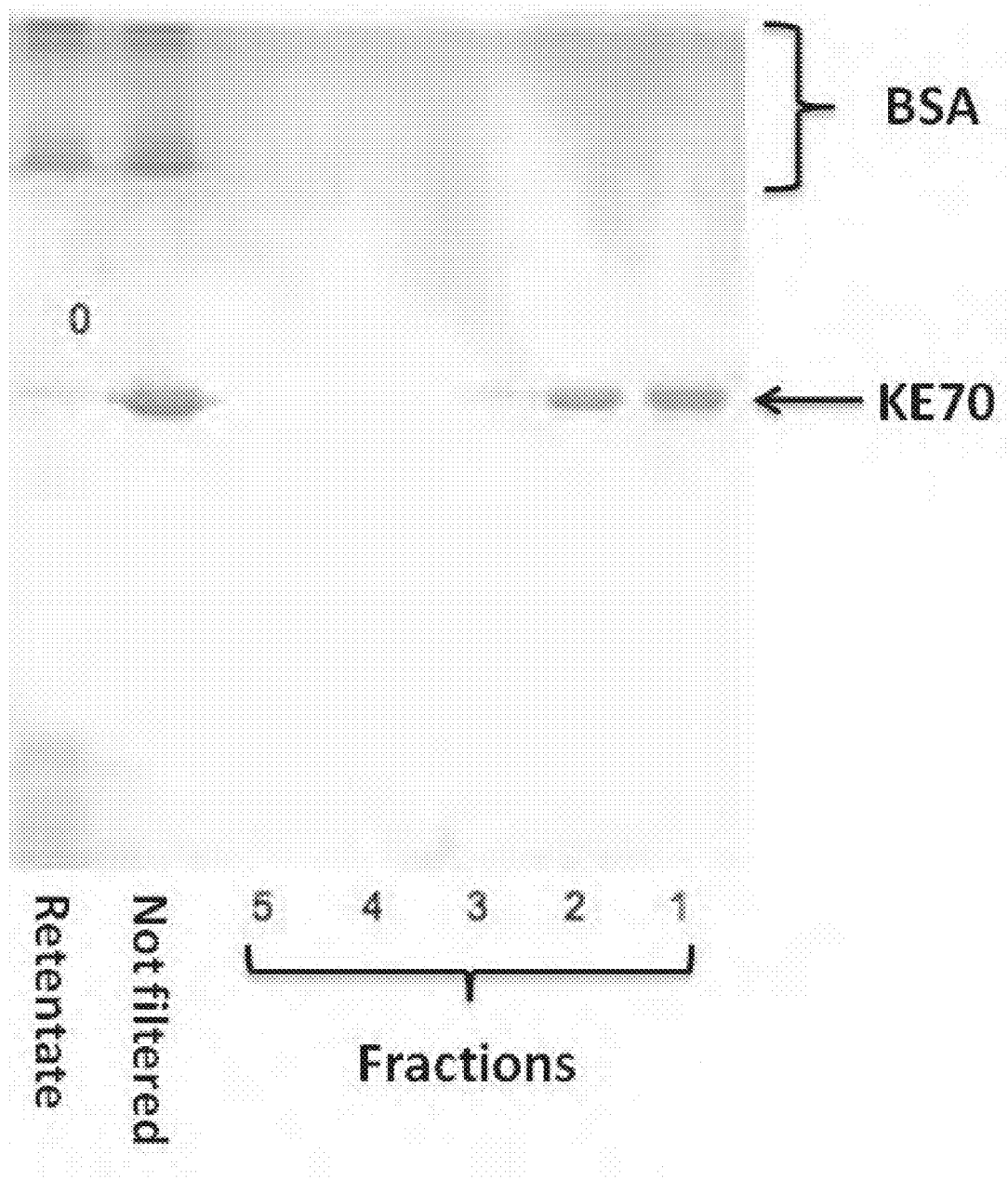
FIG. 31 SDS-PAGE of fractions 1-5, the initial protein solution (not filtered), and the retained proteins isolated from the supramolecular membrane (retentate).
Figure 32:
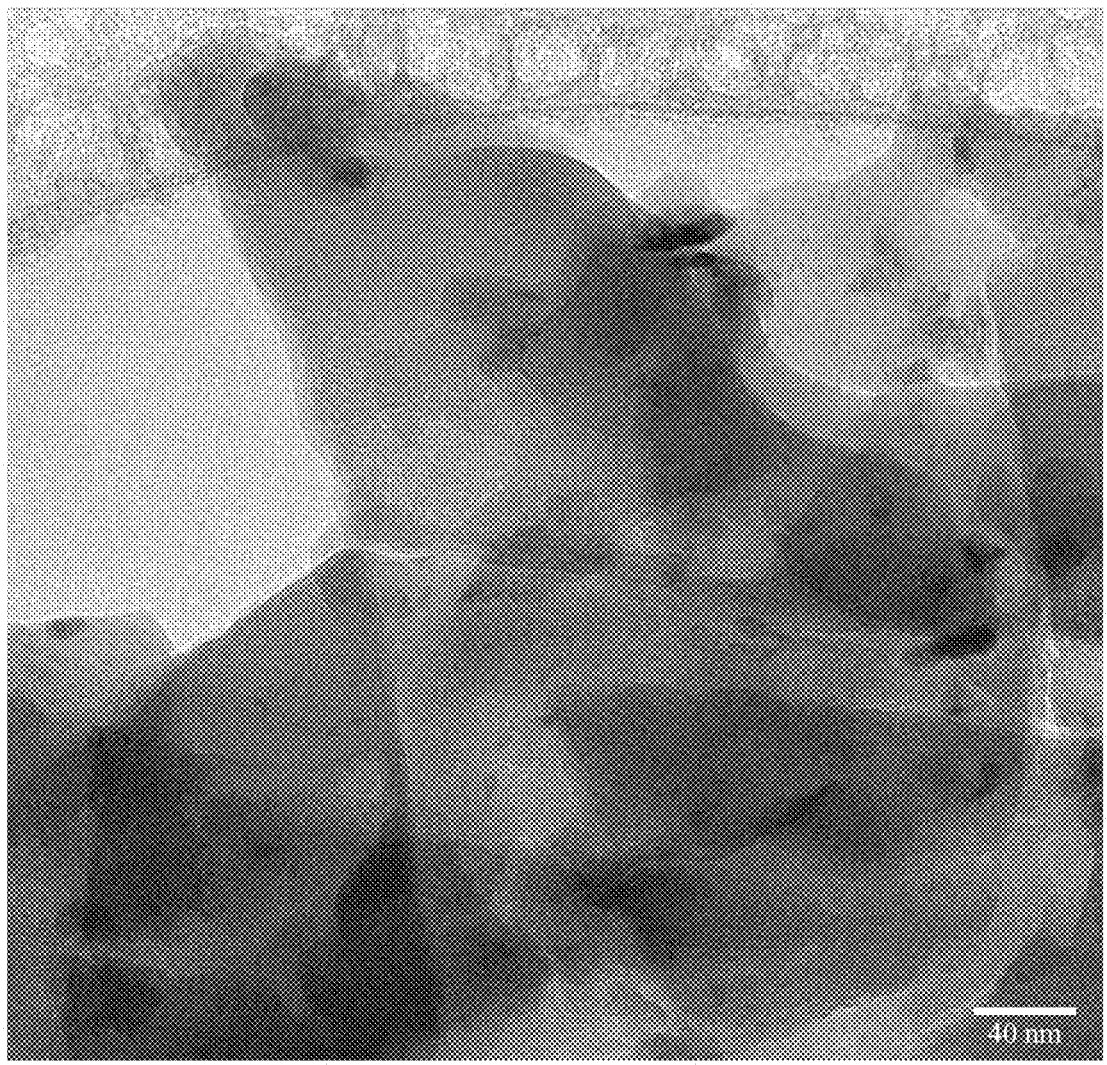
FIG. 32 depicts cryo TEM photograph of Perylene diimide VIII membrane prepared in 5% acetonitrile in water aged 20 hr in 25° C.

As indicated by SDS-PAGE (sodium dodecyl sulfate polyacrylamide gel electrophoresis), fractions 1 and 2 contain pure KE70, fraction 3 contains very small traces of KE70, and the following two fractions are void of any detectable protein concentrations (FIG. 31). In contrast, the retentate isolated from the membrane contains almost pure BSA. The findings were confirmed by the optical density (OD) measurements of the respective solutions at 280 nm (Table 3). The separation of the two proteins is in agreement with the membranes' 5 nm cut-off observed for metal and semiconductor nanoparticles.

TABLE 3

Optical densities (at 280 nm) of fractions 1-5, the initial protein solution (not filtered), and the proteins isolated from the membrane after the filtration experiment (retentate).

| Fraction | OD$_{280}$ |
|---|---|
| Membrane wash | reference |
| 1 | 0.224 |
| 2 | 0.219 |
| 3 | 0.00 |
| 4 | 0.00 |
| 5 | 0.00 |
| Not filtered (diluted proteins) | 0.137 |
| Retentate | 2.04 |

Example 14

Synthesis of Perylene Diimide VIII

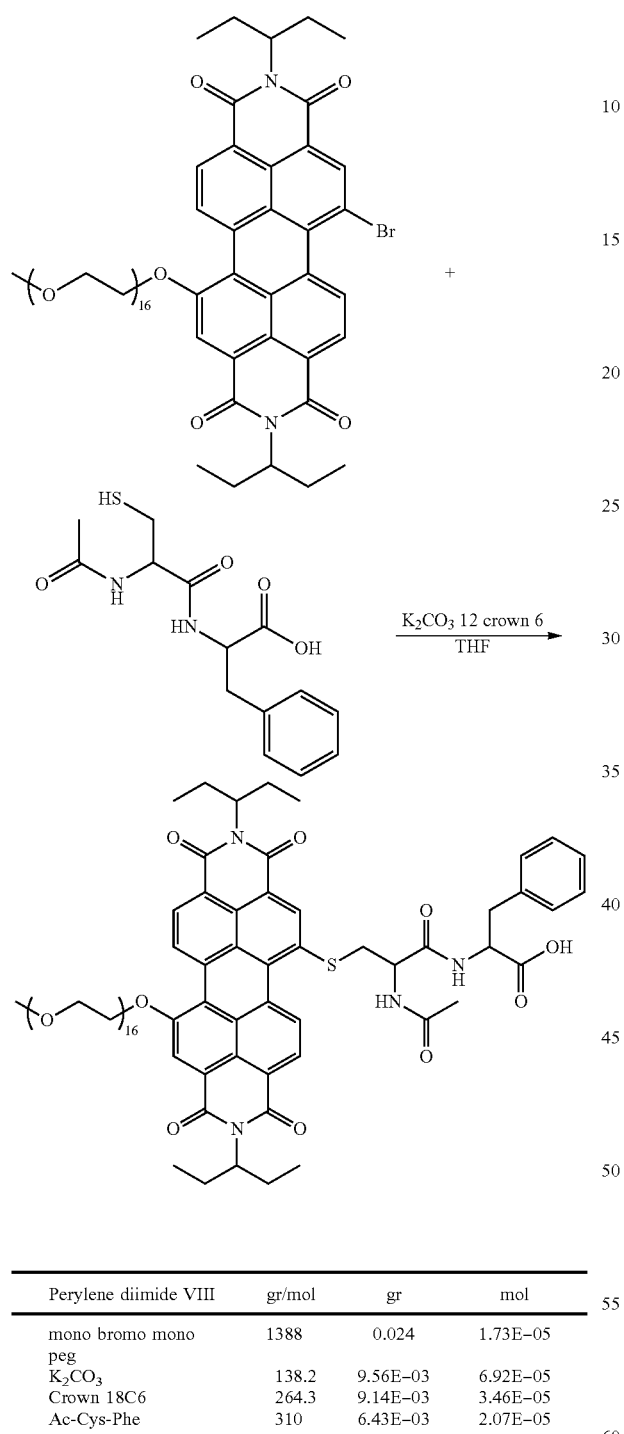

| Perylene diimide VIII | gr/mol | gr | mol |
|---|---|---|---|
| mono bromo mono peg | 1388 | 0.024 | 1.73E−05 |
| $K_2CO_3$ | 138.2 | 9.56E−03 | 6.92E−05 |
| Crown 18C6 | 264.3 | 9.14E−03 | 3.46E−05 |
| Ac-Cys-Phe | 310 | 6.43E−03 | 2.07E−05 |

All the reactants were mixed in a vial under inert gas (inside the nitrogen field glove-box) box and dissolved in dry THF. The reaction mixture was stirred for 20 hr over which it changed color from translucent pink to opaque purple. The THF was removed by evaporation and the remaining solid was dissolved in DCM (dichloromethane) and a prep TLC (thin layer chromatography) was performed in the box, in a 10% MeOH in DCM solution. The product was extracted from the silica using a 1/1 DCM MeOH solution. The product was dried and dissolved in slightly basic water. The product was transferred to a separating funnel and the aqueous phase was washed with DCM. Then the aqueous phase was acidified to pH 2 using 0.1 M HCl and extracted to DCM. The organic phase was washed 3 times with KCl brine. This process was preformed twice in order to get rid of the crown ether. The extract was concentrated and precipitated from hexane and from diethyl-ether, the precipitant was filtered and re-dissolved in DCM.

Example 15

Synthesis of Perylene Diimide XIII

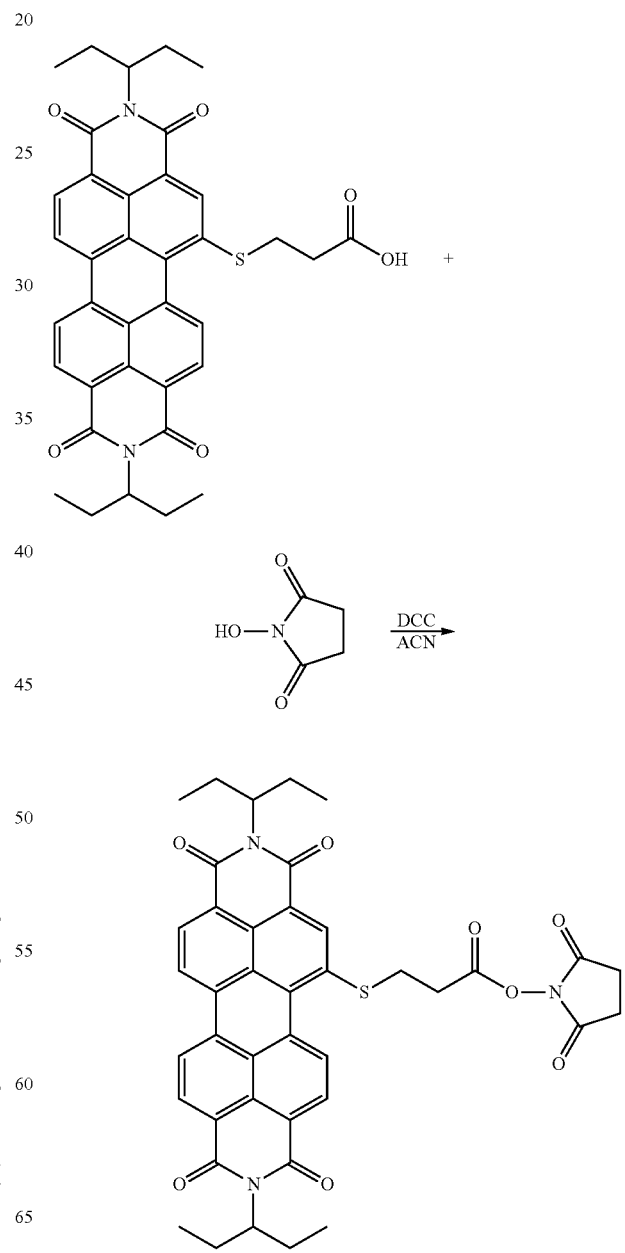

| Perylene diimide XIII | gr/mol | gr | mol | ml | mol/L | gr/ml |
|---|---|---|---|---|---|---|
| PDI-MPA | 6.35E+02 | 8.00E−03 | 1.26E−05 | | | |
| Trp | 2.04E+02 | 5.15E−03 | 2.52E−05 | | | |
| DCC | | | 1.26E−05 | 1.26E−02 | 1.00E+00 | |
| NHS | 1.15E+02 | 2.90E−03 | 2.52E−05 | | | |
| NaHCO3 | 8.40E+01 | 1.06E−03 | 1.26E−05 | | | |

The first step included preparation of the NHS (N-hydroxysuccinimide) activated ester using DCC coupling. In a vile 8 mg PDI-MPA (PDI-3-mercaptopropionic acid)(126E−05 mol) were dissolved in 5 ml acetonitrile. 2.9 mg NHS (2.52E−05 mol 1:2 ratio) were added to the PDI (perylene diimide) solution. 12.6 μl DCC 1N solution in NMP were added. The reaction was left to stir for 4 hr and was monitored by TLC. When no more change was detected the second part of the reaction was preformed.

In the second stage the ester was reacted with Tryptophan.

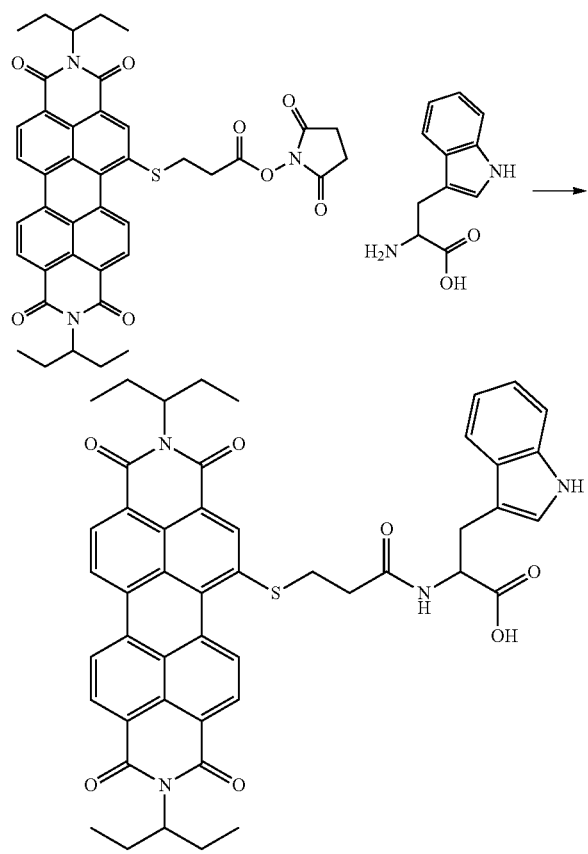

5.15 mg Trp were dissolved in a minimal amount of water by addition of a molar amount of $NaCO_3$ and sonication. The Trp solution was added to the PDI-NMP-NHS solution and was stirred over night. The compound was transferred to a separating funnel and the aqueous phase was washed with DCM. Then the aqueous phase was acidified to pH 2 using 0.1 M HCl and extracted to DCM. The organic phase was washed 3 times with KCl brine. The extract was concentrated and precipitated from hexane and from diethyl-ether, the precipitant was filtered and re-dissolved in DCM. NMR and mass were measured.

Example 16

Separation of Proteins Using the Membrane of this Invention

A mixture of six purified proteins was used to carry out filtration experiments using the membrane of this invention. The mixture included: (1) N-terminal domain of EIIBCA-Bgl residues 2-84(EIIBCA); (2) In silico designed Kemp eliminase (KE70); (3) L-carnitinedehydratase (LCD); (4) L-Fuculose-1-Phosphate Aldolase (Aldolase); (5) Citrate Synthase (CS) and (6) Bovine Serum Albumin (BSA).

This protein mixture presents a broad range of masses, making it suitable for characterization of the filtration cutoff. The proteins were dissolved in MOPS buffer solution (MOPS, 20 mM; KCl, 70 mM; $MgCl_2$, 10 mM; pH=7.0) with an overall protein concentration of 1.8 mg/ml (0.3 mg/ml for each protein). In order to evaluate the actual size of the individual proteins in solution, they were each analyzed by gel filtration chromatography (GFC) and their hydrodynamic diameters ($D_h$) were determined using dynamic light scattering (DLS). We note that not all proteins in the mixture were monomeric; CS exhibited a molecular weight of approximately 288 kDa (from GFC), corresponding to its well-known hexameric form (301 kDa), Aldolase was a tetramer, and the commercially obtained BSA was oligomeric (≥400 kDa, determined by GFC). These findings are consistent with DLS measurements, showing a size increase in the order EIIBCA<KE70<LCD<Aldolase<CS<BSA (Table 4).

TABLE 4

Size-related values of the proteins: Calculated molecular weight (MW), hydrodynamic diameter ($D_h$), and molecular dimensions estimated from X-ray structures.

| Protein | MW [kDa] | $D_h$ [nm] | Protein X-ray structure dimensions (PDB code) [nm] |
|---|---|---|---|
| EIIBCA | 8.7 | 3.4 | n.a. |
| KE70 | 29 | 5.4 | 5.0 × 4.1 × 3.8 (3Q2D) |
| LCD | 92 | 7.2 | n.a. |
| Aldolase | 158 | 8.2 | 7.0 × 7.0 × 5.5 (1DZU) |
| CS (hex.) | 301 | 11.4 | 13.1 × 12.3 × 8.2 (homologous to 1NXG) |
| BSA (olig.)[a] | ≥400 | 12.8, 57.8 | n.a. |

[a]BSA had a bimodal size distribution.

Figure 33:
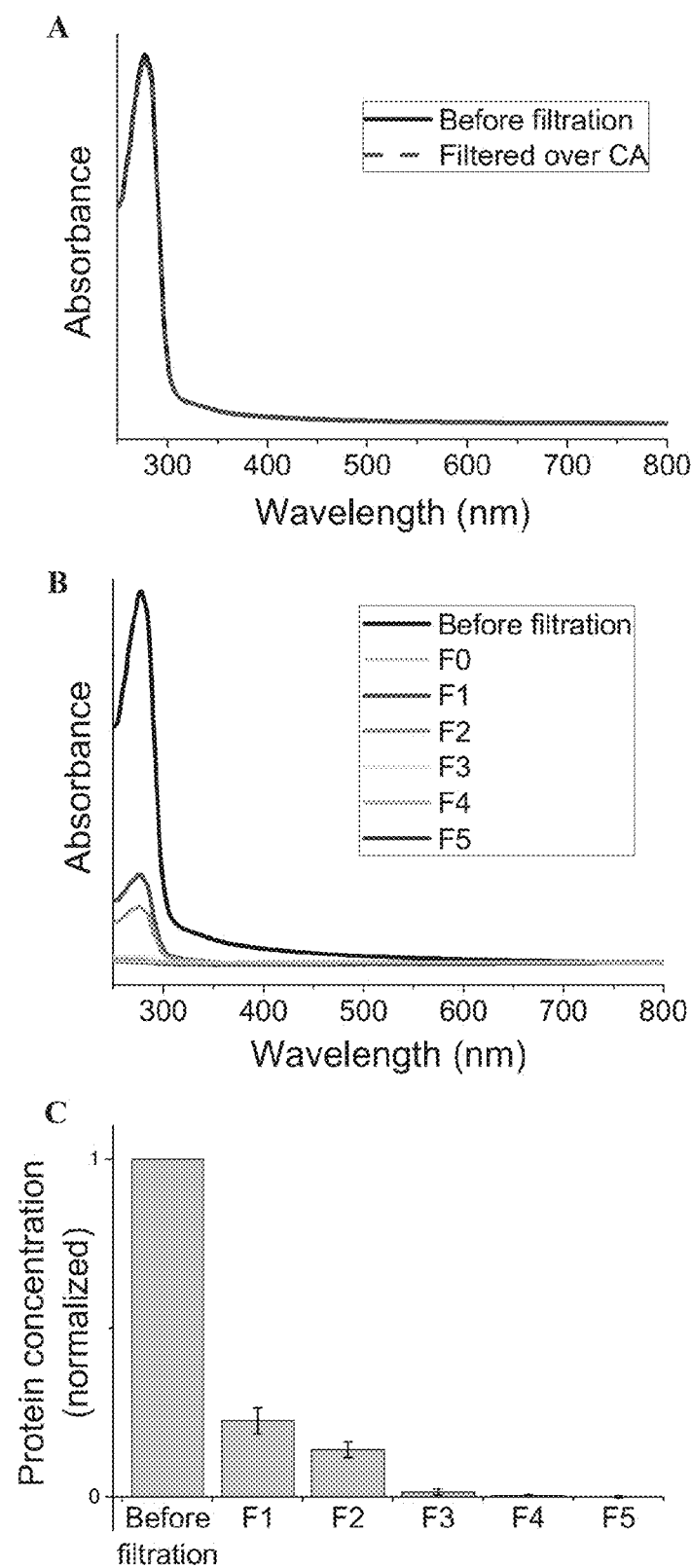
FIG. 33(A)-(C) depicts filtration results of a protein mixture of (1) N-terminal domain of EIIBCA-Bgl residues 2-84(EIIBCA); (2) In silico designed Kemp eliminase (KE70); (3). L-carnitinedehydratase (LCD); (4) L-Fuculose-1-Phosphate Aldolase (Aldolase); (5) Citrate Synthase (CS) and (6) Bovine Serum Albumin (BSA).

Filtration experiments were performed employing a flow of the protein mixture (1.5 ml) in aqueous MOPS buffer solution through a freshly prepared supramolecular membrane at 0.8 bar transmembrane pressure. After the feed solution had passed the membrane, additional clean buffer solution (6 ml) was filtered to rinse out remaining proteins from the membrane. The filtrate was collected in fractions (5×1.5 ml, F1-F5) and UV/Vis spectra were recorded (FIG. 33A-C). Relative protein concentrations for the collected fractions were quantified via absorbance at 280 nm. The fractions did not exhibit any absorption feature in the visible spectrum, showing that no detectable amount of Perylene diimide V($\lambda_{max,1}$=393 nm, $\lambda_{max,2}$=538 nm) was leaching out of the membrane during filtration. The first two filtrate fractions (F1 and F2) contained considerable amounts of protein; F3 contained only minor amounts, whereas F4 and F5 were virtually protein-free (FIG. 33C). Altogether, 38±4% of the proteins passed the membrane. In a control experiment, the protein mixture was also passed through the pristine CA membrane without the Perylene diimide V layer. As confirmed by UV/V is spectra of the filtrate, the CA membrane itself did not retain any proteins (FIG. 33A), showing that the retention is due to the supramolecular membrane only and not caused by adsorption on the support.

Figure 34:
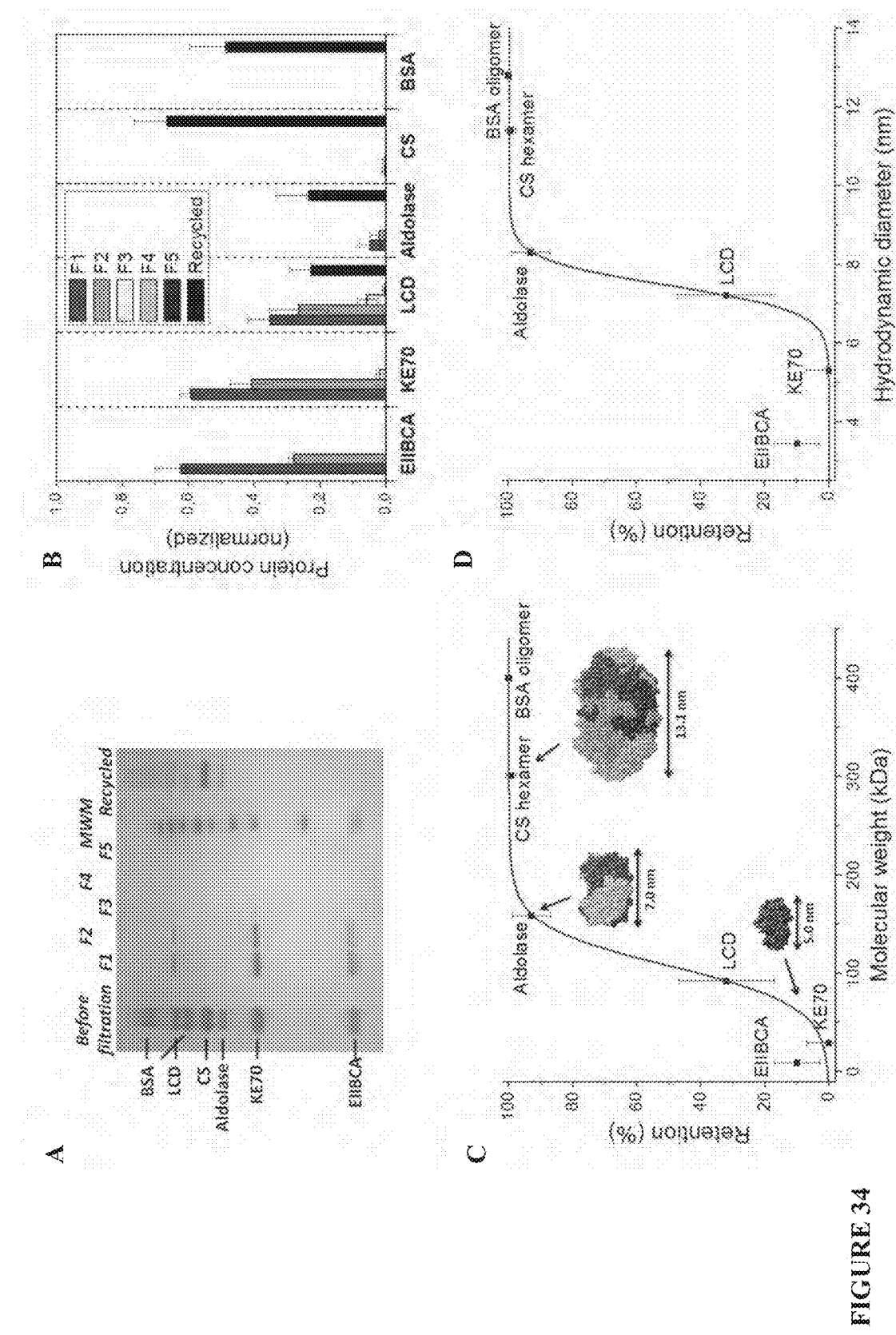
FIG. 34(A)-(D) depicts Separation of protein mixtures over the Perylene diimide V supramolecular membrane.
Figure 35:
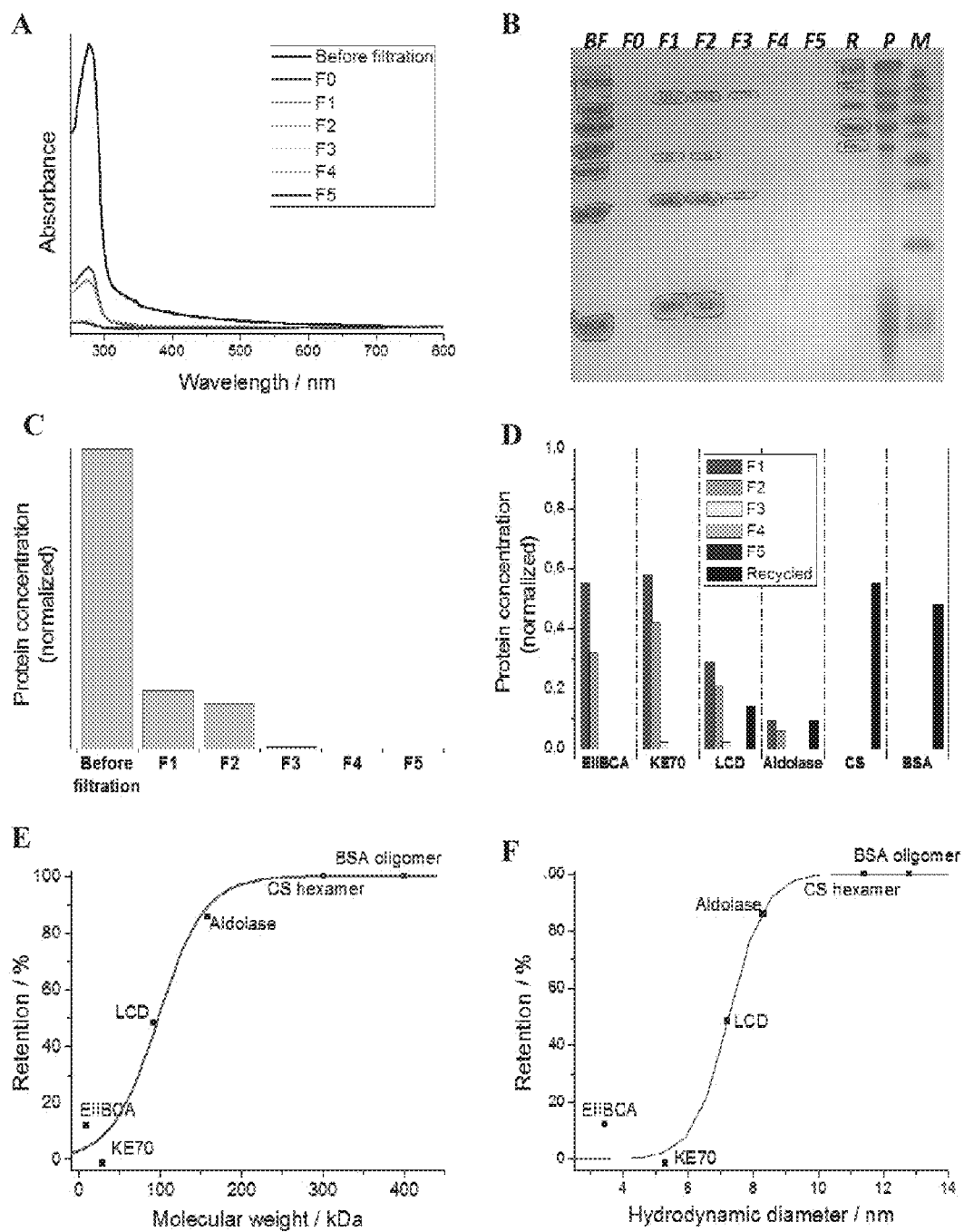
FIG. 35(A)-(F) depicts filtration of proteins over a supramolecular membrane fabricated from recycled Perylene diimide V.

Proteins that were retained on the supramolecular membrane could be partially recycled by dispersing the used membrane in buffer solution (using a vortex mixer), followed by removing the Perylene diimide V supramolecular material via centrifugation. The resulting supernatant contained retained proteins while the pellet contained Perylene diimide V together with some proteins that could not be retrieved. The filtration experiment results were analyzed by sodium dodecyl sulfate polyacrylamide gel electrophoresis (SDS-PAGE) (FIG. 34A). Individual protein concentrations in filtrate and retentate were estimated densitometrically from the gel. Filtration experiments were repeated five times using independently deposited membranes, which showed consistent separation performance.

FIG. 34C shows the retention (the percentage of proteins filtered from the solution) as a function of the molecular weight. The retained particles in the Perylene diimide V membrane are captured in the interior of the membrane rather than on the surface (depth filtration). The retention of proteins is clearly size-dependent and follows a typical sigmoid curve, indicating that size-selective capture (e.g. through mechanical sieving) plays a major role in the filtration process, rather than specific (e.g. electrostatic) protein adsorption. However, adsorption, which often takes place in depth filters, might play a minor role, for instance in the retention of small amounts (~10%) of EIIBCA. The molecular weight cutoff, defined as the theoretical weight of a molecule with 90% retention, was determined from the retention curve (FIG. 34C), as 150 kDa. In terms of hydrodynamic diameter, the membrane cutoff is 8 nm (FIG. 34D).

FIG. 34B presents the concentration of the proteins in each of the filtrate fractions and that of the retained proteins recycled from the membrane. Notably, permeation of the three smaller proteins EIIBCA, KE70, and LCD, showed a size-dependent trend: The smallest (EIIBCA) passed the membrane with a shorttime delay and was completely collected in F1 and F2, whereas the larger (KE70) exhibited a longer delay, and small amounts were detected in F3 as well. Finally, the largest of these three (LCD) was found in considerable amounts in F3, and its traces were detected in F4.

Example 17

Recycling of Proteins and Perylene Diimide V

After the filtration experiment, as described in Example 16, the filter chamber was opened and the Perylene diimide V supramolecular layer was scratched off the cellulose acetate (CA) support and suspended in MOPS buffer solution (1.5 ml). It was vortexed for 1 h in order to disentangle the Perylene diimide V supramolecular fibers, thus releasing retained proteins (R). In order to separate Perylene diimide V from the retained proteins, the solution was centrifuged for 15 minutes at 20800 g (using a desktop centrifuge). The supernatant contained retained proteins while the pellet (P) contained Perylene diimide V together with some retained proteins that could not be extracted. Both supernatant and pellet were analyzed separately by SDS-PAGE, whereby the pellet was highly concentrated due to its small volume. In order to purify Perylene diimide V in the pellet from residual proteins and other organic and inorganic contaminations, ten such pellets were dissolved in 20 ml of a water/ethanol mixture (2:3, v/v). Subsequently, Perylene diimide V was extracted with dichloromethane (40 ml). The colorless aqueous phase was discarded. The organic phase was dried in high vacuum. The solid was washed with hexane (3×50 ml), and with water (1×50 ml). Subsequently, it was purified by silica column chromatography, eluting successively with: 1) 200 ml $CHCl_3$, 2) 200 ml $CHCl_3$/MeOH (98:2, v/v), 3) 200 ml $CHCl_3$/MeOH (92:8, v/v). The product contained pure Perylene diimide V, as revealed by $^1$H-NMR. Nearly quantitative recycling was achieved.

For the retained proteins, about 66% of CS was regained from the filter, whereas only 25% of retained Aldolase could be recycled, possibly due to aggregation or irreversible entrapment within the supramolecular fibers of the membrane material.

The membrane itself can be disassembled in water/ethanol (2:3, v/v), cleaned from contaminations via chromatography over a short silica column, re-assembled, and re-used. Importantly, the membranes prepared from recycled Perylene diimide V had similar thickness and identical separation performance, as compared to the membranes prepared from non-recycled Perylene diimide V (FIG. 35A-F).

Facile recycling and reproducible separation performance after recycling can be regarded as a direct result of the noncovalent nature of the membrane material: its nanoscopic structure (i.e. the three dimensional network of supramolecular fibers) is encoded at the molecular level, allowing simple self-assembly and deposition procedures.

Example 18

Monomer/Aggregate Separation

Figure 36:
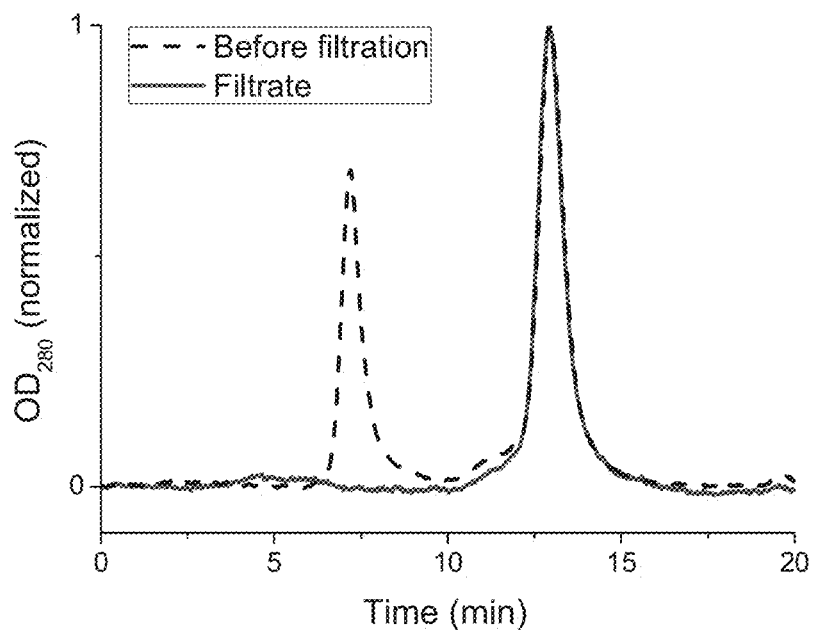
FIG. 36 presents gel filtration chromatogram of a mixture of BSA oligomers and monomers before filtration (dashed line), and its filtrate (black line). Filtration quantitatively removes BSA oligomers (≥400 kDa, retention time: 7 min) from the mixture. Smaller BSA aggregates (retention time: 11-12 min) are removed as well. The filtrate contains pure monomeric proteins (~67 kDa, retention time: 13 min).

In order to demonstrate monomer/aggregate separation, oligomeric BSA was mixed with specially prepared monomeric BSA and the mixture was filtered over the Perylene diimide V supramolecular membrane. Due to their small size, the protein oligomers ($D_h$~12.8 nm) cannot be removed by a standard desktop centrifuge (20800 g). However, as revealed by GFC, the supramolecular membrane efficiently removed oligomeric BSA from the mixture, resulting in a filtrate of pure BSA monomer (FIG. 36).

Example 19

Activity of the Filtered and Recycled Proteins

Activity of Filtered KE70

A solution of KE70 (4 ml, 0.3 mg/ml) in HEPES buffer was filtered over a freshly prepared supramolecular membrane. Due to some dilution in the filter chamber, the filtrate contained KE70 at 89.6% of its original concentration, based on absorbance at 280 nm (Table 5)

TABLE 5

Absorbance at 280 nm ($OD_{280}$) for quantification of the relative enzyme concentrations, line slope of the linear range of the kinetics plot ($\Delta OD_{380}/\Delta t$), relative KE70 concentration and activity.

| | $OD_{280}$ | $\Delta OD_{380}/\Delta t$ [min$^{-1}$] | Relative Conc. [%] | Relative activity [%] |
|---|---|---|---|---|
| Before filtration | 0.1123 | 0.2704 | 100 | 100 |
| Filtrate | 0.1007 | 0.2391 | 89.6 | 88.1 |
| Buffer only | 0.0003 | 0.0080 | 0 | 0 |

Figure 37:
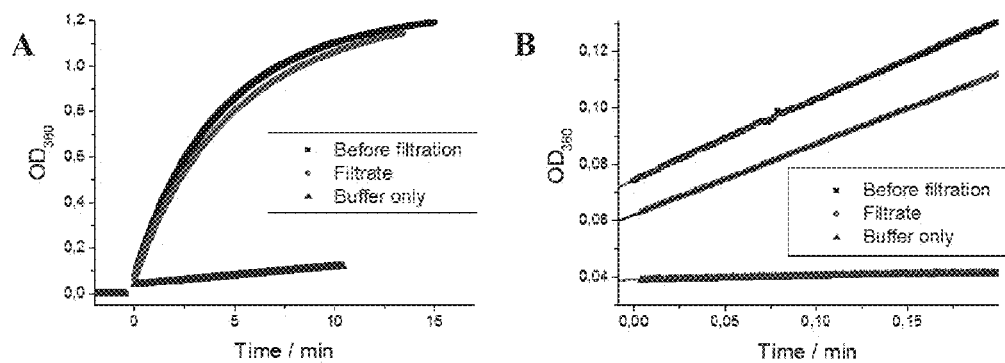
FIG. 37(A)-(B) presents kinetics of the KE70 activity before filtration, after filtration, and of neat buffer solution, as revealed by the change in absorbance at 380 nm, following addition of 5-Nitrobezisoxazole (at t=0 min).

The quantification of KE70 activity in the solution before filtration, in the filtrate, and in neat buffer solution (background reaction) was performed at 25° C. by measuring the kinetics of the enzyme-catalyzed isomerisation of 5-Nitrobezisoxazole via absorbance of the product at 380 nm ($OD_{380}$). For this, 15 µl of the test solution was diluted in 1.5 ml HEPES buffer in a UV/Vis cuvette, and $OD_{380}$ was recorded for several minutes. Then the reaction was started by addition of 1 µl 5-Nitrobezisoxazole from stock solution in acetonitrile (67 µM after dilution) and the kinetics measurement was continued for 10-15 minutes (FIG. 37A). The slope of $OD_{380}$ ($\Delta OD_{380}/\Delta t$) in the linear region of the kinetics plot (FIG. 37B) is proportional to the enzymatic activity under saturation condition. Thus, activity of the filtrate was determined to be 88.1% with respect to the original solution, whilst the concentration determined from OD at 280 nm was 89.6%. Therefore, taking into consideration dilution, the activity of filtered KE70 is ≥98%.

Activity of Recycled CS

In addition to KE70, the enzymatic activity of hexameric CS was tested after filtration. In contrast to KE70, CS was completely retained and recycled from the membrane. In case of retained enzymes, their structure and function might be affected by the extensive contact with the supramolecular material, and by the subsequent recycling procedure. CS activity before filtration and after recycling from the membrane was quantified at 25° C. according to an activity assay: measuring the kinetics of Citrate formation from Oxaloacetate and Acetyl Coenzyme A (Acetyl-CoA) by detecting the indicator of the reaction, 2-nitro-5-thiobenzoate (TNB) at 412 nm ($OD_{412}$).

CS (0.3 mg/ml) in HEPES buffer solution (1.5 ml) was filtered over a freshly prepared supramolecular membrane, followed by 6 ml neat buffer solution. The enzyme was recycled according to the regular procedure (see Example 17). Quantification of the protein concentration of recycled enzyme and of the enzyme solution before filtration was performed via Bradford test (Table 6). (Bradford et al. *Anal. Biochem.* 1976, 72, 248-254)

TABLE 6

Quantification of CS via Bradford test.

| | $OD_{600}$ | Conc. [mg/ml] | Relative Conc. [%] |
|---|---|---|---|
| Before filtration | — | 0.30 | 100 |
| Before filtration (10x diluted) | 0.38 | 0.030 | |
| Recycled | — | 0.079 | 26 |
| Recycled (5x diluted) | 0.20 | 0.016 | |

Figure 38:
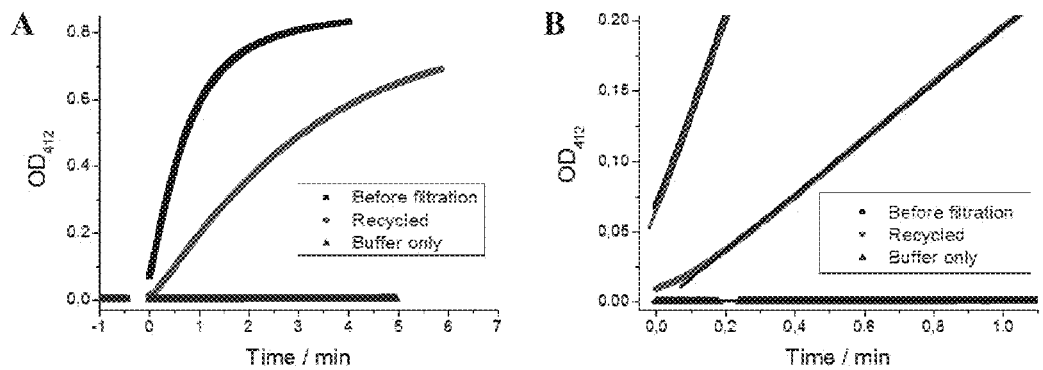
FIG. 38(A)-(B) presents kinetics of the CS activity before filtration, after filtration and recycling from the membrane, and of neat buffer solution, as revealed by the change in absorbance at 412 nm, following addition of Oxaloacetate (at t=0 min).

The activity of CS before and after filtration was quantified at 25° C. according to an activity assay. In a UV/Vis cuvette, 143 µl of the enzyme-containing solution was diluted with HEPES buffers to a total volume of 1.43 ml. Then the following reagents were added successively: 6.0 µl of Ethylenediaminetetraacetic acid (EDTA; 500 mM; final concentration: 2 mM) in water, 15 µl of 5,5'-Dithiobis(2-nitrobenzoate) (DTNB; 10 mM; final concentration: 0.1 mM) in ethanol, and 15 µl of Acetly Coenzyme A (Acetyl-CoA; 14 mM; final concentration: 0.14 mM) in HEPES buffer. Absorbance at 412 nm ($OD_{412}$) was recorded for a few minutes. Then 30 µl of Oxaloacetate (10 mM; final concentration: 0.2 mM) in HEPES buffer was added and $OD_{412}$ was recorded for another 4-5 minutes (FIG. 38A). The slope of $OD_{412}$ ($\Delta OD_{412}/\Delta t$) in the linear region of the kinetics plot (FIG. 38B) is proportional to the enzymatic activity under saturation condition. Thus, activity of the recycled enzymes was determined to be 29% with respect to the original solution (Table 7). This value is in good agreement with the concentration determined from Bradford test (26%), showing that enzymatic activity is conserved during the filtration and recycling process.

TABLE 8

Slope of the linear fits ($\Delta OD_{412}/\Delta t$) in the initial CS activity kinetics, and calculated relative activity.

| | $\Delta OD_{412}/\Delta t$ [min$^{-1}$] | Relative activity [%] |
|---|---|---|
| Before filtration | 0.6749 | 100 |
| Recycled | 0.1974 | 29 |
| Buffer only | 0.0004 | 0 |

Example 20

Biocatalytic Activity of Immobilized Proteins on the Membrane

Filtration of large enzymes results in their immobilization within the supramolecular network, keeping them exposed to the flux of solvent and solutes. Such an array (membrane/immobilized enzyme) may represent a versatile system to carry out biocatalytic reactions in a heterogeneous manner.

β-Galactosidase Activity

The enzymatic activity of membrane-immobilized β-Galactosidase (β-Gal, 465 kDa) was analyzed. β-Gal is significantly larger than the membrane cutoff, resulting in near-quantitative retention. It is ubiquitous in nature and widely utilized in molecular biology, catalyzing the hydrolysis of the glycosidic bond of β-Galactopyranosides. β-Gal and many other hydrolases do not require presence of coenzymes, making them the most relevant enzyme class for biotechnological applications in industry, e.g., β-Gal has wide application in the dairy industry for the production of low-lactose milk.

Figure 39:
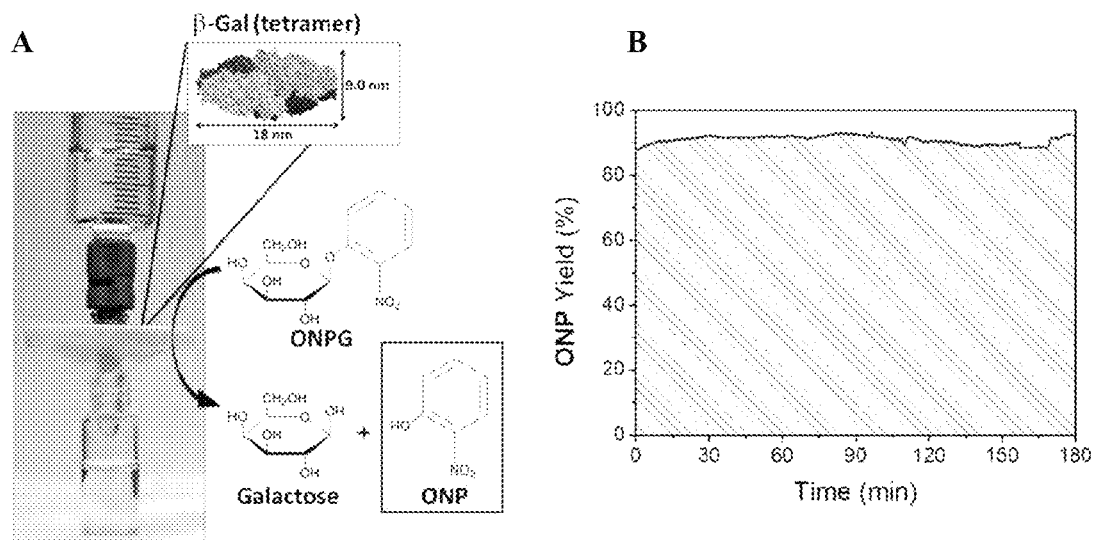
FIG. 39(A)-(B) depicts heterogeneous biocatalysis in the supramolecular membrane using immobilized β-Gal [betta-Galactosidase (b-Gal, 465 kDa)].

For immobilization, 1.5 ml of β-Gal (0.2 mg/ml) was filtered over a freshly prepared supramolecular membrane, and rinsed with 7.5 ml of clean buffer solution. Once the enzyme was retained on the membrane, the solution flux slightly dropped from 20 L h$^{-1}$ m$^{-2}$ to 17 L h$^{-1}$ m$^{-2}$. Subsequently, a typical activity assay solution containing the substrate o-Nitrophenyl β-D-galactopyranoside (ONPG, 0.05 mg/ml) was passed through the membrane. As the colorless ONPG feed solution passed through the membrane it turned yellow, indicating the β-Gal-catalyzed conversion of ONPG into o-Nitrophenol (ONP, $\lambda_{max}$=420 nm) (FIG. 39A). In order to quantify the conversion and to study performance under constant substrate flux for prolonged periods of time, the filter was connected to a UV/Vis flow cuvette, and the absorbance of the filtrate at 420 nm was recorded. Importantly, the reaction showed stable conversion over several hours of uninterrupted substrate flow with an average yield of ~90% ONP (FIG. 39B).

Small amounts of enzyme were observed to leach out of the membrane over time, as expected in immobilization that does not involve covalent attachment of the enzyme to the support. However, enzyme leaching was very low (decreasing from 0.24% to 0.046% activity with respect to the original enzyme solution; and did not influence the overall reaction yield. Emphasizing its remarkable robustness and biocompatibility, the supramolecular membrane/embedded enzyme array sustained stable operation under a constant flux of solution for overall 6 hours (incl. preparation, rinsing steps, and test of enzyme leaching), out of which 3 hours were dedicated to biocatalytic substrate conversion.

Hexameric CS Activity

Figure 40:
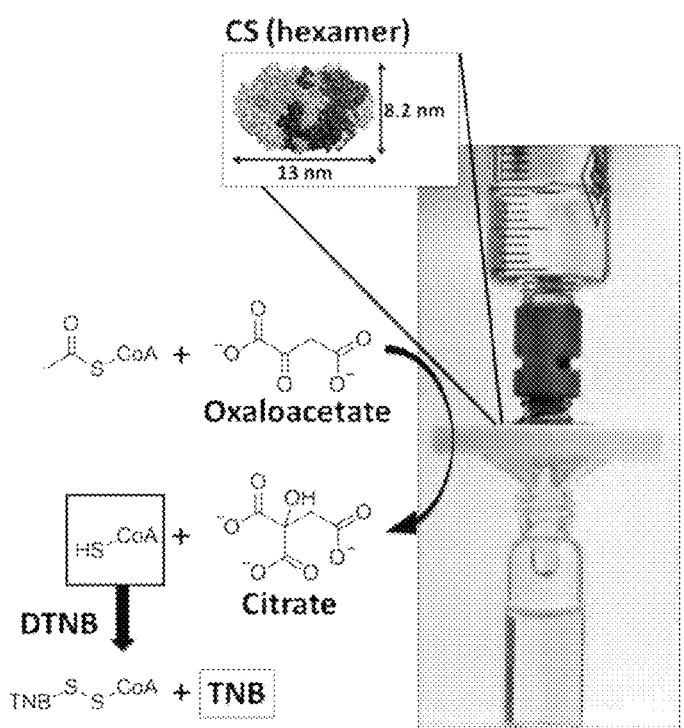
FIG. 40 presents conversion of Oxaloacetate and Acetyl-CoA into Citrate and HS-CoA over CS immobilized in a Perylene V supramolecular membrane. HS-CoA reacts with DTNB in the assay solution to release the indicator of the reaction, TNB ($\lambda_{max}$=412 nm). The color change from clear reactant feed solution to yellow filtrate indicates biocatalytic activity of the immobilized enzymes.

In an additional experiment, hexameric CS was immobilized and tested for its biocatalytic activity. While β-Gal facilitates the degradation of a complex molecule (ONPG) into smaller parts (Galactose, ONP), CS represents a distinctly different case: a simple precursor (Oxaloacetate) is converted into a more complex product (Citrate), requiring the presence of a coenzyme (Acetyl-CoA). CS immobilization was performed by simply filtering 2 ml enzyme solution (0.3 mg/ml) over a freshly prepared supramolecular membrane, followed by rinsing with 10.5 ml clean buffer solution. The activity of immobilized CS was determined using an assay solution (Srere, P. A.; Brazil, H.; Gonen, L., *Acta Chem. Scand.* 1963, 17, S129-S134). When running the mixed solution of Oxaloacetate, Acetyl-CoA, and 5,5'-Dithiobis(2-nitrobenzoate) (DTNB) through the membrane, biocatalytic formation of Citrate was indicated by the yellow color of the filtrate, which resulted from the subsequent reaction between HS-CoA and DTNB, forming TNB ($\lambda_{max}$=412 nm) (FIG. 40). Thus, conversion of Oxaloacetate into Citrate under constant flow of substrate and coenzyme was readily achieved. Similar to β-Gal, leaching of CS was low (~0.23% activity with respect to the original enzyme solution).

Example 21

Synthesis of Pegylated PDI Compounds of this Invention

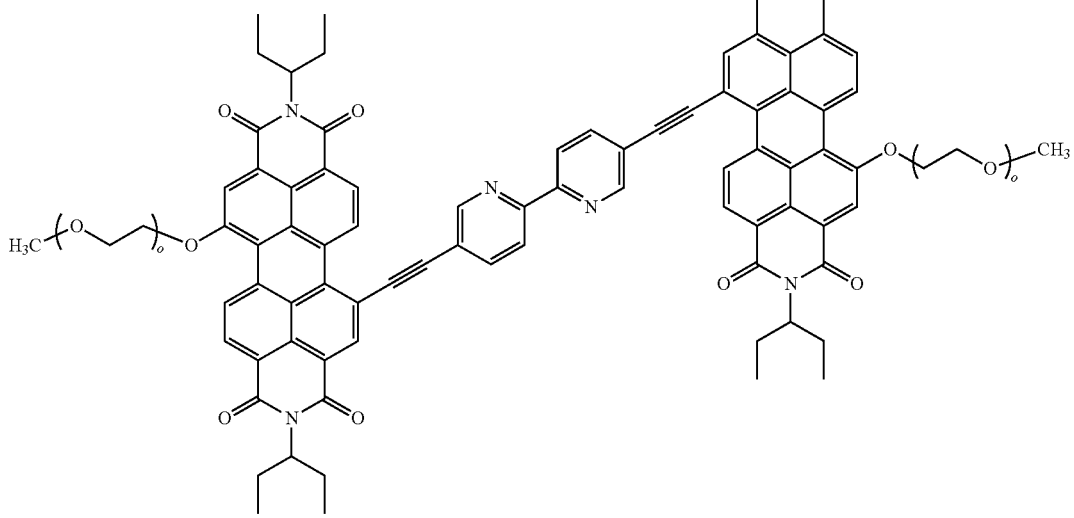

wherein o is between 1-100.

5,5'-Bis(1-PEG17-PDI-7-ethynyl)-2,2'-bipyridine (Compound XV; o=17)

Step 1:

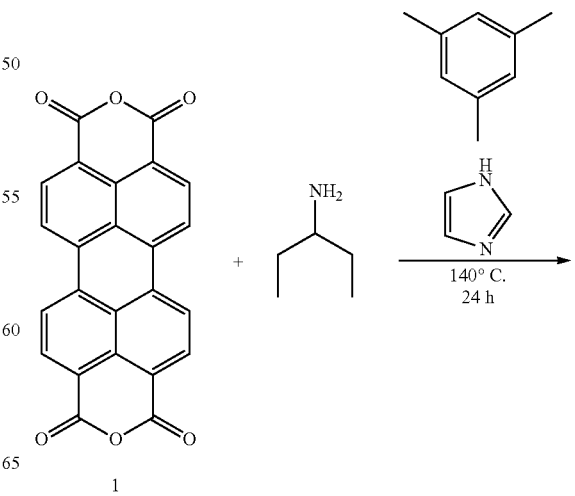

-continued

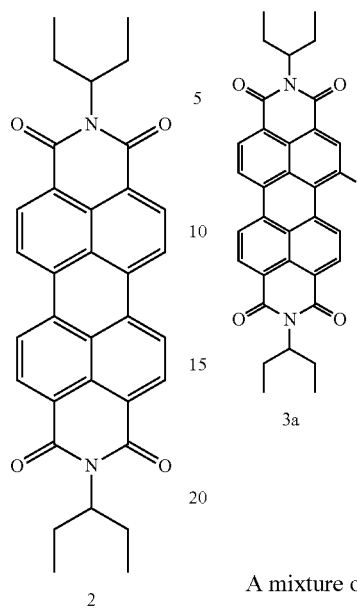

2

5 gr of perylene dianhydride (1), 18 gr imidazole, 4.5 mL ethylpropylamine (3-aminopentane) and 20 mL mesitylene (as additional solvent beside imidazole) were mixed and heated in oil bath to 140° C. deg for 24 h. 200 mL HCl 1M was added and stirred for 20 min. The solution was filtered and washed with EtOH. A red solid was obtained (2) and dried in high vacuum overnight. Yield: 76%.

Step 2

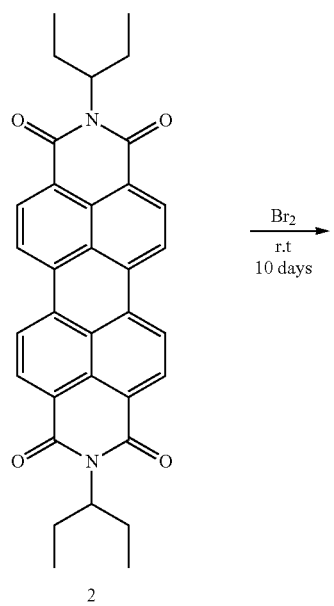

-continued

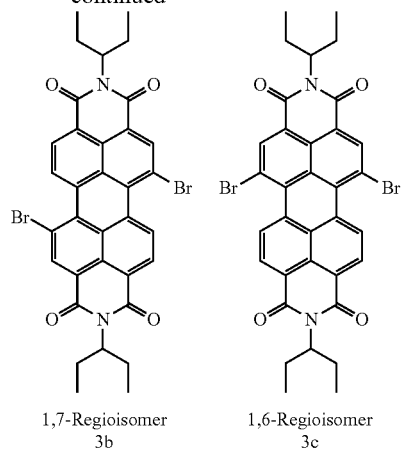

3a     1,7-Regioisomer 3b     1,6-Regioisomer 3c

A mixture of 5.14 gr of perylene diimide (PDI 2), in 150 mL dichloromethane (DCM) was cooled to 0° deg in water bath and 27 mL bromine was added slowly using dropping funnel. The reaction mixture was stirred at room temperature for 10 days (slow reaction at room temp reduces the amount of undesired 1,6 regioisomer, 3c).

The bromine and DCM were evaporated with air bubbling using outlet to $Na_2S_2O_3$ saturated solution. The monobrominated Perylene diimide (3a) was purified using silica column with DCM as eluent.

Step 3: Pegylated PDI.

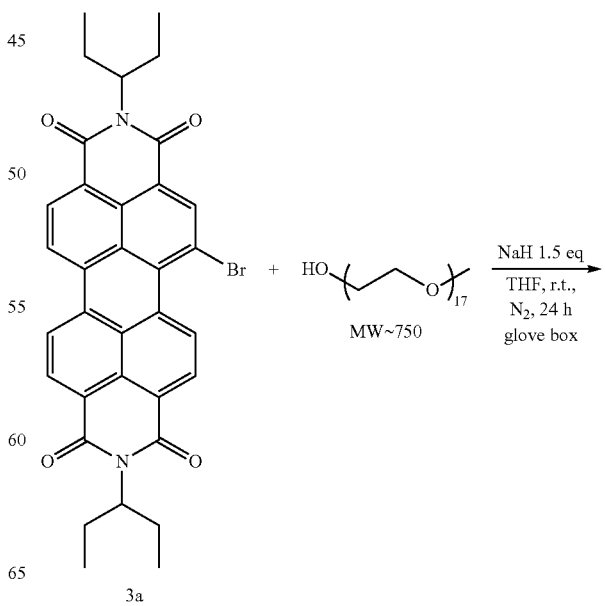

-continued

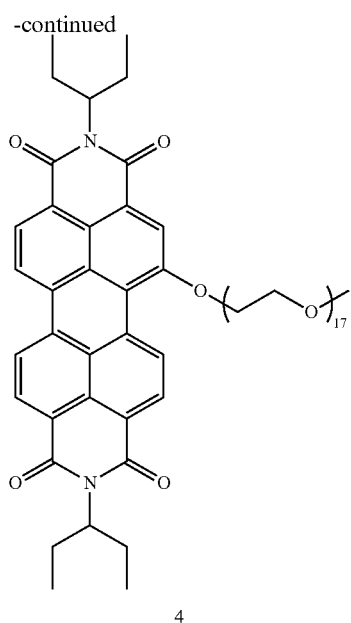

4

200 mg Br-PDI (3a) was dissolved in 30 mL of dry THF. 369 mg of dry PEG17-0H (~750 MW) and 20 mg NaH were added to the reaction mixture. The color changed to purple. The reaction mixture was stirred for 24 h. The reaction is light sensitive, and should be conducted under dark.

The solvent was evaporated. The crude was dissolved in dichloromethane. Diluted HCl 1M solution was added and the layers were separated. The organic layer was collected, the solvent was evaporated and the product (4) was purified by column chromatography using silica and CHCl$_3$/MeOH as eluent mixture.

$^1$H NMR (CDCl$_3$, 300 MHz) of 4: δ=9.72 (d, 1H, J$_{HH}$=8.5 Hz, perylene-H), 8.62 (m, 5H, perylene-H), 8.45 (s, 1H, perylene-H), 5.06 (m, 2H, N(CH(CH$_2$CH$_3$)$_2$), 4.65 (m, 2H, PEG), 4.12 (m, 2H, PEG), 3.87-3.53 (m, 60H, PEG), 3.36 (s, 3H, PEG-OCH$_3$), 2.26 (m, 4H, N(CH(CH$_2$CH$_3$)$_2$), 1.94 (m, 4H, N(CH(CH$_2$CH$_3$)$_2$, 0.92 (t, 12H, J$_{HH}$=7.4 Hz, N(CH(CH$_2$CH$_3$)$_2$)

Step 4: Monobromination of PEG-PDI

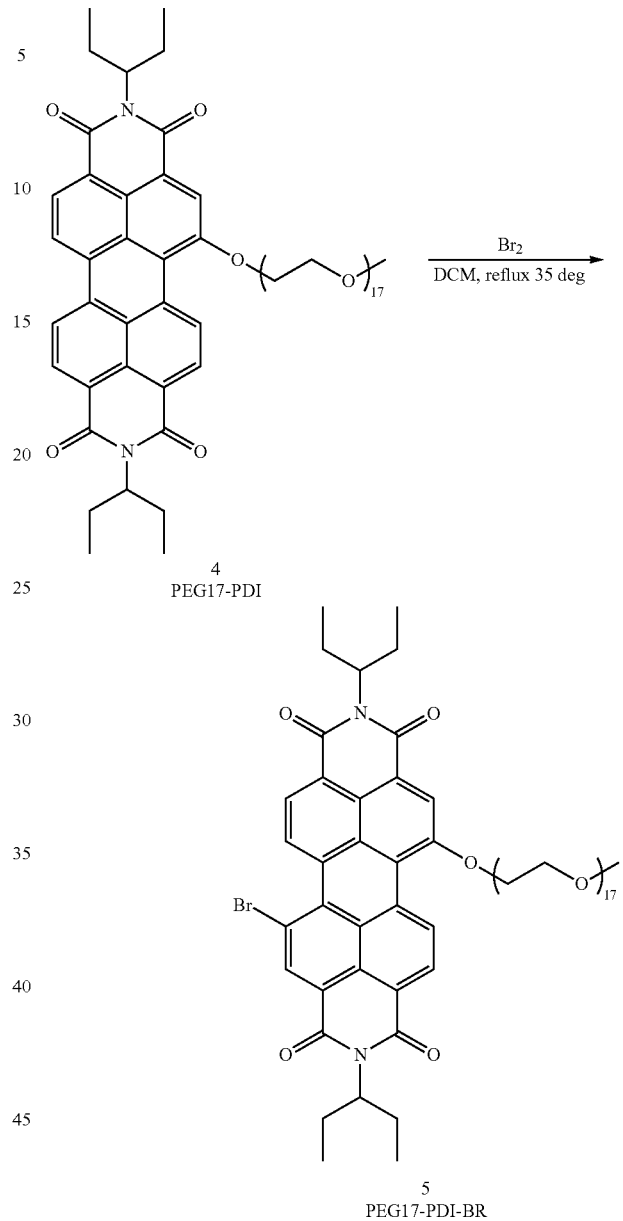

~288 mg of PEG17-PDI (4) was dissolved in 100 mL of dichloromethane (DCM). 2.2 mL of Br$_2$ (cooled in ice) was added carefully. The reaction mixture was stirred under reflux (~35 deg) while monitoring the reaction progress every 1 h using NMR. The reaction was conducted in the dark.

The bromine and DCM were evaporated with air bubbling using outlet to Na$_2$S$_2$O$_3$ saturated solution. The product was purified by column chromatography using silica and CHCl$_3$ or DCM as eluent. The product was dissolved in 10% MeOH/90% CHCl$_3$ and the PEG17-PDI-Br/PEG17-PDI mixture was filtered using PTFE filter and dried under high vacuum overnight. This mixture was used as-is in the following step.

Step 5: 5,5′-Bis(1-PEG17-PDI-7-ethynyl)-2,2′-bipyridine (Compound V)

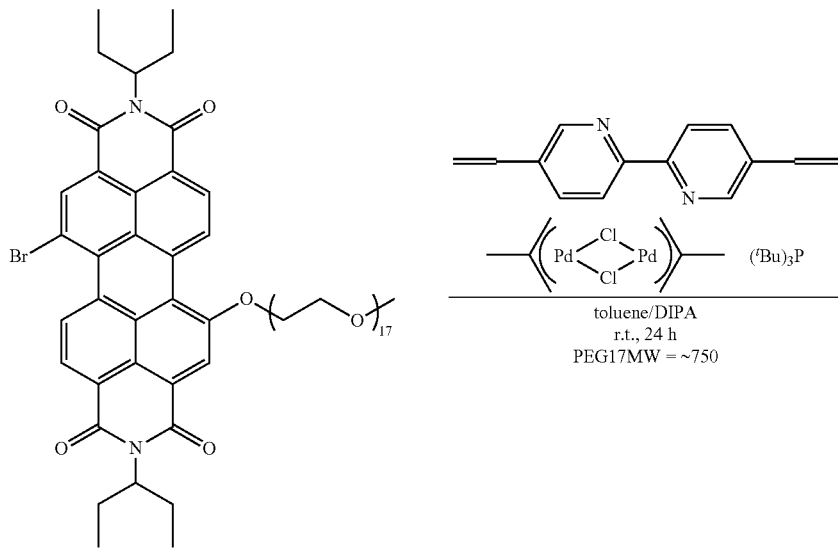

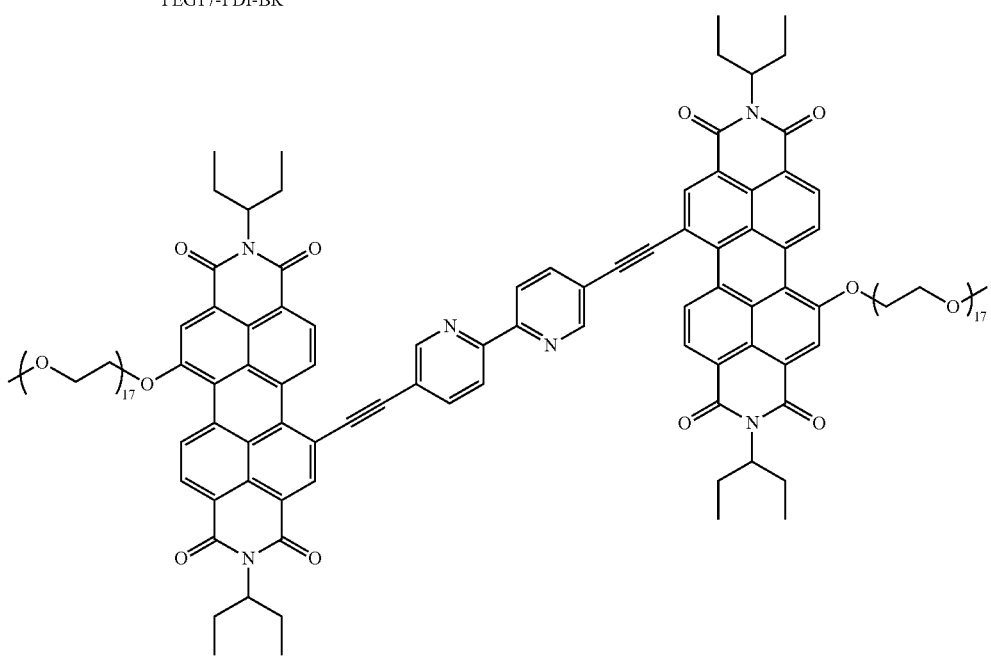

185 mg PEG-PDI-Br (calculated weight of PEG-PDI-Br in the mixture from previous step, based on NMR peak integration) was added to 3 mL dry toluene and the reaction mixture was stirred.

5.4 mg of methyl allyl palladium chloride dimer (catalyst) was added to a separate vial, mixed with 1 mL dry toluene and 55 mg/81 microliter P(tBu)$_3$ and stirred for 30 min.

The mixture in the vial was added to the PEG-PDI-Br reaction mixture and stirred for additional 30 min. 2 mL diisopropylamine (DIPA) was added and stirred for 30 min. 12.5 mg 5,5′-diethynyl-2,2′-bipyridine (as prepared in Example 11) was added and stirred at room temperature for 24 h. The reaction was conducted in the dark.

The solvents were evaporated and the crude was dried under high vacuum (to remove excess DIPA). The crude was washed with distilled H$_2$O and the organic phase was separated, dried with MgSO$_4$ and dried under high vacuum. The crude was washed with hexane following by ether. The residue was purified by column chromatography using silica, starting from acetone as an eluent, following by CHCl$_3$ and finally 10% MeOH/90% CHCl$_3$. Compound X was isolated, filtered using PTFE filter and dried under high vacuum overnight. The product was obtained in 57% yield.

$^1$H NMR (CDCl3, 300 MHz): δ=10.08 (d, 2H, $J_{HH}$=8.2 Hz, perylene-H), 9.73 (d, 2H, $J_{HH}$=8.4 Hz, perylene-H), 8.97 (s, 2H, bipy-H), 8.93 (s, 2H, perylene-H), 8.68 (dd, 4H, $J_{HH}$=8.3 Hz, 4.0 Hz, perylene-H, bpy-H), 8.62 (d, 2H, $J_{HH}$=8.2 Hz, perylene-H), 8.51 (s, 2H, perylene-H), 8.09 (d, 2H, $J_{HH}$=8.2 Hz, bpy-H), 5.08 (m, 4H, N(CH(CH$_2$CH$_3$)$_2$), 4.68 (m, 4H, PEG), 4.12 (m, 4H, PEG), 3.52-3.87 (m, 120H, PEG), 3.37 (s, 6H, PEG-OCH$_3$), 2.28 (m, 8H, N(CH(CH$_2$CH$_3$)$_2$), 1.96 (m, 8H, N(CH(CH$_2$CH$_3$)$_2$), 0.94 (m, 24H, N(CH(CH$_2$CH$_3$)$_2$).

MALDI-TOF-MS m/z calc. for C$_{152}$H$_{204}$N$_6$O$_{44}$: 2818.4. found: 2817.2 [M].

Starting materials were also purified (for recycling) by column chromatography with silica, using aceton as an eluent.

5,5'-Bis(1-PEG13-PDI-7-ethynyl)-2,2'-bipyridine (Compound XV; o=13)

5,5'-Bis(1-PEG13-PDI-7-ethynyl)-2,2'-bipyridine (Compound XV; o=13) was prepared similarly to 5,5'-Bis(1-PEG17-PDI-7-ethynyl)-2,2'-bipyridine (Compound V, Example 3 above) with the exception of using the corresponding OH-PEG13 [—O(CH$_2$CH$_2$O)$_{13}$CH$_3$].

$^1$H NMR (CDCl3, 400 MHz) of 5,5'-Bis(1-PEG13-PDI-7-ethynyl)-2,2'-bipyridine: δ=10.07 (d, 2H, J$_{HH}$=8.2 Hz, perylene-H), 9.74 (d, 2H, J$_{HH}$=8.5 Hz, perylene-H), 8.99 (s, 2H, bipy-H), 8.94 (s, 2H, perylene-H), 8.69 (m, 6H, perylene-H, bpy-H), 8.52 (s, 2H, perylene-H), 8.13 (d, 2H, J$_{HH}$=8.1 Hz, bpy-H), 5.11 (m, 4H, N(CH(CH$_2$CH$_3$)$_2$), 4.68 (m, 4H, PEG), 4.12 (m, 4H, PEG), 3.53-3.87 (m, 96H, PEG), 3.37 (s, 6H, PEG-OCH$_3$), 2.28 (m, 8H, N(CH(CH$_2$CH$_3$)$_2$), 1.96 (m, 8H, N(CH(CH$_2$CH$_3$)$_2$), 0.94 (m, 24H, N(CH(CH$_2$CH$_3$)$_2$).

MALDI-TOF-MS of 5,5'-Bis(1-PEG13-PDI-7-ethynyl)-2,2'-bipyridine m/z calc. for C$_{136}$H$_{172}$N$_6$O$_{36}$: 2466.2. found: 2446.3 [M].

5,5'-Bis(1-PEG23-PDI-7-ethynyl)-2,2'-bipyridine (Compound XV; o=23)

5,5'-Bis(1-PEG23-PDI-7-ethynyl)-2,2'-bipyridine (Compound XV; o=23) was prepared similarly to 5,5'-Bis(1-PEG17-PDI-7-ethynyl)-2,2'-bipyricline (Compound V, Example 3) with the exception of using the corresponding OH-PEG23. [—O(CH$_2$CH$_2$O)$_{23}$CH$_3$].

$^1$H NMR (CDCl3, 400 MHz) of 5,5'-Bis(1-PEG23-PDI-7-ethynyl)-2,2'-bipyridine (Compound XV; o=23): δ=10.07 (d, 2H, J$_{HH}$=8.3 Hz, perylene-H), 9.71 (d, 2H, J$_{HH}$=8.5 Hz, perylene-H), 8.96 (s, 2H, bipy-H), 8.92 (s, 2H, perylene-H), 8.67 (dd, 4H, J$_{HH}$=8.3 Hz, 3.9 Hz, perylene-H, bpy-H), 8.61 (d, 2H, J$_{HH}$=8.4 Hz, perylene-H), 8.49 (s, 2H, perylene-H), 8.08 (d, 2H, J$_{HH}$=9.0 Hz, bpy-H), 5.07 (m, 4H, N(CH(CH$_2$CH$_3$)$_2$), 4.66 (m, 4H, PEG), 4.11 (m, 4H, PEG), 3.52-3.87 (m, 176H, PEG), 3.36 (s, 6H, PEG-OCH$_3$), 2.26 (m, 8H, N(CH(CH$_2$CH$_3$)$_2$), 1.95 (m, 8H, N(CH(CH$_2$CH$_3$)$_2$), 0.94 (m, 24H, N(CH(CH$_2$CH$_3$)$_2$).

MALDI-TOF-MS of 5,5'-Bis(1-PEG23-PDI-7-ethynyl)-2,2'-bipyricline (Compound XV; o=23): m/z calc. for C$_{176}$H$_{252}$N$_6$O$_{56}$: 3346.7. found: 3348.9 [M].

5,5'-Bis(1-PEG44-PDI-7-ethynyl)-2,2'-bipyridine (Compound XV; o=44)

5,5'-Bis(1-PEG44-PDI-7-ethynyl)-2,2'-bipyridine (Compound XV; o=44) was prepared similarly to 5,5'-Bis(1-PEG17-PDI-7-ethynyl)-2,2'-bipyricline (Compound V, Example 3) with the exception of using the corresponding OH-PEG44.[—O(CH$_2$CH$_2$O)$_{44}$CH$_3$].

$^1$H NMR (CDCl3, 400 MHz) of 5,5'-Bis(1-PEG44-PDI-7-ethynyl)-2,2'-bipyridine: δ=10.07 (d, 2H, J$_{HH}$=8.2 Hz, perylene-H), 9.73 (d, 2H, J$_{HH}$=8.5 Hz, perylene-H), 8.98 (s, 2H, bipy-H), 8.94 (s, 2H, perylene-H), 8.69 (dd, 4H, J$_{HH}$=8.2 Hz, 4.5 Hz, perylene-H, bpy-H), 8.63 (d, 2H, J$_{HH}$=8.4 Hz, perylene-H), 8.51 (s, 2H, perylene-H), 8.10 (d, 2H, J$_{HH}$=9.7 Hz, bpy-H), 5.09 (m, 4H, N(CH(CH$_2$CH$_3$)$_2$), 4.67 (m, 4H, PEG), 4.11 (m, 4H, PEG), 3.52-3.87 (m, 344H, PEG), 3.37 (s, 6H, PEG-OCH$_3$), 2.28 (m, 8H, N(CH(CH$_2$CH$_3$)$_2$), 1.95 (m, 8H, N(CH(CH$_2$CH$_3$)$_2$), 0.91 (m, 24H, N(CH(CH$_2$CH$_3$)$_2$).

MALDI-TOF-MS of 5,5'-Bis(1-PEG44-PDI-7-ethynyl)-2,2'-bipyridine: m/z calc. for C$_{260}$H$_{420}$N$_6$O$_{98}$: 5196.8. found: 5211.7 [M+Na$^+$].

Example 22

Membranes of Mixtures of Perylene Diimide Compounds of this Invention as Monomeric Units Mixtures of pegylated PDI monomertic units of Compound XV with different PEG sizes in water (represented by different "o" variable) such as:
mixture of compound XV wherein o=17 (PEG 17) with Compound XV wherein o=23 (PEG 23),
mixture of compound XV wherein o=13 (PEG 13) with Compound XV wherein o=23 (PEG 23) and
mixture of Compound XV wherein o=13 (PEG 13) with Compound XV wherein o=17 (PEG 17); provided interesting supramolecular assemblies.

Preparation of Membranes Including Mixtures of Perylene Diimides of Compound XV with Different PEG Size as Monomeric Units Each component was dissolved in a known amount of CHCl$_3$ and the required volume of each component to reach the desired ratio was transferred into a 2 mL vial with septa cap, gently swirled for mixing and dried in high vacuum for several hours. The desired amount of THF was added and immediately double distilled water was added as well. The mixture was shaken vigorously and sonicated for several minutes such that the solution was homogeneous and transparent.

5% (% Mol) Perylene Diimide Monomeric Unit of Formula XV Wherein o=23 with 95% (% Mol) Perylene Diimide Monomeric Unit of Formula XV Wherein o=13 (2% THF)

5% (% mol) of compound XV, wherein o=23 (PEG23) was mixed with 95% (% mol) of Compound XV, wherein o=13 (PEG13) in water/THF (2% THF by volume)

Figure 41:
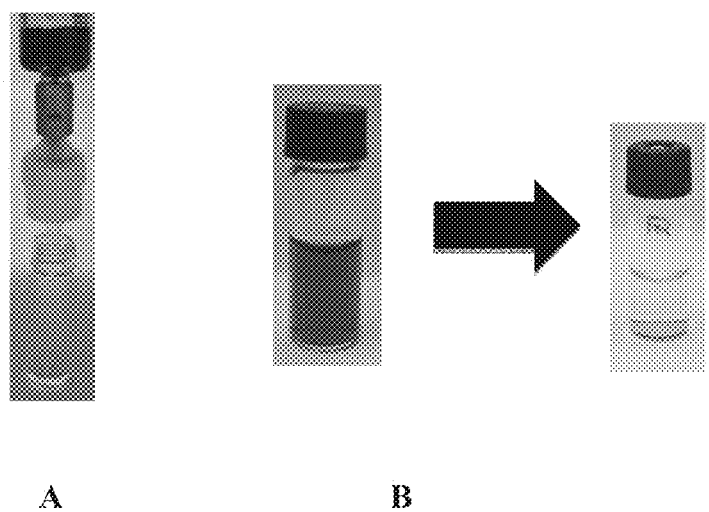
FIG. 41(A)-(C) depicts formation of a membrane from a mixture of different perylene diimide monomeric units of this invention for nanofiltration (Example 21)
Figure 41:
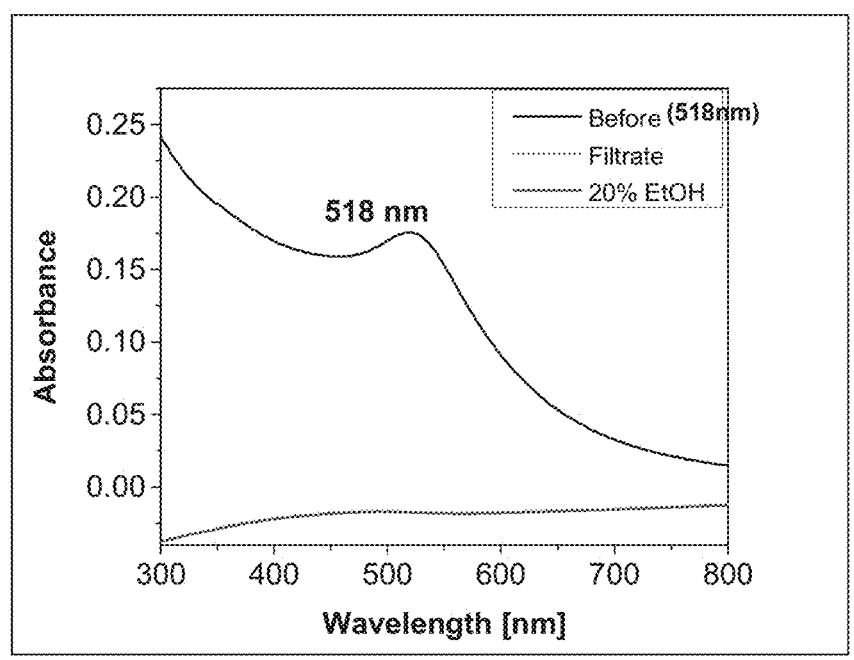

The mixture was deposited on 13 mm diameter PES (0.45 μm) support to form a membrane and was used for nanofiltration. (FIG. 41A-C). The filtration of NEG stabilized Au NP's (1-10 nm, average diameter 5.1±2.3 nm) showed membrane cutoff of ~5 nm (defined as the size larger than 95% of the particles in the filtrate).

Other ratios were disqualified due to faster precipitation (99% PEG13) or weaker fiber interactions that result in partial deposition of the 3D network (some amount passes in case of 10% PEG23). The filtration of NEG stabilized Au NP's (NEG is nonaethylene glycol, 9 units length—H (OCH2CH2)9-H) shows that the membrane cutoff before EtOH modification is ~5 nm (defined as the size larger than 95% of the particles in the filtrate).

Figure 42:
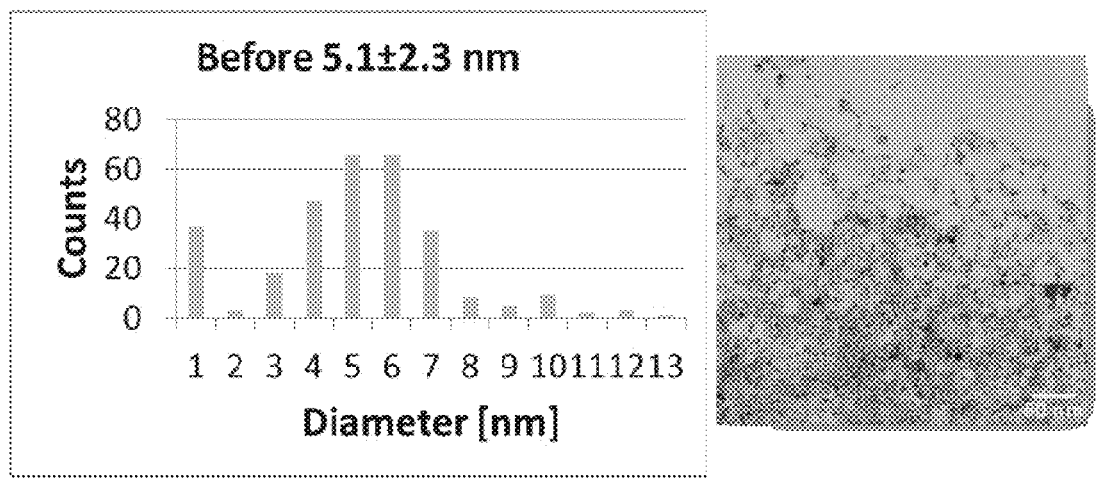
FIG. 42A depicts particle size histogram and corresponding TEM image before filtration of Au nanoparticles (1-10 nm, average diameter 5.1±2.3 nm).
FIG. 42B depicts particle size histogram and corresponding TEM image after filtration (filtrate).
Figure 42:
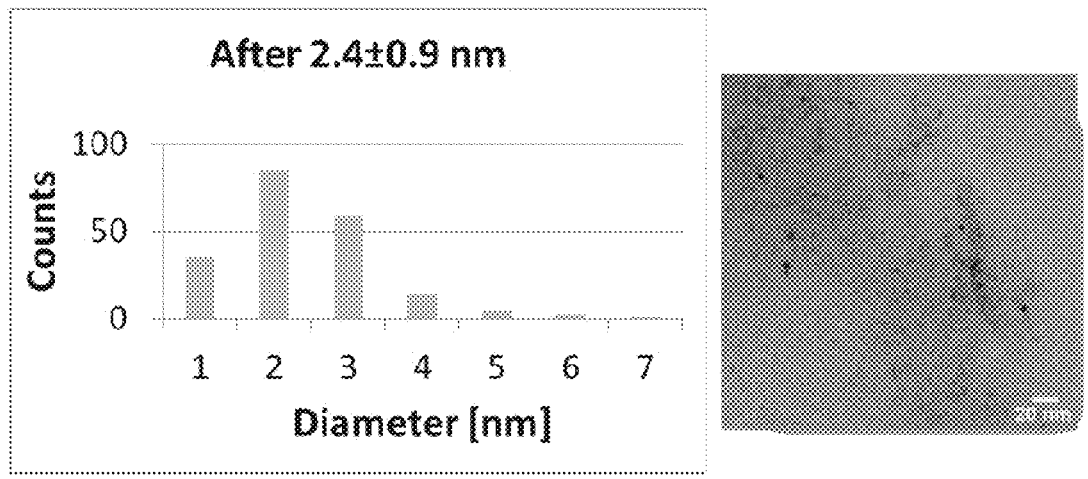

TEM images and the resulting histograms confirm quantitatively size separation of Au nanoparticles (1-10 nm, average diameter 5.1±2.3 nm) on the membrane of this invention, as the average particle size reduces of the from 5.1±2.3 nm to 2.4±0.9 nm (FIGS. 42A and 42B).

Figure 43:
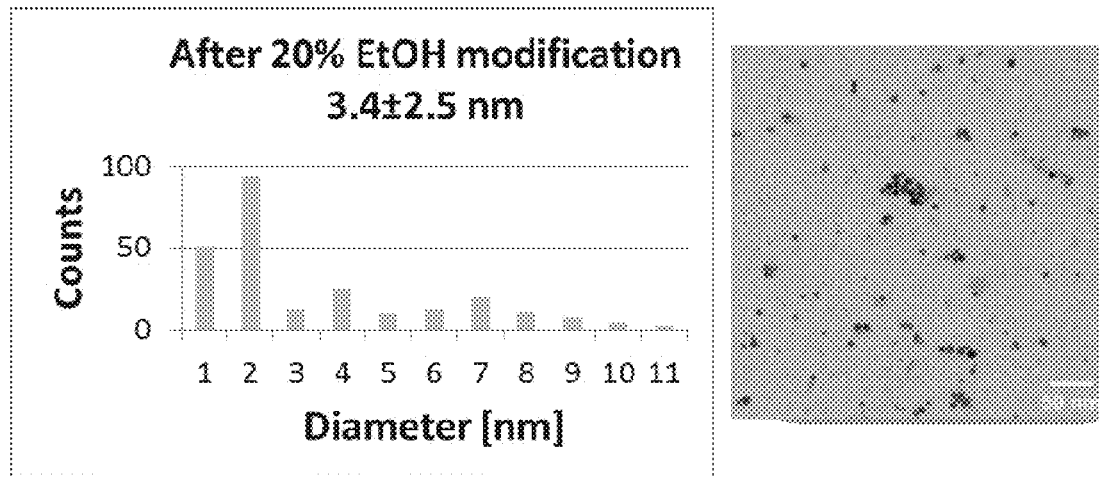
FIG. 43 depicts particle size histogram of Au nanoparticles (1-10 nm, average diameter 5.1±2.3 nm) and corresponding TEM image after filtration (modification with 20% EtOH), using a membrane comprising a mixture of 5% perylene diimide monomeric unit of formula XV wherein o=23 with 95% perylene diimide monomeric unit of formula XV wherein o=13 on 13 mm diameter PES (0.45 μm) support.

Modifying the mixed membrane by washing it with 5 mL of aqueous solution of 20% EtOH solution lead to a larger cutoff. The particles size has increased from the histogram. Meaning, in this case EtOH is increasing pore size (FIG. 43).

5% (% Mol) Perylene Diimide Monomeric Unit of Formula XV Wherein o=13 with 95% (% Mol) Perylene Diimide Monomeric Unit of Formula XV Wherein o=17 (2% THF)

5% (% mol) of compound XV, wherein o=13 (PEG13) was mixed with 95% (% mol) of Compound XV, wherein o=17 (PEG17) in a water/THF (2% THF by volume)

Figure 44:
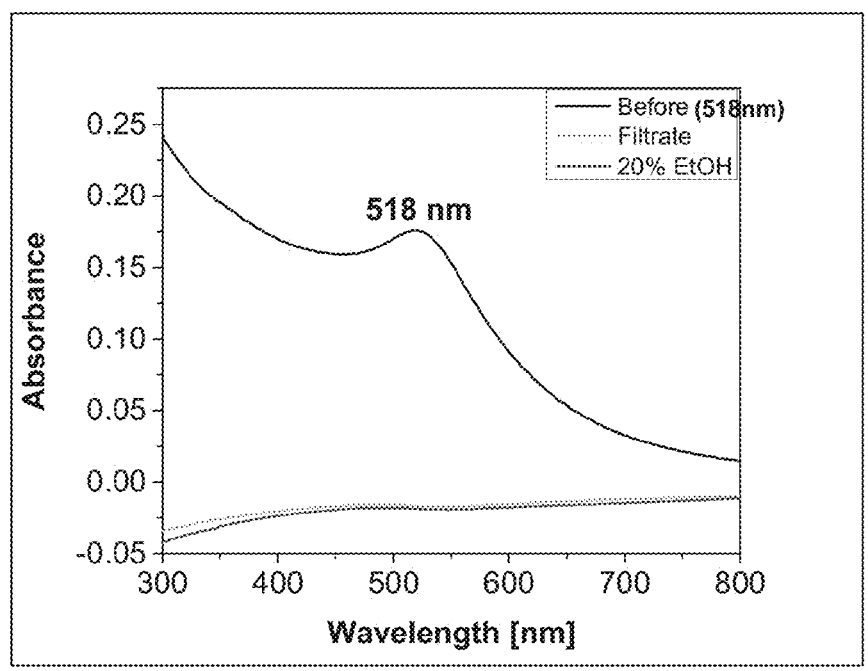
FIG. 44 UV/V is spectra of gold NP's before filtration (black), filtrate (light gray) and 20% EtOH filtrate (dark gray) on a membrane including a mixture of 0.5% (% mol) of compound XV, wherein o=13 (PEG13) was mixed with 95% (% mol,) of Compound XV, wherein o=17 (PEG17).

The mixture was deposited on 13 mm diameter PES (0.45 μm) support to form a membrane and was used for nanofiltration. (FIG. 44). The filtration of NEG stabilized Au NP's (1-10 nm, average diameter 5.1±2.3 nm) showed membrane cutoff of 8 nm (defined as the size larger than 95% of the particles in the filtrate).

In this case very small amount of larger particles had passed the membrane and it cannot be detected by UV.

Figure 45:
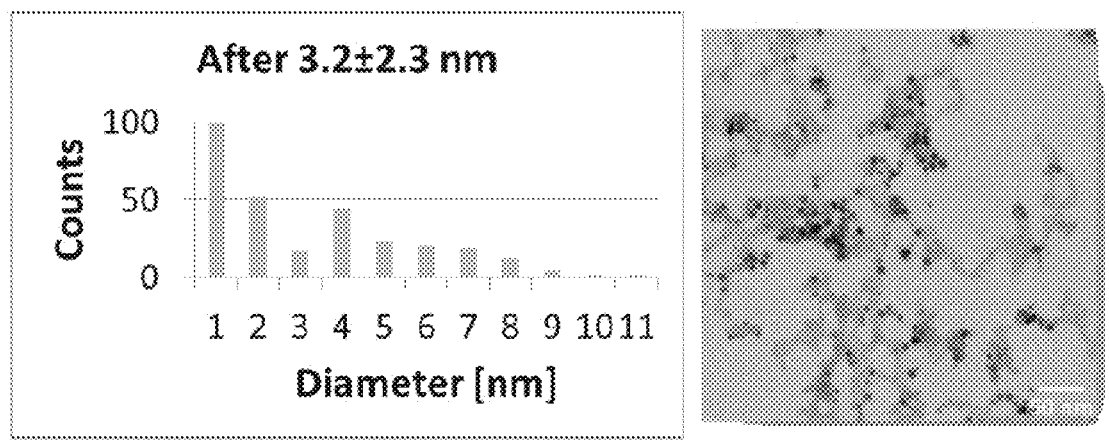
FIG. 45 depicts particle size histogram of Au nanoparticles and corresponding TEM image after filtration, using a membrane comprising a mixture of 5% (% mol) perylene diimide monomeric unit of formula XV wherein o=13 with 95% (% mol) perylene diimide monomeric unit of formula XV wherein o=17 on 13 mm diameter PES (0.45 μm) support.

TEM images and the resulting histograms confirm quantitatively the size separation and pore tuning achieved by the membrane, as the average particle size reduces from 5.1±2.3 nm to 3.2±2.3 nm (FIG. 45).

Figure 46:
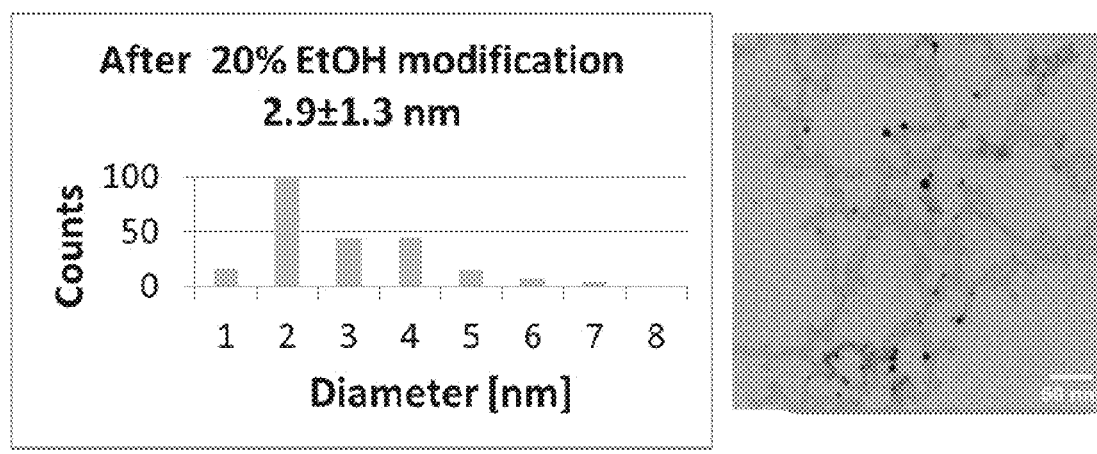
FIG. 46 depicts particle size histogram of AU nanoparticles and corresponding TEM image after filtration, and modification with 20% EtOH using a membrane comprising a mixture of 5% (% mol) perylene diimide monomeric unit of formula XV wherein o=13 with 95% (% mol) perylene diimide monomeric unit of formula XV wherein o=17 on 13 mm diameter PES (0.45 μm) support.

In contrast to the previous mixture, modifying this binary membrane with 5 mL of 20% EtOH solution leads to a decrease in pore size to 5 nm, average particle size is being reduced combined with a change in the histogram (FIG. 46).

Example 23

Membranes of this Invention on NADIR PES Support

Successful deposition of a membrane including a mixture of 5% (% mol) perylene diimide monomeric unit of formula XV wherein o=23 with 95% (% mol) perylene diimide monomeric unit of formula XV wherein o=13 (2% THF) was achieved also on small pore size 20 nm NADIR® PES support, resulting in a slow flow rate of 0.05-0.07 mL/min at 0.6 bar (~0.25 mg perylene diimide mixture/filter). The membrane was disassembled with 60% EtOH/40% $H_2O$ and sonication for 1 min., and was later recycled by transferring into $CHCl_3$ (doesn't require heating). The dry perylene diimide mixture then reassembled under the same conditions and was deposited on the 20 nm support. This system isn't applicable for Au NP's filtration as they tend to be adsorbed on the PES surface.

Example 24

Recycling the Membranes of this Invention

The membranes of this invention including mixtures of perylene diimide of formula XV with different PEG size as monomeric units were easily recycled by our standard procedure (without heating in chloroform: washed with 5 ml of water/ethanol (4:6, v/v); was extracted with 12 ml DCM. The organic phase was partially evaporated in high vacuum; Perylene diimide V was precipitated with hexane and dried in high vacuum see example 10) and could be redeposited in a similar fashion to a freshly prepared perylene diimide based assembled solution.

Figure 47:
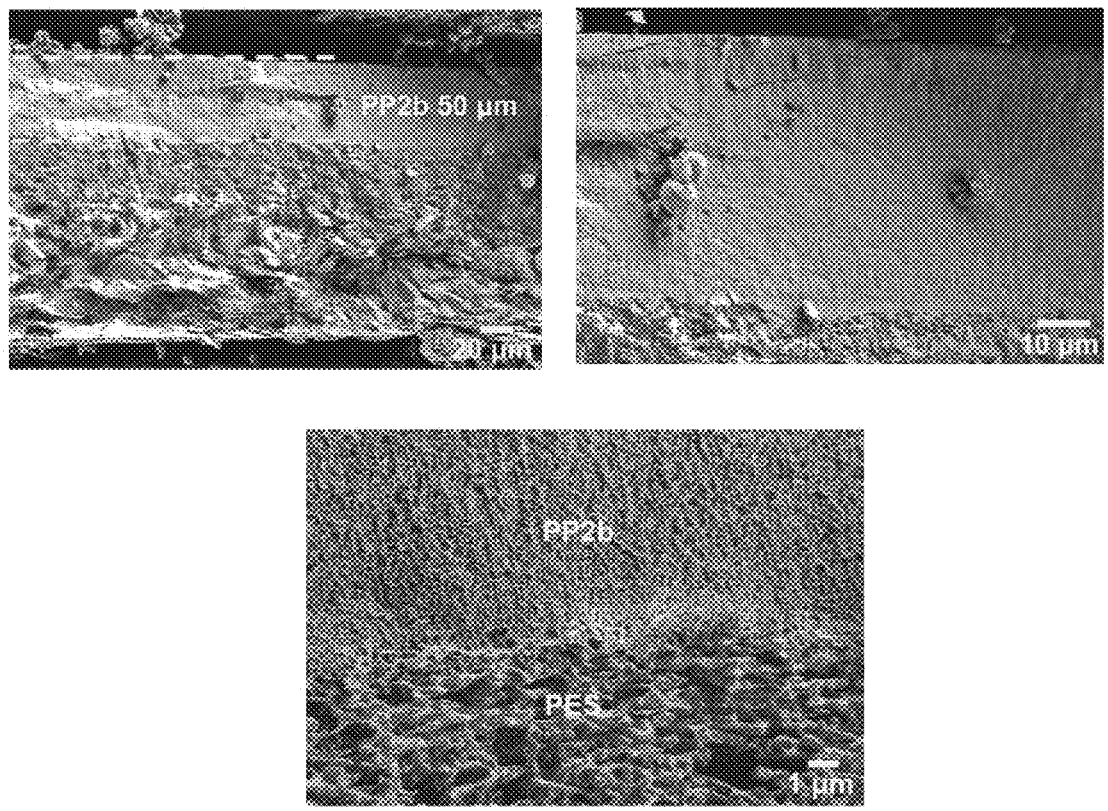
FIG. 47 depicts Cryo-SEM images of freshly prepared mixture of 5% (% mol) perylene diimide monomeric unit of formula XV wherein o=23 with 95% (% mol) perylene diimide monomeric unit of formula XV wherein o=13 supramolecular membrane cross section (~1×1 mm) deposited on the PES support. Each image refers to different magnification. Higher magnification shows the porous structure which is responsible for the size separation.
Figure 48:
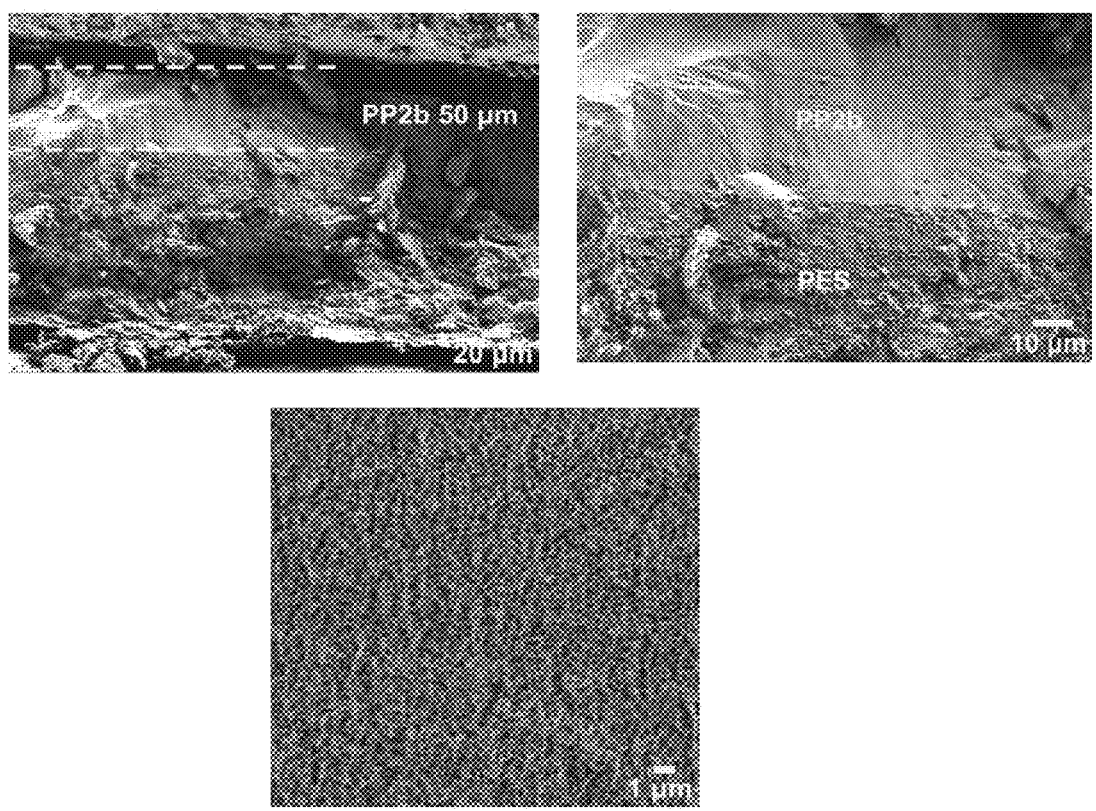
FIG. 48 depicts Cryo-SEM images of recycled mixture of 5% (% mol) perylene diimide monomeric unit of formula XV wherein o=23 with 95% (% mol) perylene monomeric diimide unit of formula XV wherein o=13 supramolecular membrane cross section (~1×1 mm) deposited on the PES support. Each image refers to different magnification. Higher magnification shows the porous structure which is responsible for the size separation.

The fresh and recycled membranes including 5% (% mol) perylene diimide monomeric unit of formula XV wherein o=23 with 95% (% mol) perylene diimide monomeric unit of formula XV wherein o=13 (2% THF) were imaged using Cryo-SEM. The membrane cross-section (FIG. 47 and FIG. 48) shows the sharp border between the PES support and the perylene diimide layer (thickness of ~50 μm), whereas higher magnifications present 3D porous network of fibers which facilitates the size separation.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. Noncovalent self-assembled porous membrane comprising a perylene diimide supramolecular structure, which provides a chromatography medium for size-selective separation of nano-material; wherein said perylene diimide supramolecular structure comprises a mixture of perylene diimide compounds, wherein each perylene diimide compound is a monomeric unit represented by the structure of formula I:

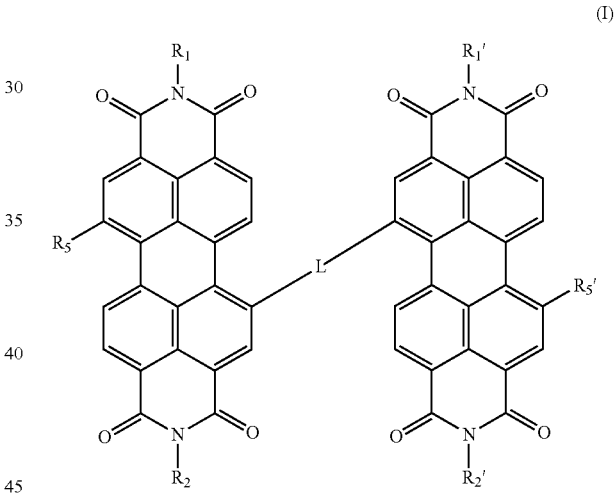

wherein
$R_1$ and $R_1'$ are each independently $[(CH_2)_qO]_rCH_3$, $[(CH_2)_qO]_rH$ $[(CH_2)_qC(O)O]_rCH_3$, $[(CH_2)_qC(O)NH]_rCH_3$, $[(CH_2)_qCH_2{=}CH_2]_rCH_3$, $[(CH_2)_qCH{=}CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2{=}CH_2]_rCH_3$, $[(alkylene)_qCH{=}CH]_rCH_3$, $[(alkylene)_qNH]_rCH_3$, $(C_1$-$C_{32})$alkyl, $(C_3$-$C_8)$cycloalkyl, aryl, heteroaryl, chiral group, $(C_1$-$C_{32})$alkyl-COOH, $(C_1$-$C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1$-$C_6$ alkyl) or O—$(C_1$-$C_6$ alkyl); wherein A comprises three same or different of the following substituents Cl, Br, I, $O(C_1$-$C_8)$alkyl or $(C_1$-$C_8)$alkyl; and wherein $R_3$ in said $[C(O)CHR_3NH]_pH$ is an alkyl, haloalkyl, hydroxyalkyl, hydroxyl, aryl, phenyl, alkylphenyl, alkylamino and independently the same or different when p is larger than 1;

$R_2$ and $R_2'$ are each independently $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$alkyl, $(C_3-C_8)$ cycloalkyl, aryl, heteroaryl, chiral group, $(C_1-C_{32})$ alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are each independently $R_5$ and $R_5'$ are each independently H, —$OR_x$ where $R_x$ is $C_1-C_6$ alkyl, $[(CH_2)_nO]_oCH_3$ or $[(CH_2)_nO]_oH$; $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, aryl, heteroaryl, C≡C—$R_7$, CH=$CR_8R_9$, $NR_{10}R_{11}$, chiral group, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_7$ is H, halo, $(C_1-C_{32})$alkyl, aryl, $NH_2$, alkyl-amino, COOH, C(O)H, alkyl-COOH heteroaryl, $Si(H)_3$ or $Si[(C_1-C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$alkyl);

$R_8$, $R_9$, $R_{10}$ and $R_{11}$ are each independently H, $(C_1-C_{32})$alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

L is ethynyl group or a diethynylbenzene group;
n is an integer from 1-5;
o is an integer from 1-100;
p is an integer from 1-100;
q is an integer from 1-5;
r is an integer from 1-100; and
s is an integer from 1-100;

wherein if $R_5$ and/or $R_5'$ are chiral; said membrane will form a chiral membrane; wherein said mixture comprises between 2 to 10 different perylene diimide compounds of formula I.

2. The porous membrane of claim 1, wherein the pores size of said membrane have a cutoff size of between 2-100 nm.

3. The porous membrane of claim 1, wherein said nanomaterials are nanoparticles or biomolecules.

4. The porous membrane of claim 1, wherein the size of said pores depends on the thickness of the membrane, wherein the thickness of said membrane is between 5-100 μm.

5. A method of preparing a noncovalent self-assembled perylene diimide based membrane of claim 1 comprising:
  a. preparing an organic solution of a mixture of perylene diimide compounds, wherein the organic solvent in said organic solution is miscible in water;
  b. adding excess of water to said solution of (a); wherein the ratio between said organic solvent to water is between about 1:99% to 8:92% v/v;
  c. evaporating said organic solvent; and
  d. transferring the remaining aqueous solution or emulsion through a solid support;
  thereby obtaining a noncovalent self-assembled perylene diimide based membrane.

6. The method of claim 5, wherein said method comprises further washing said membrane with ethanol.

7. The method of claim 5, wherein said organic solvent is tetrahydrofuran (THF), dimethylacetamide (DMA), dimethylformamide (DMF), acetonitrile, acetone, methanol, ethanol or any combination thereof.

8. The method of claim 5, wherein said solid support is a microfiltration filter comprising cellulose acetate (CA), PES, teflon (PTFE) or polycarbonate, or microfiltration filter with pores smaller or equal to 0.45 microns.

9. A method of separation/filtration or purification of nanoparticles comprising (a) transferring an aqueous solution or emulsion comprising a membrane of claim 1 through porous solid support, thereby forming a noncovalent self assembled perylene diimide based membrane on said porous solid support; (b) transferring nanoparticles through said noncovalent self-assembled perylene diimide based membrane of step (a); wherein the particles which are larger than the pores of said membrane remain on said membrane.

10. The method of claim 9, wherein said noncovalent self-assembled perylene diimide based membrane is further recycled.

11. The method of claim 10, wherein said recycling comprises; (a) washing said solid support with the noncovalent self-assembled perylene diimide based membrane and the retentate deposited thereon, with a solution of alcohol and water; (b) extracting said perylene diimide structure from said solution with an organic solvent; and (c) isolating said perylene diimide from said organic solvent.

12. The method of claim 11, wherein said isolated perylene diimide can be further used to form a noncovalent self-assembled perylene diimide based membrane in aqueous conditions.

13. Noncovalent self-assembled porous membrane comprising a perylene diimide supramolecular structure, which provides a chromatography medium for size-selective separation of nano-material; wherein said perylene diimide supramolecular structure comprises a mixture of perylene diimide compounds, wherein each perylene diimide compound is a monomeric unit represented by the structure of formula I:

(I)

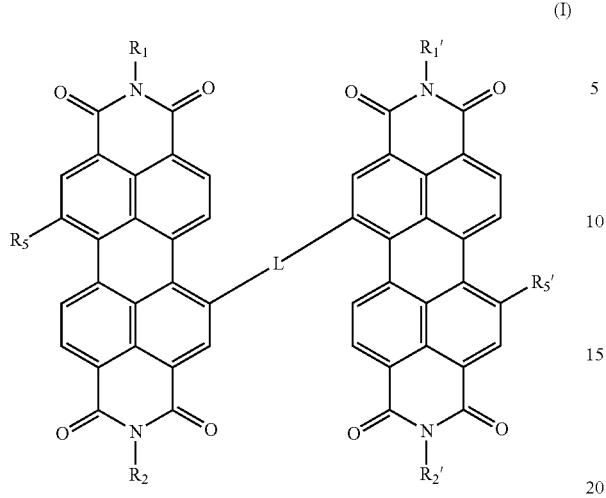

wherein

R$_1$ and R$_1$' are each independently [(CH$_2$)$_q$O]$_r$CH$_3$, [(CH$_2$)$_q$O]$_r$H [(CH$_2$)$_q$C(O)O]$_r$CH$_3$, [(CH$_2$)$_q$C(O)NH]$_r$CH$_3$, [(CH$_2$)$_q$CH=CH$_2$]$_r$CH$_3$, [(CH$_2$)$_q$CH≡CH]$_r$CH$_3$, [(CH$_2$)$_q$NH]$_r$CH$_3$, [(alkylene)$_q$O]$_r$CH$_3$, [(alkylene)$_q$C(O)O]$_r$CH$_3$, [(alkylene)$_q$C(O)NH]$_r$CH$_3$, [(alkylene)$_q$CH$_2$=CH$_2$]$_r$CH$_3$, [(alkylene)$_q$ CH≡CH]$_r$CH$_3$, [(alkylene)$_q$NH]$_r$CH$_3$, (C$_1$-C$_{32}$)alkyl, (C$_3$-C$_8$)cycloalkyl, aryl, heteroaryl, chiral group, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$)alkyl; and wherein R$_3$ in said [C(O)CHR$_3$NH]$_p$H is an alkyl, haloalkyl, hydroxyalkyl, hydroxyl, aryl, phenyl, alkylphenyl, alkylamino and independently the same or different when p is larger than 1;

R$_2$ and R$_2$' are each independently [(CH$_2$)$_q$O]$_r$CH$_3$, [(CH$_2$)$_q$C(O)O]$_r$CH$_3$, [(CH$_2$)$_q$C(O)NH]$_r$CH$_3$, [(CH$_2$)$_q$CH$_2$=CH$_2$]$_r$CH$_3$, [(CH$_2$)$_q$CH≡CH]$_r$CH$_3$, [(CH$_2$)$_q$NH]$_r$CH$_3$, [(alkylene)$_q$O]$_r$CH$_3$, [(alkylene)$_q$C(O)O]$_r$CH$_3$, [(alkylene)$_q$C(O)NH]$_r$CH$_3$, [(alkylene)$_q$CH$_2$=CH$_2$]$_r$CH$_3$, [(alkylene)$_q$CH=CH]$_r$CH$_3$, [(alkylene)$_q$NH]$_r$CH$_3$, (C$_1$-C$_{32}$)alkyl, (C$_3$-C$_8$)cycloalkyl, aryl, heteroaryl, chiral group, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$)alkyl; and wherein R$_4$ in said [C(O)CHR$_4$NH]$_s$H is an alkyl, haloalkyl, hydroxyalkyl, hydroxyl, aryl, phenyl, alkylphenyl, alkylamino and independently the same or different when s is larger than 1;

R$_5$ and R$_5$' are each independently R$_5$ and R$_5$' are each independently H, —OR$_x$ where R$_x$ is C$_1$-C$_6$ alkyl, [(CH$_2$)$_n$O]$_o$CH$_3$ or [(CH$_2$)$_n$O]$_o$H; [(CH$_2$)$_n$C(O)O]$_o$CH$_3$, [(CH$_2$)$_n$C(O)NH]$_o$CH$_3$, [(CH$_2$)$_n$CH$_2$=CH$_2$]$_o$CH$_3$, [(CH$_2$)$_n$CH≡CH]$_o$CH$_3$, [(CH$_2$)$_n$NH]$_o$CH$_3$, [(alkylene)$_n$O]$_o$CH$_3$, [(alkylene)$_n$C(O)O]$_o$CH$_3$, [(alkylene)$_n$C(O)NH]$_o$CH$_3$, [(alkylene)$_n$CH$_2$=CH$_2$]$_o$CH$_3$, [(alkylene)$_n$CH=CH]$_o$CH$_3$, [(alkylene)$_n$NH]$_o$CH$_3$, aryl, heteroaryl, C≡C—R$_7$, CH=CR$_8$R$_9$, NR$_{10}$R$_{11}$, chiral group, amino acid, peptide or a saturated carbocyclic or heterocyclic ring wherein said saturated heterocyclic ring or heteroaryl contains at least one nitrogen atom and R$_5$ or R$_5$' are connected via the nitrogen atom and wherein said saturated carbocyclic ring, heterocyclic ring, aryl and heteroaryl groups are optionally substituted by 1-3 groups comprising halide, aryl, heteroaryl, CN, CO$_2$H, OH, SH, NH$_2$, CO$_2$—(C$_1$-C$_6$ alkyl) or O—(C$_1$-C$_6$ alkyl);

R$_7$ is H, halo, (C$_1$-C$_{32}$)alkyl, aryl, NH$_2$, alkyl-amino, COOH, C(O)H, alkyl-COOH heteroaryl, Si(H)$_3$ or Si[(C$_1$-C$_8$)alkyl]$_3$ wherein said aryl or heteroaryl groups are optionally substituted by 1-3 groups comprising halide, aryl, heteroaryl, CN, CO$_2$H, OH, SH, NH$_2$, CO$_2$—(C$_1$-C$_6$ alkyl) or O—(C$_1$-C$_6$ alkyl);

R$_8$, R$_9$, R$_{10}$ and R$_{11}$ are each independently H, (C$_1$-C$_{32}$)alkyl, aryl, NH$_2$, alkyl-amino, COOH, C(O)H, alkyl-COOH or heteroaryl wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl);

L diethynyldipyridine group;

n is an integer from 1-5;

o is an integer from 1-100;

p is an integer from 1-100;

q is an integer from 1-5;

r is an integer from 1-100; and s is an integer from 1-100;

wherein if R$_5$ and/or R$_5$' are chiral; said membrane will form a chiral membrane;

wherein said mixture comprises between 2 to 10 different perylene diimide compounds of formula I;

wherein if R$_1$, R$_1$', R$_2$ and R$_2$' are isopentyl and both R$_5$ and R$_5$' are [(CH$_2$)$_n$O]$_o$CH$_3$] and n is 2, then o is different for each compound and o is between 15-20 or 30-60.

14. The membrane of claim 13, wherein said perylene diimide supramolecular structure comprises a mixture of perylene diimide compounds, wherein each compound is a monomeric unit represented by the structure of formula XV:

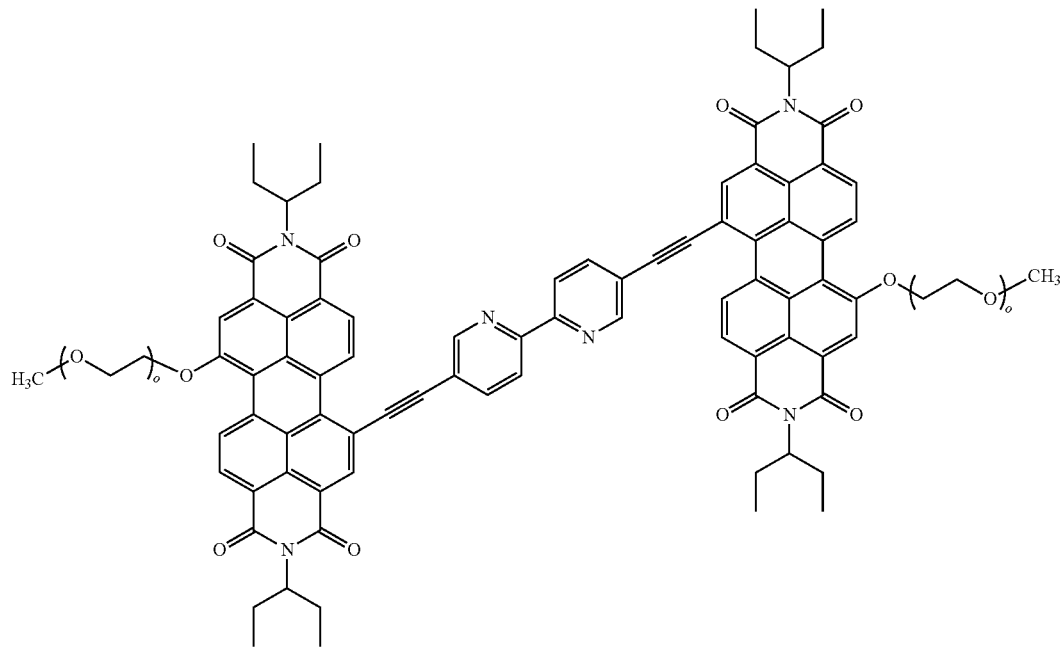

(XV)

wherein said mixture comprises between 2 to 10 different perylene diimide compounds of formula XV, each with a different "o" integer.

15. The membrane of claim 14, wherein said perylene diimide supramolecular structure comprises a mixture of two different perylene diimide compounds.

16. Noncovalent self-assembled porous membrane comprising a perylene diimide supramolecular structure, which provides a chromatography medium for size-selective separation of nano-material; wherein said perylene diimide supramolecular structure comprises a mixture of perylene diimide compounds, wherein each perylene diimide compound is a monomeric unit represented by the structure of formula XV:

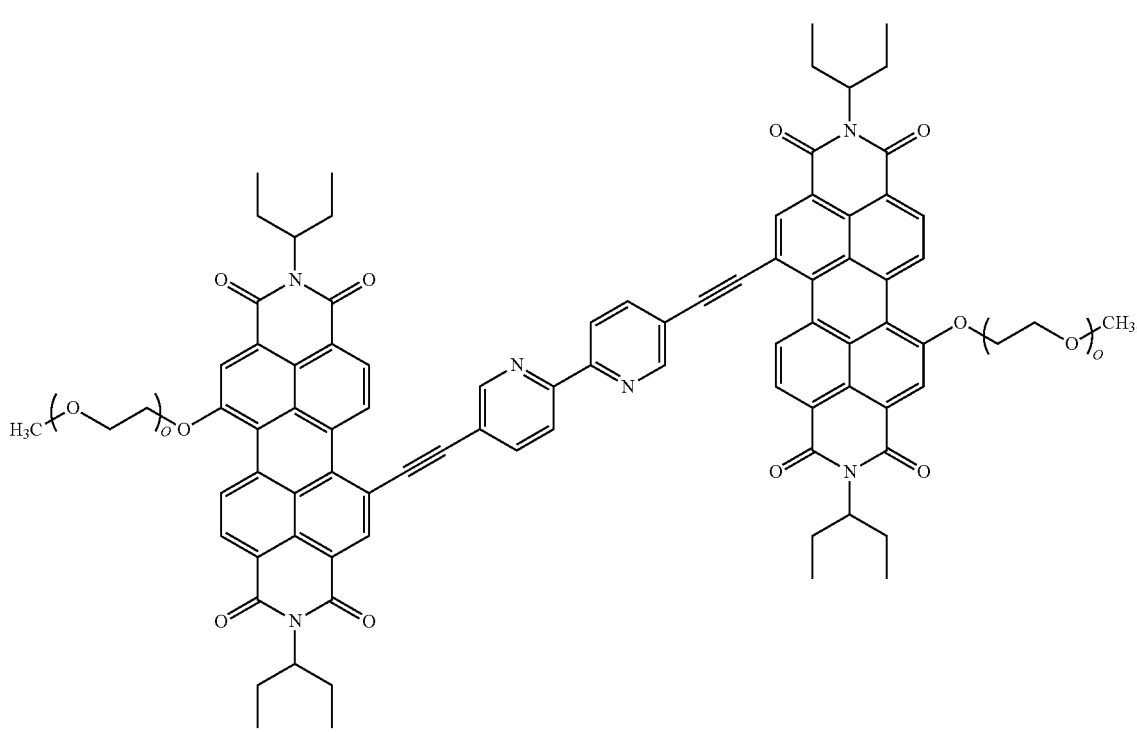

(XV)

wherein said mixture comprises 95% (molar ratio) of compound of formula XV wherein o is 17 and 5% (molar ratio) of a compound of formula XV, wherein o is 23.

17. Noncovalent self-assembled porous membrane comprising a perylene diimide supramolecular structure, which provides a chromatography medium for size-selective separation of nano-material; wherein said perylene diimide supramolecular structure comprises a mixture of perylene diimide compounds, wherein each perylene diimide compound is a monomeric unit represented by the structure of formula XV:

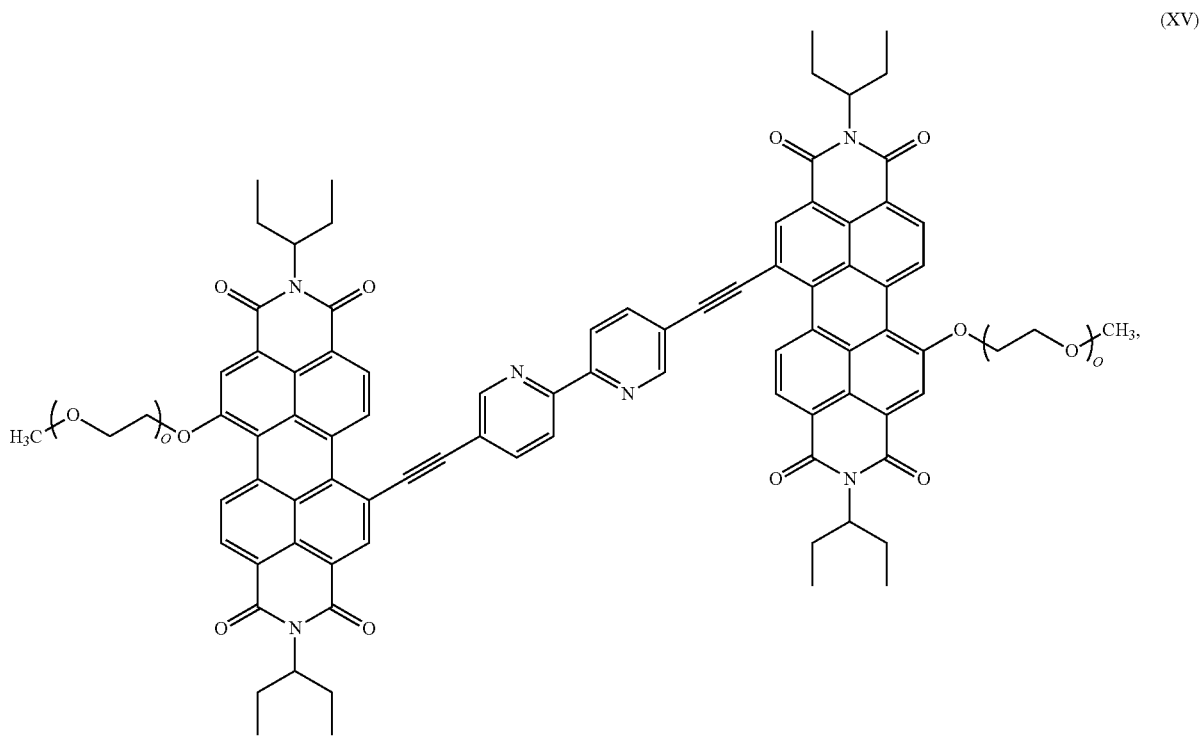

(XV)

wherein said mixture comprises 95% (molar ratio) of compound of formula XV wherein o is 17 and 5% (molar ratio) of a compound of formula XV, wherein o is 13.

18. Noncovalent self-assembled porous membrane comprising a perylene diimide supramolecular structure, which provides a chromatography medium for size-selective separation of nano-material; wherein said perylene diimide supramolecular structure comprises a mixture of perylene diimide compounds, wherein each perylene diimide compound is a monomeric unit represented by the structure of formula XV:

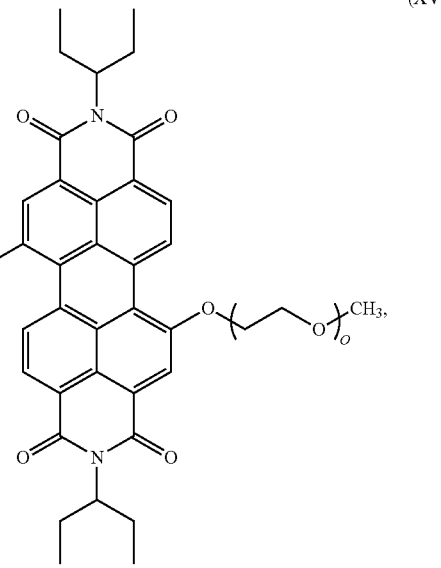
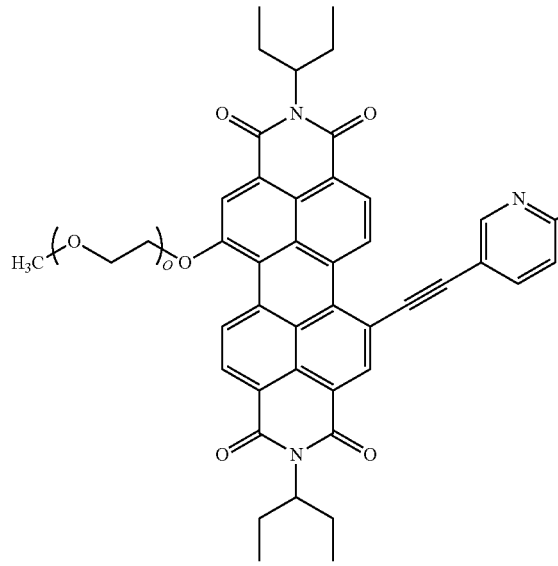

(XV)

wherein said mixture comprises 95% (molar ratio) of compound of formula XV wherein o is 13 and 5% (molar ratio) of a compound of formula XV, wherein o is 23.

19. The membrane of claim 17, wherein the pores size of said membrane have a cutoff size of about 8 nm.

20. The membrane of claim 18, wherein the pores size of said membrane have a cutoff size of about 5 nm.

21. The porous membrane of claim 13, wherein the pores size of said membrane have a cutoff size of between 2-100 nm.

22. The porous membrane of claim 13, wherein said nano-materials are nanoparticles or biomolecules.

23. The porous membrane of claim 13, wherein the size of said pores depends on the thickness of the membrane, wherein the thickness of said membrane is between 5-100 µm.

24. A method of preparing a noncovalent self-assembled perylene diimide based membrane of claim 13 comprising:
a. preparing an organic solution of a mixture of perylene diimide compounds, wherein the organic solvent in said organic solution is miscible in water;
b. adding excess of water to said solution of (a); wherein the ratio between said organic solvent to water is between about 1:99% to 8:92% v/v;
c. evaporating said organic solvent; and
d. transferring the remaining aqueous solution or emulsion through a solid support: thereby obtaining a noncovalent self-assembled perylene diimide based membrane.

25. The method of claim 24, wherein said method comprises further washing said membrane with ethanol.

26. The method of claim 24, wherein said organic solvent is tetrahydrofuran (THF), dimethylacetamide (DMA), dimethylformamide (DMF), acetonitrile, acetone, methanol, ethanol or any combination thereof.

27. The method of claim 24, wherein said solid support is a microfiltration filter comprising cellulose acetate (CA), PES, teflon (PTFE) or polycarbonate, or microfiltration filter with pores smaller or equal to 0.45 microns.

28. A method of separation/filtration or purification of nanoparticles comprising (a) transferring an aqueous solution or emulsion comprising a membrane of claim 20 through porous solid support, thereby forming a noncovalent self assembled perylene diimide based membrane on said porous solid support: (b) transferring nanoparticles through said noncovalent self-assembled perylene diimide based membrane of step (a): wherein the particles which are larger than the pores of said membrane remain on said membrane.

29. The method of claim 28, wherein said noncovalent self-assembled perylene diimide based membrane is further recycled.

30. The method of claim 29, wherein said recycling comprises: (a) washing said solid support with the noncovalent self-assembled perylene diimide based membrane and the retentate deposited thereon, with a solution of alcohol and water; (b) extracting said perylene diimide structure from said solution with an organic solvent; and (c) isolating said perylene diimide from said organic solvent.

31. The method of claim 30, wherein said isolated perylene diimide can be further used to form a noncovalent self-assembled perylene diimide based membrane in aqueous conditions.

* * * * *